US011498955B2

(12) United States Patent
Giaccia et al.

(10) Patent No.: US 11,498,955 B2
(45) Date of Patent: Nov. 15, 2022

(54) SPD-1 VARIANT# FC FUSION PROTEINS

(71) Applicants: The Board of Trustees of the Leland Stanford Junior University, Stanford, CA (US); AKSO Biopharmaceutical, Inc., Menlo Park, CA (US)

(72) Inventors: Amato J. Giaccia, Stanford, CA (US); Todd A. Aguilera, Stanford, CA (US); Mihalis S. Kariolis, Stanford, CA (US); Yu Miao, Stanford, CA (US); Kaushik Thakkar, Stanford, CA (US); Xin Eric Zhang, Menlo Park, CA (US)

(73) Assignees: The Board of Trustees of the Leland Stanford Junior University, Stanford, CA (US); AKSO Biopharmaceutical, Inc., Menlo Park, CA (US)

(*) Notice: Subject to any disclaimer, the term of this patent is extended or adjusted under 35 U.S.C. 154(b) by 476 days.

(21) Appl. No.: 16/569,105

(22) Filed: Sep. 12, 2019

(65) Prior Publication Data
US 2020/0181231 A1 Jun. 11, 2020

Related U.S. Application Data

(63) Continuation of application No. PCT/US2019/050742, filed on Sep. 12, 2019.

(60) Provisional application No. 62/731,488, filed on Sep. 14, 2018, provisional application No. 62/888,320, filed on Aug. 16, 2019.

(51) Int. Cl.
*C07K 14/705* (2006.01)
*A61K 38/00* (2006.01)
*C12N 15/62* (2006.01)
*A61P 31/00* (2006.01)
*A61P 35/00* (2006.01)
*C07K 16/28* (2006.01)

(52) U.S. Cl.
CPC .... *C07K 14/70521* (2013.01); *C07K 16/2827* (2013.01); *A61K 38/00* (2013.01); *C07K 2317/524* (2013.01); *C07K 2317/526* (2013.01); *C07K 2317/53* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| 10,588,938 | B2* | 3/2020 | Giaccia | A61P 31/22 |
| 10,919,950 | B2* | 2/2021 | Jensen | C07K 14/70503 |
| 2012/0121634 | A1* | 5/2012 | Chen | A61P 35/00 604/20 |
| 2019/0358263 | A1* | 11/2019 | Walchli | C07K 14/70521 |
| 2020/0360474 | A1* | 11/2020 | Giaccia | A61P 31/14 |
| 2021/0363219 | A1* | 11/2021 | Swanson | C12N 15/86 |

FOREIGN PATENT DOCUMENTS

| WO | 2014124217 A1 | 8/2014 |
| WO | 2016023001 A1 | 2/2016 |
| WO | 2016164428 A1 | 10/2016 |
| WO | 2017055547 A1 | 4/2017 |
| WO | 2017123548 A1 | 7/2017 |

OTHER PUBLICATIONS

Dong et al., "PD-1 and its Ligands are Important Immune Checkpoints in Cancer," Oncotarget, vol. 8, No. 2, Jan. 10, 2017, pp. 2171-2186.
Du et al., "The Design of High Affinity Human PD-1 Mutants by Using Molecular Dynamics Simulations (MD)," Cell Communication and Signaling, vol. 16, No. 25, Jun. 7, 2018, pp. 1-16.
Iwai et al., "Cancer Immunotherapies Targeting the PD-1 Signaling Pathway," Journal of Biomedical Science, vol. 24, No. 26, Apr. 4, 2017, pp. 1-11.
Maute et al., "Engineering High-Affinity PD-1 Variants for Optimized Immunotherapy and Immuno-PET Imaging," Proceedings of the National Academy of Sciences, vol. 112, No. 47, Nov. 10, 2015, pp. E6506-E6514.
Pascolutti et al., "Structure and Dynamics of PD-L1 and an Ultra-High-Affinity PD-1 Receptor Mutant," Structure, vol. 24, No. 10, Oct. 4, 2016, pp. 1719-1728.
PCT/US2019/050742, "International Search Report and Written Opinion," Dec. 12, 2019, 17 pages.
Shi et al., "Understanding the Structural and Energetic Basis of PD-1 and Monoclonal Antibodies Bound to PD-L1: A Molecular Modeling Perspective," Biochimica et Biophysica Acta, vol. 1862, No. 3, 2018, pp. 576-588.
Sun et al., "Regulation and Function of the PD-L1 Checkpoint," Immunity, vol. 48, No. 3, Mar. 1, 2018, pp. 434-452.
Zak et al., "Structural Biology of the Immune Checkpoint Receptor PD-1 and Its Ligands PD-L1/PD-L2," Structure, vol. 25, No. 8, Aug. 1, 2017, pp. 1163-1174.

* cited by examiner

*Primary Examiner* — Ilia I Ouspenski
(74) *Attorney, Agent, or Firm* — Kilpatrick Townsend & Stockton LLP

(57) ABSTRACT

The invention is directed to novel sPD-1 variant—Fc fusion proteins.

38 Claims, 123 Drawing Sheets
Specification includes a Sequence Listing.

FIG. 1

```
PD1 WT    1  MQIPQAPWPVVWAVLQLGWRPGWFLDSPDRPWNPPTFSPALLVVTEGDNATFTCSFSNTS
PD1 V1    1  MQIPQAPWPVVWAVLQLGWRPGWFLDSPDRPWNPPTFSPALLVVTEGDNATFTCSFSNTS
PD1 V2    1  MQIPQAPWPVVWAVLQLGWRPGWFLDSPDRPWNPPTFSPALLVVTEGDNATFTCSFSNTS

PD1 WT   61  ESFVLNWYRMSPSNQTDKLAAFPEDRSQPGQDCRFRVTQLPNGRDFHMSVVRARRNDSGT
PD1 V1   61  EGFVLNWYRMSPSNQTDKLAAFPEDRGQLGQDCRFRVTQLPNGRDFHMSVVRARRSDSGT
PD1 V2   61  EGFVLNWYRMSPSNQTDKLAAFPEDRGQLGQDCRFRVTQLPNGRDFHMSVVRARRNDSGT

PD1 WT  121  YLCGAISLAPKAQIKESLRAELRVTERRAEVPTAHPSPSPRPAGQFQTLVGGGGS
PD1 V1  121  YLCSAIVLAPKIQIKESLRVELRVTERRAEVPTAHPSPSPRPAGQFQTLVGGGGS
PD1 V2  121  YLCSAIVLAPKIQIKESLRVELRVTERRAEVPTAHPSPSPRPAGQFQTLVGGGGS
```

*Italic* – the signaling peptide domain

Bold – mutated residue

Bold and underlining – mutated N-glycosylation site

Double underlining – Linker

```
IgG4 S228P    1  ESKYGPPCPPCPAPEFLGGPSVFLFPPKPKDTLMISRTPEVTCVVVDVSQEDPEVQFNWY
IgG4 S228P   61  VDGVEVHNAKTKPREEQFNSTYRVVSVLTVLHQDWLNGKEYKCKVSNKGLPSSIEKTISK
IgG4 S228P  121  AKGQPREPQVYTLPPSQEEMTKNQVSLTCLVKGFYPSDIAVEWESNGQPENNYKTTPPVL
IgG4 S228P  181  DSDGSFFLYSRLTVDKSRWQEGNVFSCSVMHEALHNHYTQKSLSLSLGK
```

| Analyte | Ligand | ka (1/Ms) | kd (1/s) | KD (M) |
|---|---|---|---|---|
| Human PD-L1 | s-h-PD1-ECD-Fc version 1 | 2.038E+6 | 6.941E-4 | 3.406E-10 |
| | s-h-PD1-ECD-Fc version 2 | 2.139E+6 | 7.500E-4 | 3.420E-10 |
| | s-h-PD1-ECD-Fc | N/A | N/A | 2.743E-6 |
| Human PD-L2 | s-h-PD1-ECD-Fc version 1 | 4.366E+6 | 0.01288 | 2.949E-9 |
| | s-h-PD1-ECD-Fc version 2 | 4.479E+6 | 0.01524 | 3.402E-9 |
| | s-h-PD1-ECD-Fc | 1.811E+5 | 0.1029 | 5.471E-7 |

FIG. 12

Hinge sequence of Human IgG1:

EPKSCDKTHTCPPCPAPELLGGP

Hinge sequence of Human IgG2:

ERKCCVECPPCPAPPVAGP

Hinge sequence of Human IgG3:

ELKTPLGDTTHTCPRCPEPKSCDTPPPCPRCPEPKSCDTPPPCPRCPEPKSCDTPPPCPRCPAPEFLGGP

Hinge sequence of Human IgG4:

ESKYGPPCPSCPAPEFLGGP

FIG. 17A

1-WT (SEQ ID NO: 11)

PGWFLDSPDRPWNPPTFSPALLVVTEGDNATFTCSFSNTSESFVLNWYRMSPSNQTDKLAAFPEDRSQPGQD
CRFRVTQLPNGRDFHMSVVRARRNDSGTYLCGAISLAPKAQIKESLRAELRVTERRAEVPTAHPSPSPRPAG
QFQTLV

2-7 mutations (SEQ ID NO:12)

PGWFLDSPDRPWNPPTFSPALLVVTEGDNATFTCSFSNTSEGFVLNWYRMSPSNQTDKLAAFPEDRGQLGQ
DCRFRVTQLPNGRDFHMSVVRARRNDSGTYLCSAIVLAPKIQIKESLRVELRVTERRAEVPTAHPSPSPRPAG
QFQTLV

3-1 mutation (SEQ ID NO:13)

PGWFLDSPDRPWNPPTFSPALLVVTEGDNATFTCSFSNTSEGFVLNWYRMSPSNQTDKLAAFPEDRSQPGQ
DCRFRVTQLPNGRDFHMSVVRARRNDSGTYLCGAISLAPKAQIKESLRAELRVTERRAEVPTAHPSPSPRPA
GQFQTLV

4-1 mutation (SEQ ID NO:14)

PGWFLDSPDRPWNPPTFSPALLVVTEGDNATFTCSFSNTSESFVLNWYRMSPSNQTDKLAAFPEDRGQPGQ
DCRFRVTQLPNGRDFHMSVVRARRNDSGTYLCGAISLAPKAQIKESLRAELRVTERRAEVPTAHPSPSPRPA
GQFQTLV

5-1 mutation (SEQ ID NO:15)

PGWFLDSPDRPWNPPTFSPALLVVTEGDNATFTCSFSNTSESFVLNWYRMSPSNQTDKLAAFPEDRSQLGQ
DCRFRVTQLPNGRDFHMSVVRARRNDSGTYLCGAISLAPKAQIKESLRAELRVTERRAEVPTAHPSPSPRPA
GQFQTLV

6-1 mutation (SEQ ID NO:16)

PGWFLDSPDRPWNPPTFSPALLVVTEGDNATFTCSFSNTSESFVLNWYRMSPSNQTDKLAAFPEDRSQPGQD
CRFRVTQLPNGRDFHMSVVRARRNDSGTYLCSAISLAPKAQIKESLRAELRVTERRAEVPTAHPSPSPRPAG
QFQTLV

7-1 mutation (SEQ ID NO:17)

PGWFLDSPDRPWNPPTFSPALLVVTEGDNATFTCSFSNTSESFVLNWYRMSPSNQTDKLAAFPEDRSQPGQD
CRFRVTQLPNGRDFHMSVVRARRNDSGTYLCGAIVLAPKAQIKESLRAELRVTERRAEVPTAHPSPSPRPAG
QFQTLV

8-1 mutation (SEQ ID NO:18)

PGWFLDSPDRPWNPPTFSPALLVVTEGDNATFTCSFSNTSESFVLNWYRMSPSNQTDKLAAFPEDRSQPGQD
CRFRVTQLPNGRDFHMSVVRARRNDSGTYLCGAISLAPKIQIKESLRAELRVTERRAEVPTAHPSPSPRPAGQ
FQTLV

9-1 mutation (SEQ ID NO:19)

PGWFLDSPDRPWNPPTFSPALLVVTEGDNATFTCSFSNTSESFVLNWYRMSPSNQTDKLAAFPEDRSQPGQD
CRFRVTQLPNGRDFHMSVVRARRNDSGTYLCGAISLAPKAQIKESLRVELRVTERRAEVPTAHPSPSPRPAG
QFQTLV

FIG. 17B

10-2 mutations (SEQ ID NO:20)

PGWFLDSPDRPWNPPTFSPALLVVTEGDNATFTCSFSNTSEGFVLNWYRMSPSNQTDKLAAFPEDRGQPGQ
DCRFRVTQLPNGRDFHMSVVRARRNDSGTYLCGAISLAPKAQIKESLRAELRVTERRAEVPTAHPSPSRPA
GQFQTLV

11-2 mutations (SEQ ID NO:21)

PGWFLDSPDRPWNPPTFSPALLVVTEGDNATFTCSFSNTSEGFVLNWYRMSPSNQTDKLAAFPEDRSQLGQ
DCRFRVTQLPNGRDFHMSVVRARRNDSGTYLCGAISLAPKAQIKESLRAELRVTERRAEVPTAHPSPSRPA
GQFQTLV

12-2 mutations (SEQ ID NO:22)

PGWFLDSPDRPWNPPTFSPALLVVTEGDNATFTCSFSNTSEGFVLNWYRMSPSNQTDKLAAFPEDRSQPGQ
DCRFRVTQLPNGRDFHMSVVRARRNDSGTYLCSAISLAPKAQIKESLRAELRVTERRAEVPTAHPSPSRPA
GQFQTLV

13-2 mutations (SEQ ID NO:23)

PGWFLDSPDRPWNPPTFSPALLVVTEGDNATFTCSFSNTSEGFVLNWYRMSPSNQTDKLAAFPEDRSQPGQ
DCRFRVTQLPNGRDFHMSVVRARRNDSGTYLCGAIVLAPKAQIKESLRAELRVTERRAEVPTAHPSPSRPA
GQFQTLV

14-2 mutations (SEQ ID NO:24)

PGWFLDSPDRPWNPPTFSPALLVVTEGDNATFTCSFSNTSEGFVLNWYRMSPSNQTDKLAAFPEDRSQPGQ
DCRFRVTQLPNGRDFHMSVVRARRNDSGTYLCGAISLAPKIQIKESLRAELRVTERRAEVPTAHPSPSRPAG
QFQTLV

15-2 mutations (SEQ ID NO:25)

PGWFLDSPDRPWNPPTFSPALLVVTEGDNATFTCSFSNTSEGFVLNWYRMSPSNQTDKLAAFPEDRSQPGQ
DCRFRVTQLPNGRDFHMSVVRARRNDSGTYLCGAISLAPKAQIKESLRVELRVTERRAEVPTAHPSPSRPA
GQFQTLV

16-2 mutations (SEQ ID NO:26)

PGWFLDSPDRPWNPPTFSPALLVVTEGDNATFTCSFSNTSESFVLNWYRMSPSNQTDKLAAFPEDRGQLGQ
DCRFRVTQLPNGRDFHMSVVRARRNDSGTYLCGAISLAPKAQIKESLRAELRVTERRAEVPTAHPSPSRPA
GQFQTLV

17-2 mutations (SEQ ID NO:27)

PGWFLDSPDRPWNPPTFSPALLVVTEGDNATFTCSFSNTSESFVLNWYRMSPSNQTDKLAAFPEDRGQPGQ
DCRFRVTQLPNGRDFHMSVVRARRNDSGTYLCSAISLAPKAQIKESLRAELRVTERRAEVPTAHPSPSRPA
GQFQTLV

18-2 mutations (SEQ ID NO:28)

PGWFLDSPDRPWNPPTFSPALLVVTEGDNATFTCSFSNTSESFVLNWYRMSPSNQTDKLAAFPEDRGQPGQ
DCRFRVTQLPNGRDFHMSVVRARRNDSGTYLCGAIVLAPKAQIKESLRAELRVTERRAEVPTAHPSPSRPA
GQFQTLV

FIG. 17C

19-2 mutations (SEQ ID NO:29)

PGWFLDSPDRPWNPPTFSPALLVVTEGDNATFTCSFSNTSESFVLNWYRMSPSNQTDKLAAFPEDRGQPGQ
DCRFRVTQLPNGRDFHMSVVRARRNDSGTYLCGAISLAPKIQIKESLRAELRVTERRAEVPTAHPSPSPRPAG
QFQTLV

20-2 mutations (SEQ ID NO:30)

PGWFLDSPDRPWNPPTFSPALLVVTEGDNATFTCSFSNTSESFVLNWYRMSPSNQTDKLAAFPEDRGQPGQ
DCRFRVTQLPNGRDFHMSVVRARRNDSGTYLCGAISLAPKAQIKESLRVELRVTERRAEVPTAHPSPSPRPA
GQFQTLV

21-2 mutations (SEQ ID NO:31)

PGWFLDSPDRPWNPPTFSPALLVVTEGDNATFTCSFSNTSESFVLNWYRMSPSNQTDKLAAFPEDRSQLGQ
DCRFRVTQLPNGRDFHMSVVRARRNDSGTYLCSAISLAPKAQIKESLRAELRVTERRAEVPTAHPSPSPRPA
GQFQTLV

22-2 mutations (SEQ ID NO:32)

PGWFLDSPDRPWNPPTFSPALLVVTEGDNATFTCSFSNTSESFVLNWYRMSPSNQTDKLAAFPEDRSQLGQ
DCRFRVTQLPNGRDFHMSVVRARRNDSGTYLCGAIVLAPKAQIKESLRAELRVTERRAEVPTAHPSPSPRPA
GQFQTLV

23-2 mutations (SEQ ID NO:33)

PGWFLDSPDRPWNPPTFSPALLVVTEGDNATFTCSFSNTSESFVLNWYRMSPSNQTDKLAAFPEDRSQLGQ
DCRFRVTQLPNGRDFHMSVVRARRNDSGTYLCGAISLAPKIQIKESLRAELRVTERRAEVPTAHPSPSPRPAG
QFQTLV

24-2 mutations (SEQ ID NO:34)

PGWFLDSPDRPWNPPTFSPALLVVTEGDNATFTCSFSNTSESFVLNWYRMSPSNQTDKLAAFPEDRSQLGQ
DCRFRVTQLPNGRDFHMSVVRARRNDSGTYLCGAISLAPKAQIKESLRVELRVTERRAEVPTAHPSPSPRPA
GQFQTLV

25-2 mutations (SEQ ID NO:35)

PGWFLDSPDRPWNPPTFSPALLVVTEGDNATFTCSFSNTSESFVLNWYRMSPSNQTDKLAAFPEDRSQPGQD
CRFRVTQLPNGRDFHMSVVRARRNDSGTYLCSAIVLAPKAQIKESLRAELRVTERRAEVPTAHPSPSPRPAG
QFQTLV

26-2 mutations (SEQ ID NO:36)

PGWFLDSPDRPWNPPTFSPALLVVTEGDNATFTCSFSNTSESFVLNWYRMSPSNQTDKLAAFPEDRSQPGQD
CRFRVTQLPNGRDFHMSVVRARRNDSGTYLCSAISLAPKIQIKESLRAELRVTERRAEVPTAHPSPSPRPAGQ
FQTLV

27-2 mutations (SEQ ID NO:37)

PGWFLDSPDRPWNPPTFSPALLVVTEGDNATFTCSFSNTSESFVLNWYRMSPSNQTDKLAAFPEDRSQPGQD
CRFRVTQLPNGRDFHMSVVRARRNDSGTYLCSAISLAPKAQIKESLRVELRVTERRAEVPTAHPSPSPRPAG
QFQTLV

FIG. 17D

28-2 mutations (SEQ ID NO:38)

PGWFLDSPDRPWNPPTFSPALLVVTEGDNATFTCSFSNTSESFVLNWYRMSPSNQTDKLAAFPEDRSQPGQD
CRFRVTQLPNGRDFHMSVVRARRNDSGTYLCGAIVLAPKIQIKESLRAELRVTERRAEVPTAHPSPSPRPAG
QFQTLV

29-2 mutations (SEQ ID NO:39)

PGWFLDSPDRPWNPPTFSPALLVVTEGDNATFTCSFSNTSESFVLNWYRMSPSNQTDKLAAFPEDRSQPGQD
CRFRVTQLPNGRDFHMSVVRARRNDSGTYLCGAIVLAPKAQIKESLRVELRVTERRAEVPTAHPSPSPRPAG
QFQTLV

30-2 mutations (SEQ ID NO:40)

PGWFLDSPDRPWNPPTFSPALLVVTEGDNATFTCSFSNTSESFVLNWYRMSPSNQTDKLAAFPEDRSQPGQD
CRFRVTQLPNGRDFHMSVVRARRNDSGTYLCGAISLAPKIQIKESLRVELRVTERRAEVPTAHPSPSPRPAGQ
FQTLV

31-3 mutations (SEQ ID NO:41)

PGWFLDSPDRPWNPPTFSPALLVVTEGDNATFTCSFSNTSEGFVLNWYRMSPSNQTDKLAAFPEDRGQLGQ
DCRFRVTQLPNGRDFHMSVVRARRNDSGTYLCGAISLAPKAQIKESLRAELRVTERRAEVPTAHPSPSPRPA
GQFQTLV

32-3 mutations (SEQ ID NO:42)

PGWFLDSPDRPWNPPTFSPALLVVTEGDNATFTCSFSNTSEGFVLNWYRMSPSNQTDKLAAFPEDRGQPGQ
DCRFRVTQLPNGRDFHMSVVRARRNDSGTYLCSAISLAPKAQIKESLRAELRVTERRAEVPTAHPSPSPRPA
GQFQTLV

33-3 mutations (SEQ ID NO:43)

PGWFLDSPDRPWNPPTFSPALLVVTEGDNATFTCSFSNTSEGFVLNWYRMSPSNQTDKLAAFPEDRGQPGQ
DCRFRVTQLPNGRDFHMSVVRARRNDSGTYLCGAIVLAPKAQIKESLRAELRVTERRAEVPTAHPSPSPRPA
GQFQTLV

34-3 mutations (SEQ ID NO:44)

PGWFLDSPDRPWNPPTFSPALLVVTEGDNATFTCSFSNTSEGFVLNWYRMSPSNQTDKLAAFPEDRGQPGQ
DCRFRVTQLPNGRDFHMSVVRARRNDSGTYLCGAISLAPKIQIKESLRAELRVTERRAEVPTAHPSPSPRPAG
QFQTLV

35-3 mutations (SEQ ID NO:45)

PGWFLDSPDRPWNPPTFSPALLVVTEGDNATFTCSFSNTSEGFVLNWYRMSPSNQTDKLAAFPEDRGQPGQ
DCRFRVTQLPNGRDFHMSVVRARRNDSGTYLCGAISLAPKAQIKESLRVELRVTERRAEVPTAHPSPSPRPA
GQFQTLV

36-3 mutations (SEQ ID NO:46)

PGWFLDSPDRPWNPPTFSPALLVVTEGDNATFTCSFSNTSEGFVLNWYRMSPSNQTDKLAAFPEDRSQLGQ
DCRFRVTQLPNGRDFHMSVVRARRNDSGTYLCSAISLAPKAQIKESLRAELRVTERRAEVPTAHPSPSPRPA
GQFQTLV

FIG. 17E

37-3 mutations (SEQ ID NO:47)

PGWFLDSPDRPWNPPTFSPALLVVTEGDNATFTCSFSNTSEGFVLNWYRMSPSNQTDKLAAFPEDRSQLGQ
DCRFRVTQLPNGRDFHMSVVRARRNDSGTYLCGAIVLAPKAQIKESLRAELRVTERRAEVPTAHPSPSPRPA
GQFQTLV

38-3 mutations (SEQ ID NO:48)

PGWFLDSPDRPWNPPTFSPALLVVTEGDNATFTCSFSNTSEGFVLNWYRMSPSNQTDKLAAFPEDRSQLGQ
DCRFRVTQLPNGRDFHMSVVRARRNDSGTYLCGAISLAPKIQIKESLRAELRVTERRAEVPTAHPSPSPRPAG
QFQTLV

39-3 mutations (SEQ ID NO:49)

PGWFLDSPDRPWNPPTFSPALLVVTEGDNATFTCSFSNTSEGFVLNWYRMSPSNQTDKLAAFPEDRSQLGQ
DCRFRVTQLPNGRDFHMSVVRARRNDSGTYLCGAISLAPKAQIKESLRVELRVTERRAEVPTAHPSPSPRPA
GQFQTLV

40-3 mutations (SEQ ID NO:50)

PGWFLDSPDRPWNPPTFSPALLVVTEGDNATFTCSFSNTSEGFVLNWYRMSPSNQTDKLAAFPEDRSQPGQ
DCRFRVTQLPNGRDFHMSVVRARRNDSGTYLCSAIVLAPKAQIKESLRAELRVTERRAEVPTAHPSPSPRPA
GQFQTLV

41-3 mutations (SEQ ID NO:51)

PGWFLDSPDRPWNPPTFSPALLVVTEGDNATFTCSFSNTSEGFVLNWYRMSPSNQTDKLAAFPEDRSQPGQ
DCRFRVTQLPNGRDFHMSVVRARRNDSGTYLCSAISLAPKIQIKESLRAELRVTERRAEVPTAHPSPSPRPAG
QFQTLV

42-3 mutations (SEQ ID NO:52)

PGWFLDSPDRPWNPPTFSPALLVVTEGDNATFTCSFSNTSEGFVLNWYRMSPSNQTDKLAAFPEDRSQPGQ
DCRFRVTQLPNGRDFHMSVVRARRNDSGTYLCSAISLAPKAQIKESLRVELRVTERRAEVPTAHPSPSPRPA
GQFQTLV

43-3 mutations (SEQ ID NO:53)

PGWFLDSPDRPWNPPTFSPALLVVTEGDNATFTCSFSNTSEGFVLNWYRMSPSNQTDKLAAFPEDRSQPGQ
DCRFRVTQLPNGRDFHMSVVRARRNDSGTYLCGAIVLAPKIQIKESLRAELRVTERRAEVPTAHPSPSPRPA
GQFQTLV

44-3 mutations (SEQ ID NO:54)

PGWFLDSPDRPWNPPTFSPALLVVTEGDNATFTCSFSNTSEGFVLNWYRMSPSNQTDKLAAFPEDRSQPGQ
DCRFRVTQLPNGRDFHMSVVRARRNDSGTYLCGAIVLAPKAQIKESLRVELRVTERRAEVPTAHPSPSPRPA
GQFQTLV

45-3 mutations (SEQ ID NO:55)

PGWFLDSPDRPWNPPTFSPALLVVTEGDNATFTCSFSNTSEGFVLNWYRMSPSNQTDKLAAFPEDRSQPGQ
DCRFRVTQLPNGRDFHMSVVRARRNDSGTYLCGAISLAPKIQIKESLRVELRVTERRAEVPTAHPSPSPRPAG
QFQTLV

FIG. 17F

46-3 mutations (SEQ ID NO:56)

PGWFLDSPDRPWNPPTFSPALLVVTEGDNATFTCSFSNTSESFVLNWYRMSPSNQTDKLAAFPEDRGQLGQ
DCRFRVTQLPNGRDFHMSVVRARRNDSGTYLCSAISLAPKAQIKESLRAELRVTERRAEVPTAHPSPSPRPA
GQFQTLV

47-3 mutations (SEQ ID NO:57)

PGWFLDSPDRPWNPPTFSPALLVVTEGDNATFTCSFSNTSESFVLNWYRMSPSNQTDKLAAFPEDRGQLGQ
DCRFRVTQLPNGRDFHMSVVRARRNDSGTYLCGAIVLAPKAQIKESLRAELRVTERRAEVPTAHPSPSPRPA
GQFQTLV

48-3 mutations (SEQ ID NO:58)

PGWFLDSPDRPWNPPTFSPALLVVTEGDNATFTCSFSNTSESFVLNWYRMSPSNQTDKLAAFPEDRGQLGQ
DCRFRVTQLPNGRDFHMSVVRARRNDSGTYLCGAISLAPKIQIKESLRAELRVTERRAEVPTAHPSPSPRPAG
QFQTLV

49-3 mutations (SEQ ID NO:59)

PGWFLDSPDRPWNPPTFSPALLVVTEGDNATFTCSFSNTSESFVLNWYRMSPSNQTDKLAAFPEDRGQLGQ
DCRFRVTQLPNGRDFHMSVVRARRNDSGTYLCGAISLAPKAQIKESLRVELRVTERRAEVPTAHPSPSPRPA
GQFQTLV

50-3 mutations (SEQ ID NO:60)

PGWFLDSPDRPWNPPTFSPALLVVTEGDNATFTCSFSNTSESFVLNWYRMSPSNQTDKLAAFPEDRGQPGQ
DCRFRVTQLPNGRDFHMSVVRARRNDSGTYLCSAIVLAPKAQIKESLRAELRVTERRAEVPTAHPSPSPRPA
GQFQTLV

51-3 mutations (SEQ ID NO:61)

PGWFLDSPDRPWNPPTFSPALLVVTEGDNATFTCSFSNTSESFVLNWYRMSPSNQTDKLAAFPEDRGQPGQ
DCRFRVTQLPNGRDFHMSVVRARRNDSGTYLCSAISLAPKIQIKESLRAELRVTERRAEVPTAHPSPSPRPAG
QFQTLV

52-3 mutations (SEQ ID NO:62)

PGWFLDSPDRPWNPPTFSPALLVVTEGDNATFTCSFSNTSESFVLNWYRMSPSNQTDKLAAFPEDRGQPGQ
DCRFRVTQLPNGRDFHMSVVRARRNDSGTYLCSAISLAPKAQIKESLRVELRVTERRAEVPTAHPSPSPRPA
GQFQTLV

53-3 mutations (SEQ ID NO:63)

PGWFLDSPDRPWNPPTFSPALLVVTEGDNATFTCSFSNTSESFVLNWYRMSPSNQTDKLAAFPEDRGQPGQ
DCRFRVTQLPNGRDFHMSVVRARRNDSGTYLCGAIVLAPKIQIKESLRAELRVTERRAEVPTAHPSPSPRPA
GQFQTLV

54-3 mutations (SEQ ID NO:64)

PGWFLDSPDRPWNPPTFSPALLVVTEGDNATFTCSFSNTSESFVLNWYRMSPSNQTDKLAAFPEDRGQPGQ
DCRFRVTQLPNGRDFHMSVVRARRNDSGTYLCGAIVLAPKAQIKESLRVELRVTERRAEVPTAHPSPSPRPA
GQFQTLV

FIG. 17G

55-3 mutations (SEQ ID NO:65)

PGWFLDSPDRPWNPPTFSPALLVVTEGDNATFTCSFSNTSESFVLNWYRMSPSNQTDKLAAFPEDRGQPGQ
DCRFRVTQLPNGRDFHMSVVRARRNDSGTYLCGAISLAPKIQIKESLRVELRVTERRAEVPTAHPSPSPRPAG
QFQTLV

56-3 mutations (SEQ ID NO:66)

PGWFLDSPDRPWNPPTFSPALLVVTEGDNATFTCSFSNTSESFVLNWYRMSPSNQTDKLAAFPEDRSQLGQ
DCRFRVTQLPNGRDFHMSVVRARRNDSGTYLCSAIVLAPKAQIKESLRAELRVTERRAEVPTAHPSPSPRPA
GQFQTLV

57-3 mutations (SEQ ID NO:67)

PGWFLDSPDRPWNPPTFSPALLVVTEGDNATFTCSFSNTSESFVLNWYRMSPSNQTDKLAAFPEDRSQLGQ
DCRFRVTQLPNGRDFHMSVVRARRNDSGTYLCSAISLAPKIQIKESLRAELRVTERRAEVPTAHPSPSPRPAG
QFQTLV

58-3 mutations (SEQ ID NO:68)

PGWFLDSPDRPWNPPTFSPALLVVTEGDNATFTCSFSNTSESFVLNWYRMSPSNQTDKLAAFPEDRSQLGQ
DCRFRVTQLPNGRDFHMSVVRARRNDSGTYLCSAISLAPKAQIKESLRVELRVTERRAEVPTAHPSPSPRPA
GQFQTLV

59-3 mutations (SEQ ID NO:69)

PGWFLDSPDRPWNPPTFSPALLVVTEGDNATFTCSFSNTSESFVLNWYRMSPSNQTDKLAAFPEDRSQLGQ
DCRFRVTQLPNGRDFHMSVVRARRNDSGTYLCGAIVLAPKIQIKESLRAELRVTERRAEVPTAHPSPSPRPA
GQFQTLV

60-3 mutations (SEQ ID NO:70)

PGWFLDSPDRPWNPPTFSPALLVVTEGDNATFTCSFSNTSESFVLNWYRMSPSNQTDKLAAFPEDRSQLGQ
DCRFRVTQLPNGRDFHMSVVRARRNDSGTYLCGAIVLAPKAQIKESLRVELRVTERRAEVPTAHPSPSPRPA
GQFQTLV

61-3 mutations (SEQ ID NO:71)

PGWFLDSPDRPWNPPTFSPALLVVTEGDNATFTCSFSNTSESFVLNWYRMSPSNQTDKLAAFPEDRSQLGQ
DCRFRVTQLPNGRDFHMSVVRARRNDSGTYLCGAISLAPKIQIKESLRVELRVTERRAEVPTAHPSPRPAG
QFQTLV

62-3 mutations (SEQ ID NO:72)

PGWFLDSPDRPWNPPTFSPALLVVTEGDNATFTCSFSNTSESFVLNWYRMSPSNQTDKLAAFPEDRSQPGQD
CRFRVTQLPNGRDFHMSVVRARRNDSGTYLCSAIVLAPKIQIKESLRAELRVTERRAEVPTAHPSPSPRPAGQ
FQTLV

63-3 mutations (SEQ ID NO:73)

PGWFLDSPDRPWNPPTFSPALLVVTEGDNATFTCSFSNTSESFVLNWYRMSPSNQTDKLAAFPEDRSQPGQD
CRFRVTQLPNGRDFHMSVVRARRNDSGTYLCSAIVLAPKAQIKESLRVELRVTERRAEVPTAHPSPSPRPAG
QFQTLV

FIG. 17H

64-3 mutations (SEQ ID NO:74)

PGWFLDSPDRPWNPPTFSPALLVVTEGDNATFTCSFSNTSESFVLNWYRMSPSNQTDKLAAFPEDRSQPGQD
CRFRVTQLPNGRDFHMSVVRARRNDSGTYLCSAISLAPKIQIKESLRVELRVTERRAEVPTAHPSPSRPAGQ
FQTLV

65-3 mutations (SEQ ID NO:75)

PGWFLDSPDRPWNPPTFSPALLVVTEGDNATFTCSFSNTSESFVLNWYRMSPSNQTDKLAAFPEDRSQPGQD
CRFRVTQLPNGRDFHMSVVRARRNDSGTYLCGAIVLAPKIQIKESLRVELRVTERRAEVPTAHPSPSRPAG
QFQTLV

66-4 mutations (SEQ ID NO:76)

PGWFLDSPDRPWNPPTFSPALLVVTEGDNATFTCSFSNTSEGFVLNWYRMSPSNQTDKLAAFPEDRGQLGQ
DCRFRVTQLPNGRDFHMSVVRARRNDSGTYLCSAISLAPKAQIKESLRAELRVTERRAEVPTAHPSPSRPA
GQFQTLV

67-4 mutations (SEQ ID NO:77)

PGWFLDSPDRPWNPPTFSPALLVVTEGDNATFTCSFSNTSEGFVLNWYRMSPSNQTDKLAAFPEDRGQLGQ
DCRFRVTQLPNGRDFHMSVVRARRNDSGTYLCGAIVLAPKAQIKESLRAELRVTERRAEVPTAHPSPSRPA
GQFQTLV

68-4 mutations (SEQ ID NO:78)

PGWFLDSPDRPWNPPTFSPALLVVTEGDNATFTCSFSNTSEGFVLNWYRMSPSNQTDKLAAFPEDRGQLGQ
DCRFRVTQLPNGRDFHMSVVRARRNDSGTYLCGAISLAPKIQIKESLRAELRVTERRAEVPTAHPSPSRPAG
QFQTLV

69-4 mutations (SEQ ID NO:79)

PGWFLDSPDRPWNPPTFSPALLVVTEGDNATFTCSFSNTSEGFVLNWYRMSPSNQTDKLAAFPEDRGQLGQ
DCRFRVTQLPNGRDFHMSVVRARRNDSGTYLCGAISLAPKAQIKESLRVELRVTERRAEVPTAHPSPSRPA
GQFQTLV

70-4 mutations (SEQ ID NO:80)

PGWFLDSPDRPWNPPTFSPALLVVTEGDNATFTCSFSNTSEGFVLNWYRMSPSNQTDKLAAFPEDRGQPGQ
DCRFRVTQLPNGRDFHMSVVRARRNDSGTYLCSAIVLAPKAQIKESLRAELRVTERRAEVPTAHPSPSRPA
GQFQTLV

71-4 mutations (SEQ ID NO:81)

PGWFLDSPDRPWNPPTFSPALLVVTEGDNATFTCSFSNTSEGFVLNWYRMSPSNQTDKLAAFPEDRGQPGQ
DCRFRVTQLPNGRDFHMSVVRARRNDSGTYLCSAISLAPKIQIKESLRAELRVTERRAEVPTAHPSPSRPAG
QFQTLV

72-4 mutations (SEQ ID NO:82)

PGWFLDSPDRPWNPPTFSPALLVVTEGDNATFTCSFSNTSEGFVLNWYRMSPSNQTDKLAAFPEDRGQPGQ
DCRFRVTQLPNGRDFHMSVVRARRNDSGTYLCSAISLAPKAQIKESLRVELRVTERRAEVPTAHPSPSRPA
GQFQTLV

FIG. 17I

73-4 mutations (SEQ ID NO:83)

PGWFLDSPDRPWNPPTFSPALLVVTEGDNATFTCSFSNTSEGFVLNWYRMSPSNQTDKLAAFPEDRGQPGQ
DCRFRVTQLPNGRDFHMSVVRARRNDSGTYLCGAIVLAPKIQIKESLRAELRVTERRAEVPTAHPSPSRPA
GQFQTLV

74-4 mutations (SEQ ID NO:84)

PGWFLDSPDRPWNPPTFSPALLVVTEGDNATFTCSFSNTSEGFVLNWYRMSPSNQTDKLAAFPEDRGQPGQ
DCRFRVTQLPNGRDFHMSVVRARRNDSGTYLCGAIVLAPKAQIKESLRVELRVTERRAEVPTAHPSPSRPA
GQFQTLV

75-4 mutations (SEQ ID NO:85)

PGWFLDSPDRPWNPPTFSPALLVVTEGDNATFTCSFSNTSEGFVLNWYRMSPSNQTDKLAAFPEDRGQPGQ
DCRFRVTQLPNGRDFHMSVVRARRNDSGTYLCGAISLAPKIQIKESLRVELRVTERRAEVPTAHPSPSRPAG
QFQTLV

76-4 mutations (SEQ ID NO:86)

PGWFLDSPDRPWNPPTFSPALLVVTEGDNATFTCSFSNTSEGFVLNWYRMSPSNQTDKLAAFPEDRSQLGQ
DCRFRVTQLPNGRDFHMSVVRARRNDSGTYLCSAIVLAPKAQIKESLRAELRVTERRAEVPTAHPSPSRPA
GQFQTLV

77-4 mutations (SEQ ID NO:87)

PGWFLDSPDRPWNPPTFSPALLVVTEGDNATFTCSFSNTSEGFVLNWYRMSPSNQTDKLAAFPEDRSQLGQ
DCRFRVTQLPNGRDFHMSVVRARRNDSGTYLCSAISLAPKIQIKESLRAELRVTERRAEVPTAHPSPSRPAG
QFQTLV

78-4 mutations (SEQ ID NO:88)

PGWFLDSPDRPWNPPTFSPALLVVTEGDNATFTCSFSNTSEGFVLNWYRMSPSNQTDKLAAFPEDRSQLGQ
DCRFRVTQLPNGRDFHMSVVRARRNDSGTYLCSAISLAPKAQIKESLRVELRVTERRAEVPTAHPSPSRPA
GQFQTLV

79-4 mutations (SEQ ID NO:89)

PGWFLDSPDRPWNPPTFSPALLVVTEGDNATFTCSFSNTSEGFVLNWYRMSPSNQTDKLAAFPEDRSQLGQ
DCRFRVTQLPNGRDFHMSVVRARRNDSGTYLCGAIVLAPKIQIKESLRAELRVTERRAEVPTAHPSPSRPA
GQFQTLV

80-4 mutations (SEQ ID NO:90)

PGWFLDSPDRPWNPPTFSPALLVVTEGDNATFTCSFSNTSEGFVLNWYRMSPSNQTDKLAAFPEDRSQLGQ
DCRFRVTQLPNGRDFHMSVVRARRNDSGTYLCGAIVLAPKAQIKESLRVELRVTERRAEVPTAHPSPSRPA
GQFQTLV

81-4 mutations (SEQ ID NO:91)

PGWFLDSPDRPWNPPTFSPALLVVTEGDNATFTCSFSNTSEGFVLNWYRMSPSNQTDKLAAFPEDRSQLGQ
DCRFRVTQLPNGRDFHMSVVRARRNDSGTYLCGAISLAPKIQIKESLRVELRVTERRAEVPTAHPSPSRPAG
QFQTLV

FIG. 17J

82-4 mutations (SEQ ID NO:92)

PGWFLDSPDRPWNPPTFSPALLVVTEGDNATFTCSFSNTSEGFVLNWYRMSPSNQTDKLAAFPEDRSQPGQ
DCRFRVTQLPNGRDFHMSVVRARRNDSGTYLCSAIVLAPKIQIKESLRAELRVTERRAEVPTAHPSPSPRPAG
QFQTLV

83-4 mutations (SEQ ID NO:93)

PGWFLDSPDRPWNPPTFSPALLVVTEGDNATFTCSFSNTSEGFVLNWYRMSPSNQTDKLAAFPEDRSQPGQ
DCRFRVTQLPNGRDFHMSVVRARRNDSGTYLCSAIVLAPKAQIKESLRVELRVTERRAEVPTAHPSPSPRPA
GQFQTLV

84-4 mutations (SEQ ID NO:94)

PGWFLDSPDRPWNPPTFSPALLVVTEGDNATFTCSFSNTSEGFVLNWYRMSPSNQTDKLAAFPEDRSQPGQ
DCRFRVTQLPNGRDFHMSVVRARRNDSGTYLCSAISLAPKIQIKESLRVELRVTERRAEVPTAHPSPSPRPAG
QFQTLV

85-4 mutations (SEQ ID NO:95)

PGWFLDSPDRPWNPPTFSPALLVVTEGDNATFTCSFSNTSEGFVLNWYRMSPSNQTDKLAAFPEDRSQPGQ
DCRFRVTQLPNGRDFHMSVVRARRNDSGTYLCGAIVLAPKIQIKESLRVELRVTERRAEVPTAHPSPSPRPA
GQFQTLV

86-4 mutations (SEQ ID NO:96)

PGWFLDSPDRPWNPPTFSPALLVVTEGDNATFTCSFSNTSESFVLNWYRMSPSNQTDKLAAFPEDRGQLGQ
DCRFRVTQLPNGRDFHMSVVRARRNDSGTYLCSAIVLAPKAQIKESLRAELRVTERRAEVPTAHPSPSPRPA
GQFQTLV

87-4 mutations (SEQ ID NO:97)

PGWFLDSPDRPWNPPTFSPALLVVTEGDNATFTCSFSNTSESFVLNWYRMSPSNQTDKLAAFPEDRGQLGQ
DCRFRVTQLPNGRDFHMSVVRARRNDSGTYLCSAISLAPKIQIKESLRAELRVTERRAEVPTAHPSPSPRPAG
QFQTLV

88-4 mutations (SEQ ID NO:98)

PGWFLDSPDRPWNPPTFSPALLVVTEGDNATFTCSFSNTSESFVLNWYRMSPSNQTDKLAAFPEDRGQLGQ
DCRFRVTQLPNGRDFHMSVVRARRNDSGTYLCSAISLAPKAQIKESLRVELRVTERRAEVPTAHPSPSPRPA
GQFQTLV

89-4 mutations (SEQ ID NO:99)

PGWFLDSPDRPWNPPTFSPALLVVTEGDNATFTCSFSNTSESFVLNWYRMSPSNQTDKLAAFPEDRGQLGQ
DCRFRVTQLPNGRDFHMSVVRARRNDSGTYLCGAIVLAPKIQIKESLRAELRVTERRAEVPTAHPSPSPRPA
GQFQTLV

90-4 mutations (SEQ ID NO:100)

PGWFLDSPDRPWNPPTFSPALLVVTEGDNATFTCSFSNTSESFVLNWYRMSPSNQTDKLAAFPEDRGQLGQ
DCRFRVTQLPNGRDFHMSVVRARRNDSGTYLCGAIVLAPKAQIKESLRVELRVTERRAEVPTAHPSPSPRPA
GQFQTLV

FIG. 17K

91-4 mutations (SEQ ID NO:101)

PGWFLDSPDRPWNPPTFSPALLVVTEGDNATFTCSFSNTSESFVLNWYRMSPSNQTDKLAAFPEDRGQLGQ
DCRFRVTQLPNGRDFHMSVVRARRNDSGTYLCGAISLAPKIQIKESLRVELRVTERRAEVPTAHPSPSRPAG
QFQTLV

92-4 mutations (SEQ ID NO:102)

PGWFLDSPDRPWNPPTFSPALLVVTEGDNATFTCSFSNTSESFVLNWYRMSPSNQTDKLAAFPEDRGQPGQ
DCRFRVTQLPNGRDFHMSVVRARRNDSGTYLCSAIVLAPKIQIKESLRAELRVTERRAEVPTAHPSPSRPAG
QFQTLV

93-4 mutations (SEQ ID NO:103)

PGWFLDSPDRPWNPPTFSPALLVVTEGDNATFTCSFSNTSESFVLNWYRMSPSNQTDKLAAFPEDRGQPGQ
DCRFRVTQLPNGRDFHMSVVRARRNDSGTYLCSAIVLAPKAQIKESLRVELRVTERRAEVPTAHPSPSRPA
GQFQTLV

94-4 mutations (SEQ ID NO:104)

PGWFLDSPDRPWNPPTFSPALLVVTEGDNATFTCSFSNTSESFVLNWYRMSPSNQTDKLAAFPEDRGQPGQ
DCRFRVTQLPNGRDFHMSVVRARRNDSGTYLCSAISLAPKIQIKESLRVELRVTERRAEVPTAHPSPSRPAG
QFQTLV

95-4 mutations (SEQ ID NO:105)

PGWFLDSPDRPWNPPTFSPALLVVTEGDNATFTCSFSNTSESFVLNWYRMSPSNQTDKLAAFPEDRGQPGQ
DCRFRVTQLPNGRDFHMSVVRARRNDSGTYLCGAIVLAPKIQIKESLRVELRVTERRAEVPTAHPSPSRPA
GQFQTLV

96-4 mutations (SEQ ID NO:106)

PGWFLDSPDRPWNPPTFSPALLVVTEGDNATFTCSFSNTSESFVLNWYRMSPSNQTDKLAAFPEDRSQLGQ
DCRFRVTQLPNGRDFHMSVVRARRNDSGTYLCSAIVLAPKIQIKESLRAELRVTERRAEVPTAHPSPSRPAG
QFQTLV

97-4 mutations (SEQ ID NO:107)

PGWFLDSPDRPWNPPTFSPALLVVTEGDNATFTCSFSNTSESFVLNWYRMSPSNQTDKLAAFPEDRSQLGQ
DCRFRVTQLPNGRDFHMSVVRARRNDSGTYLCSAIVLAPKAQIKESLRVELRVTERRAEVPTAHPSPSRPA
GQFQTLV

98-4 mutations (SEQ ID NO:108)

PGWFLDSPDRPWNPPTFSPALLVVTEGDNATFTCSFSNTSESFVLNWYRMSPSNQTDKLAAFPEDRSQLGQ
DCRFRVTQLPNGRDFHMSVVRARRNDSGTYLCSAISLAPKIQIKESLRVELRVTERRAEVPTAHPSPSRPAG
QFQTLV

99-4 mutations (SEQ ID NO:109)

PGWFLDSPDRPWNPPTFSPALLVVTEGDNATFTCSFSNTSEFVLNWYRMSPSNQTDKLAAFPEDRSQLGQD
CRFRVTQLPNGRDFHMSVVRARRNDSGTYLCGAIVLAPKIQIKESLRVELRVTERRAEVPTAHPSPSRPAG
QFQTLV

FIG. 17L

100-4 mutations (SEQ ID NO:110)

PGWFLDSPDRPWNPPTFSPALLVVTEGDNATFTCSFSNTSESFVLNWYRMSPSNQTDKLAAFPEDRSQPGQD
CRFRVTQLPNGRDFHMSVVRARRNDSGTYLCSAIVLAPKIQIKESLRVELRVTERRAEVPTAHPSPSRPAGQ
FQTLV

101-5 mutations (SEQ ID NO:111)

PGWFLDSPDRPWNPPTFSPALLVVTEGDNATFTCSFSNTSEGFVLNWYRMSPSNQTDKLAAFPEDRGQLGQ
DCRFRVTQLPNGRDFHMSVVRARRNDSGTYLCSAIVLAPKAQIKESLRAELRVTERRAEVPTAHPSPSRPA
GQFQTLV

102-5 mutations (SEQ ID NO:112)

PGWFLDSPDRPWNPPTFSPALLVVTEGDNATFTCSFSNTSEGFVLNWYRMSPSNQTDKLAAFPEDRGQLGQ
DCRFRVTQLPNGRDFHMSVVRARRNDSGTYLCSAISLAPKIQIKESLRAELRVTERRAEVPTAHPSPSRPAG
QFQTLV

103-5 mutations (SEQ ID NO:113)

PGWFLDSPDRPWNPPTFSPALLVVTEGDNATFTCSFSNTSEGFVLNWYRMSPSNQTDKLAAFPEDRGQLGQ
DCRFRVTQLPNGRDFHMSVVRARRNDSGTYLCSAISLAPKAQIKESLRVELRVTERRAEVPTAHPSPSRPA
GQFQTLV

104-5 mutations (SEQ ID NO:114)

PGWFLDSPDRPWNPPTFSPALLVVTEGDNATFTCSFSNTSEGFVLNWYRMSPSNQTDKLAAFPEDRGQLGQ
DCRFRVTQLPNGRDFHMSVVRARRNDSGTYLCGAIVLAPKIQIKESLRAELRVTERRAEVPTAHPSPSRPA
GQFQTLV

105-5 mutations (SEQ ID NO:115)

PGWFLDSPDRPWNPPTFSPALLVVTEGDNATFTCSFSNTSEGFVLNWYRMSPSNQTDKLAAFPEDRGQLGQ
DCRFRVTQLPNGRDFHMSVVRARRNDSGTYLCGAIVLAPKAQIKESLRVELRVTERRAEVPTAHPSPSRPA
GQFQTLV

106-5 mutations (SEQ ID NO:116)

PGWFLDSPDRPWNPPTFSPALLVVTEGDNATFTCSFSNTSEGFVLNWYRMSPSNQTDKLAAFPEDRGQLGQ
DCRFRVTQLPNGRDFHMSVVRARRNDSGTYLCGAISLAPKIQIKESLRVELRVTERRAEVPTAHPSPSRPAG
QFQTLV

107-5 mutations (SEQ ID NO:117)

PGWFLDSPDRPWNPPTFSPALLVVTEGDNATFTCSFSNTSEGFVLNWYRMSPSNQTDKLAAFPEDRGQPGQ
DCRFRVTQLPNGRDFHMSVVRARRNDSGTYLCSAIVLAPKIQIKESLRAELRVTERRAEVPTAHPSPSRPAG
QFQTLV

108-5 mutations (SEQ ID NO:118)

PGWFLDSPDRPWNPPTFSPALLVVTEGDNATFTCSFSNTSEGFVLNWYRMSPSNQTDKLAAFPEDRGQPGQ
DCRFRVTQLPNGRDFHMSVVRARRNDSGTYLCSAIVLAPKAQIKESLRVELRVTERRAEVPTAHPSPSRPA
GQFQTLV

FIG. 17M

109-5 mutations (SEQ ID NO:119)

PGWFLDSPDRPWNPPTFSPALLVVTEGDNATFTCSFSNTSEGFVLNWYRMSPSNQTDKLAAFPEDRGQPGQ
DCRFRVTQLPNGRDFHMSVVRARRNDSGTYLCSAISLAPKIQIKESLRVELRVTERRAEVPTAHPSPSPRPAG
QFQTLV

110-5 mutations (SEQ ID NO:120)

PGWFLDSPDRPWNPPTFSPALLVVTEGDNATFTCSFSNTSEGFVLNWYRMSPSNQTDKLAAFPEDRGQPGQ
DCRFRVTQLPNGRDFHMSVVRARRNDSGTYLCGAIVLAPKIQIKESLRVELRVTERRAEVPTAHPSPSPRPA
GQFQTLV

111-5 mutations (SEQ ID NO:121)

PGWFLDSPDRPWNPPTFSPALLVVTEGDNATFTCSFSNTSEGFVLNWYRMSPSNQTDKLAAFPEDRSQLGQ
DCRFRVTQLPNGRDFHMSVVRARRNDSGTYLCSAIVLAPKIQIKESLRAELRVTERRAEVPTAHPSPSPRPAG
QFQTLV

112-5 mutations (SEQ ID NO:122)

PGWFLDSPDRPWNPPTFSPALLVVTEGDNATFTCSFSNTSEGFVLNWYRMSPSNQTDKLAAFPEDRSQLGQ
DCRFRVTQLPNGRDFHMSVVRARRNDSGTYLCSAIVLAPKAQIKESLRVELRVTERRAEVPTAHPSPSPRPA
GQFQTLV

113-5 mutations (SEQ ID NO:123)

PGWFLDSPDRPWNPPTFSPALLVVTEGDNATFTCSFSNTSEGFVLNWYRMSPSNQTDKLAAFPEDRSQLGQ
DCRFRVTQLPNGRDFHMSVVRARRNDSGTYLCSAISLAPKIQIKESLRVELRVTERRAEVPTAHPSPSPRPAG
QFQTLV

114-5 mutations (SEQ ID NO:124)

PGWFLDSPDRPWNPPTFSPALLVVTEGDNATFTCSFSNTSEGFVLNWYRMSPSNQTDKLAAFPEDRSQLGQ
DCRFRVTQLPNGRDFHMSVVRARRNDSGTYLCGAIVLAPKIQIKESLRVELRVTERRAEVPTAHPSPSPRPA
GQFQTLV

115-5 mutations (SEQ ID NO:125)

PGWFLDSPDRPWNPPTFSPALLVVTEGDNATFTCSFSNTSEGFVLNWYRMSPSNQTDKLAAFPEDRSQPGQ
DCRFRVTQLPNGRDFHMSVVRARRNDSGTYLCSAIVLAPKIQIKESLRVELRVTERRAEVPTAHPSPSPRPAG
QFQTLV

116-5 mutations (SEQ ID NO:126)

PGWFLDSPDRPWNPPTFSPALLVVTEGDNATFTCSFSNTSESFVLNWYRMSPSNQTDKLAAFPEDRGQLGQ
DCRFRVTQLPNGRDFHMSVVRARRNDSGTYLCSAIVLAPKIQIKESLRAELRVTERRAEVPTAHPSPSPRPAG
QFQTLV

117-5 mutations (SEQ ID NO:127)

PGWFLDSPDRPWNPPTFSPALLVVTEGDNATFTCSFSNTSESFVLNWYRMSPSNQTDKLAAFPEDRGQLGQ
DCRFRVTQLPNGRDFHMSVVRARRNDSGTYLCSAIVLAPKAQIKESLRVELRVTERRAEVPTAHPSPSPRPA
GQFQTLV

FIG. 17N

118-5 mutations (SEQ ID NO:128)

PGWFLDSPDRPWNPPTFSPALLVVTEGDNATFTCSFSNTSESFVLNWYRMSPSNQTDKLAAFPEDRGQLGQ
DCRFRVTQLPNGRDFHMSVVRARRNDSGTYLCSAISLAPKIQIKESLRVELRVTERRAEVPTAHPSPSPRPAG
QFQTLV

119-5 mutations (SEQ ID NO:129)

PGWFLDSPDRPWNPPTFSPALLVVTEGDNATFTCSFSNTSESFVLNWYRMSPSNQTDKLAAFPEDRGQLGQ
DCRFRVTQLPNGRDFHMSVVRARRNDSGTYLCGAIVLAPKIQIKESLRVELRVTERRAEVPTAHPSPSPRPA
GQFQTLV

120-5 mutations (SEQ ID NO:130)

PGWFLDSPDRPWNPPTFSPALLVVTEGDNATFTCSFSNTSESFVLNWYRMSPSNQTDKLAAFPEDRGQPGQ
DCRFRVTQLPNGRDFHMSVVRARRNDSGTYLCSAIVLAPKIQIKESLRVELRVTERRAEVPTAHPSPSPRPAG
QFQTLV

121-5 mutations (SEQ ID NO:131)

PGWFLDSPDRPWNPPTFSPALLVVTEGDNATFTCSFSNTSESFVLNWYRMSPSNQTDKLAAFPEDRSQLGQ
DCRFRVTQLPNGRDFHMSVVRARRNDSGTYLCSAIVLAPKIQIKESLRVELRVTERRAEVPTAHPSPSPRPAG
QFQTLV

122-6 mutations (SEQ ID NO:132)

PGWFLDSPDRPWNPPTFSPALLVVTEGDNATFTCSFSNTSEGFVLNWYRMSPSNQTDKLAAFPEDRGQLGQ
DCRFRVTQLPNGRDFHMSVVRARRNDSGTYLCSAIVLAPKIQIKESLRAELRVTERRAEVPTAHPSPSPRPAG
QFQTLV

123-6 mutations (SEQ ID NO:133)

PGWFLDSPDRPWNPPTFSPALLVVTEGDNATFTCSFSNTSEGFVLNWYRMSPSNQTDKLAAFPEDRGQLGQ
DCRFRVTQLPNGRDFHMSVVRARRNDSGTYLCSAIVLAPKAQIKESLRVELRVTERRAEVPTAHPSPSPRPA
GQFQTLV

124-6 mutations (SEQ ID NO:134)

PGWFLDSPDRPWNPPTFSPALLVVTEGDNATFTCSFSNTSEGFVLNWYRMSPSNQTDKLAAFPEDRGQLGQ
DCRFRVTQLPNGRDFHMSVVRARRNDSGTYLCSAISLAPKIQIKESLRVELRVTERRAEVPTAHPSPSPRPAG
QFQTLV

125-6 mutations (SEQ ID NO:135)

PGWFLDSPDRPWNPPTFSPALLVVTEGDNATFTCSFSNTSEGFVLNWYRMSPSNQTDKLAAFPEDRGQLGQ
DCRFRVTQLPNGRDFHMSVVRARRNDSGTYLCGAIVLAPKIQIKESLRVELRVTERRAEVPTAHPSPSPRPA
GQFQTLV

126-6 mutations (SEQ ID NO:136)

PGWFLDSPDRPWNPPTFSPALLVVTEGDNATFTCSFSNTSEGFVLNWYRMSPSNQTDKLAAFPEDRGQPGQ
DCRFRVTQLPNGRDFHMSVVRARRNDSGTYLCSAIVLAPKIQIKESLRVELRVTERRAEVPTAHPSPSPRPAG
QFQTLV

FIG. 17O

127-6 mutations (SEQ ID NO:137)

PGWFLDSPDRPWNPPTFSPALLVVTEGDNATFTCSFSNTSEGFVLNWYRMSPSNQTDKLAAFPEDRSQLGQ
DCRFRVTQLPNGRDFHMSVVRARRNDSGTYLCSAIVLAPKIQIKESLRVELRVTERRAEVPTAHPSPSRPAG
QFQTLV

128-6 mutations (SEQ ID NO:138)

PGWFLDSPDRPWNPPTFSPALLVVTEGDNATFTCSFSNTSESFVLNWYRMSPSNQTDKLAAFPEDRGQLGQ
DCRFRVTQLPNGRDFHMSVVRARRNDSGTYLCSAIVLAPKIQIKESLRVELRVTERRAEVPTAHPSPSRPAG
QFQTLV

129-8 mutations (SEQ ID NO:139)

PGWFLDSPDRPWNPPTFSPALLVVTEGDNATFTCSFSNTSEGFVLNWYRMSPSNQTDKLAAFPEDRGQLGQ
DCRFRVTQLPNGRDFHMSVVRARRSDSGTYLCSAIVLAPKIQIKESLRVELRVTERRAEVPTAHPSPSRPAG
QFQTLV

FIG. 18B
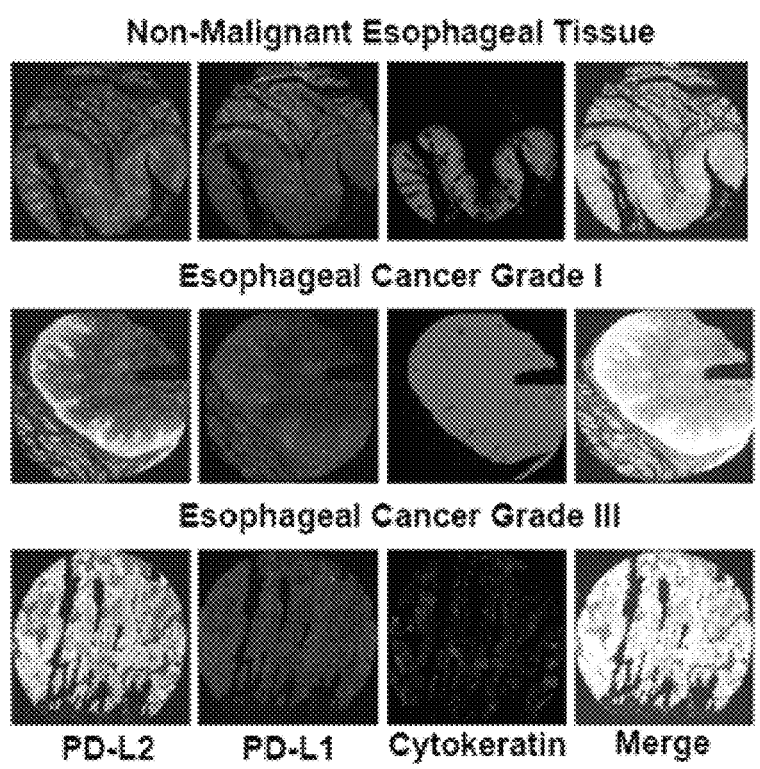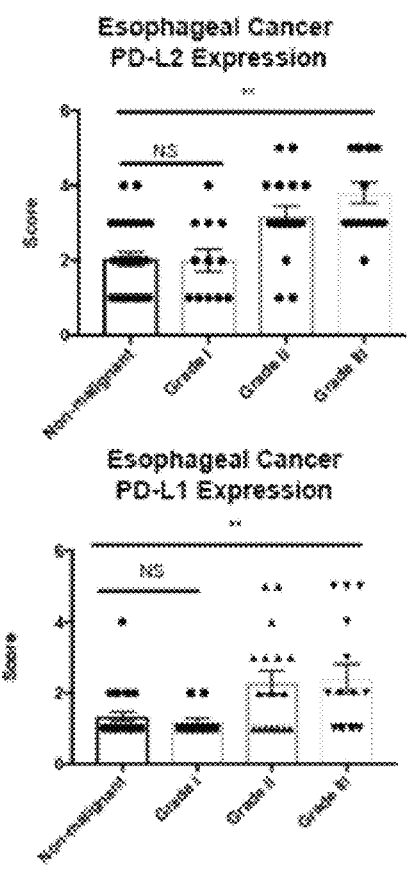

FIG. 18E
Non-Malignant Ovary Tissue with Blood Vessel
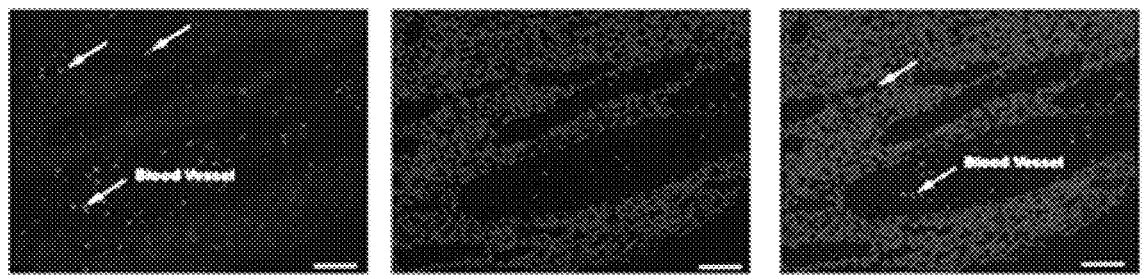
Ovarian Cancer Tissue CD8 Positive
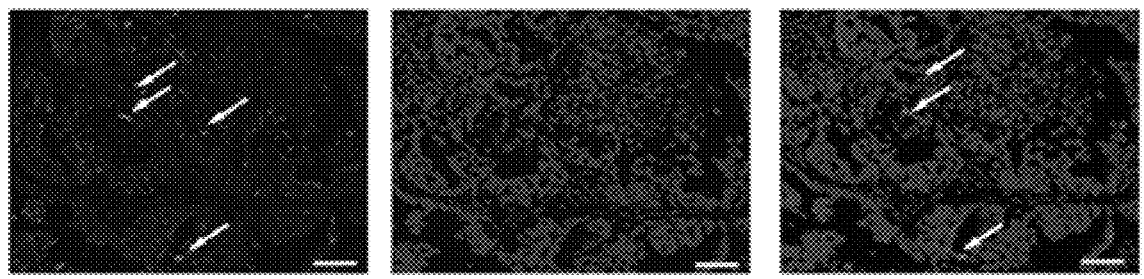
Ovarian Cancer Tissue CD8 Negative
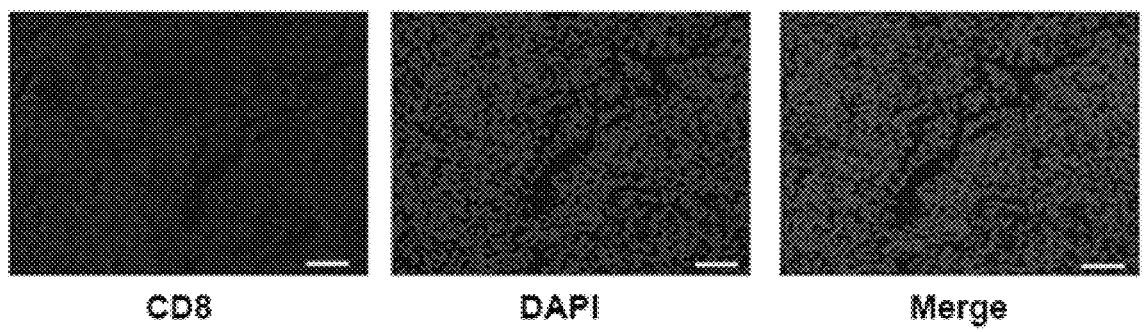
CD8  DAPI  Merge FIG. 18F
Non-Malignant Esophageal Tissue
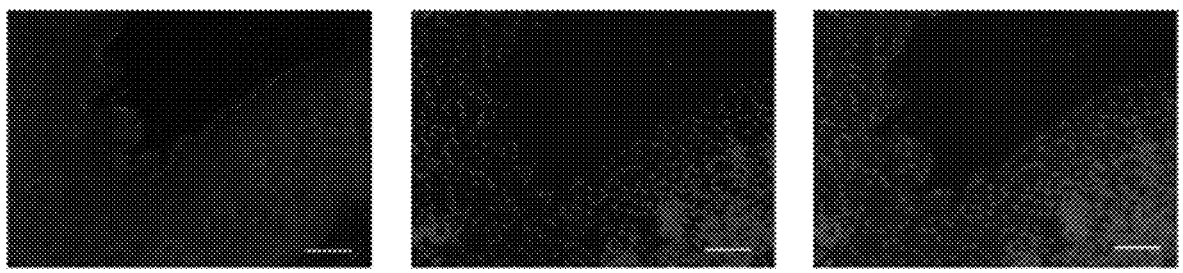
Inflammed Esophageal Tissue CD8 Positive
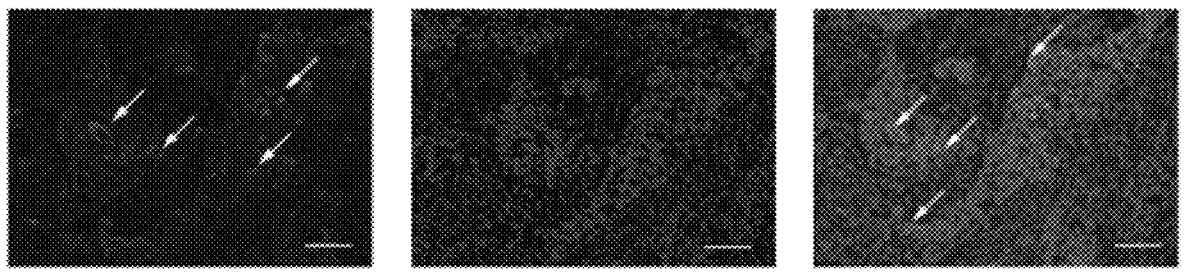
Esophageal Cancer Tissue CD8 Negative
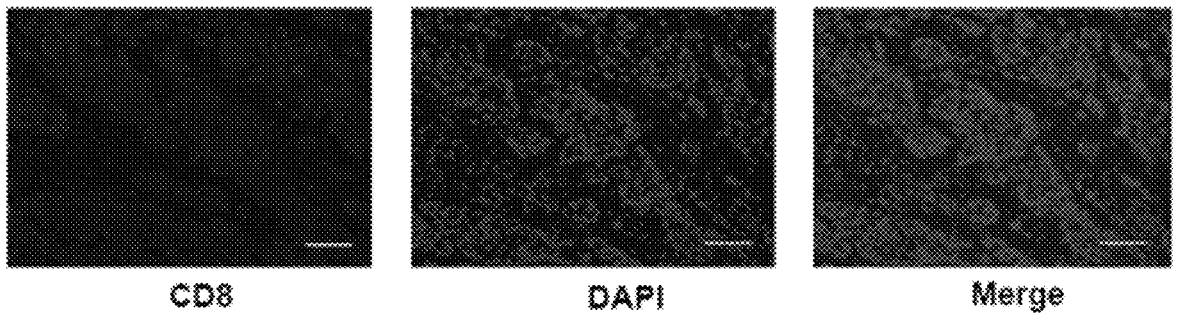
CD8　　　　　　　　DAPI　　　　　　　　Merge

FIG. 19C
sPD-1 Mutant V1 Binding Kinetics to PD-L1
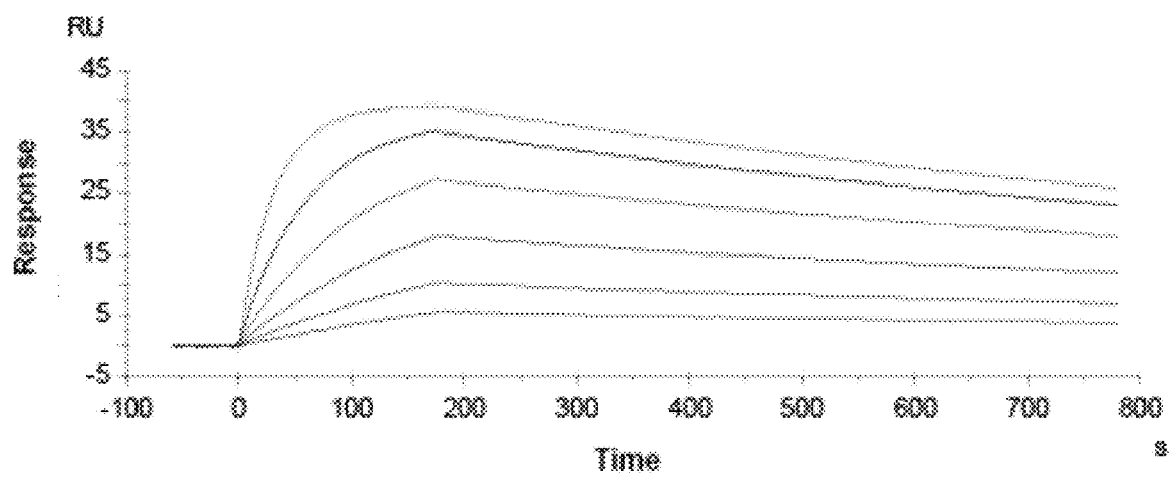
sPD-1 Wild Type Binding Kinetics to PD-L1
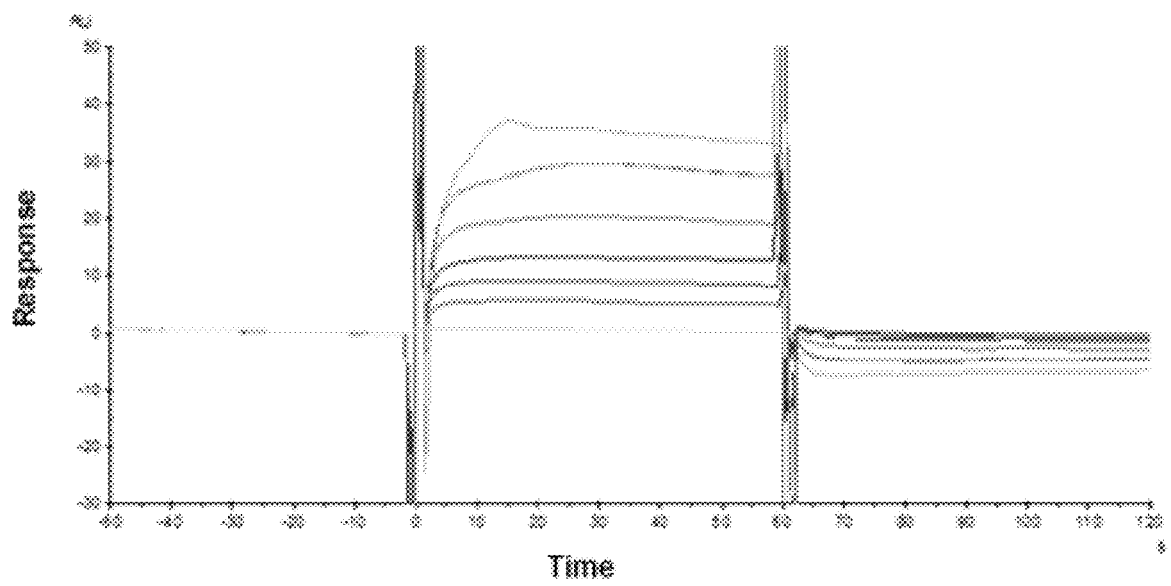

FIG. 19D sPD-1 Mutant V1 Binding Kinetics to PD-L2 sPD-1 Wild Type Binding Kinetics to PD-L2

Surface Complementarity with PD-L1

Surface Complementarity with PD-L2

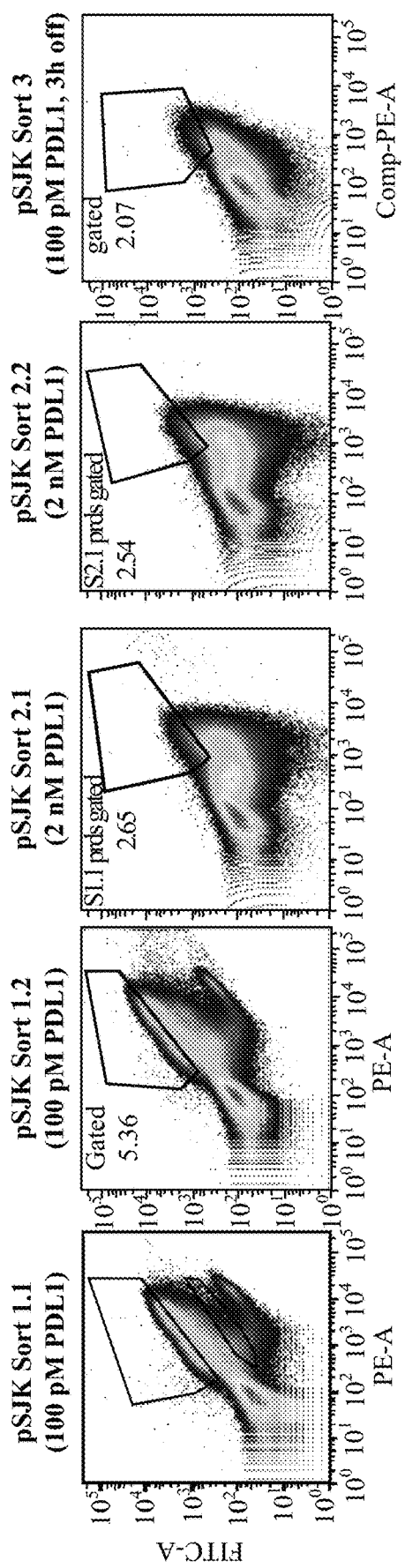
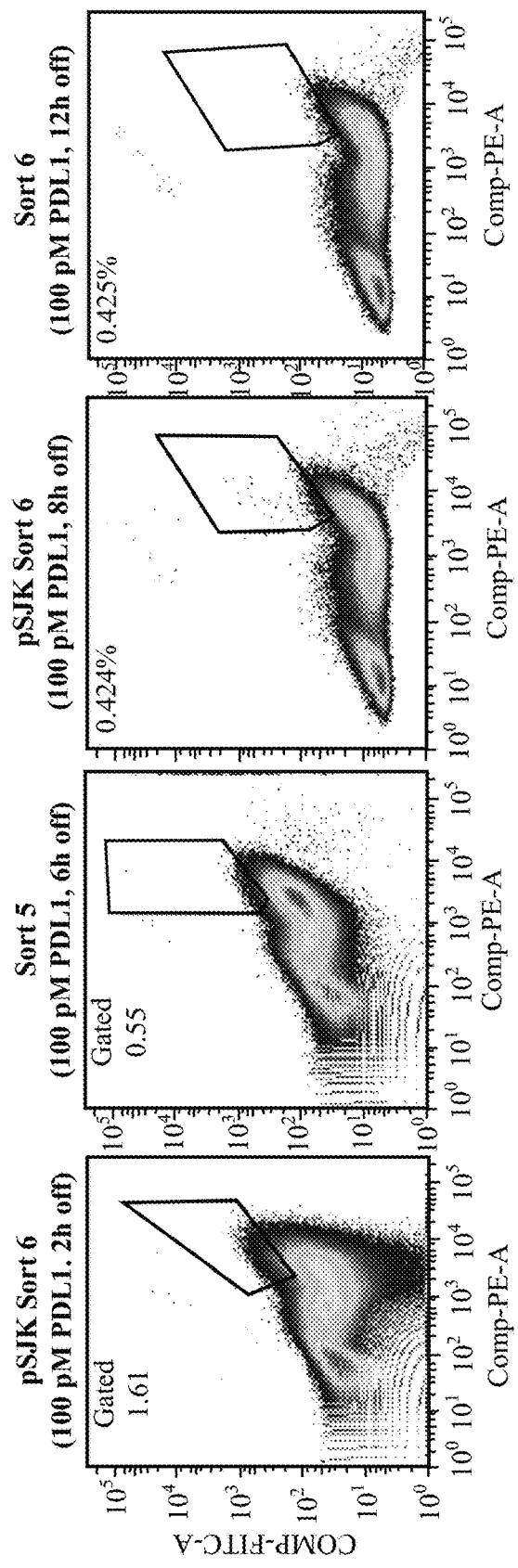
FIG. 26 CON'T

M: Maker
1: Reduced (2ug)
2: Non-reduced (1ug)

M: Maker
1: Reduced (2ug)
2: Non-reduced (1ug)

FIG. 29

| Site in PD-1 | Surface Complementarity | | Hydrogen Bond with PD-L1 | |
|---|---|---|---|---|
| | WT | Single mutation | WT | Single mutation |
| G124S | 0.93 | 0.75 | 0 | 1 to Y123 |
| S127V | 0.89 | 0.64 | 0 | 0 |
| A132I | 0.72 | 0.85 | 1 to Q66 | 2 to Q66 |

FIG. 30

| Site in PD1 | Surface Complementarity | | Hydrogen bond with PD-L2 | |
|---|---|---|---|---|
| | WT | Single mutation | WT | Single mutation |
| G124S | 0.80 | 0.85 | 0 | 0 |
| A132I | 0.83 | 0.86 | 1 to Q60 | 1 to Q60 |

FIG. 32A

| | | cells\|Freq. of Parent (%) | cells\|Mean (Alexa Fluor 488-A) | coresponding specimen |
|---|---|---|---|---|
| 1E6/well during transduction | 3F3 | 86 | 4973.6 | Specimen_001_A1_A01_001.fcs |
| | 4G10 | | 4730.4 | Specimen_001_A2_A02_002.fcs |
| | 4C3 | | 4259.3 | Specimen_001_A3_A03_003.fcs |
| | 5E9 | | 4322.7 | Specimen_001_A4_A04_004.fcs |
| | 4C7 | | | Specimen_001_A5_A05_005.fcs |
| | 4F11 | 65 | 3711.2 | Specimen_001_A6_A06_006.fcs |
| | 4F12 | | | Specimen_001_A7_A07_007.fcs |
| | 4E8 | | | Specimen_001_A8_A08_008.fcs |
| 5E5/well during transduction | 5B11 | 95.1 | 7515 | Specimen_001_B1_B01_011.fcs |
| | 5C10 | | 6117.9 | Specimen_001_B2_B02_013.fcs |
| | 4H7 | | | Specimen_001_B3_B03_013.fcs |
| | 4B6 | | 5717.5 | Specimen_001_B4_B04_014.fcs |
| | 5A10 | | 4869.3 | Specimen_001_B5_B05_015.fcs |
| | 5D4 | | | Specimen_001_B6_B06_016.fcs |
| | 5D12 | | 10118 | Specimen_001_B7_B07_017.fcs |
| | 5E2 | | | Specimen_001_B8_B08_018.fcs |
| | 5E5 | 89.7 | 3820.5 | Specimen_001_B9_B09_019.fcs |
| | 5F5 | | 5485.8 | Specimen_001_B10_B10_020.fcs |
| | 5A7 | | | Specimen_001_B11_B11_021.fcs |
| | 5F8 | | 7278 | Specimen_001_B12_B12_022.fcs |
| | 4G6 | | | Specimen_002_C1_C01_023.fcs |
| MC38 | stained | | | Specimen_001_A11_A11_009.fcs |
| blank | unstained | 0.5 | 351.8 | Specimen_001_A12_A12_010.fcs |

Sample set 3 (50%-60%) +ve cells

Sample set 4 (>60%) +ve cells

FIG. 33A

| Clone | Alexa488 MFI | P3 %Parent | Peak number |
|---|---|---|---|
| Hep3B blank+Ab2 | 53.1 | 0.3 | 1 |
| Hep3B blank+Ab1+Ab2 | 2699 | 75.7 | 1 |
| 5C5 | 34409 | 98.4 | 1 |
| 5D8 | 53268 | 95.9 | 1 |
| 5E8 | 50584.3 | 95.3 | 1 |
| 5F8 | 32883.8 | 98.8 | 1 |
| 5F5 | 28832.1 | 98.9 | 1 |
| 4B9 | 41703.5 | 98.5 | 1 |
| 4G6 | 34652.9 | 98.1 | 1 |
| 4E2 | 38126.1 | 99.1 | 1 |
| 4F2 | 46515.5 | 92.7 | 1 |
| 4E7 | 32394.5 | 98.7 | 1 |
| 5E7 | 50304.4 | 98.6 | 1 |
| 5F7 | 39739.9 | 97.1 | 1 |
| 4F9 | 42523.6 | 96.4 | 1 |
| 5G3 | 43873.9 | 98.4 | 1 |
| 5G6 | 33266.8 | 98.5 | 1 |
| 5G9 | 61274.1 | 97.8 | 1 |

| Clone | Alexa488 MFI |
|---|---|
| 5G9 | 61274.1 |
| 5D8 | 53268 |
| 5E8 | 50584.3 |
| 5E7 | 50304.4 |
| 4F2 | 46515.5 |
| 5G3 | 43873.9 |
| 4F9 | 42523.6 |
| 4B9 | 41703.5 |
| 5F7 | 39739.9 |
| 4E2 | 38126.1 |
| 4G6 | 34652.9 |
| 5C5 | 34409 |
| 5G6 | 33266.8 |
| 5F8 | 32883.8 |
| 4E7 | 32394.5 |
| 5F5 | 28832.1 |

FIG. 37 (CON'T)

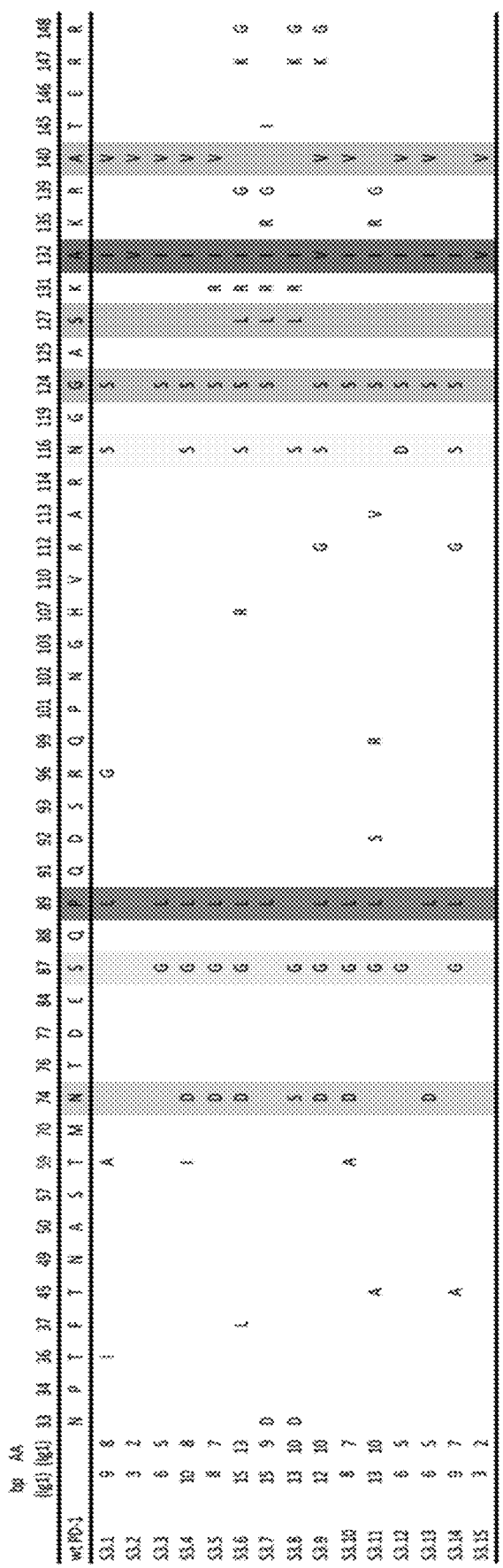
FIG. 37 (CON'T)

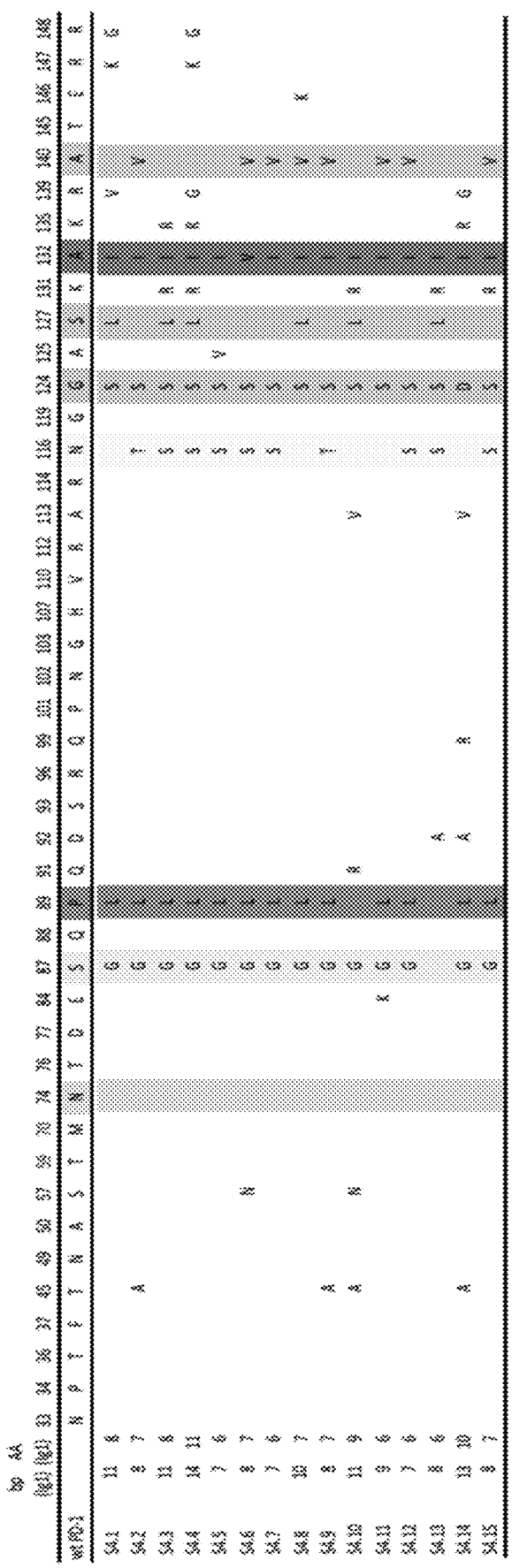
FIG. 37 (CON'T)

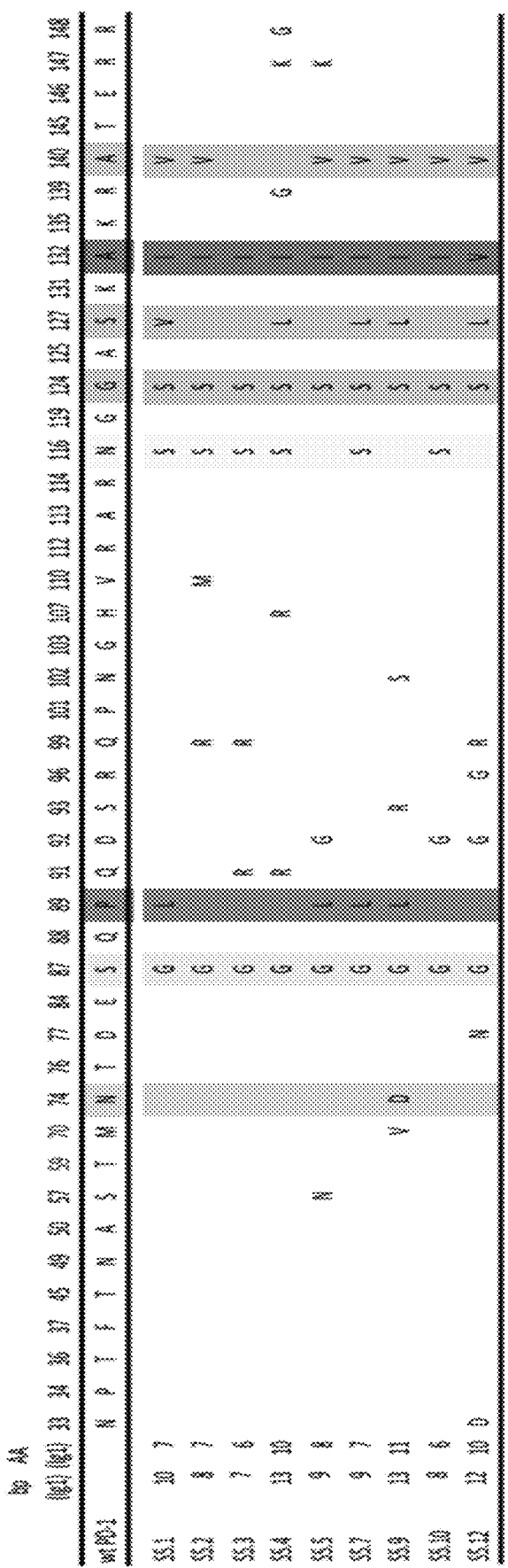
FIG. 37 (CON'T)

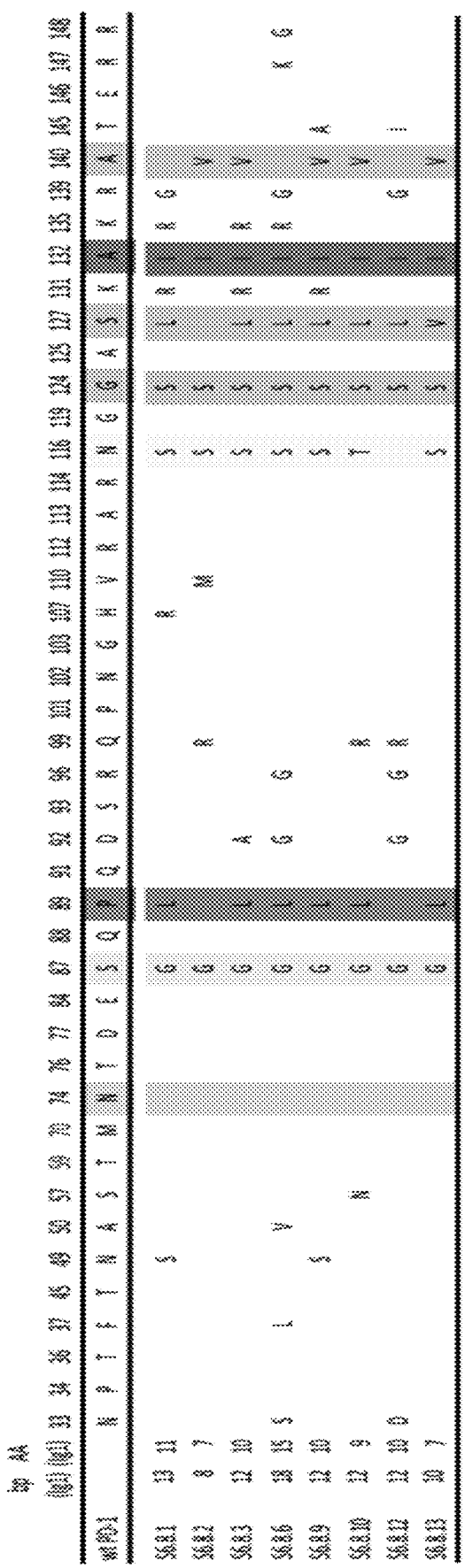
FIG. 37 (CON'T)

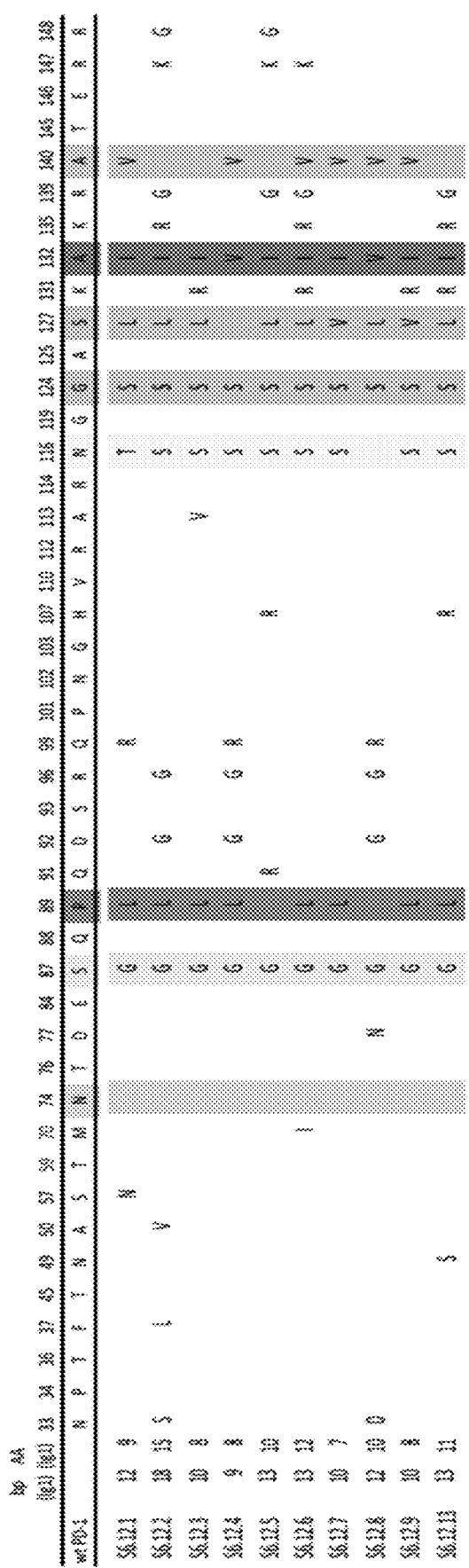
FIG. 37 (CON'T)

Refined clones to test in the binding assay

FIG. 38B

| | |
|---|---|
| Clone#1 | 89-124-127-132-140 |
| Clone#2 | 87-124-127-132-140 |
| Clone#3 | 87-89-124-127-132-140 |
| Clone#4 | 124-127-132-140 |
| Clone#5 | 124-127-132 |

Original Mutant PD1
(62-87-89-124-127-132-140)

Kd = 0.44 nM

Clone#1
89-124-127-132-140

Kd = 0.03 nM

Clone#3
87-89-124-127-132-140

Kd = 0.06 nM

Kd = 0.08 nM

Refined clones to test in the binding assay for PDL1

FIG. 40B

| | | |
|---|---|---|
| Original Mutant | 62-87-89-124-127-132-140 | Kd: 0.44 nM |
| Clone#1 | 89-124-127-132-140 | Kd: 0.03 nM or 30 pM |
| Clone#2 | 87-124-127-132-140 | Kd: 0.12 nM |
| Clone#3 | 87-89-124-127-132-140 | Kd: 0.06 nM |
| Clone#4 | 124-127-132-140 | Kd: 0.08 nM or 80 pM |
| Clone#5 | 124-127-132 | Kd: 0.8 nM |

Clone#2
87-124-127-132-140

Kd = 0.11 nM, Bmax: 1409

Clone#4
124-127-132-140

Kd = 0.87 nM, Bmax: 1370

Refined clones to test in the binding assay for PDL2

FIG. 42B

| | | |
|---|---|---|
| Original Mutant | 62-87-89-124-127-132-140 | Kd: 2.6 nM |
| Clone#1 | 89-124-127-132-140 | Kd: 1.4 nM |
| Clone#2 | 87-124-127-132-140 | Kd: 0.11 nM |
| Clone#3 | 87-89-124-127-132-140 | Kd: 1.1 nM |
| Clone#4 | 124-127-132-140 | Kd: 0.87 nM |
| Clone#5 | 124-127-132 | Kd: 4.1 nM |

SEQUENCE LISTING

<160> NUMBER OF SEQ ID NOS: 163

<210> SEQ ID NO 1
<211> LENGTH: 150
<212> TYPE: PRT
<213> ORGANISM: Homo sapiens

<400> SEQUENCE: 1

```
Pro Gly Trp Phe Leu Asp Ser Pro Asp Arg Pro Trp Asn Pro Pro Thr
1               5                  10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
```

```
                65                  70                  75                  80
Pro Asn Gly Arg Asp Phe His Met Ser Val Val Arg Ala Arg Arg Asn
                85                  90                  95
Asp Ser Gly Thr Tyr Leu Cys Gly Ala Ile Ser Leu Ala Pro Lys Ala
                100                 105                 110
Gln Ile Lys Glu Ser Leu Arg Ala Glu Leu Arg Val Thr Glu Arg Arg
                115                 120                 125
Ala Glu Val Pro Thr Ala His Pro Ser Pro Ser Pro Arg Pro Ala Gly
                130                 135                 140
Gln Phe Gln Thr Leu Val
145                 150

<210> SEQ ID NO 2
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Pro Gly Trp Phe Leu Asp Ser Pro Asp Arg Pro Trp Asn Pro Pro Thr
1               5                   10                  15
Phe Ser Pro Ala Leu Leu Val Val Thr Glu Gly Asp Asn Ala Thr Phe
                20                  25                  30
Thr Cys Ser Phe Ser Asn Thr Ser Glu Gly Phe Val Leu Asn Trp Tyr
                35                  40                  45
Arg Met Ser Pro Ser Asn Gln Thr Asp Lys Leu Ala Ala Phe Pro Glu
                50                  55                  60
Asp Arg Gly Gln Leu Gly Gln Asp Cys Arg Phe Arg Val Thr Gln Leu
65                  70                  75                  80
Pro Asn Gly Arg Asp Phe His Met Ser Val Val Arg Ala Arg Arg Ser
                85                  90                  95
Asp Ser Gly Thr Tyr Leu Cys Ser Ala Ile Val Leu Ala Pro Lys Ile
                100                 105                 110
Gln Ile Lys Glu Ser Leu Arg Val Glu Leu Arg Val Thr Glu Arg Arg
                115                 120                 125
Ala Glu Val Pro Thr Ala His Pro Ser Pro Ser Pro Arg Pro Ala Gly
                130                 135                 140
Gln Phe Gln Thr Leu Val
145                 150

<210> SEQ ID NO 3
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Pro Gly Trp Phe Leu Asp Ser Pro Asp Arg Pro Trp Asn Pro Pro Thr
1               5                   10                  15
Phe Ser Pro Ala Leu Leu Val Val Thr Glu Gly Asp Asn Ala Thr Phe
                20                  25                  30
Thr Cys Ser Phe Ser Asn Thr Ser Glu Gly Phe Val Leu Asn Trp Tyr
                35                  40                  45
```

```
Arg Met Ser Pro Ser Asn Gln Thr Asp Lys Leu Ala Ala Phe Pro Glu
         50                  55                  60

Asp Arg Gly Gln Leu Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Leu Cys Ser Ala Ile Val Leu Ala Pro Lys Ile
                100                 105                 110

Gln Ile Lys Glu Ser Leu Arg Val Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 4
<211> LENGTH: 384
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Pro Gly Trp Phe Leu Asp Ser Pro Asp Arg Pro Trp Asn Pro Pro Thr
 1               5                  10                  15

Phe Ser Pro Ala Leu Leu Val Val Thr Glu Gly Asp Asn Ala Thr Phe
             20                  25                  30

Thr Cys Ser Phe Ser Asn Thr Ser Glu Ser Phe Val Leu Asn Trp Tyr
         35                  40                  45

Arg Met Ser Pro Ser Asn Gln Thr Asp Lys Leu Ala Ala Phe Pro Glu
         50                  55                  60

Asp Arg Ser Gln Pro Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val Gly Gly Gly Ser Glu Ser Lys Tyr Gly
145                 150                 155                 160

Pro Pro Cys Pro Pro Cys Pro Ala Pro Glu Phe Leu Gly Gly Pro Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser Gln Glu Asp Pro
        195                 200                 205

Glu Val Gln Phe Asn Trp Tyr Val Asp Gly Val Glu Val His Asn Ala
    210                 215                 220

Lys Thr Lys Pro Arg Glu Glu Gln Phe Asn Ser Thr Tyr Arg Val Val
225                 230                 235                 240
```

```
Ser Val Leu Thr Val Leu His Gln Asp Trp Leu Asn Gly Lys Glu Tyr
                245                 250                 255

Lys Cys Lys Val Ser Asn Lys Gly Leu Pro Ser Ser Ile Glu Lys Thr
        260                 265                 270

Ile Ser Lys Ala Lys Gly Gln Pro Arg Glu Pro Gln Val Tyr Thr Leu
            275                 280                 285

Pro Pro Ser Gln Glu Glu Met Thr Lys Asn Gln Val Ser Leu Thr Cys
290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Arg Leu Thr Val Asp Lys Ser
            340                 345                 350

Arg Trp Gln Glu Gly Asn Val Phe Ser Cys Ser Val Met His Glu Ala
        355                 360                 365

Leu His Asn His Tyr Thr Gln Lys Ser Leu Ser Leu Ser Leu Gly Lys
    370                 375                 380

<210> SEQ ID NO 5
<211> LENGTH: 384
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Ser
                85                  90                  95

Asp Ser Gly Thr Tyr Leu Cys Ser Ala Ile Val Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Gly Gly Gly Ser Glu Ser Lys Tyr Gly
145                 150                 155                 160

Pro Pro Cys Pro Pro Cys Pro Ala Pro Glu Phe Leu Gly Gly Pro Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser Gln Glu Asp Pro
        195                 200                 205

Glu Val Gln Phe Asn Trp Tyr Val Asp Gly Val Glu Val His Asn Ala
```

```
                210                 215                 220
Lys Thr Lys Pro Arg Glu Glu Gln Phe Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Gly Leu Pro Ser Ser Ile Glu Lys Thr
                260                 265                 270

Ile Ser Lys Ala Lys Gly Gln Pro Arg Glu Pro Gln Val Tyr Thr Leu
                275                 280                 285

Pro Pro Ser Gln Glu Glu Met Thr Lys Asn Gln Val Ser Leu Thr Cys
                290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Arg Leu Thr Val Asp Lys Ser
                340                 345                 350

Arg Trp Gln Glu Gly Asn Val Phe Ser Cys Ser Val Met His Glu Ala
                355                 360                 365

Leu His Asn His Tyr Thr Gln Lys Ser Leu Ser Leu Ser Leu Gly Lys
                370                 375                 380

<210> SEQ ID NO 6
<211> LENGTH: 384
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
                35                  40                  45

Arg Met Ser Pro Ser Asn Gln Thr Asp Lys Leu Ala Ala Phe Pro Glu
50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ile
                100                 105                 110

Gln Ile Lys Glu Ser Leu Arg Val Glu Leu Arg Val Thr Glu Arg Arg
                115                 120                 125

Ala Glu Val Pro Thr Ala His Pro Ser Pro Ser Pro Arg Pro Ala Gly
130                 135                 140

Gln Phe Gln Thr Leu Val Gly Gly Gly Ser Glu Ser Lys Tyr Gly
145                 150                 155                 160

Pro Pro Cys Pro Pro Cys Pro Ala Pro Glu Phe Leu Gly Gly Pro Ser
                165                 170                 175

Val Phe Leu Phe Pro Pro Lys Pro Lys Asp Thr Leu Met Ile Ser Arg
                180                 185                 190
```

```
Thr Pro Glu Val Thr Cys Val Val Asp Val Ser Gln Glu Asp Pro
            195                 200                 205

Glu Val Gln Phe Asn Trp Tyr Val Asp Gly Val Glu Val His Asn Ala
210                 215                 220

Lys Thr Lys Pro Arg Glu Gln Phe Asn Ser Thr Tyr Arg Val Val
225                 230                 235                 240

Ser Val Leu Thr Val Leu His Gln Asp Trp Leu Asn Gly Lys Glu Tyr
            245                 250                 255

Lys Cys Lys Val Ser Asn Lys Gly Leu Pro Ser Ser Ile Glu Lys Thr
            260                 265                 270

Ile Ser Lys Ala Lys Gly Gln Pro Arg Glu Pro Gln Val Tyr Thr Leu
            275                 280                 285

Pro Pro Ser Gln Glu Glu Met Thr Lys Asn Gln Val Ser Leu Thr Cys
            290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Arg Leu Thr Val Asp Lys Ser
            340                 345                 350

Arg Trp Gln Glu Gly Asn Val Phe Ser Cys Ser Val Met His Glu Ala
            355                 360                 365

Leu His Asn His Tyr Thr Gln Lys Ser Leu Ser Leu Ser Leu Gly Lys
            370                 375                 380

<210> SEQ ID NO 7
<211> LENGTH: 20
<212> TYPE: PRT
<213> ORGANISM: Homo sapiens

<400> SEQUENCE: 7

Met Gln Ile Pro Gln Ala Pro Trp Pro Val Val Trp Ala Val Leu Gln
1               5                   10                  15

Leu Gly Trp Arg
            20

<210> SEQ ID NO 8
<211> LENGTH: 404
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
            50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
```

```
                85                  90                  95
Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
                115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Gly Gly Gly Ser Glu
                165                 170                 175

Ser Lys Tyr Gly Pro Pro Cys Pro Pro Cys Pro Ala Pro Glu Phe Leu
                180                 185                 190

Gly Gly Pro Ser Val Phe Leu Phe Pro Pro Lys Pro Lys Asp Thr Leu
                195                 200                 205

Met Ile Ser Arg Thr Pro Glu Val Thr Cys Val Val Val Asp Val Ser
            210                 215                 220

Gln Glu Asp Pro Glu Val Gln Phe Asn Trp Tyr Val Asp Gly Val Glu
225                 230                 235                 240

Val His Asn Ala Lys Thr Lys Pro Arg Glu Glu Gln Phe Asn Ser Thr
                245                 250                 255

Tyr Arg Val Val Ser Val Leu Thr Val Leu His Gln Asp Trp Leu Asn
                260                 265                 270

Gly Lys Glu Tyr Lys Cys Lys Val Ser Asn Lys Gly Leu Pro Ser Ser
                275                 280                 285

Ile Glu Lys Thr Ile Ser Lys Ala Lys Gly Gln Pro Arg Glu Pro Gln
            290                 295                 300

Val Tyr Thr Leu Pro Pro Ser Gln Glu Glu Met Thr Lys Asn Gln Val
305                 310                 315                 320

Ser Leu Thr Cys Leu Val Lys Gly Phe Tyr Pro Ser Asp Ile Ala Val
                325                 330                 335

Glu Trp Glu Ser Asn Gly Gln Pro Glu Asn Asn Tyr Lys Thr Thr Pro
                340                 345                 350

Pro Val Leu Asp Ser Asp Gly Ser Phe Phe Leu Tyr Ser Arg Leu Thr
            355                 360                 365

Val Asp Lys Ser Arg Trp Gln Glu Gly Asn Val Phe Ser Cys Ser Val
                370                 375                 380

Met His Glu Ala Leu His Asn His Tyr Thr Gln Lys Ser Leu Ser Leu
385                 390                 395                 400

Ser Leu Gly Lys

<210> SEQ ID NO 9
<211> LENGTH: 404
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30
```

```
Asn Pro Pro Thr Phe Ser Pro Ala Leu Leu Val Val Thr Glu Gly Asp
             35                  40                  45

Asn Ala Thr Phe Thr Cys Ser Phe Ser Asn Thr Ser Glu Gly Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Gly Gln Leu Gly Gln Asp Cys Arg Phe Arg
                 85                  90                  95

Val Thr Gln Leu Pro Asn Gly Arg Asp Phe His Met Ser Val Val Arg
            100                 105                 110

Ala Arg Arg Ser Asp Ser Gly Thr Tyr Leu Cys Ser Ala Ile Val Leu
            115                 120                 125

Ala Pro Lys Ile Gln Ile Lys Glu Ser Leu Arg Val Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Gly Gly Gly Ser Glu
            165                 170                 175

Ser Lys Tyr Gly Pro Pro Cys Pro Pro Cys Pro Ala Pro Glu Phe Leu
            180                 185                 190

Gly Gly Pro Ser Val Phe Leu Phe Pro Pro Lys Pro Lys Asp Thr Leu
            195                 200                 205

Met Ile Ser Arg Thr Pro Glu Val Thr Cys Val Val Val Asp Val Ser
            210                 215                 220

Gln Glu Asp Pro Glu Val Gln Phe Asn Trp Tyr Val Asp Gly Val Glu
225                 230                 235                 240

Val His Asn Ala Lys Thr Lys Pro Arg Glu Glu Gln Phe Asn Ser Thr
            245                 250                 255

Tyr Arg Val Val Ser Val Leu Thr Val Leu His Gln Asp Trp Leu Asn
            260                 265                 270

Gly Lys Glu Tyr Lys Cys Lys Val Ser Asn Lys Gly Leu Pro Ser Ser
            275                 280                 285

Ile Glu Lys Thr Ile Ser Lys Ala Lys Gly Gln Pro Arg Glu Pro Gln
            290                 295                 300

Val Tyr Thr Leu Pro Pro Ser Gln Glu Glu Met Thr Lys Asn Gln Val
305                 310                 315                 320

Ser Leu Thr Cys Leu Val Lys Gly Phe Tyr Pro Ser Asp Ile Ala Val
            325                 330                 335

Glu Trp Glu Ser Asn Gly Gln Pro Glu Asn Asn Tyr Lys Thr Thr Pro
            340                 345                 350

Pro Val Leu Asp Ser Asp Gly Ser Phe Phe Leu Tyr Ser Arg Leu Thr
            355                 360                 365

Val Asp Lys Ser Arg Trp Gln Glu Gly Asn Val Phe Ser Cys Ser Val
            370                 375                 380

Met His Glu Ala Leu His Asn His Tyr Thr Gln Lys Ser Leu Ser Leu
385                 390                 395                 400

Ser Leu Gly Lys

<210> SEQ ID NO 10
<211> LENGTH: 404
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 10

```
Met Gln Ile Pro Gln Ala Pro Trp Pro Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Gly Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Gly Gln Leu Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Ser Ala Ile Val Leu
            115                 120                 125

Ala Pro Lys Ile Gln Ile Lys Glu Ser Leu Arg Val Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Gly Gly Gly Ser Glu
                165                 170                 175

Ser Lys Tyr Gly Pro Pro Cys Pro Cys Pro Ala Pro Glu Phe Leu
            180                 185                 190

Gly Gly Pro Ser Val Phe Leu Phe Pro Pro Lys Pro Lys Asp Thr Leu
            195                 200                 205

Met Ile Ser Arg Thr Pro Glu Val Thr Cys Val Val Val Asp Val Ser
    210                 215                 220

Gln Glu Asp Pro Glu Val Gln Phe Asn Trp Tyr Val Asp Gly Val Glu
225                 230                 235                 240

Val His Asn Ala Lys Thr Lys Pro Arg Glu Glu Gln Phe Asn Ser Thr
                245                 250                 255

Tyr Arg Val Val Ser Val Leu Thr Val Leu His Gln Asp Trp Leu Asn
                260                 265                 270

Gly Lys Glu Tyr Lys Cys Lys Val Ser Asn Lys Gly Leu Pro Ser Ser
            275                 280                 285

Ile Glu Lys Thr Ile Ser Lys Ala Lys Gly Gln Pro Arg Glu Pro Gln
    290                 295                 300

Val Tyr Thr Leu Pro Pro Ser Gln Glu Glu Met Thr Lys Asn Gln Val
305                 310                 315                 320

Ser Leu Thr Cys Leu Val Lys Gly Phe Tyr Pro Ser Asp Ile Ala Val
                325                 330                 335

Glu Trp Glu Ser Asn Gly Gln Pro Glu Asn Asn Tyr Lys Thr Thr Pro
            340                 345                 350

Pro Val Leu Asp Ser Asp Gly Ser Phe Phe Leu Tyr Ser Arg Leu Thr
            355                 360                 365

Val Asp Lys Ser Arg Trp Gln Glu Gly Asn Val Phe Ser Cys Ser Val
        370                 375                 380

Met His Glu Ala Leu His Asn His Tyr Thr Gln Lys Ser Leu Ser Leu
385                 390                 395                 400
```

Ser Leu Gly Lys

```
<210> SEQ ID NO 11
<211> LENGTH: 150
<212> TYPE: PRT
<213> ORGANISM: Unknown
<220> FEATURE:
<221> NAME/KEY: source
<223> OTHER INFORMATION: /note="Description of Unknown:
      PD1 sequence"

<400> SEQUENCE: 11
```

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

```
<210> SEQ ID NO 12
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12
```

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 13
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 14
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145             150

<210> SEQ ID NO 15
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145             150

<210> SEQ ID NO 16
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu

```
                65                  70                  75                  80
Pro Asn Gly Arg Asp Phe His Met Ser Val Val Arg Ala Arg Arg Asn
                    85                  90                  95

Asp Ser Gly Thr Tyr Leu Cys Ser Ala Ile Ser Leu Ala Pro Lys Ala
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 17
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                    85                  90                  95

Asp Ser Gly Thr Tyr Leu Cys Gly Ala Ile Val Leu Ala Pro Lys Ala
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 18
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45
```

Arg Met Ser Pro Ser Asn Gln Thr Asp Lys Leu Ala Ala Phe Pro Glu
         50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                 85                  90                  95

Asp Ser Gly Thr Tyr Leu Cys Gly Ala Ile Ser Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 19
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 20
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Pro Gly Trp Phe Leu Asp Ser Pro Asp Arg Pro Trp Asn Pro Pro Thr
1               5                   10                  15

```
Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
 50                  55                  60

Asp Arg Gly Gln Pro Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
130                 135                 140

Gln Phe Gln Thr Leu Val
145                 150

<210> SEQ ID NO 21
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Pro Gly Trp Phe Leu Asp Ser Pro Asp Arg Pro Trp Asn Pro Pro Thr
 1               5                  10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
 50                  55                  60

Asp Arg Ser Gln Leu Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
130                 135                 140

Gln Phe Gln Thr Leu Val
145                 150

<210> SEQ ID NO 22
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 22

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 23
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 24
<211> LENGTH: 150
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic polypeptide"

<400> SEQUENCE: 24

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 25
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 25

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 26
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 27
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ala
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly 130                 135                 140

Gln Phe Gln Thr Leu Val
145                 150

<210> SEQ ID NO 28
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
    50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 29
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
    50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ile
            100                 105                 110

```
Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 30
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 31
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80
```

```
Pro Asn Gly Arg Asp Phe His Met Ser Val Val Arg Ala Arg Asn
                85                  90                  95

Asp Ser Gly Thr Tyr Leu Cys Ser Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 32
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 33
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
```

```
                50                  55                  60
Asp Arg Ser Gln Leu Gly Gln Asp Cys Arg Phe Arg Val Thr Gln Leu
 65                  70                  75                  80

Pro Asn Gly Arg Asp Phe His Met Ser Val Val Arg Ala Arg Asn
                 85                  90                  95

Asp Ser Gly Thr Tyr Leu Cys Gly Ala Ile Ser Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
            130                 135                 140

Gln Phe Gln Thr Leu Val
145                 150

<210> SEQ ID NO 34
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Pro Gly Trp Phe Leu Asp Ser Pro Asp Arg Pro Trp Asn Pro Pro Thr
 1               5                  10                  15

Phe Ser Pro Ala Leu Leu Val Val Thr Glu Gly Asp Asn Ala Thr Phe
                 20                  25                  30

Thr Cys Ser Phe Ser Asn Thr Ser Glu Ser Phe Val Leu Asn Trp Tyr
             35                  40                  45

Arg Met Ser Pro Ser Asn Gln Thr Asp Lys Leu Ala Ala Phe Pro Glu
         50                  55                  60

Asp Arg Ser Gln Leu Gly Gln Asp Cys Arg Phe Arg Val Thr Gln Leu
 65                  70                  75                  80

Pro Asn Gly Arg Asp Phe His Met Ser Val Val Arg Ala Arg Asn
                 85                  90                  95

Asp Ser Gly Thr Tyr Leu Cys Gly Ala Ile Ser Leu Ala Pro Lys Ala
                100                 105                 110

Gln Ile Lys Glu Ser Leu Arg Val Glu Leu Arg Val Thr Glu Arg Arg
            115                 120                 125

Ala Glu Val Pro Thr Ala His Pro Ser Pro Ser Pro Arg Pro Ala Gly
            130                 135                 140

Gln Phe Gln Thr Leu Val
145                 150

<210> SEQ ID NO 35
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Pro Gly Trp Phe Leu Asp Ser Pro Asp Arg Pro Trp Asn Pro Pro Thr
 1               5                  10                  15

Phe Ser Pro Ala Leu Leu Val Val Thr Glu Gly Asp Asn Ala Thr Phe
                 20                  25                  30
```

```
Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ala
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150
```

<210> SEQ ID NO 36
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150
```

<210> SEQ ID NO 37
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 37

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ala
                100                 105                 110

Gln Ile Lys Glu Ser Leu Arg Val Glu Leu Arg Val Thr Glu Arg Arg
                115                 120                 125

Ala Glu Val Pro Thr Ala His Pro Ser Pro Ser Pro Arg Pro Ala Gly
    130                 135                 140

Gln Phe Gln Thr Leu Val
145             150
```

<210> SEQ ID NO 38
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ile
                100                 105                 110

Gln Ile Lys Glu Ser Leu Arg Ala Glu Leu Arg Val Thr Glu Arg Arg
                115                 120                 125

Ala Glu Val Pro Thr Ala His Pro Ser Pro Ser Pro Arg Pro Ala Gly
    130                 135                 140

Gln Phe Gln Thr Leu Val
145             150
```

<210> SEQ ID NO 39
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 40
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 41

-continued

```
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 42
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
    50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140
```

```
Gln Phe Gln Thr Leu Val
145                 150

<210> SEQ ID NO 43
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 44
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ile
            100                 105                 110

Gln Ile Lys Glu Ser Leu Arg Ala Glu Leu Arg Val Thr Glu Arg Arg
```

```
                115                 120                 125
Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 45
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 46
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95
```

```
Asp Ser Gly Thr Tyr Leu Cys Ser Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145             150

<210> SEQ ID NO 47
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145             150

<210> SEQ ID NO 48
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60
```

```
Asp Arg Ser Gln Leu Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Leu Cys Gly Ala Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 49
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Pro Gly Trp Phe Leu Asp Ser Pro Asp Arg Pro Trp Asn Pro Pro Thr
  1               5                  10                  15

Phe Ser Pro Ala Leu Leu Val Val Thr Glu Gly Asp Asn Ala Thr Phe
                 20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
 50                  55                  60

Asp Arg Ser Gln Leu Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Leu Cys Gly Ala Ile Ser Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 50
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Pro Gly Trp Phe Leu Asp Ser Pro Asp Arg Pro Trp Asn Pro Pro Thr
  1               5                  10                  15

Phe Ser Pro Ala Leu Leu Val Val Thr Glu Gly Asp Asn Ala Thr Phe
                 20                  25                  30

Thr Cys Ser Phe Ser Asn Thr Ser Glu Gly Phe Val Leu Asn Trp Tyr
```

```
                35                  40                  45
Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 51
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 52
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Pro Gly Trp Phe Leu Asp Ser Pro Asp Arg Pro Trp Asn Pro Pro Thr
1               5                   10                  15
```

```
Phe Ser Pro Ala Leu Leu Val Val Thr Glu Gly Asp Asn Ala Thr Phe
             20                  25                  30

Thr Cys Ser Phe Ser Asn Thr Ser Glu Gly Phe Val Leu Asn Trp Tyr
         35                  40                  45

Arg Met Ser Pro Ser Asn Gln Thr Asp Lys Leu Ala Ala Phe Pro Glu
 50                  55                  60

Asp Arg Ser Gln Pro Gly Gln Asp Cys Arg Phe Arg Val Thr Gln Leu
 65                  70                  75                  80

Pro Asn Gly Arg Asp Phe His Met Ser Val Val Arg Ala Arg Asn
                 85                  90                  95

Asp Ser Gly Thr Tyr Leu Cys Ser Ala Ile Ser Leu Ala Pro Lys Ala
                100                 105                 110

Gln Ile Lys Glu Ser Leu Arg Val Glu Leu Arg Val Thr Glu Arg Arg
            115                 120                 125

Ala Glu Val Pro Thr Ala His Pro Ser Pro Ser Pro Arg Pro Ala Gly
            130                 135                 140

Gln Phe Gln Thr Leu Val
145                 150

<210> SEQ ID NO 53
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Pro Gly Trp Phe Leu Asp Ser Pro Asp Arg Pro Trp Asn Pro Pro Thr
 1               5                  10                  15

Phe Ser Pro Ala Leu Leu Val Val Thr Glu Gly Asp Asn Ala Thr Phe
             20                  25                  30

Thr Cys Ser Phe Ser Asn Thr Ser Glu Gly Phe Val Leu Asn Trp Tyr
         35                  40                  45

Arg Met Ser Pro Ser Asn Gln Thr Asp Lys Leu Ala Ala Phe Pro Glu
 50                  55                  60

Asp Arg Ser Gln Pro Gly Gln Asp Cys Arg Phe Arg Val Thr Gln Leu
 65                  70                  75                  80

Pro Asn Gly Arg Asp Phe His Met Ser Val Val Arg Ala Arg Asn
                 85                  90                  95

Asp Ser Gly Thr Tyr Leu Cys Gly Ala Ile Val Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
            130                 135                 140

Gln Phe Gln Thr Leu Val
145                 150

<210> SEQ ID NO 54
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 54

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 55
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 56
<211> LENGTH: 150
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 56

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150
```

<210> SEQ ID NO 57
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 57

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150
```

<210> SEQ ID NO 58
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 59
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Val Glu Leu Arg Val Thr Glu Arg Arg
        115                 120                 125

-continued

Ala Glu Val Pro Thr Ala His Pro Ser Pro Ser Pro Arg Pro Ala Gly
130                 135                 140

Gln Phe Gln Thr Leu Val
145                 150

<210> SEQ ID NO 60
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val
145                 150

<210> SEQ ID NO 61
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ile

```
                    100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 62
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 63
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Pro Gly Gln Asp Cys Arg Phe Arg Val Thr Gln Leu
65                  70                  75                  80
```

```
Pro Asn Gly Arg Asp Phe His Met Ser Val Val Arg Ala Arg Asn
                85                  90                  95

Asp Ser Gly Thr Tyr Leu Cys Gly Ala Ile Val Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 64
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 65
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45
```

```
Arg Met Ser Pro Ser Asn Gln Thr Asp Lys Leu Ala Ala Phe Pro Glu
    50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 66
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 67
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
```

```
                    20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 68
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 69
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69
```

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 70
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 71
<211> LENGTH: 150
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic polypeptide"

<400> SEQUENCE: 71

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 72
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

-continued

```
<210> SEQ ID NO 73
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 74
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140
```

```
Gln Phe Gln Thr Leu Val
145                 150

<210> SEQ ID NO 75
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 76
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ala
            100                 105                 110
```

```
Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 77
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 78
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
```

```
                 85                  90                  95

Asp Ser Gly Thr Tyr Leu Cys Gly Ala Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 79
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Pro Gly Trp Phe Leu Asp Ser Pro Asp Arg Pro Trp Asn Pro Pro Thr
1               5                  10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 80
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Pro Gly Trp Phe Leu Asp Ser Pro Asp Arg Pro Trp Asn Pro Pro Thr
1               5                  10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60
```

```
Asp Arg Gly Gln Pro Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Leu Cys Ser Ala Ile Val Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 81
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Pro Gly Trp Phe Leu Asp Ser Pro Asp Arg Pro Trp Asn Pro Pro Thr
 1               5                  10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Gly Gln Pro Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Leu Cys Ser Ala Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 82
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Pro Gly Trp Phe Leu Asp Ser Pro Asp Arg Pro Trp Asn Pro Pro Thr
 1               5                  10                  15

Phe Ser Pro Ala Leu Leu Val Val Thr Glu Gly Asp Asn Ala Thr Phe
                20                  25                  30
```

```
Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
 50                  55                  60

Asp Arg Gly Gln Pro Gly Gln Asp Cys Arg Phe Arg Val Thr Gln Leu
 65                  70                  75                  80

Pro Asn Gly Arg Asp Phe His Met Ser Val Val Arg Ala Arg Asn
                 85                  90                  95

Asp Ser Gly Thr Tyr Leu Cys Ser Ala Ile Ser Leu Ala Pro Lys Ala
                100                 105                 110

Gln Ile Lys Glu Ser Leu Arg Val Glu Leu Arg Val Thr Glu Arg Arg
                115                 120                 125

Ala Glu Val Pro Thr Ala His Pro Ser Pro Ser Pro Arg Pro Ala Gly
                130                 135                 140

Gln Phe Gln Thr Leu Val
145                 150

<210> SEQ ID NO 83
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Pro Gly Trp Phe Leu Asp Ser Pro Asp Arg Pro Trp Asn Pro Pro Thr
 1               5                  10                  15

Phe Ser Pro Ala Leu Leu Val Val Thr Glu Gly Asp Asn Ala Thr Phe
                 20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
 50                  55                  60

Asp Arg Gly Gln Pro Gly Gln Asp Cys Arg Phe Arg Val Thr Gln Leu
 65                  70                  75                  80

Pro Asn Gly Arg Asp Phe His Met Ser Val Val Arg Ala Arg Asn
                 85                  90                  95

Asp Ser Gly Thr Tyr Leu Cys Gly Ala Ile Val Leu Ala Pro Lys Ile
                100                 105                 110

Gln Ile Lys Glu Ser Leu Arg Ala Glu Leu Arg Val Thr Glu Arg Arg
                115                 120                 125

Ala Glu Val Pro Thr Ala His Pro Ser Pro Ser Pro Arg Pro Ala Gly
                130                 135                 140

Gln Phe Gln Thr Leu Val
145                 150

<210> SEQ ID NO 84
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Pro Gly Trp Phe Leu Asp Ser Pro Asp Arg Pro Trp Asn Pro Pro Thr
```

```
                1               5                   10                  15
            Phe Ser Pro Ala Leu Leu Val Val Thr Glu Gly Asp Asn Ala Thr Phe
                            20                  25                  30

Thr Cys Ser Phe Ser Asn Thr Ser Glu Gly Phe Val Leu Asn Trp Tyr
                        35                  40                  45

Arg Met Ser Pro Ser Asn Gln Thr Asp Lys Leu Ala Ala Phe Pro Glu
                    50                  55                  60

Asp Arg Gly Gln Pro Gly Gln Asp Cys Arg Phe Arg Val Thr Gln Leu
            65                  70                  75                  80

Pro Asn Gly Arg Asp Phe His Met Ser Val Val Arg Ala Arg Arg Asn
                            85                  90                  95

Asp Ser Gly Thr Tyr Leu Cys Gly Ala Ile Val Leu Ala Pro Lys Ala
                        100                 105                 110

Gln Ile Lys Glu Ser Leu Arg Val Glu Leu Arg Val Thr Glu Arg Arg
                    115                 120                 125

Ala Glu Val Pro Thr Ala His Pro Ser Pro Ser Pro Arg Pro Ala Gly
                130                 135                 140

Gln Phe Gln Thr Leu Val
            145                 150

<210> SEQ ID NO 85
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Pro Gly Trp Phe Leu Asp Ser Pro Asp Arg Pro Trp Asn Pro Pro Thr
            1               5                   10                  15

Phe Ser Pro Ala Leu Leu Val Val Thr Glu Gly Asp Asn Ala Thr Phe
                            20                  25                  30

Thr Cys Ser Phe Ser Asn Thr Ser Glu Gly Phe Val Leu Asn Trp Tyr
                        35                  40                  45

Arg Met Ser Pro Ser Asn Gln Thr Asp Lys Leu Ala Ala Phe Pro Glu
                    50                  55                  60

Asp Arg Gly Gln Pro Gly Gln Asp Cys Arg Phe Arg Val Thr Gln Leu
            65                  70                  75                  80

Pro Asn Gly Arg Asp Phe His Met Ser Val Val Arg Ala Arg Arg Asn
                            85                  90                  95

Asp Ser Gly Thr Tyr Leu Cys Gly Ala Ile Ser Leu Ala Pro Lys Ile
                        100                 105                 110

Gln Ile Lys Glu Ser Leu Arg Val Glu Leu Arg Val Thr Glu Arg Arg
                    115                 120                 125

Ala Glu Val Pro Thr Ala His Pro Ser Pro Ser Pro Arg Pro Ala Gly
                130                 135                 140

Gln Phe Gln Thr Leu Val
            145                 150

<210> SEQ ID NO 86
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 86

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150
```

<210> SEQ ID NO 87
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 87

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150
```

<210> SEQ ID NO 88
<211> LENGTH: 150

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88
```

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val
145                 150

```
<210> SEQ ID NO 89
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89
```

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val 145             150

<210> SEQ ID NO 90
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145             150

<210> SEQ ID NO 91
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 92
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 93
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

```
Asp Ser Gly Thr Tyr Leu Cys Ser Ala Ile Val Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145             150

<210> SEQ ID NO 94
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145             150

<210> SEQ ID NO 95
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
```

```
              65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 96
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 97
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45
```

```
Arg Met Ser Pro Ser Asn Gln Thr Asp Lys Leu Ala Ala Phe Pro Glu
        50                  55                  60

Asp Arg Gly Gln Leu Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 98
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Pro Gly Trp Phe Leu Asp Ser Pro Asp Arg Pro Trp Asn Pro Pro Thr
 1               5                  10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Gly Gln Leu Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ala
                100                 105                 110

Gln Ile Lys Glu Ser Leu Arg Val Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 99
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Pro Gly Trp Phe Leu Asp Ser Pro Asp Arg Pro Trp Asn Pro Pro Thr
 1               5                  10                  15
```

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
 50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Arg Ala Arg Arg Asn
                85                  90                  95

Asp Ser Gly Thr Tyr Leu Cys Gly Ala Ile Val Leu Ala Pro Lys Ile
            100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 100
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
 50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Arg Ala Arg Arg Asn
                85                  90                  95

Asp Ser Gly Thr Tyr Leu Cys Gly Ala Ile Val Leu Ala Pro Lys Ala
            100                 105                 110

Gln Ile Lys Glu Ser Leu Arg Val Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 101
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150
```

<210> SEQ ID NO 102
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 102

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150
```

<210> SEQ ID NO 103
<211> LENGTH: 150
<212> TYPE: PRT
<213> ORGANISM: Artificial Sequence -continued

```
<220> FEATURE:
<221> NAME/KEY: source
<223> OTHER INFORMATION: /note="Description of Artificial Sequence:
      Synthetic polypeptide"

<400> SEQUENCE: 103
```

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

```
<210> SEQ ID NO 104
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104
```

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

```
<210> SEQ ID NO 105
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 106
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
```

```
        130                 135                 140
Gln Phe Gln Thr Leu Val
145                 150

<210> SEQ ID NO 107
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 108
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ile
            100                 105                 110
```

```
Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 109
<211> LENGTH: 149
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 109

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Phe Val Leu Asn Trp Tyr Arg
            35                  40                  45

Met Ser Pro Ser Asn Gln Thr Asp Lys Leu Ala Ala Phe Pro Glu Asp
    50                  55                  60

Arg Ser Gln Leu Gly Gln Asp Cys Arg Phe Arg Val Thr Gln Leu Pro
65                  70                  75                  80

Asn Gly Arg Asp Phe His Met Ser Val Val Arg Ala Arg Arg Asn Asp
                85                  90                  95

Ser Gly Thr Tyr Leu Cys Gly Ala Ile Val Leu Ala Pro Lys Ile Gln
            100                 105                 110

Ile Lys Glu Ser Leu Arg Val Glu Leu Arg Val Thr Glu Arg Arg Ala
        115                 120                 125

Glu Val Pro Thr Ala His Pro Ser Pro Ser Pro Arg Pro Ala Gly Gln
    130                 135                 140

Phe Gln Thr Leu Val
145

<210> SEQ ID NO 110
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80
```

Pro Asn Gly Arg Asp Phe His Met Ser Val Val Arg Ala Arg Asn
                85                  90                  95

Asp Ser Gly Thr Tyr Leu Cys Ser Ala Ile Val Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 111
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Pro Gly Trp Phe Leu Asp Ser Pro Asp Arg Pro Trp Asn Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 112
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Pro Gly Trp Phe Leu Asp Ser Pro Asp Arg Pro Trp Asn Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu

```
Asp Arg Gly Gln Leu Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Leu Cys Ser Ala Ile Ser Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 113
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

Pro Gly Trp Phe Leu Asp Ser Pro Asp Arg Pro Trp Asn Pro Pro Thr
  1               5                  10                  15

Phe Ser Pro Ala Leu Leu Val Val Thr Glu Gly Asp Asn Ala Thr Phe
                 20                  25                  30

Thr Cys Ser Phe Ser Asn Thr Ser Glu Gly Phe Val Leu Asn Trp Tyr
             35                  40                  45

Arg Met Ser Pro Ser Asn Gln Thr Asp Lys Leu Ala Ala Phe Pro Glu
         50                  55                  60

Asp Arg Gly Gln Leu Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Leu Cys Ser Ala Ile Ser Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 114
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Pro Gly Trp Phe Leu Asp Ser Pro Asp Arg Pro Trp Asn Pro Pro Thr
  1               5                  10                  15

Phe Ser Pro Ala Leu Leu Val Val Thr Glu Gly Asp Asn Ala Thr Phe
                 20                  25                  30
```

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 115
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 116
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
            85                  90                  95

Asp Ser Gly Thr Tyr Leu Cys Gly Ala Ile Ser Leu Ala Pro Lys Ile
            100                 105                 110

Gln Ile Lys Glu Ser Leu Arg Val Glu Leu Arg Val Thr Glu Arg Arg
            115                 120                 125

Ala Glu Val Pro Thr Ala His Pro Ser Pro Ser Pro Arg Pro Ala Gly
            130                 135                 140

Gln Phe Gln Thr Leu Val
145                 150

<210> SEQ ID NO 117
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
            85                  90                  95

Asp Ser Gly Thr Tyr Leu Cys Ser Ala Ile Val Leu Ala Pro Lys Ile
            100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
            130                 135                 140

Gln Phe Gln Thr Leu Val
145                 150

<210> SEQ ID NO 118
<211> LENGTH: 150
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 118

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 119
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 120

```
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120
```

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

```
<210> SEQ ID NO 121
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121
```

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

```
Gln Phe Gln Thr Leu Val
145                 150

<210> SEQ ID NO 122
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 123
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ile
            100                 105                 110

Gln Ile Lys Glu Ser Leu Arg Val Glu Leu Arg Val Thr Glu Arg Arg
```

```
                    115                 120                 125

Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 124
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 125
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95
```

```
Asp Ser Gly Thr Tyr Leu Cys Ser Ala Ile Val Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 126
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ile
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 127
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60
```

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 128
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 129
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr

```
                35                  40                  45
Arg Met Ser Pro Ser Asn Gln Thr Asp Lys Leu Ala Ala Phe Pro Glu
 50                  55                  60

Asp Arg Gly Gln Leu Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Leu Cys Gly Ala Ile Val Leu Ala Pro Lys Ile
                100                 105                 110

Gln Ile Lys Glu Ser Leu Arg Val Glu Leu Arg Val Thr Glu Arg Arg
                115                 120                 125

Ala Glu Val Pro Thr Ala His Pro Ser Pro Ser Pro Arg Pro Ala Gly
130                 135                 140

Gln Phe Gln Thr Leu Val
145                 150

<210> SEQ ID NO 130
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Pro Gly Trp Phe Leu Asp Ser Pro Asp Arg Pro Trp Asn Pro Pro Thr
 1               5                  10                  15

Phe Ser Pro Ala Leu Leu Val Val Thr Glu Gly Asp Asn Ala Thr Phe
                 20                  25                  30

Thr Cys Ser Phe Ser Asn Thr Ser Glu Ser Phe Val Leu Asn Trp Tyr
                 35                  40                  45

Arg Met Ser Pro Ser Asn Gln Thr Asp Lys Leu Ala Ala Phe Pro Glu
 50                  55                  60

Asp Arg Gly Gln Pro Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Leu Cys Ser Ala Ile Val Leu Ala Pro Lys Ile
                100                 105                 110

Gln Ile Lys Glu Ser Leu Arg Val Glu Leu Arg Val Thr Glu Arg Arg
                115                 120                 125

Ala Glu Val Pro Thr Ala His Pro Ser Pro Ser Pro Arg Pro Ala Gly
130                 135                 140

Gln Phe Gln Thr Leu Val
145                 150

<210> SEQ ID NO 131
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

Pro Gly Trp Phe Leu Asp Ser Pro Asp Arg Pro Trp Asn Pro Pro Thr
 1               5                  10                  15
```

```
Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
 50                  55                  60

Asp Arg Ser Gln Leu Gly Gln Asp Cys Arg Phe Arg Val Thr Gln Leu
 65                  70                  75                  80

Pro Asn Gly Arg Asp Phe His Met Ser Val Val Arg Ala Arg Asn
                 85                  90                  95

Asp Ser Gly Thr Tyr Leu Cys Ser Ala Ile Val Leu Ala Pro Lys Ile
                100                 105                 110

Gln Ile Lys Glu Ser Leu Arg Val Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 132
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
 50                  55                  60

Asp Arg Gly Gln Leu Gly Gln Asp Cys Arg Phe Arg Val Thr Gln Leu
 65                  70                  75                  80

Pro Asn Gly Arg Asp Phe His Met Ser Val Val Arg Ala Arg Asn
                 85                  90                  95

Asp Ser Gly Thr Tyr Leu Cys Ser Ala Ile Val Leu Ala Pro Lys Ile
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 133
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 133

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ala
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145             150

<210> SEQ ID NO 134
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Ser Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145             150

<210> SEQ ID NO 135
<211> LENGTH: 150
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 135

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
                35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Val Leu Ala Pro Lys Ile
                100                 105                 110

Gln Ile Lys Glu Ser Leu Arg Val Glu Leu Arg Val Thr Glu Arg Arg
                115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 136
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 136

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
                35                  40                  45

Arg Met Ser Pro Ser Asn Gln Thr Asp Lys Leu Ala Ala Phe Pro Glu
    50                  55                  60

Asp Arg Gly Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ile
                100                 105                 110

Gln Ile Lys Glu Ser Leu Arg Val Glu Leu Arg Val Thr Glu Arg Arg
                115                 120                 125

Ala Glu Val Pro Thr Ala His Pro Ser Pro Ser Pro Arg Pro Ala Gly
    130                 135                 140

Gln Phe Gln Thr Leu Val
145                 150
```

<210> SEQ ID NO 137
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 137

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Gly Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150
```

<210> SEQ ID NO 138
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 138

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Ser Ala Ile Val Leu Ala Pro Lys Ile
            100                 105                 110

Gln Ile Lys Glu Ser Leu Arg Val Glu Leu Arg Val Thr Glu Arg Arg
        115                 120                 125
```

```
Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 139
<211> LENGTH: 150
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 139

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Gly Phe Val Leu Asn Trp Tyr
            35                  40                  45

Arg Met Ser Pro Ser Asn Gln Thr Asp Lys Leu Ala Ala Phe Pro Glu
50                  55                  60

Asp Arg Gly Gln Leu Gly Gln Asp Cys Arg Phe Arg Val Thr Gln Leu
65                  70                  75                  80

Pro Asn Gly Arg Asp Phe His Met Ser Val Val Arg Ala Arg Arg Ser
                85                  90                  95

Asp Ser Gly Thr Tyr Leu Cys Ser Ala Ile Val Leu Ala Pro Lys Ile
            100                 105                 110

Gln Ile Lys Glu Ser Leu Arg Val Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 140
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(10)
<223> OTHER INFORMATION: /note="This sequence may encompass 1-5 'Gly
      Ser' repeating units"

<400> SEQUENCE: 140

Gly Ser Gly Ser Gly Ser Gly Ser Gly Ser
1               5                   10

<210> SEQ ID NO 141
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
```

```
<222> LOCATION: (1)..(25)
<223> OTHER INFORMATION: /note="This sequence may encompass 1-5 'Gly Ser
      Gly Gly Ser' repeating units"

<400> SEQUENCE: 141

Gly Ser Gly Gly Ser Gly Ser Gly Gly Ser Gly Ser Gly Gly Ser Gly
1               5                   10                  15

Ser Gly Gly Ser Gly Ser Gly Gly Ser
            20                  25

<210> SEQ ID NO 142
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(25)
<223> OTHER INFORMATION: /note="This sequence may encompass 1-5 'Gly Gly
      Gly Gly Ser' repeating units"

<400> SEQUENCE: 142

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 143
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(20)
<223> OTHER INFORMATION: /note="This sequence may encompass 1-5 'Gly Gly
      Gly Ser' repeating units"

<400> SEQUENCE: 143

Gly Gly Gly Ser Gly Gly Gly Ser Gly Gly Gly Ser Gly Gly Gly Ser
1               5                   10                  15

Gly Gly Gly Ser
            20

<210> SEQ ID NO 144
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Gly Gly Gly Gly Ser
1               5

<210> SEQ ID NO 145
<211> LENGTH: 20
<212> TYPE: PRT
<213> ORGANISM: Homo sapiens
```

-continued

```
<400> SEQUENCE: 145

Glu Ser Lys Tyr Gly Pro Pro Cys Pro Ser Cys Pro Ala Pro Glu Phe
1               5                   10                  15

Leu Gly Gly Pro
            20

<210> SEQ ID NO 146
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"

<400> SEQUENCE: 146

Gly Ser Gly Gly Ser
1               5

<210> SEQ ID NO 147
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"

<400> SEQUENCE: 147

Gly Gly Gly Gly Ser
1               5

<210> SEQ ID NO 148
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"

<400> SEQUENCE: 148

Gly Gly Gly Ser
1

<210> SEQ ID NO 149
<211> LENGTH: 175
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 149

Met Gln Ile Pro Gln Ala Pro Trp Pro Val Val Trp Ala Val Leu Gln
1               5                   10                  15
```

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Gly Gly Gly Ser
                165                 170                 175

<210> SEQ ID NO 150
<211> LENGTH: 175
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 150

Met Gln Ile Pro Gln Ala Pro Trp Pro Val Val Trp Ala Val Leu Gln
 1               5                  10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Gly Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Gly Gln Leu Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Ser Asp Ser Gly Thr Tyr Leu Cys Ser Ala Ile Val Leu
        115                 120                 125

Ala Pro Lys Ile Gln Ile Lys Glu Ser Leu Arg Val Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Gly Gly Gly Ser
                165                 170                 175

<210> SEQ ID NO 151
<211> LENGTH: 175

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 151
```

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Gly Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Gly Gln Leu Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Ser Ala Ile Val Leu
        115                 120                 125

Ala Pro Lys Ile Gln Ile Lys Glu Ser Leu Arg Val Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Gly Gly Gly Ser
                165                 170                 175

```
<210> SEQ ID NO 152
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 152
```

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln

```
            130                 135                 140
Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
            210                 215                 220

Leu Ser Leu Gly Lys
225

<210> SEQ ID NO 153
<211> LENGTH: 119
<212> TYPE: PRT
<213> ORGANISM: Homo sapiens

<400> SEQUENCE: 153

Asp Arg Pro Trp Asn Pro Pro Thr Phe Ser Pro Ala Leu Leu Val Val
1               5                   10                  15

Thr Glu Gly Asp Asn Ala Thr Phe Thr Cys Ser Phe Ser Asn Thr Ser
                20                  25                  30

Glu Ser Phe Val Leu Asn Trp Tyr Arg Met Ser Pro Ser Asn Gln Thr
            35                  40                  45

Asp Lys Leu Ala Ala Phe Pro Glu Asp Arg Ser Gln Pro Gly Gln Asp
        50                  55                  60

Cys Arg Phe Arg Val Thr Gln Leu Pro Asn Gly Arg Asp Phe His Met
65                  70                  75                  80

Ser Val Val Arg Ala Arg Arg Asn Asp Ser Gly Thr Tyr Leu Cys Gly
                85                  90                  95

Ala Ile Ser Leu Ala Pro Lys Ala Gln Ile Lys Glu Ser Leu Arg Ala
            100                 105                 110

Glu Leu Arg Val Thr Glu Arg
        115

<210> SEQ ID NO 154
<211> LENGTH: 118
<212> TYPE: PRT
<213> ORGANISM: Homo sapiens

<400> SEQUENCE: 154

Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
                20                  25                  30

Leu Asn Trp Tyr Arg Met Ser Pro Ser Asn Gln Thr Asp Lys Leu Ala
            35                  40                  45

Ala Phe Pro Glu Asp Arg Ser Gln Pro Gly Gln Asp Ser Arg Phe Arg
        50                  55                  60

Val Thr Gln Leu Pro Asn Gly Arg Asp Phe His Met Ser Val Val Arg
65                  70                  75                  80

Ala Arg Arg Asn Asp Ser Gly Thr Tyr Leu Cys Gly Ala Ile Ser Leu
                85                  90                  95

Ala Pro Lys Ala Gln Ile Lys Glu Ser Leu Arg Ala Glu Leu Arg Val
```

-continued

```
                100                 105                 110
Thr Glu Arg Arg Ala Glu
        115

<210> SEQ ID NO 155
<211> LENGTH: 129
<212> TYPE: PRT
<213> ORGANISM: Homo sapiens

<400> SEQUENCE: 155

Gly Pro Gly Ser Asp Ser Pro Asp Arg Pro Trp Asn Pro Thr Phe
1               5                   10                  15

Ser Pro Ala Leu Leu Val Val Thr Glu Gly Asp Asn Ala Thr Phe Thr
            20                  25                  30

Cys Ser Phe Ser Asn Thr Ser Glu Ser Phe His Val Val Trp His Arg
        35                  40                  45

Glu Ser Pro Ser Gly Gln Thr Asp Thr Leu Ala Ala Phe Pro Glu Asp
    50                  55                  60

Arg Ser Gln Pro Gly Gln Asp Ala Arg Phe Arg Val Thr Gln Leu Pro
65                  70                  75                  80

Asn Gly Arg Asp Phe His Met Ser Val Val Arg Ala Arg Arg Asn Asp
                85                  90                  95

Ser Gly Thr Tyr Val Cys Gly Val Ile Ser Leu Ala Pro Lys Ile Gln
            100                 105                 110

Ile Lys Glu Ser Leu Arg Ala Glu Leu Arg Val Thr Glu Arg Ala Ala
        115                 120                 125

Ala

<210> SEQ ID NO 156
<211> LENGTH: 202
<212> TYPE: PRT
<213> ORGANISM: Homo sapiens

<400> SEQUENCE: 156

Ala Leu Phe Thr Val Thr Val Pro Lys Glu Leu Tyr Ile Ile Glu His
1               5                   10                  15

Gly Ser Asn Val Thr Leu Glu Cys Asn Phe Asp Thr Gly Ser His Val
            20                  25                  30

Asn Leu Gly Ala Ile Thr Ala Ser Leu Gln Lys Val Glu Asn Asp Thr
        35                  40                  45

Ser Pro His Arg Glu Arg Ala Thr Leu Leu Glu Glu Gln Leu Pro Leu
    50                  55                  60

Gly Lys Ala Ser Phe His Ile Pro Gln Val Gln Val Arg Asp Glu Gly
65                  70                  75                  80

Gln Tyr Gln Cys Ile Ile Ile Tyr Gly Val Ala Trp Asp Tyr Lys Tyr
                85                  90                  95

Leu Thr Leu Lys Val Lys Ala Ser Tyr Arg Lys Ile Asn Thr His Ile
            100                 105                 110

Leu Lys Val Pro Glu Thr Asp Glu Val Glu Leu Thr Cys Gln Ala Thr
        115                 120                 125

Gly Tyr Pro Leu Ala Glu Val Ser Trp Pro Asn Val Ser Val Pro Ala
    130                 135                 140

Asn Thr Ser His Ser Arg Thr Pro Glu Gly Leu Tyr Gln Val Thr Ser
145                 150                 155                 160

Val Leu Arg Leu Lys Pro Pro Pro Gly Arg Asn Phe Ser Cys Val Phe
                165                 170                 175
```

```
Trp Asn Thr His Val Arg Glu Leu Thr Leu Ala Ser Ile Asp Leu Gln
            180                 185                 190

Ser Gln Met Glu Pro Arg Thr His Pro Thr
        195                 200
```

<210> SEQ ID NO 157
<211> LENGTH: 201
<212> TYPE: PRT
<213> ORGANISM: Mus sp.

<400> SEQUENCE: 157

```
Leu Phe Thr Val Thr Ala Pro Lys Glu Val Tyr Thr Val Asp Val Gly
1               5                   10                  15

Ser Ser Val Ser Leu Glu Cys Asp Phe Asp Phe Glu Cys Thr Glu
            20                  25                  30

Leu Glu Gly Ile Arg Ala Ser Leu Gln Lys Val Glu Asn Asp Thr Ser
        35                  40                  45

Leu Gln Ser Glu Arg Ala Thr Leu Leu Glu Glu Gln Leu Pro Leu Gly
    50                  55                  60

Lys Ala Leu Phe His Ile Pro Ser Val Gln Val Arg Asp Ser Gly Gln
65                  70                  75                  80

Tyr Arg Cys Leu Val Ile Cys Gly Ala Ala Trp Asp Tyr Lys Tyr Leu
                85                  90                  95

Thr Val Lys Val Lys Ala Ser Tyr Met Arg Ile Asp Thr Arg Ile Leu
            100                 105                 110

Glu Val Pro Gly Thr Gly Glu Val Gln Leu Thr Cys Gln Ala Arg Gly
        115                 120                 125

Tyr Pro Leu Ala Glu Val Ser Trp Gln Asn Val Ser Val Pro Ala Asn
    130                 135                 140

Thr Ser His Ile Arg Thr Pro Glu Gly Leu Tyr Gln Val Thr Ser Val
145                 150                 155                 160

Leu Arg Leu Lys Pro Gln Pro Ser Arg Asn Phe Ser Cys Met Phe Trp
                165                 170                 175

Asn Ala His Met Lys Glu Leu Thr Ser Ala Ile Ile Asp Pro Leu Ser
            180                 185                 190

Arg Met Glu Pro Lys Val Pro Arg Thr
        195                 200
```

<210> SEQ ID NO 158
<211> LENGTH: 202
<212> TYPE: PRT
<213> ORGANISM: Mus sp.

<400> SEQUENCE: 158

```
Met Leu Phe Thr Val Thr Ala Pro Lys Glu Val Tyr Thr Val Asp Val
1               5                   10                  15

Gly Ser Ser Val Ser Leu Glu Cys Asp Phe Asp Phe Glu Cys Thr
            20                  25                  30

Glu Leu Glu Gly Ile Arg Ala Ser Leu Gln Lys Val Glu Asn Asp Thr
        35                  40                  45

Ser Leu Gln Ser Glu Arg Ala Thr Leu Leu Glu Glu Gln Leu Pro Leu
    50                  55                  60

Gly Lys Ala Leu Phe His Ile Pro Ser Val Gln Val Arg Asp Ser Gly
65                  70                  75                  80

Gln Tyr Arg Cys Leu Val Ile Cys Gly Ala Ala Trp Asp Tyr Lys Tyr
                85                  90                  95
```

Leu Thr Val Lys Val Lys Ala Ser Tyr Met Arg Ile Asp Thr Arg Ile
            100                 105                 110

Leu Glu Val Pro Gly Thr Gly Glu Val Gln Leu Thr Cys Gln Ala Arg
            115                 120                 125

Gly Tyr Pro Leu Ala Glu Val Ser Trp Gln Asn Val Ser Val Pro Ala
            130                 135                 140

Asn Thr Ser His Ile Arg Thr Pro Glu Gly Leu Tyr Gln Val Thr Ser
145                 150                 155                 160

Val Leu Arg Leu Lys Pro Gln Pro Ser Arg Asn Phe Ser Cys Met Phe
                165                 170                 175

Trp Asn Ala His Met Lys Glu Leu Thr Ser Ala Ile Ile Asp Pro Leu
                180                 185                 190

Ser Arg Met Glu Pro Lys Val Pro Arg Thr
            195                 200

<210> SEQ ID NO 159
<211> LENGTH: 29
<212> TYPE: PRT
<213> ORGANISM: Homo sapiens

<400> SEQUENCE: 159

Ala Leu Phe Thr Val Glu Leu Thr Ser Gln Thr Ser Pro His Gln Gln
1               5                   10                  15

Cys Ile Ile Tyr Gly Val Ala Trp Asp Tyr Lys Tyr Leu
            20                  25

<210> SEQ ID NO 160
<211> LENGTH: 29
<212> TYPE: PRT
<213> ORGANISM: Mus sp.

<400> SEQUENCE: 160

Met Leu Phe Thr Ala Glu Val Arg Ser Gln Thr Ser Leu Gln Gln Arg
1               5                   10                  15

Cys Leu Ile Cys Gly Ala Ala Trp Asp Tyr Lys Tyr Leu
            20                  25

<210> SEQ ID NO 161
<211> LENGTH: 23
<212> TYPE: PRT
<213> ORGANISM: Homo sapiens

<400> SEQUENCE: 161

Glu Pro Lys Ser Cys Asp Lys Thr His Thr Cys Pro Pro Cys Pro Ala
1               5                   10                  15

Pro Glu Leu Leu Gly Gly Pro
            20

<210> SEQ ID NO 162
<211> LENGTH: 19
<212> TYPE: PRT
<213> ORGANISM: Homo sapiens

<400> SEQUENCE: 162

Glu Arg Lys Cys Cys Val Glu Cys Pro Pro Cys Pro Ala Pro Pro Val
1               5                   10                  15

Ala Gly Pro

<210> SEQ ID NO 163

```
<211> LENGTH: 70
<212> TYPE: PRT
<213> ORGANISM: Homo sapiens

<400> SEQUENCE: 163

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45

Pro Lys Ser Cys Asp Thr Pro Pro Pro Cys Pro Arg Cys Pro Ala Pro
    50                  55                  60

Glu Phe Leu Gly Gly Pro
65                  70
```

US 11,498,955 B2

SPD-1 VARIANT# FC FUSION PROTEINS

I. CROSS REFERENCE TO RELATED APPLICATIONS

This application is a continuation of International Application No. PCT/US19/50742, filed on Sep. 12, 2019, which claims priority to U.S. Provisional Patent Application No. 62/731,488, filed on Sep. 14, 2018, and U.S. Provisional Patent Application No. 62/888,320, filed on Aug. 16, 2019, which are entirely incorporated herein by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file SequenceListing_079445-001920US-1155026.txt, created on Dec. 16, 2019, 234,665 bytes, machine format IBM-PC, MS-Windows operating system, is hereby incorporated by reference.

II. FIELD OF THE INVENTION

This invention relates to sPD-1 variant—Fc fusion proteins, polynucleotides encoding the sPD-1 variant—Fc fusion proteins, methods of making the sPD-1 variant—Fc fusion proteins, and methods of using the sPD-1 variant—Fc fusion proteins, for example, in treating diseases such as cancers, infections, etc.

III. BACKGROUND OF THE INVENTION

PD-1 (programmed cell death 1) is an important immune checkpoint receptor expressed by activated T cell and B cells. It functions to mediate immunosuppression. PD-1 is expressed on activated T cells, B cells, and natural killer (NK) cells. The ligands for PD-1 are programmed cell death 1 ligand 1 (PD-L1, alternatively B7-H1) and programmed cell death 1 ligand 2 (PD-L2, alternatively B7-DC) which are expressed on many tumor cells and antigen-presenting cells, such as monocytes, dendritic cells (DC) and macrophages.

PD-1 is a member of the immunoglobulin (Ig) superfamily that contains a single Ig V-like domain in its extracellular region. The PD-1 cytoplasmic domain contains two tyrosines, with the most membrane-proximal tyrosine located within an immuno-receptor tyrosine-based inhibitory motif (ITIM). PD-1 attenuates antigen receptor signaling by recruiting cytoplasmic phosphatases via its cytoplasmic domain. Human and murine PD-1 proteins share about 60% amino acid identity with conservation of four potential N-glycosylation sites, and residues that define the Ig-V domain.

PD-1 acts to deliver a negative immune response signal when induced in T cells. Activation of PD-1 via selective binding to one of its ligands activates an inhibitory immune response that decreases T cell proliferation and/or the intensity and/or duration of a T cell response. PD-1 also regulates effector T cell activity in peripheral tissues in response to infection or tumor progression (Pardoll, Nat Rev Cancer, 2012, 12(4):252-264)

Endogenous immune checkpoints, such as the PD-1 signaling pathway, that normally terminate immune responses to mitigate collateral tissue damage can be co-opted by tumors to evade immune destruction. The interaction between PD-L1 and PD-1 in cancers can decrease the number of tumor-infiltrating immune cells, and inhibit an immune response to the cancer cells. Downregulation of T cell activation and cytokine secretion upon binding to PD-1 has been observed in several human cancers (Freeman et al., J Exp Med, 2000, 192(7): 1027-34; Latchman et al, Nat Immunol, 2001, 2(3):261-8). In addition, the PD-1 ligand PD-L1 is overexpressed in many cancers, including breast cancer, colon cancer, esophageal cancer, gastric cancer, glioma, leukemia, lung cancer, melanoma, multiple myeloma, ovarian cancer, pancreatic cancer, renal cell carcinoma, and urothelial cancer. It has also been shown that patients with cancer have a limited or reduced adaptive immune response due to increased PD-1/PD-L1 interactions by immune cells. This increase in activated PD-1 signaling has also been seen in patients with viral infections. For instance, hepatitis B and C viruses can induce overexpression of PD-1 ligands on hepatocytes and activate PD-1 signaling in effector T-cells. This, in turn, leads to T-cell exhaustion and immune tolerance to the viral infection (Boni et al., J Virol, 2007, 81:4215-4225; Golden-Mason et al, J Immunol, 2008, 180:3637-3641).

Current PD-1 antagonists, such as pidilizumab, pembrolizumab (Keytruda®) and nivolumab (Opdivo®) are antibodies that target PD-1 on all lymphatic cells of the body. These antibodies have nanomolar affinities to PD-1, which is weaker than the interaction between PD-1 and its ligands within the immune synapse, e.g., the interface between an antigen-presenting cell and a lymphocyte.

There is a need in the art for effective protein-based therapeutic treatment that can alleviate or reverse the inhibition of adaptive immunity in patients with cancer or infection. The present invention satisfies this and other needs.

It is an object of the present invention to provide sPD-1 variant—Fc fusion proteins having improved properties (e.g. increased binding affinity for PD-L1 and/or PD-L2, and increased protein stability, etc.) as well as methods of making and using such sPD-1 variant—Fc fusion proteins in treating patients with cancers and/or infections.

IV. BRIEF SUMMARY OF THE INVENTION

The present invention provides, inter alia, sPD-1 variant—Fc fusion proteins, polynucleotides encoding the sPD-1 variant—Fc fusion proteins, methods of making the sPD-1 variant—Fc fusion proteins, and methods of using the sPD-1 variant—Fc fusion proteins, particularly for treating a disease or disorder in which the adaptive immune system is suppressed or an increase in the magnitude or level of immune response is needed. In some embodiments, the sPD-1 variant—Fc fusion proteins can be used to treat cancer or chronic viral infection. In other embodiments, the sPD-1 variant—Fc fusion protein described herein can be used as adjuvant therapy for the treatment of cancer.

In one aspect, the invention provides an sPD-1 variant—Fc fusion protein comprising:
  a) a soluble PD-1 (sPD-1) variant domain comprising an amino acid substitution as compared to SEQ ID NO:1, wherein said amino acid substitution is at a position number selected from the group consisting of 120, 112, 107, 104, 67, 69, 96 and 42;
  b) an optional linker; and
  c) an Fc domain.

In an additional aspect, the invention provides the sPD-1 variant—Fc fusion protein as described above, where the Fc fusion protein comprises, from N- to C-terminal:

a) the sPD-1 variant domain;
b) the optional linker; and
c) the Fc domain.

In a further aspect, the invention provides the sPD-1 variant—Fc fusion protein as described above, where the Fc fusion protein comprises, from N- to C-terminal:
a) the Fc domain;
b) the optional linker; and
c) the sPD-1 variant domain.

In an additional aspect, the invention provides the sPD-1 variant—Fc fusion protein as described above, where the sPD-1 variant domain exhibits at least 95% identity to SEQ ID NO:1.

In a further aspect, the invention provides the sPD-1 variant—Fc fusion protein as described above, where the sPD-1 variant domain has amino acid substitution(s) at one of said positions, two of said positions, three of said positions, four of said positions, five of said positions, six of said positions, seven of said positions or eight of said positions.

In an additional aspect, the invention provides the sPD-1 variant—Fc fusion protein as described above, where the sPD-1 variant domain comprises the amino acid substitution selected from the group consisting of: A120V, A112I, S107V, G104S, S67G, P69L, N96S and S42G.

In a further aspect, the invention provides the sPD-1 variant—Fc fusion protein as described above, where the sPD-1 variant domain comprises a set of amino acid substitutions selected from the group consisting of S42G/S67G/P69L/G104S/S107V/A112I/A120V, S42G/S67G/P69L/N96S/G104S/S107V/A112I/A120V, P69L/G104S/S107V/A112I/A120V, S67G/G104S/S107V/A112I/A120V, S67G/P69L/G104S/S107V/A112I/A120V, G104S/S107V/A112I/A120V, and G104S/S107V/A112I.

In an additional aspect, the invention provides the sPD-1 variant—Fc fusion protein as described above, where the sPD-1 variant domain comprises a set of amino acid substitutions of S42G/S67G/P69L/G104S/S107V/A112I/A120V.

In a further aspect, the invention provides the sPD-1 variant—Fc fusion protein as described above, where the sPD-1 variant domain comprises a set of amino acid substitutions of S42G/S67G/P69L/N96S/G104S/S107V/A112I/A120V.

In an additional aspect, the invention provides the sPD-1 variant—Fc fusion protein as described above, wherein said sPD-1 variant domain comprises a set of amino acid substitutions of P69L/G104S/S107V/A112I/A120V.

In a further aspect, the invention provides the sPD-1 variant—Fc fusion protein as described above, wherein said sPD-1 variant domain comprises a set of amino acid substitutions of S67G/G104S/S107V/A112I/A120V.

In an additional aspect, the invention provides the sPD-1 variant—Fc fusion protein as described above, wherein said sPD-1 variant domain comprises a set of amino acid substitutions of S67G/P69L/G104S/S107V/A112I/A120V.

In a further aspect, the invention provides the sPD-1 variant—Fc fusion protein as described above, wherein said sPD-1 variant domain comprises a set of amino acid substitutions of G104S/S107V/A112I/A120V.

In an additional aspect, the invention provides the sPD-1 variant—Fc fusion protein as described above, wherein said sPD-1 variant domain comprises a set of amino acid substitutions of G104S/S107V/A112I.

In an additional aspect, the invention provides the sPD-1 variant—Fc fusion protein as described herein, wherein the sPD-1 variant domain has SEQ ID NO:2.

In a further aspect, the invention provides the sPD-1 variant—Fc fusion protein as described herein, wherein the sPD-1 variant domain has SEQ ID NO:3.

In an additional aspect, the invention provides the sPD-1 variant—Fc fusion protein as described herein, wherein the sPD-1 variant domain has SEQ ID NO:72.

In a further aspect, the invention provides the sPD-1 variant—Fc fusion protein as described herein, wherein the sPD-1 variant domain has SEQ ID NO:110.

In an additional aspect, the invention provides the sPD-1 variant—Fc fusion protein as described herein, wherein the sPD-1 variant domain has SEQ ID NO:130.

In a further aspect, the invention provides the sPD-1 variant—Fc fusion protein as described herein, wherein the sPD-1 variant domain has SEQ ID NO:131.

In an additional aspect, the invention provides the sPD-1 variant—Fc fusion protein as described herein, wherein the sPD-1 variant domain has SEQ ID NO:138.

In an additional aspect, the invention provides the sPD-1 variant—Fc fusion protein as described above, wherein the Fc domain is a human IgG Fc domain or a variant human IgG Fc domain.

In a further aspect, the invention provides the sPD-1 variant—Fc fusion protein as described above, where the human IgG Fc domain comprises the hinge-CH2-CH3 of human IgG4.

In an additional aspect, the invention provides the sPD-1 variant—Fc fusion protein as described above, where the Fc domain is a variant human IgG Fc domain.

In a further aspect, the invention provides the sPD-1 variant—Fc fusion protein as described above, where the variant human IgG Fc domain comprises the hinge-CH2-CH3 of human IgG4 with a S228P amino acid substitution according to the EU numbering index.

In an additional aspect, the invention provides the sPD-1 variant—Fc fusion protein as described above, where the linker is selected from the group consisting of (GS)n, (GSGGS)n, (GGGGS)n, and (GGGS)n, wherein n is selected from the group consisting of 1, 2, 3, 4 and 5.

In a further aspect, the invention provides the sPD-1 variant—Fc fusion protein as described above, where the linker is GGGGS.

In an additional aspect, the invention provides the sPD-1 variant—Fc fusion protein as described above, where the Fc fusion protein has SEQ ID NO:5.

In a further aspect, the invention provides the sPD-1 variant—Fc fusion protein as described above, where the Fc fusion protein has SEQ ID NO:6.

In an additional aspect, the invention provides a nucleic acid encoding the sPD-1 variant—Fc fusion protein as described above.

In a further aspect, the invention provides an expression vector comprising the nucleic acid as described above.

In an additional aspect, the invention provides a host cell comprising the nucleic acid or the expression vector as described above.

In a further aspect, the invention provides a method of making an sPD-1 variant—Fc fusion protein comprising: a) culturing the host cell as described above under conditions wherein the Fc fusion protein is expressed; and b) recovering the Fc fusion protein.

In an additional aspect, the invention provides a method of treating, reducing or preventing metastasis or invasion of a tumor in a subject with cancer, the method comprising administering to the subject a therapeutically effective dose of one or more said sPD-1 variant—Fc fusion proteins as described above.

In a further aspect, the invention provides a method of treating, reducing or preventing metastasis or invasion of a tumor in a subject with cancer as described above, where the cancer is selected from the group consisting of melanoma, glioma, lymphoma, myeloma, head and neck cancer, esophageal cancer, kidney cancer, lung cancer, breast cancer, liver cancer, colorectal cancer, gallbladder cancer, gastric cancer, pancreatic cancer, prostate cancer, cervical cancer, uterine cancer, ovarian cancer, testicular cancer, and any other solid tumor cancer.

In an additional aspect, the invention provides a method of treating a subject with an infection, where the method comprises administering to the subject a therapeutically effective dose of one or more said sPD-1 variant—Fc fusion proteins as described above.

In a further aspect, the invention provides a method of treating a subject with an infection as described above, where the infection is a fungal infection, bacterial infection or viral infection.

In an additional aspect, the invention provides a method of treating a subject with an infection as described above, where the viral infection is selected from the group consisting of a hepatitis B virus infection, hepatitis C virus infection, human papilloma virus infection, human immunodeficiency virus (HIV) infection, human T-lymphotrophic virus (HTLV) infection, Epstein-Barr virus infection, herpes virus infection, cytomegalovirus infection, and any other chronic viral infection.

In a further aspect, the invention provides a method of treating, reducing or preventing metastasis or invasion of a tumor in a subject with cancer as described above, or a method of treating a subject with an infection as described above, where the effective dose of the one or more sPD-1 variant—Fc fusion proteins inhibits, reduces, or modulates signal transduction mediated by the wild-type PD-1 in the subject.

In an additional aspect, the invention provides a method of treating, reducing or preventing metastasis or invasion of a tumor in a subject with cancer as described above, or a method of treating a subject with an infection as described above, where the effective dose of the one or more Fc fusion proteins increases a T cell response in the subject.

V. BRIEF DESCRIPTION OF THE DRAWINGS

FIG. 1 provides a schematic of the domains of wild type PD-1 polypeptide (PD1 WT), sPD-1 variant version 1 (PD1 V1), sPD-1 variant version 2 (PD1 V2) and IgG4. The signal peptide region is from residues 1 to 20 and italic, and the extracellular domain (ECD) is from residues 21 to 170. A mutated N-glycosylation site is bolded and underlined. Other mutated residues are bolded. Linkers are double-underlined. Sequence numbering starts from the first amino acid of the signal peptide region.

FIG. 2 provides a sequence alignment result of human PD-1, chain B of 4ZQK and chain A of 5IUS. The identical residues are marked in blue, the residues missing in both crystal structures are marked in red, residues missing only in 4ZQK are marked in cyan.

FIG. 3 provides an overlay of human PD-1 model and crystal structure of human PD-1/PD-L1 (PDBID: 4ZQK). The crystal structures of PD-1 and PD-L1 in 4ZQK are shown in blue and green respectively. The 7 residues (Ser62, Ser87, Pro89, Gly124, Ser127, Ala132 and Ala140 with the position numbering starting from the signal region) on PD-1 for mutation are shown in orange sticks, the N-glycosylation site (Asn116) is shown in magenta sticks. Position numbering starts from the first amino acid of the signal peptide region.

FIG. 4 shows a time-evolution of backbone atom-positional RMSD for WT PD-1/PD-L1 (in blue), PD-1/PD-L1 with 3 interface mutations (in red) and PD-1/PD-L1 with all 8 interface mutations (in green).

FIG. 5A shows the sequence alignment results of human PD-L2 and mouse PD-L2 (PDBID: 3RNQ, 3BP6 and 3BP5). The sequence identity between human PD-L2 and mouse PD-L2 is about 72%. FIG. 5B shows the consensus model of human PD-L2. The identical residues are marked in blue. The residues in missing loop are marked in red.

FIG. 6 provides a PD-1 binding interface comparison between human PD-L2 model and mouse PD-L2 crystal structure (PDBID: 3BP5). The interface residues are shown in lines. The interface residues are marked in green in the human PD-L2 model (shown in dark blue). The crystal structure of mouse PD-L2 is shown in pink.

FIG. 7 provides an Overlay of human PD-1/PD-L2 model and mouse PD-1/PD-L2 crystal structure (PDBID: 3BP5). Human PD-1 and PD-L2 models are shown in cyan and dark blue, mouse PD-1 and PD-L2 structures are shown in yellow and pink, respectively.

FIG. 8 shows the binding affinity of sPD-1 variant—Fc fusion proteins to PD-L1 and PD-L2. sPD-1 variant—Fc fusion protein demonstrates about 10,000-fold improvement in PD-L1 binding compared with a WT PD-1—Fc fusion protein ("parent Fc fusion protein"), and about 200-fold improvement in PD-L2 binding compared with the parent Fc fusion protein.

FIG. 9A shows the binding activity of sPD-1 variant—Fc fusion proteins (i.e. sPD-1 variant version 1—Fc fusion protein, and sPD-1 variant version 2—Fc fusion protein) on MC38 hPD-L1 knock-in cells. Both sPD-1 variant—Fc fusion proteins bind much better than the group of wild type (i.e. the group of wild type PD-1—Fc fusion protein) on MC38-PD-L1 knock-in cells. FIG. 9B shows the binding activity of sPD-1 variant—Fc fusion proteins (i.e. sPD-1 variant version 1—Fc fusion protein, and sPD-1 variant version 2—Fc fusion protein) on MC38 parental cells. sPD-1 variant—Fc fusion proteins also bind to parental MC38 cells but is lower.

FIG. 10 shows T cell activation in the presence of Hep3B-hPD-L1 cells upon incubation with different concentrations of sPD-1 mutants, sPD-1 wild type and hIgG4. T cell activity is measured by IFN-γ. Error bars represent the mean and standard deviation of technical triplicate. Experiment was conducted twice independently with PBMC isolated from different donors.

FIG. 11A shows sPD-1 variant version 2—Fc fusion protein demonstrating superior anti-tumor activity compared to anti-PD-L1 antibody as evidenced by reduced tumor volume in the group of PD-1-ECD-Fc (i.e. the group of sPD-1 variant version 2—Fc fusion protein) compared to that in the group of positive control (i.e. the group of anti-PD-L1 antibody). FIG. 11B shows sPD-1 variant version 2—Fc fusion protein demonstrating superior anti-tumor activity compared to anti-PD-L1 antibody as evidenced by increased tumor growth inhibition in the group of PD-1-ECD-Fc (i.e. the group of sPD-1 variant version 2—Fc fusion protein) compared to that in the group of positive control (i.e. the group of anti-PD-L1 antibody). FIG. 11C shows sPD-1 variant version 2—Fc fusion protein demonstrating superior anti-tumor activity compared to anti-PD-L1 antibody as evidenced by increased survival rate in the group of PD-1-ECD-Fc (i.e. the group of sPD-1 variant version 2—Fc fusion protein) compared to that in the group of positive control (i.e. the group of anti-PD-L1 antibody). FIG. 11D shows relative changes of body weight in the groups of vehicle control, PD-1-ECD-Fc (i.e. the group of sPD-1 variant version 2—Fc fusion protein), and positive control (i.e. the group of anti-PD-L1 antibody).

FIG. 12 shows hinge sequences of Human IgG1, IgG2, IgG3, and IgG4.

FIGS. 17A-17O shows the amino acid sequences of the mature extracellular domain (ECD) of PD1 WT (SEQ ID NO:11) and different sPD-1 variants (SEQ ID NOs:12-139) as compared to the PD1 WT. A signal peptide region, e.g. the one as set forth in SEQ ID NO:7 can be added before each of the sequences as shown in FIGS. 17A-17O. A linker domain, e.g. GGGGS can be added after each of the sequences as shown in FIGS. 17A-17O. A mutated N-glycosylation site is bolded and underlined. Other mutated residues are bolded. The mutation(s) in each colony are summarized in Table 10 with the sequence numbering starting from its mature region. FIG. 17A shows the amino acid sequences of PD1 WT (SEQ ID NO:11) and different sPD-1 variants (SEQ ID NOS:12-19). FIG. 17B shows the amino acid sequences of different sPD-1 variants (SEQ ID NOS:20-28). FIG. 17C shows the amino acid sequences of different sPD-1 variants (SEQ ID NOS:29-37). FIG. 17D shows the amino acid sequences of different sPD-1 variants (SEQ ID NOS:38-46). FIG. 17E shows the amino acid sequences of different sPD-1 variants (SEQ ID NOS:47-55). FIG. 17F shows the amino acid sequences of different sPD-1 variants (SEQ ID NOS:56-64). FIG. 17G shows the amino acid sequences of different sPD-1 variants (SEQ ID NOS: 65-73). FIG. 17H shows the amino acid sequences of different sPD-1 variants (SEQ ID NOS:74-82). FIG. 17I shows the amino acid sequences of different sPD-1 variants (SEQ ID NOS:83-91). FIG. 17J shows the amino acid sequences of different sPD-1 variants (SEQ ID NOS:92-100). FIG. 17K shows the amino acid sequences of different sPD-1 variants (SEQ ID NOS:101-109). FIG. 17L shows the amino acid sequences of different sPD-1 variants (SEQ ID NOS:110-118). FIG. 17M shows the amino acid sequences of different sPD-1 variants (SEQ ID NOS:119-127). FIG. 17N shows the amino acid sequences of different sPD-1 variants (SEQ ID NOS:128-136). FIG. 17O shows the amino acid sequences of different sPD-1 variants (SEQ ID NOS:137-139).

Figure 18A:
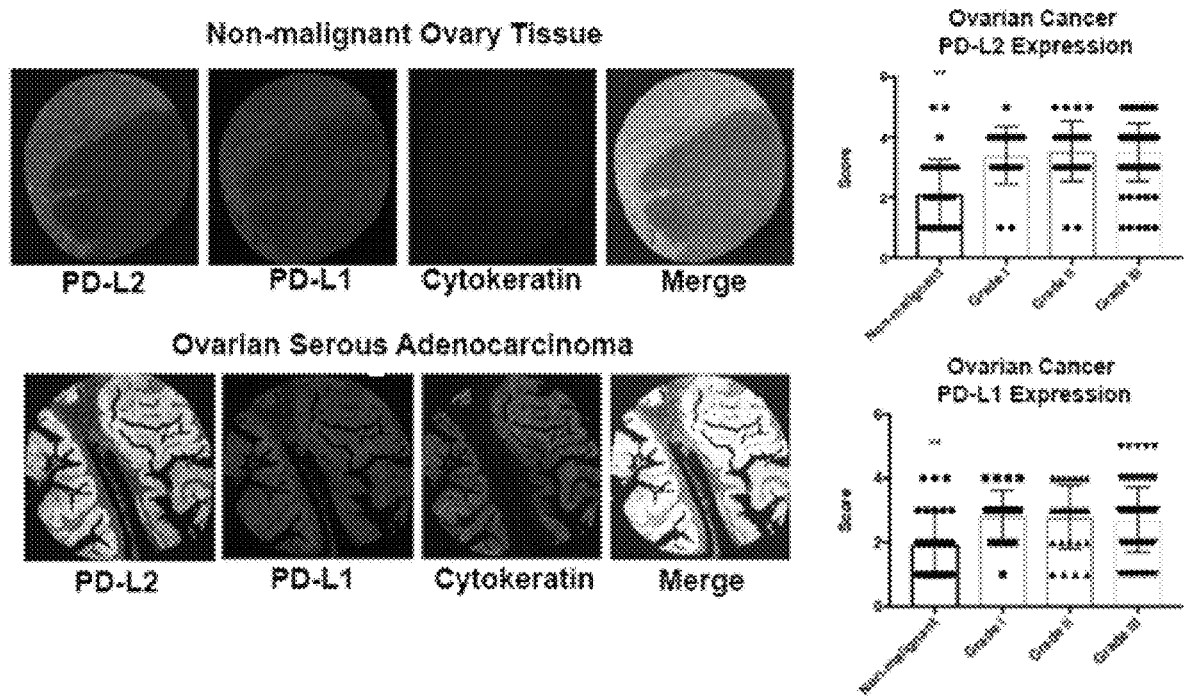
Figure 18C:
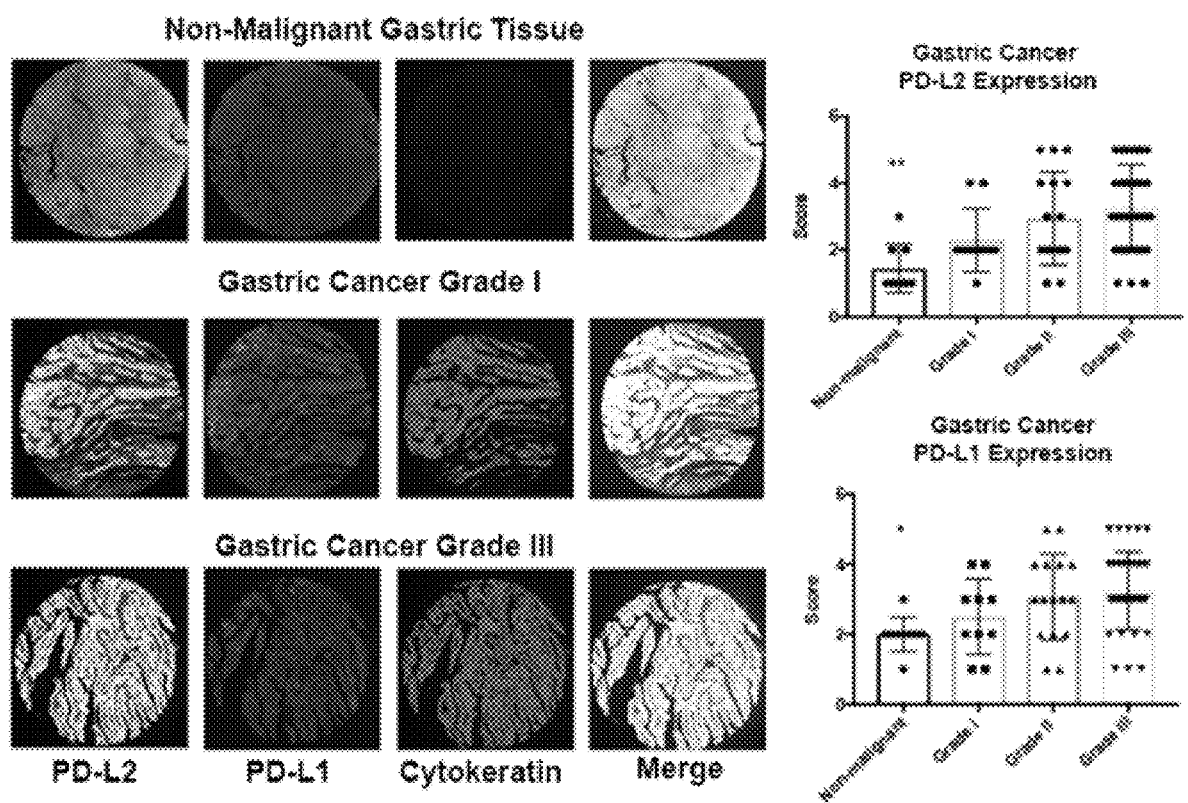
Figure 18D:
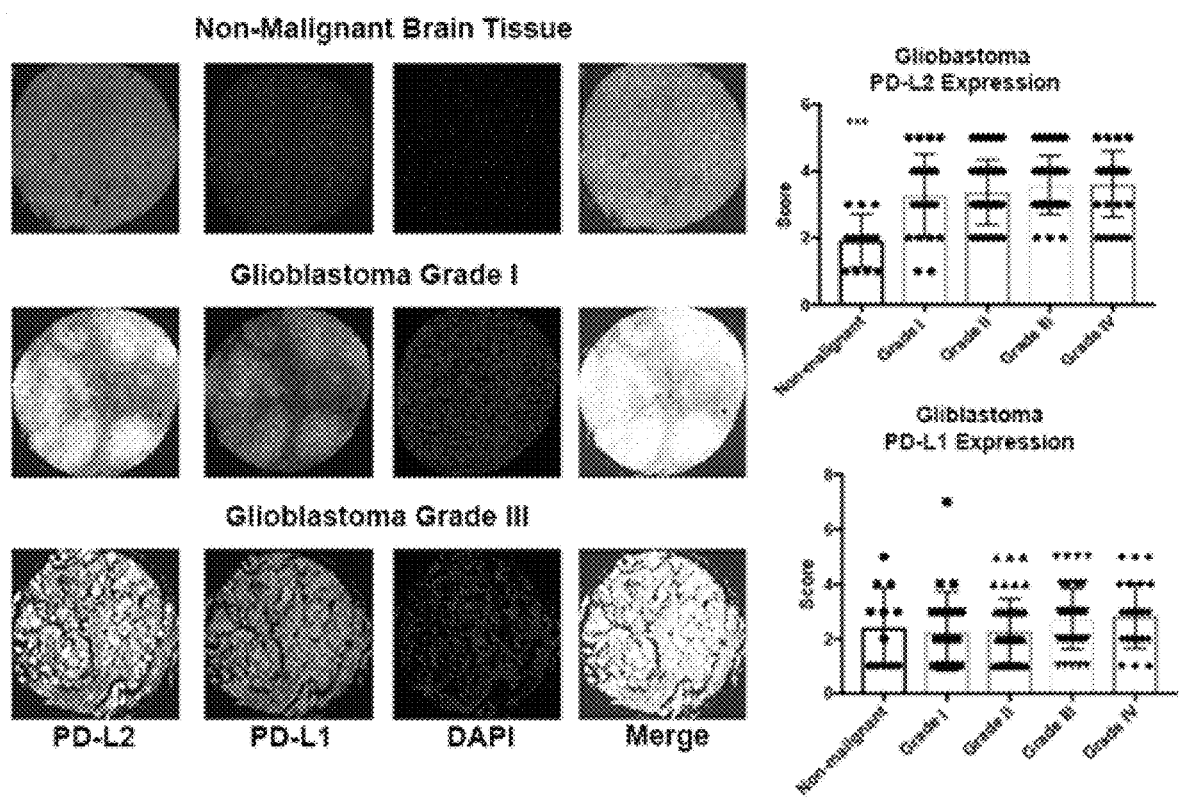

FIGS. 18A-18F shows PD-L2, PD-L1 and CD8+ T cell expression in human tissue microarray of ovarian, esophageal, gastric and brain tumors. FIG. 18A shows that representative images of ovarian cancer tissue microarray containing both normal and malignant samples (N=156) were stained with anti-human PD-L2 (gray), anti-human PD-L1 (Latchman, Wood et al.) and cytokeratin (red) by fluorescent immunohistochemistry. The intensity of each sample stained was scored and quantified according to the tumor grade (Top right, PD-L2. Bottom right, PD-L1). FIG. 18B shows that representative images of normal and cancerous esophageal tissues (N=72) were stained with anti-human PD-L2 (gray), anti-human PD-L1 (Latchman, Wood et al.) and cytokeratin (red) by fluorescent immunohistochemistry. Each sample was scored and quantified to show both PD-L2 (Top right) and PD-L1 (Bottom right) expression according to tumor grading. FIG. 18C shows that representative images of gastric cancer tissue microarray (N=76) were stained then quantified for both PD-L2 (Top right) and PD-L1 (Bottom right) expression based on tumor grading. FIG. 18D shows that representative images of Glioblastoma tissue microarray (N=152) were stained and then quantified for PD-L2 (Top right) and PD-L1 (Bottom right) expression based on tumor grading, DAPI staining marks the presence of a nuclei. FIG. 18E shows that ovarian cancer tissue microarray containing same samples examined in FIG. 18A were stained for anti-human CD8 (red) and DAPI (blue) with representative images shown here. Positive CD8 cells were annotated with arrows and scale bar represents 100 μM. FIG. 18F shows that esophageal cancer tissue microarray containing same samples examined in FIG. 18B were stained for anti-human CD8 (red) and DAPI (blue) with representative images shown. Positive CD8 cells were annotated with arrows and scale bar represents 100 μm. Each sample was quantified showing no. of positive nuclei per field and graphed according to tumor grading (right). All quantification data were plotted showing the score or the no. of positive nuclei per patient sample with mean and Standard deviation calculated. Statistical analysis was conducted with One-way ANOVA comparing between treatment groups. P value *=<0.05, =<0.01 and *=<0.001.

Figure 19A:
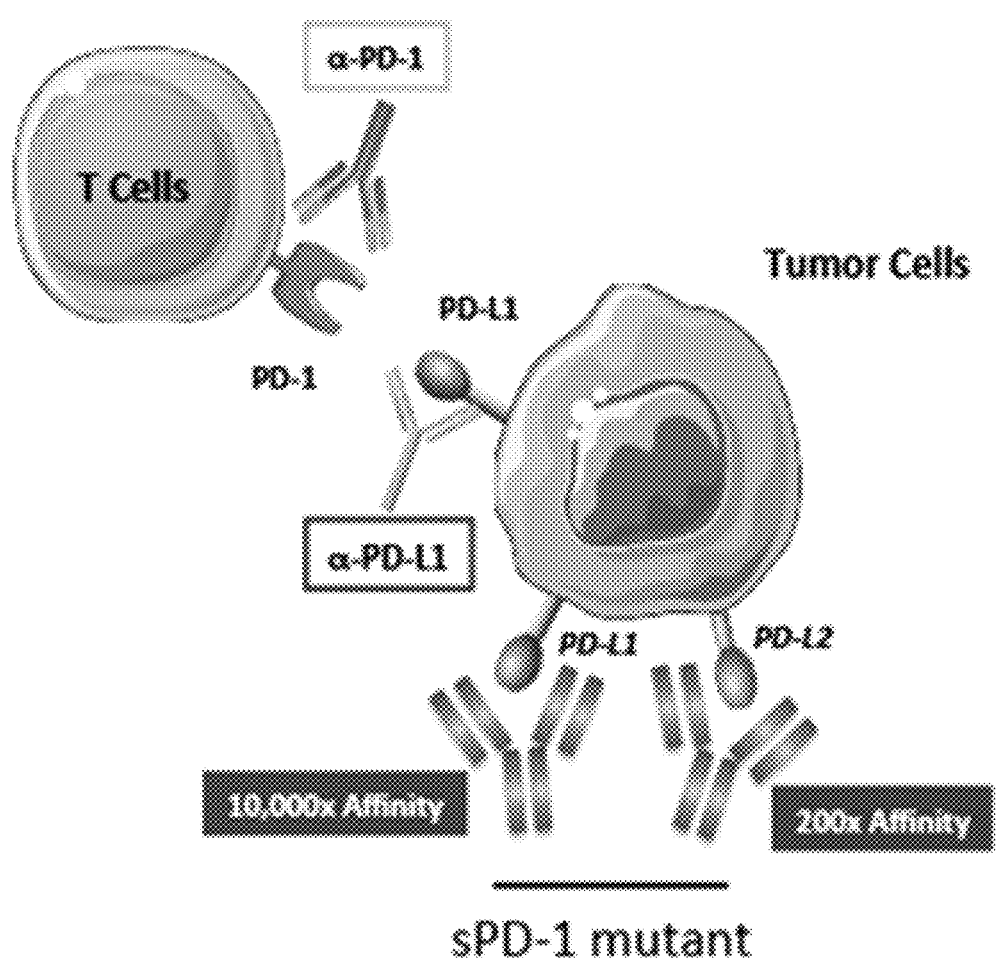
Figure 19B:
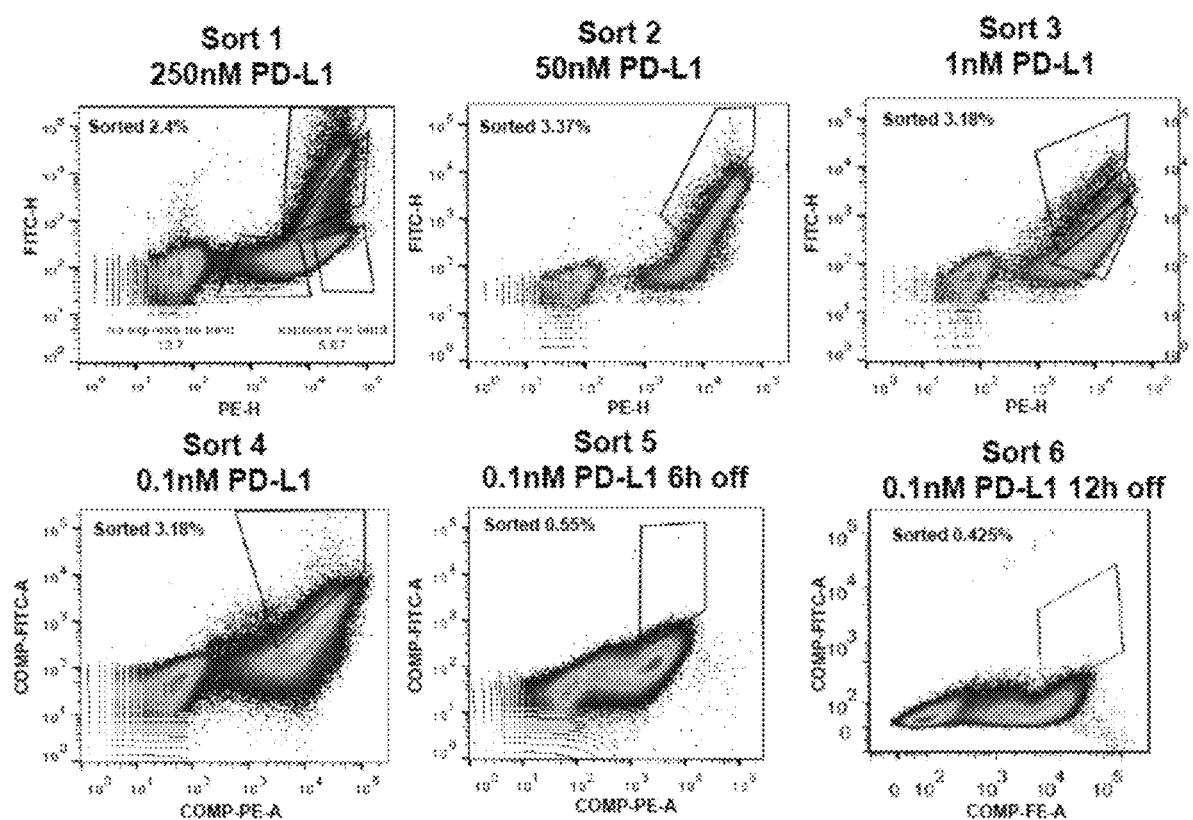

FIGS. 19A-19D shows engineering sPD-1 mutants with superior binding affinity to PD-L1 and PD-L2. FIG. 19A shows graphic illustration of three different strategies to inhibit the PD-1 signaling. FIG. 19B demonstrates representative flow cytometry dot plots showing yeast-displayed sPD-1 Mutant library binding to PD-L1. Clones with strongest binding to PD-L1 were selected through sequential decrease of PD-L1 concentration (sort 1 to sort 4) followed by increase in incubation time (sort 5 and sort 6). FIG. 19C shows that kinetics of sPD-1 Mutant Version 1 (Topalian, Hodi et al. 2012, N Engl J Med 366(26): 2443-2454, hereby entirely incorporated by reference) and wild type PD-1 (bottom) binding to human PD-L1 was determined by BIAcore Surface Plasmon Resonance system. Each curve represents a single concentration of the analyte. FIG. 19D shows that kinetics of sPD-1 Mutant Version 1 (Topalian, Hodi et al. 2012, N Engl J Med 366(26): 2443-2454, hereby entirely incorporated by reference) and wild type PD-1 (bottom) binding to human PD-L2 was determined by BIAcore Surface Plasmon Resonance system. Each curve represents a single concentration of analyte.

Figure 20A:
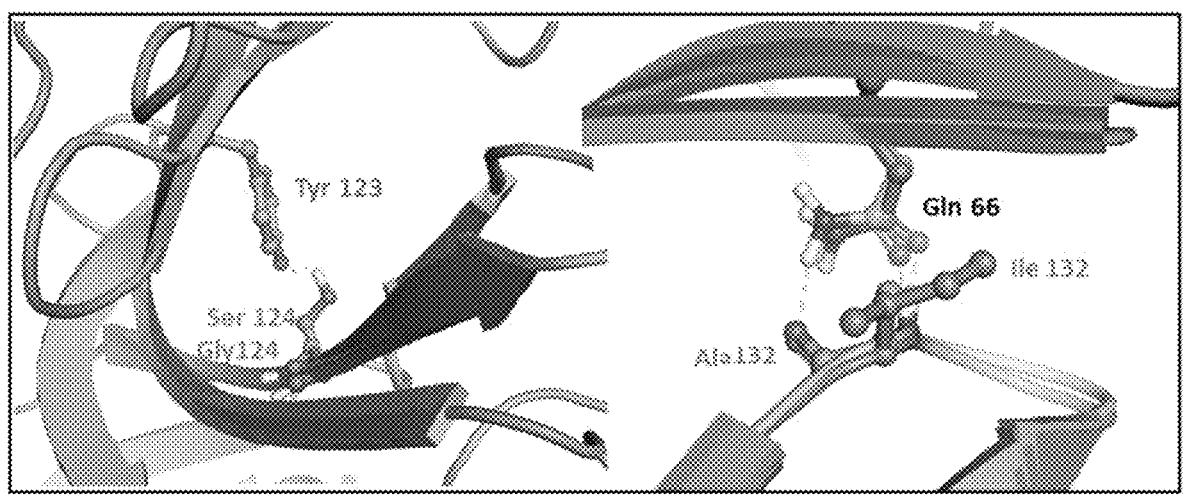
Figure 20B:
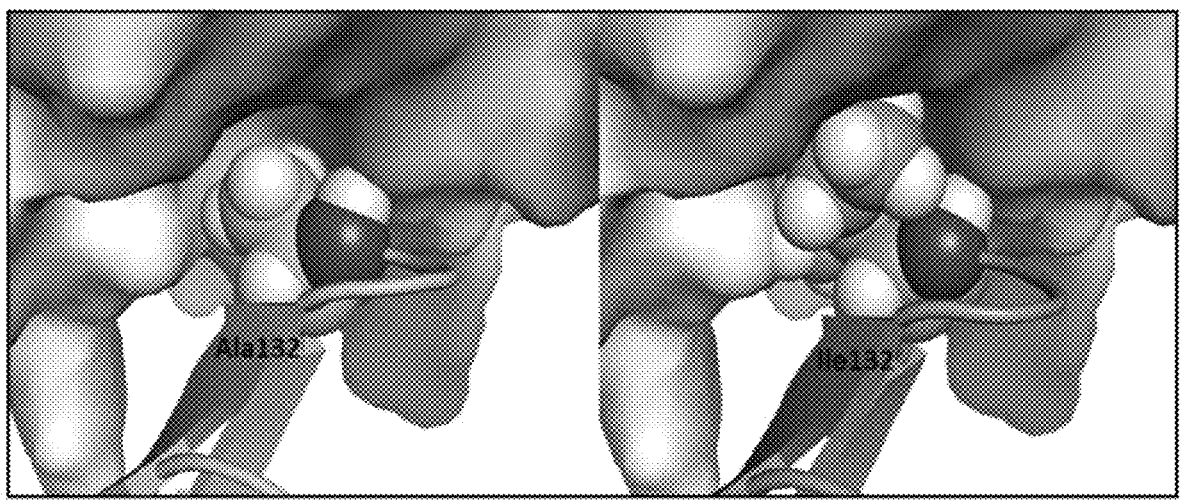
Figure 20C:
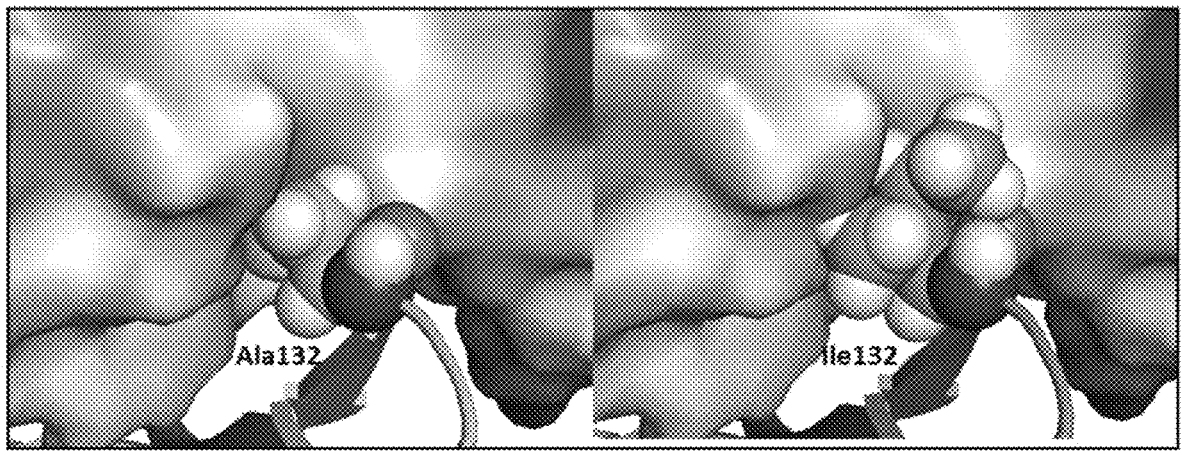

FIGS. 20A-20C shows computational modeling based structural analysis of sPD-1 Mutants in co-complex with human PD-L1 and PD-L2. FIG. 20A shows that left panel demonstrates the sPD-1 mutation G124S (orange) makes a hydrogen bond with PD-L1 Tyr123 (green and red sticks). Wild type PD-1 structure is shown in cyan. Right panel shows mutation A132I makes one more hydrogen bond with PD-L1 Gln166. Wild type PD-1 structure (cyan), mutated PD-1 structure (orange). Crystal PD-L1 structure is shown in pink and PD-L1 co-complex with sPD-1 mutant is shown in green. FIG. 20B shows comparison of surface complementarity of mutation A132I. PD-L1 binding site is marked to reveal electrostatic potential surface. Red indicates negative electrostatic potential, blue indicates positive electrostatic potential and grey indicates hydrophobic regions. Wild type PD-1 is shown in cyan cartoon and balls (left panel); mutated PD-1 is shown in orange cartoon and balls (right panel). FIG. 20C shows comparison of surface complementarity of mutation A132I with PD-L2 with same color annotation as FIG. 20B.

Figure 21A:
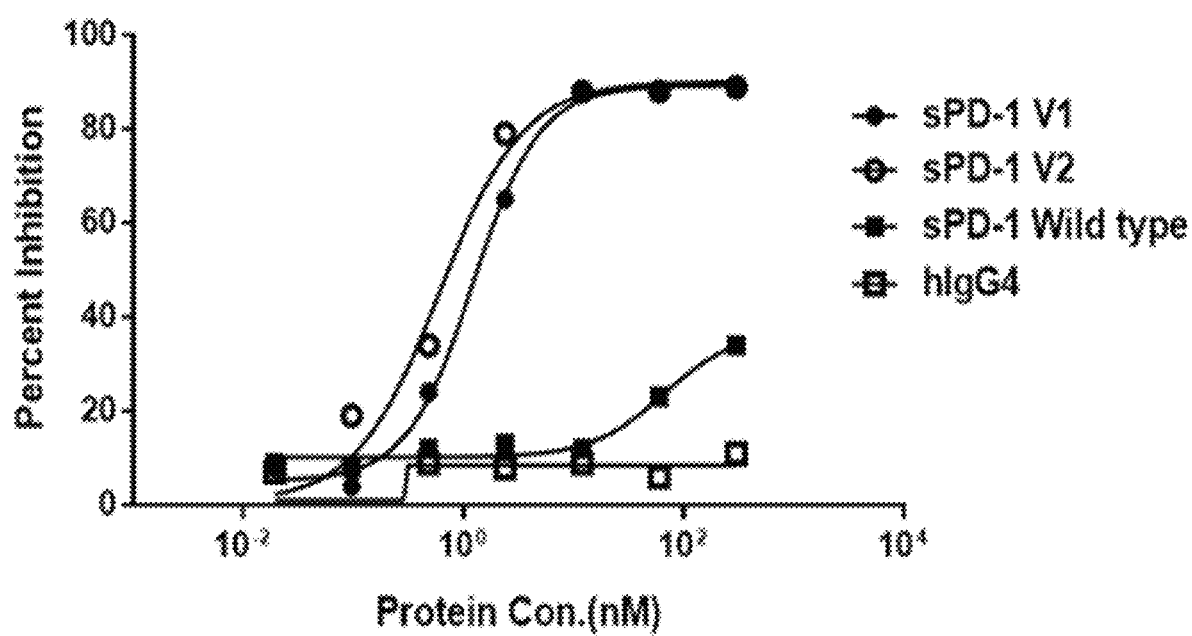
Figure 21B:
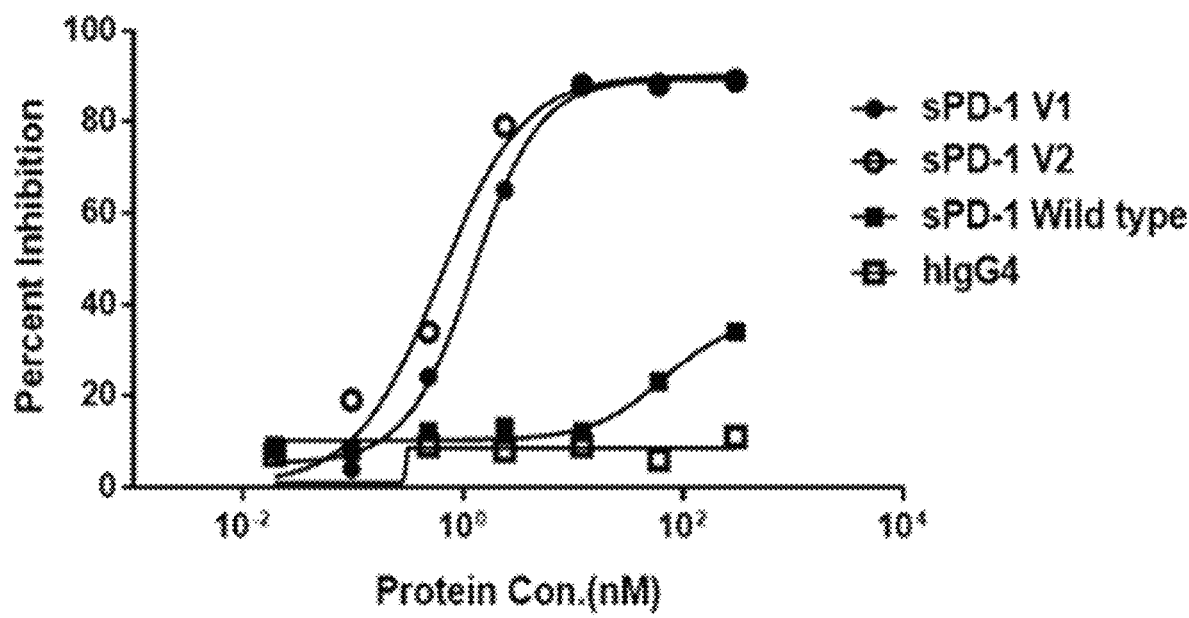
Figure 21C:
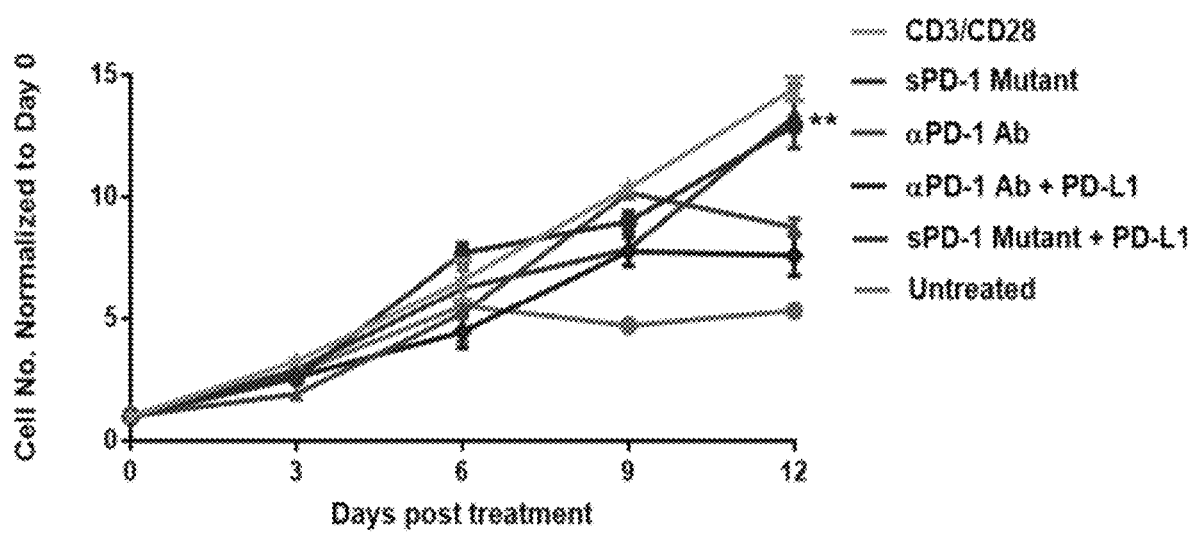

FIGS. 21A-21C demonstrates that sPD-1 mutants showed superior capability in blocking PD-L1 and PD-L2 mediated activities in a ligand-dependent manner without affecting T cell viability. FIG. 21A shows cell based receptor-blocking assay demonstrating percent inhibition of Hep3B-hPD-L1 binding to Biotin conjugated PD-1 wild type in competition with PD-1 wild type, hIgG4 and sPD-1 mutants. One of the two independent experiments shown here with individual points representing the mean of two technical repeats. FIG. 21B shows cell based receptor-blocking assay showing percent inhibition of Hep3B-hPD-L2 cell binding to Biotin conjugated PD-1 wild type in competition with sPD-1 wild type, hIgG4 and sPD-1 mutant version 1 and 2. One of the two independent experiments shown here with individual points representing the mean of two technical repeats. FIG. 21C shows T cell proliferation over-time in the presence of sPD-1 mutant version 2 and αPD-1 antibody with or without recombinant PD-L1 added. T cells treated with CD3/CD28 antigen were used as positive control and untreated T cells served as negative control. Each data points shows the mean and standard deviation of technical duplicate. Experiment was repeated with T cells isolated from a different donor. Statistical analysis was conducted with One-way ANOVA for comparing between treatment groups and repeated ANOVA for changes over time. P value *=<0.05, **=<0.01.

Figure 22A:
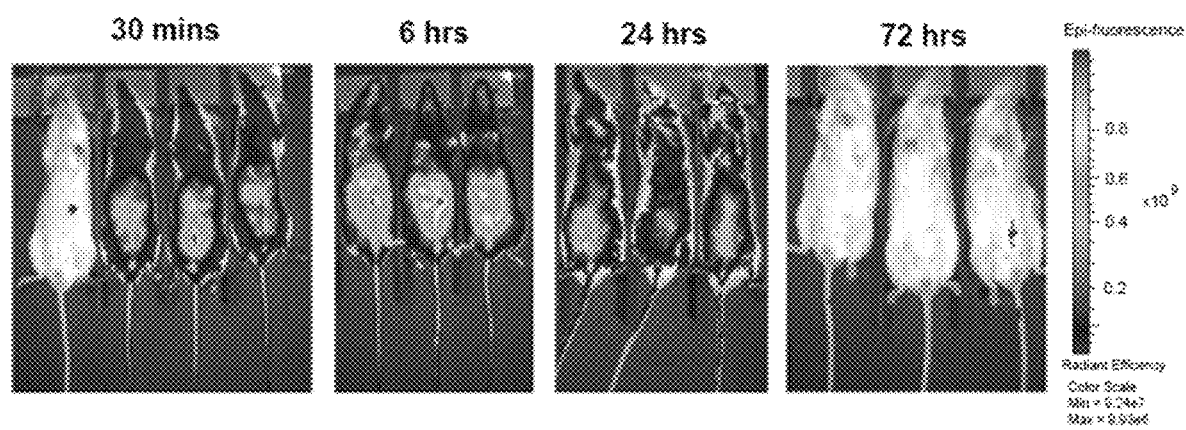
Figure 22B:
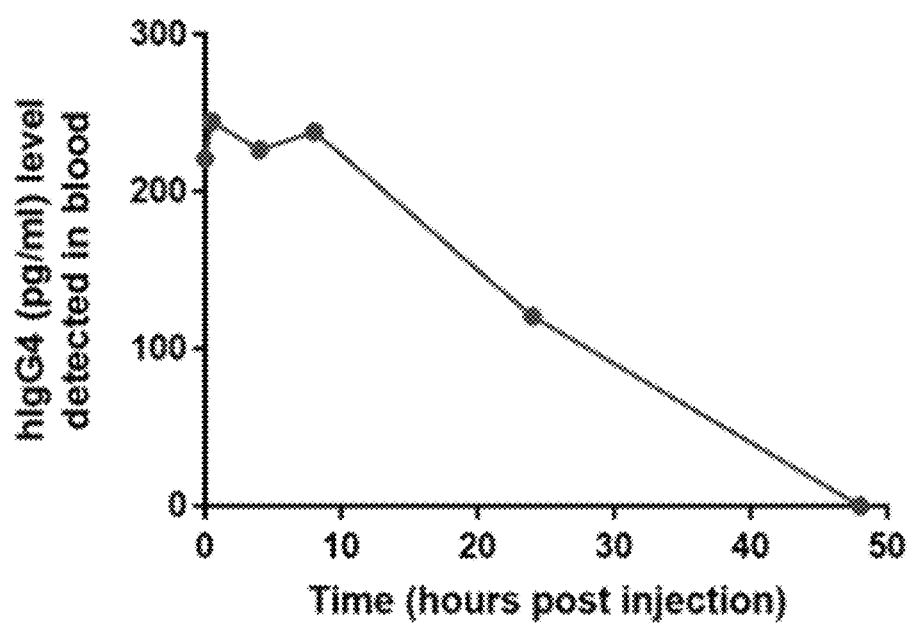
Figure 22C:
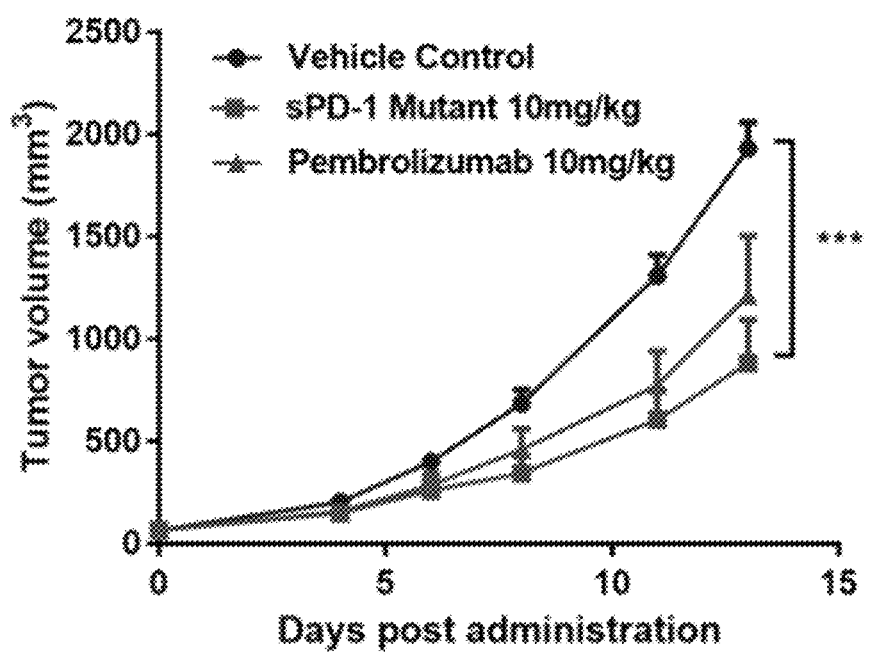
Figure 22D:
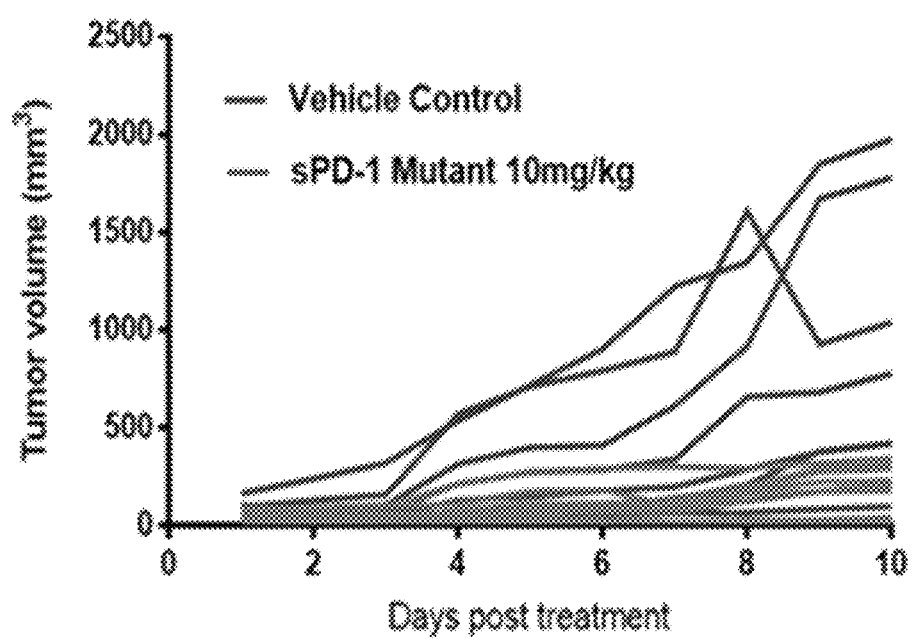
Figure 22E:
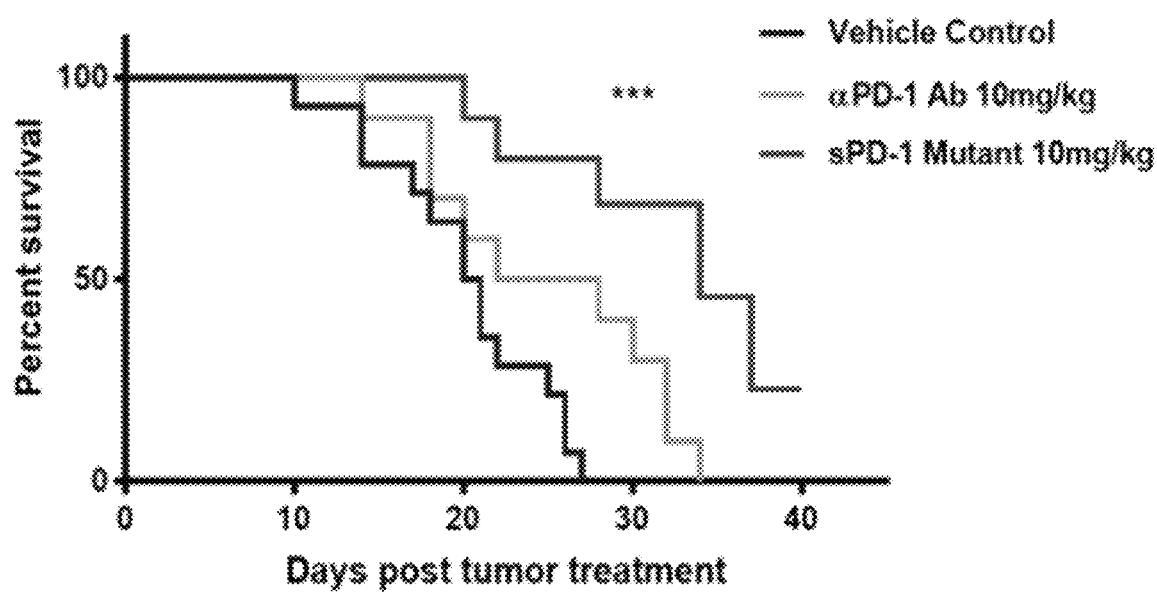
Figure 22F:
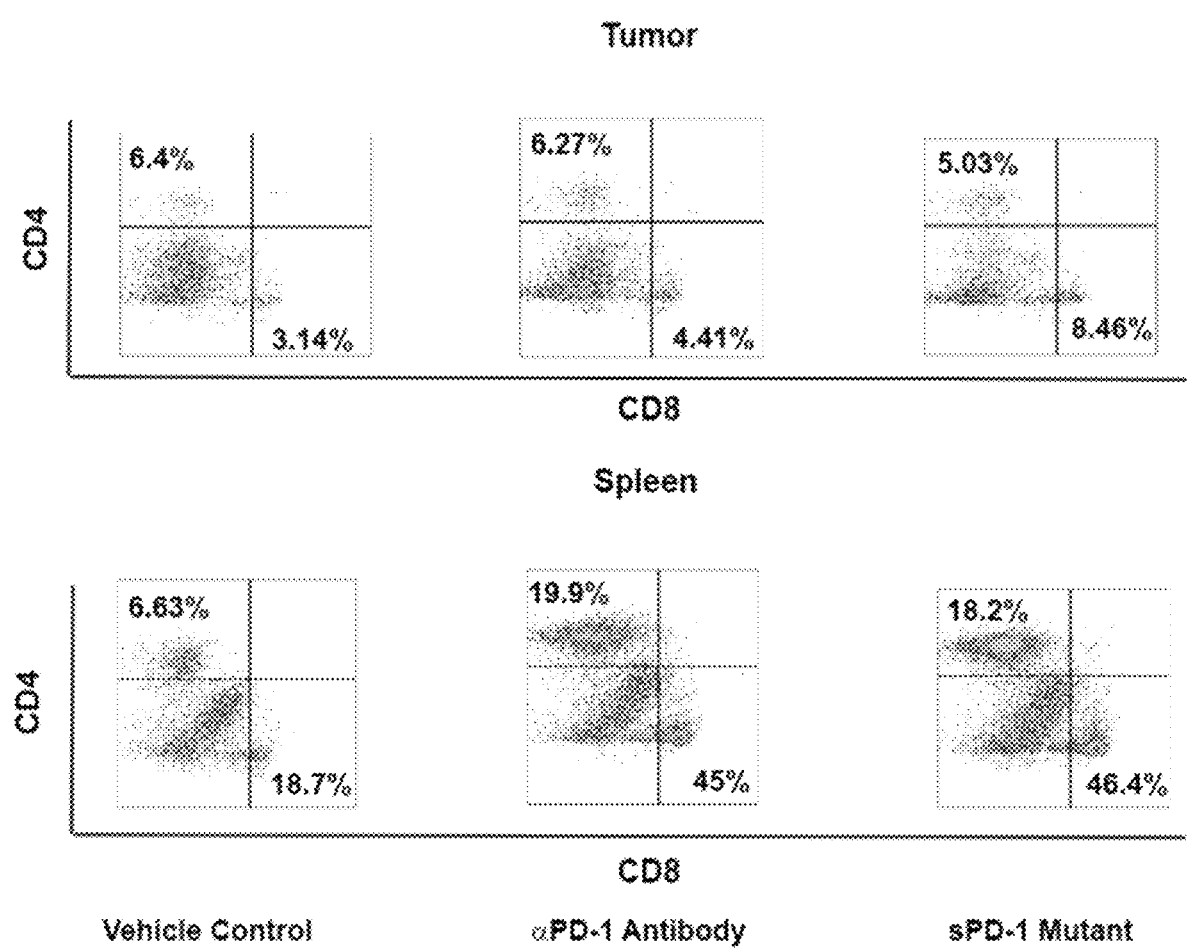
Figure 22G:
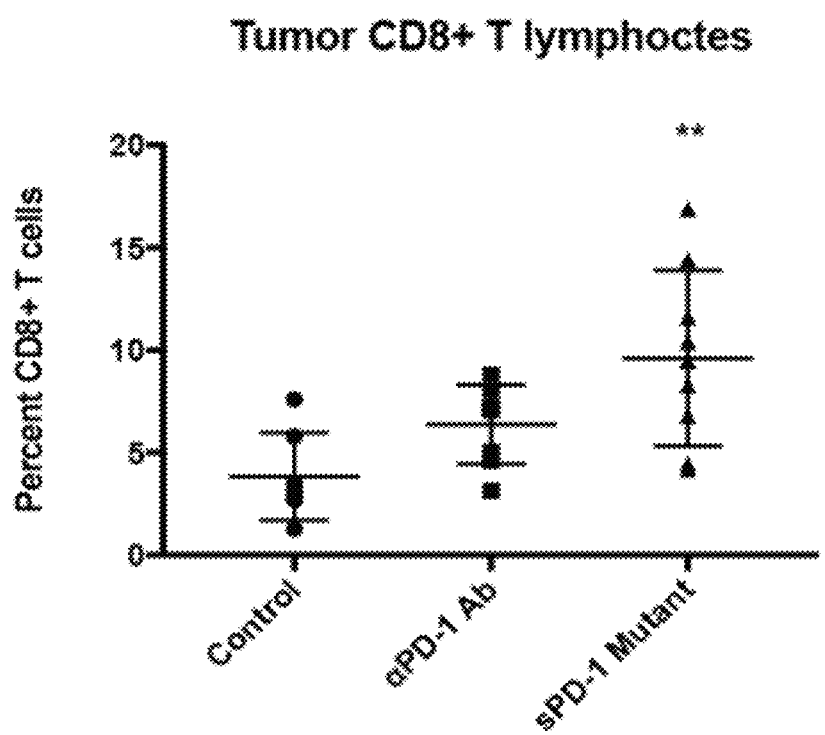
Figure 22H:
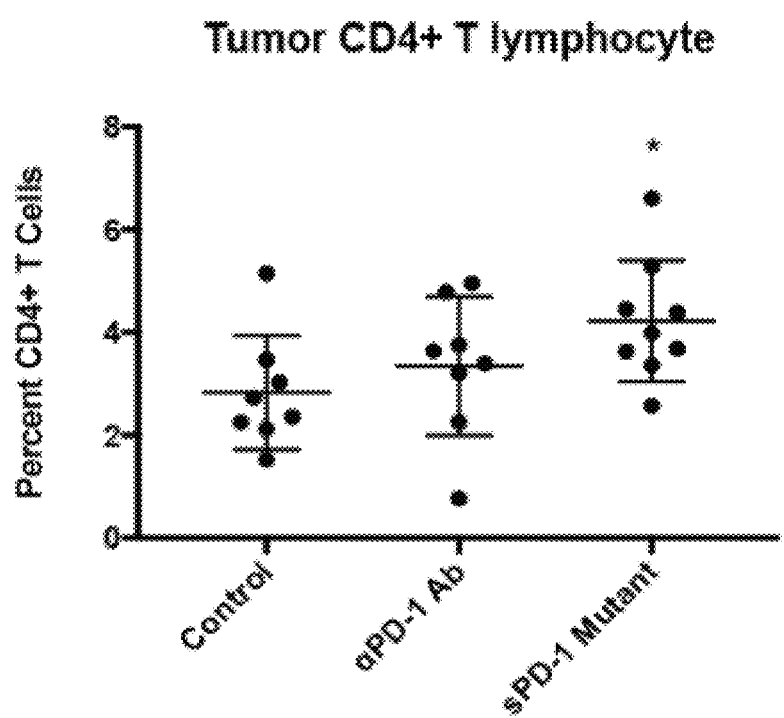

FIGS. 22A-22H shows that sPD-1 mutant inhibits tumor growth in mouse tumor models of colorectal cancer, melanoma and ovarian cancer. FIG. 22A shows that biodistribution of sPD-1 mutant labeled with Alexa Fluor® 488 were imaged over-time. FIG. 22B shows biodistribution of sPD-1 mutant in mouse serum after a single dose of molecule at 10 mg/kg detected using ELISA against human IgG4. Each data points represent the mean of two animals collected at the same time point. FIG. 22C shows tumor growth over-time in C57B/6 mice inoculated with MC39-hPD-L2 colorectal cancer then assigned to vehicle control, sPD-1 mutant 10 mg/kg or Pembrolizumab 10 mg/kg. Each data point represents mean and SEM of individual tumor measured over-time. FIG. 22D shows tumor growth over-time in C57B/6 mice inoculated with B16/OVA melanoma cells then treated with to vehicle controls or sPD-1 mutant 10 mg/kg. Each line represents individual tumor growth over-time. FIG. 22E shows Kaplan Meier survival plot of C57B/6 mice orthotopically inoculated with ID8 mouse ovarian tumor cells treated with vehicle control, anti-mouse αPD-1 blocking antibody 10 mg/kg and sPD-1 mutant 10 mg/kg. Animals terminated upon development of ascites. FIG. 22F shows representative flow cytometry dot plots of CD4+ and CD8+ cytotoxic T-cells isolated from tumor (upper panel) and spleen (lower panel) of B16/OVA melanoma tumors treated with vehicle control, anti-mouse αPD-1 blocking antibody 10 mg/kg and sPD-1 mutant 10 mg/kg. FIG. 22G shows CD8+ T cells isolated and analyzed from MC38-hPD-L2 tumors treated with vehicle control, anti-mouse αPD-1 blocking antibody 10 mg/kg and sPD-1 mutant 10 mg/kg. FIG. 22H shows CD4+ T cells isolated and analyzed from MC38-hPD-L2 tumors treated with vehicle control, anti-mouse αPD-1 blocking antibody 10 mg/kg and sPD-1 mutant 10 mg/kg. Statistical analysis was conducted using One-way ANOVA for comparing between treatment groups and repeated ANOVA for changes occur over-time. Kaplan Meier estimator was calculated for survival curves. P value *=<0.05, =<0.01. *=<0.001.

Figure 23A:
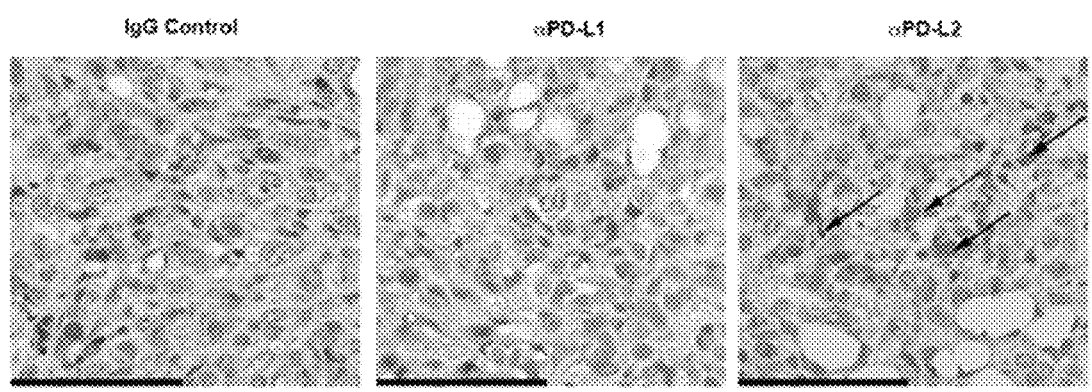
Figure 23B:
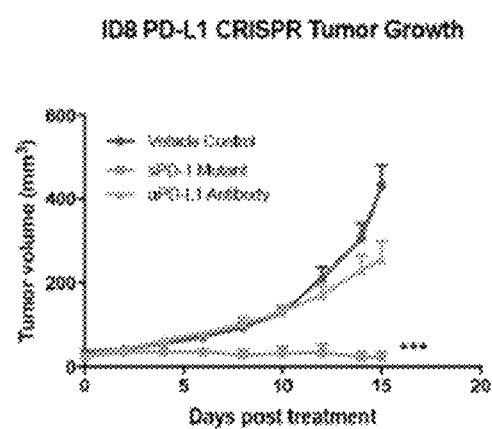
Figure 23C:
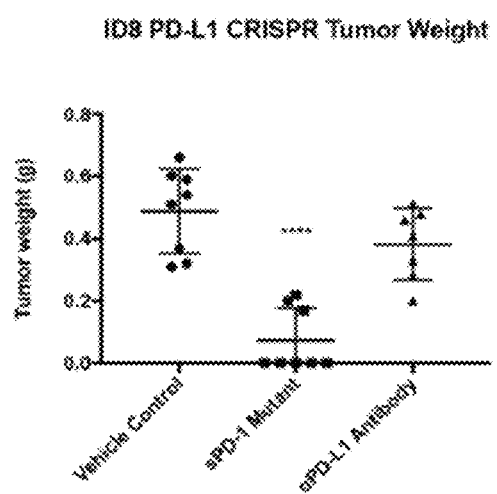
Figure 23D:
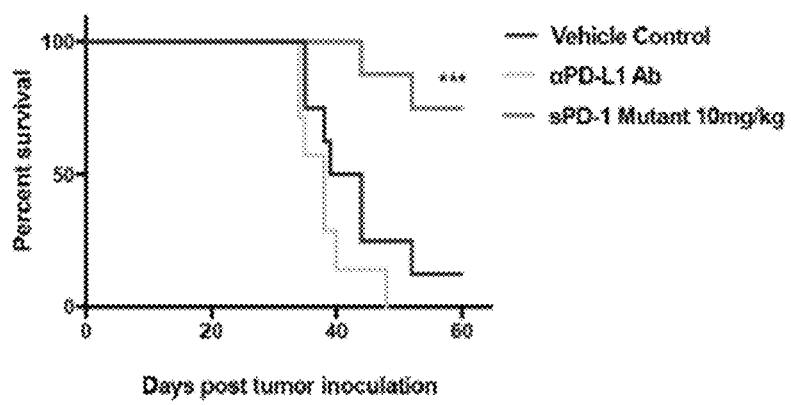
Figure 23E:
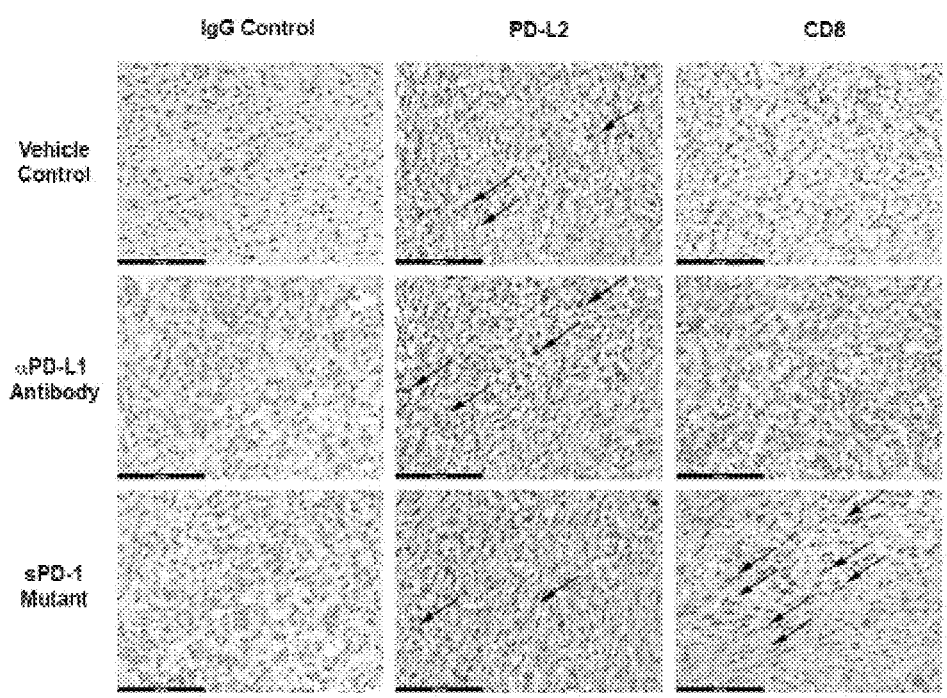

FIGS. 23A-23E shows that sPD-1 mutant is capable of suppressing tumor growth in ovarian cancer model that is PD-L2 dependent. FIG. 23A shows that ID8 PD-L1 CRSIPR KO tumors inoculated into PD-L1 KO mice and stained for PD-L1 and PD-L2 expression. Scale bar 100 μm. FIG. 23B shows that subcutaneous tumor growth over-time for in C57B/6 PD-L1 KO mice inoculated with ID8 PD-L1 CRSIPR KO tumors then treated with vehicle control, anti-mouse αPD-L1 blocking antibody 10 mg/kg and sPD-1 mutant 10 mg/kg. FIG. 23C shows total tumor weight of ID8 PD-L1 CRISPR KO tumors at the time of termination. FIG. 23D shows Kaplan Meier survival analysis of C57B/6 PD-L1 KO mice orthotopically inoculated with ID8 PD-L1 CRISPR KO mouse ovarian tumor cells treated with vehicle control, anti-mouse αPD-L1 blocking antibody 10 mg/kg and sPD-1 mutant 10 mg/kg. Animals terminated upon development of ascites. FIG. 23E IHC staining of PD-L1 and PD-L2 in ID8 tumors treated with vehicle control, anti-mouse αPD-L1 blocking antibody 10 mg/kg and sPD-1 mutant 10 mg/kg. Scale bar 100 μm. Statistical analysis was conducted using One-way ANOVA for comparing between treatment groups and repeated ANOVA for changes occur over time. Kaplan Meier estimator was calculated for survival curves. P value *=<0.05, =<0.01. *=<0.001.

Figure 24A:
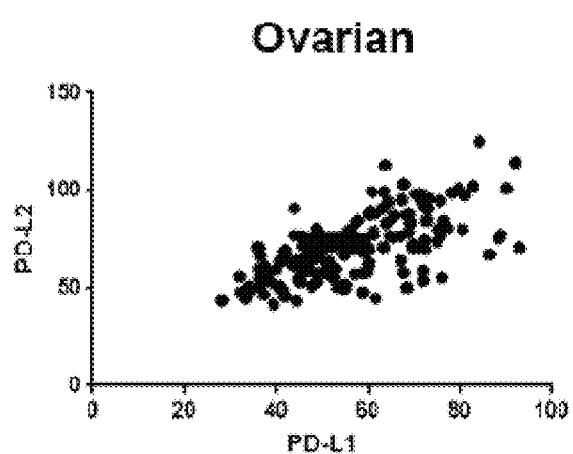
Figure 24B:
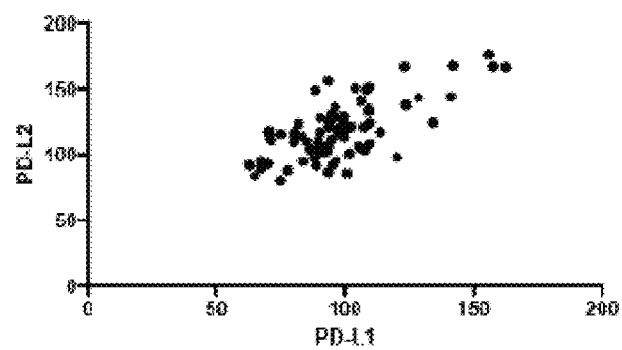
Figure 24C:
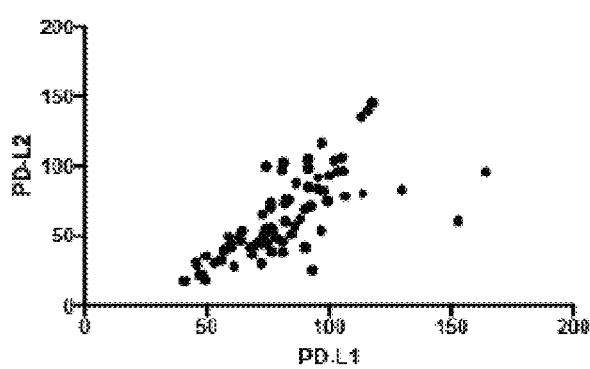
Figure 24D:
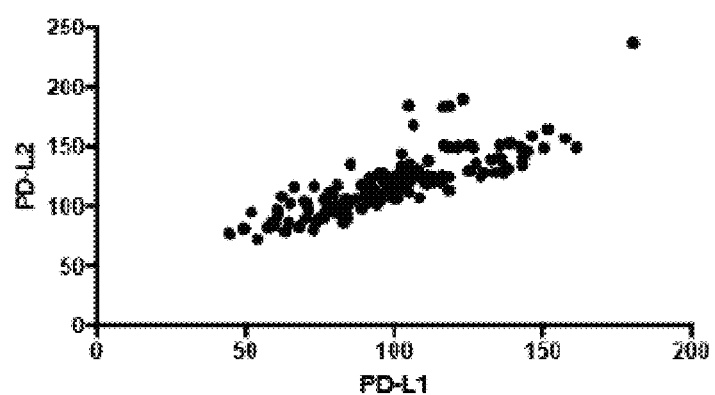
Figure 24E:
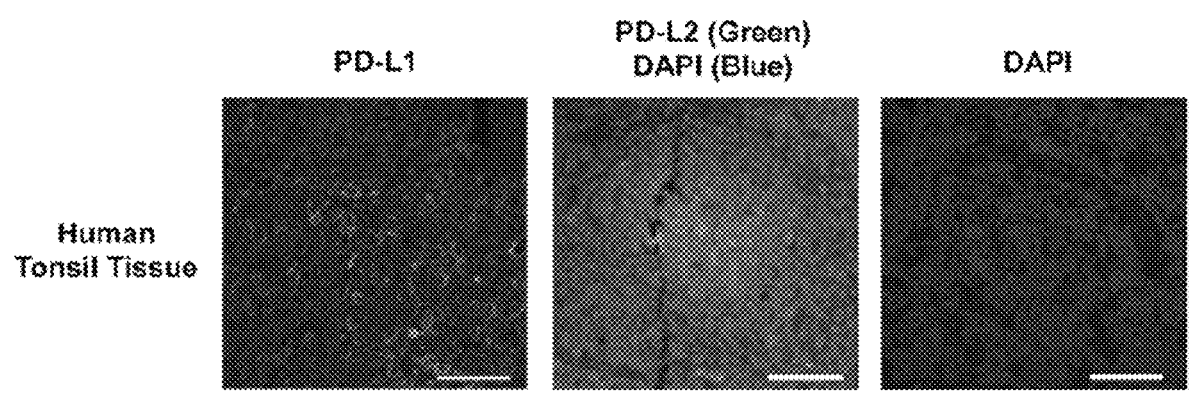

FIGS. 24A-24E shows that PD-L1 and PD-L2 expression is positively correlated in patient tumor samples. FIG. 24A shows Pearson correlation plot of PD-L1 and PD-L2 expression in ovarian cancer. FIG. 24B shows Pearson correlation plot of PD-L1 and PD-L2 expression in esophageal cancer. FIG. 24C shows Pearson correlation plot of PD-L1 and PD-L2 expression in gastric cancer. FIG. 24D shows Pearson correlation plot of PD-L1 and PD-L2 expression in glioblastoma. FIG. 24E shows IHC staining of human PD-L1 and PD-L2 on normal Tonsil tissue showing specific staining pattern.

Figure 25A:
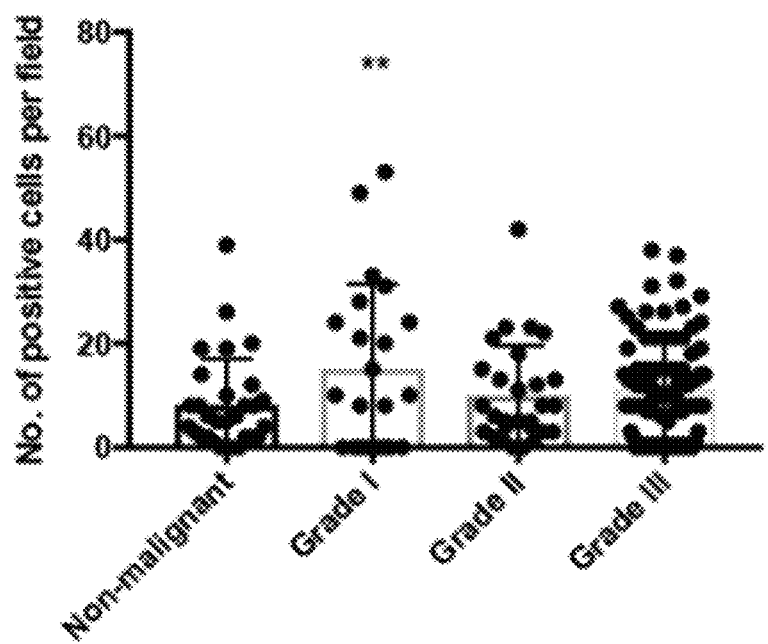
Figure 25B:
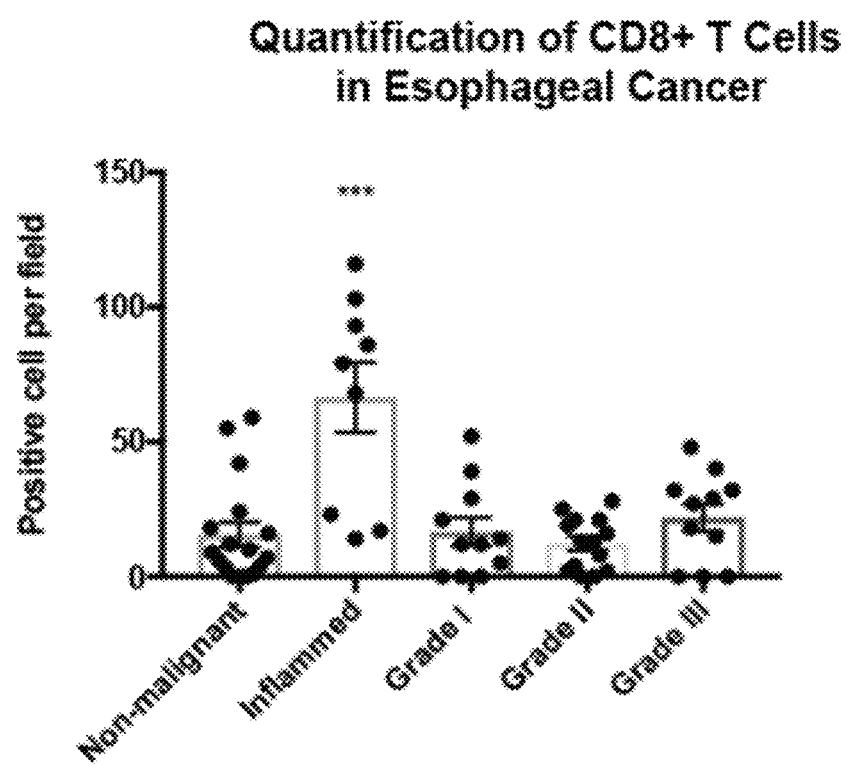

FIGS. 25A-25B shows that CD8 expression in ovarian and esophageal cancer patient samples. FIG. 25A shows that ovarian cancer specimens were quantified with no. of CD8 positive nuclei per field and graphed according to tumor grading. FIG. 25B shows that esophageal cancer specimens were quantified with no. of CD8 positive nuclei per field and graphed according to tumor grading.

Figure 26:
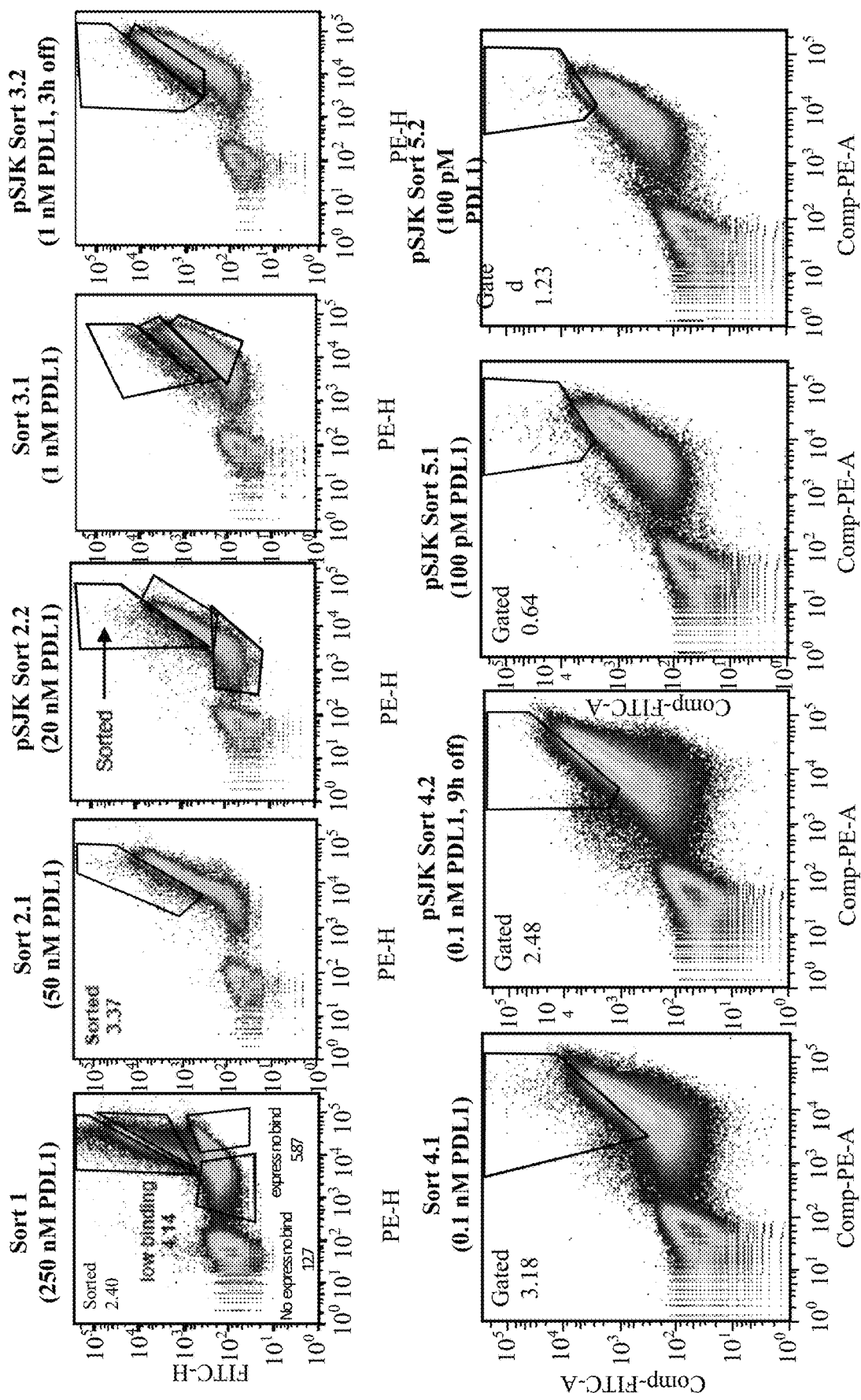

FIG. 26 shows directed evolution based sorting of mutant clones exhibiting superior binding characteristics. The first two sorts were performed by decreasing the amount of PD-L1 incubated with the library in a sequential manner. Sort three to sort six was screened based on a combination of both decreasing the concentration of the ligand and kinetics off-rate sorting strategy in which clones were isolated based on the ability to bind PD-L1 in the presence of lower ligand concentration and longer incubation time in the presence of competitors. Percentages in each panel correspond to the gated subpopulation collected.

Figure 27A:
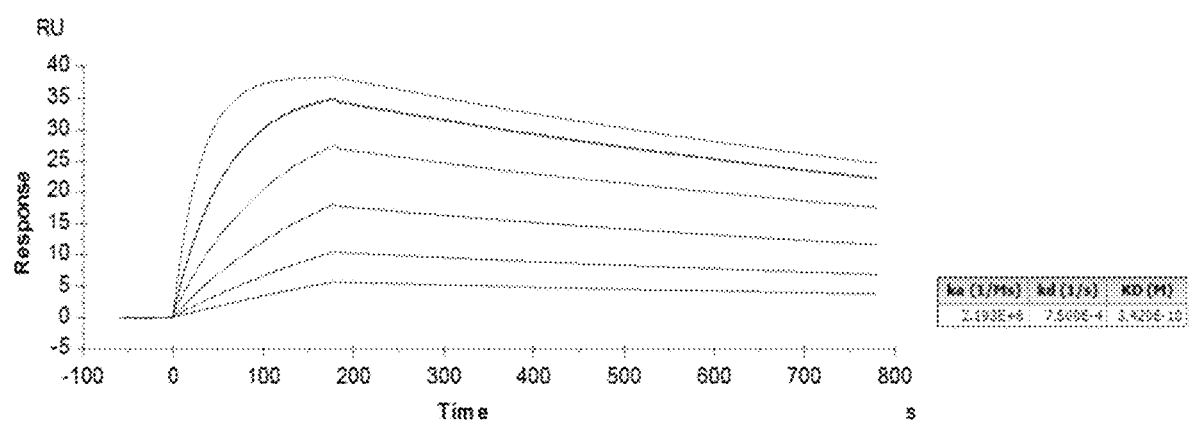
Figure 27B:
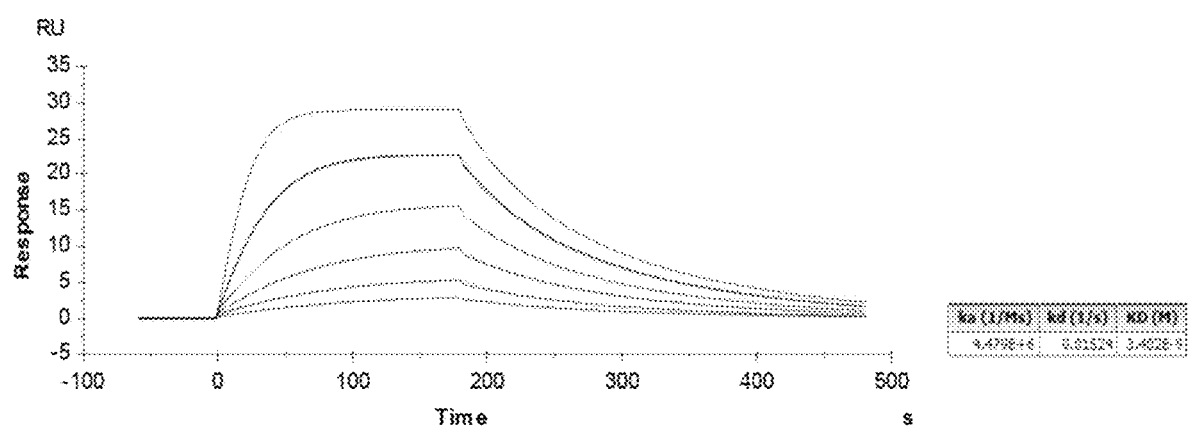

FIGS. 27A and 27B shows analysis of sPD-1 mutant V2 binding kinetics to PD-L1 and PD-L2. FIG. 27A shows binding analysis of sPD-1 mutant version 2 binding to kinetics to PD-L1 by a BIAcore T200 at 25° C. FIG. 27B shows binding analysis of sPD-1 mutant version 2 binding to kinetics to PD-L2 by a BIAcore T200 at 25° C.

Figure 28A:
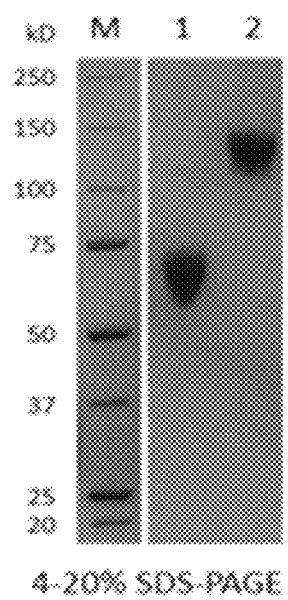
Figure 28B:
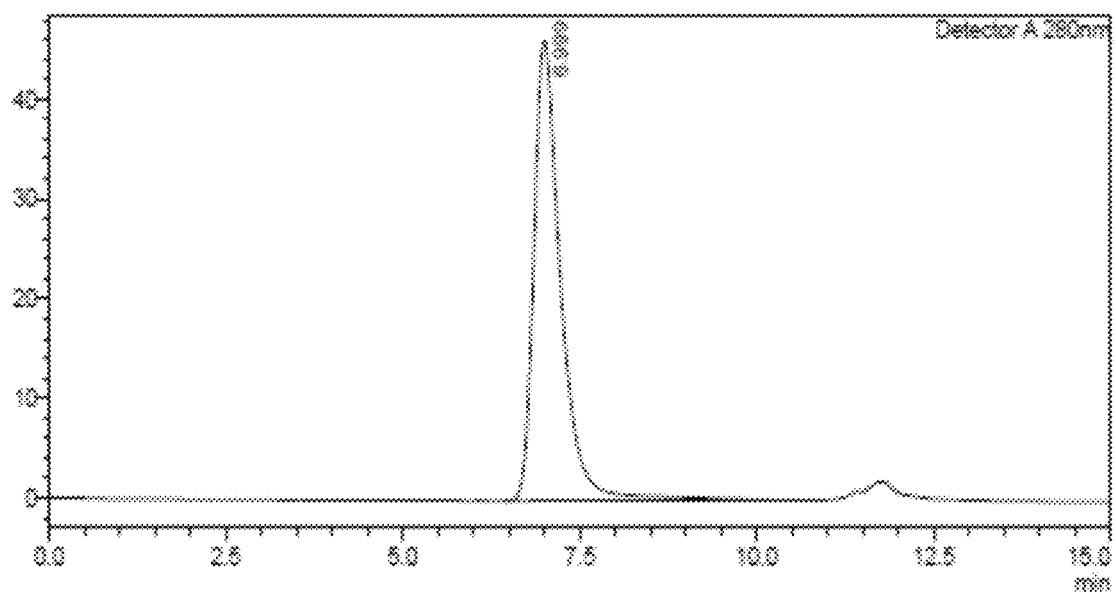
Figure 28C:
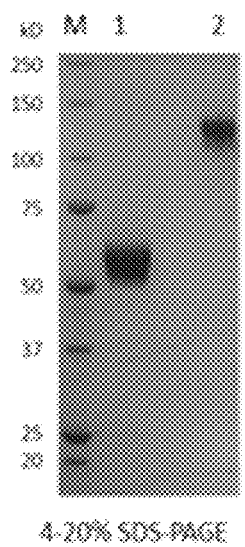
Figure 28D:
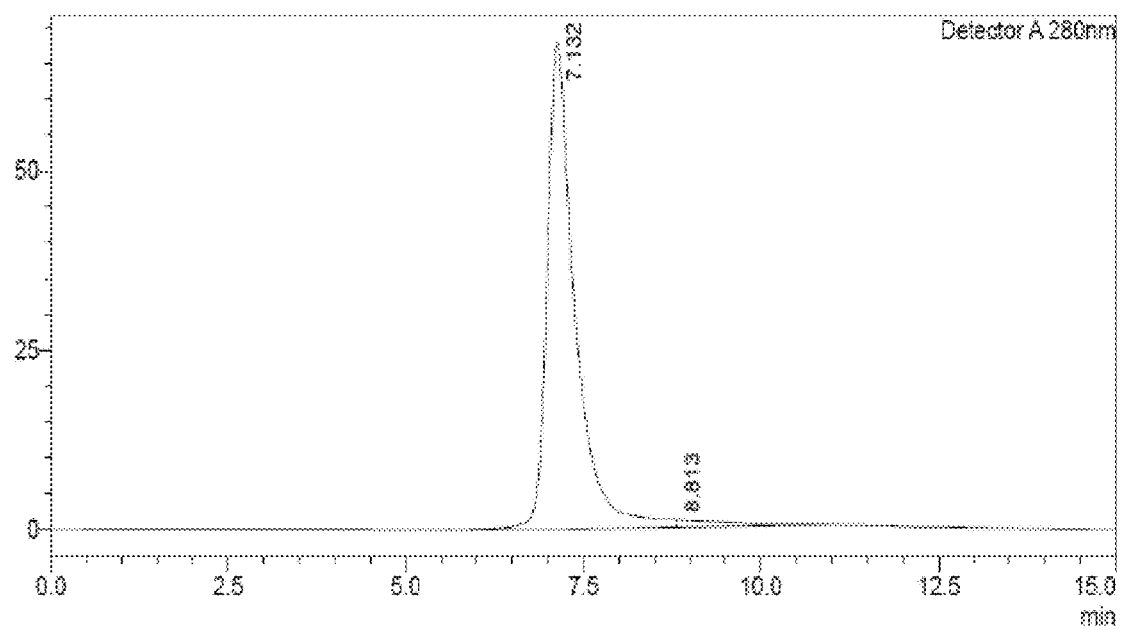
Figure 28E:
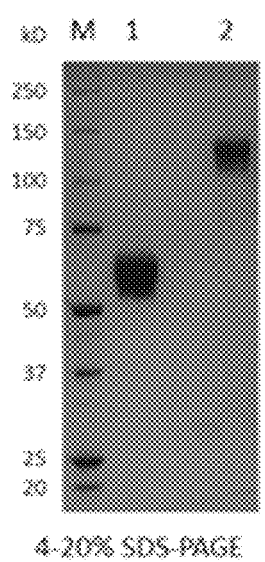
Figure 28F:
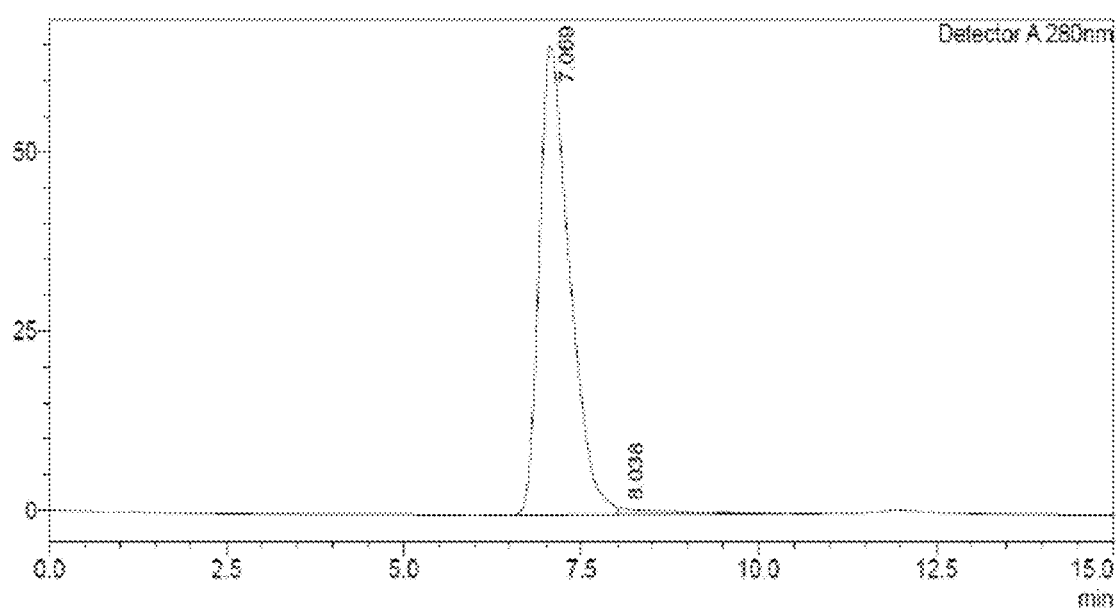

FIGS. 28A-28F shows recombinant protein production of sPD-1 mutants. FIG. 28A shows SDS-PAGE of purified wild type sPD-1 Fc, lane 1 reduced and lane 2 non-reduced. FIG. 28B shows SEC-HPLC analysis of purified wild type sPD-1 Fc and endotoxin levels shown on the table below. FIG. 28C shows SDS-PAGE of purified sPD-1 mutant version 1, lane 1 reduced and lane 2 non-reduced. FIG. 28D shows SEC-HPLC analysis of purified sPD-1 mutant version 1 and endotoxin levels shown on the table below. FIG. 28E shows SDS-PAGE of purified sPD-1 mutant version 2, lane 1 reduced and lane 2 non-reduced. FIG. 28F shows SEC-HPLC analysis of purified sPD-1 mutant version 2 and endotoxin levels shown on the table below.

FIG. 29 shows protein interaction between sPD-1 mutant and PD-L1 and analysis of surface complementarity and hydrogen bond for each of the three mutations within the binding interface of PD-1 and PD-L1.

FIG. 30 compares protein interaction for wild type and mutated human PD-1/PD-L2 model, and shows analysis results of surface complementarity and hydrogen bond for 2 mutations within the binding interface of PD-1 and PD-L2.

Figure 31:
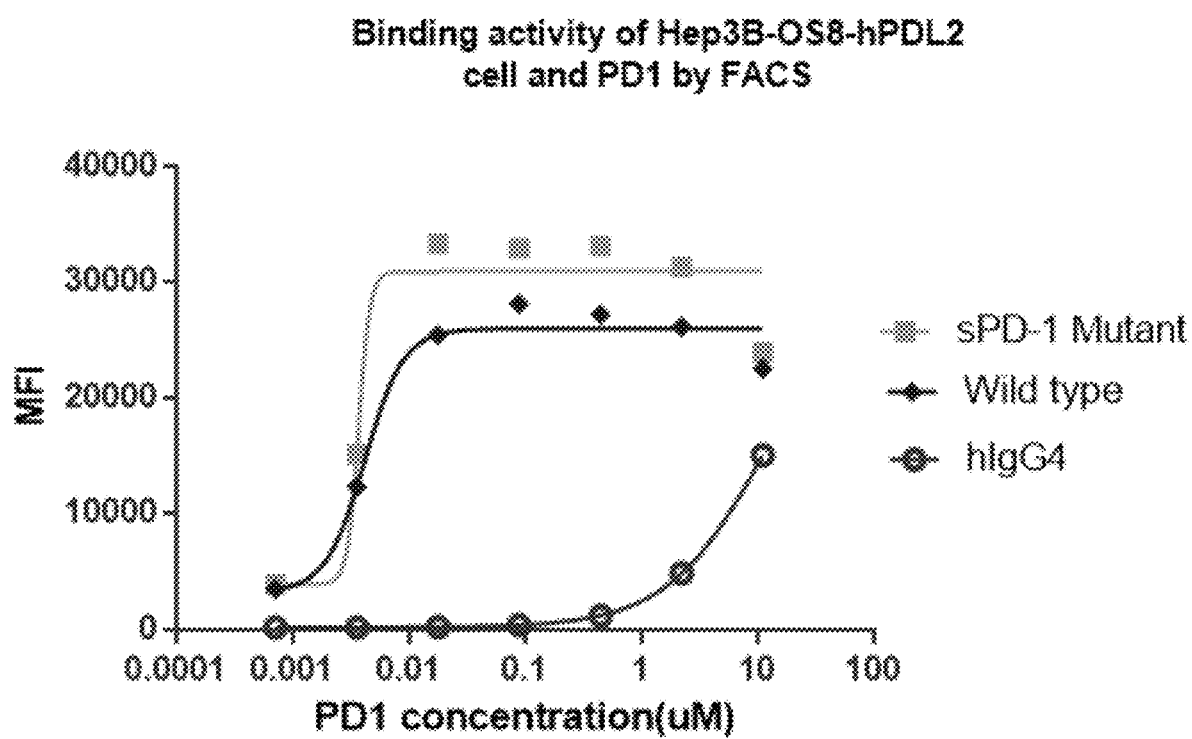

FIG. 31 shows FACs based analysis between wild type sPD-1, PD-1 mutant version 2 and IgG4 to Hep3B cells over-expressing PD-L2.

Figure 32B:
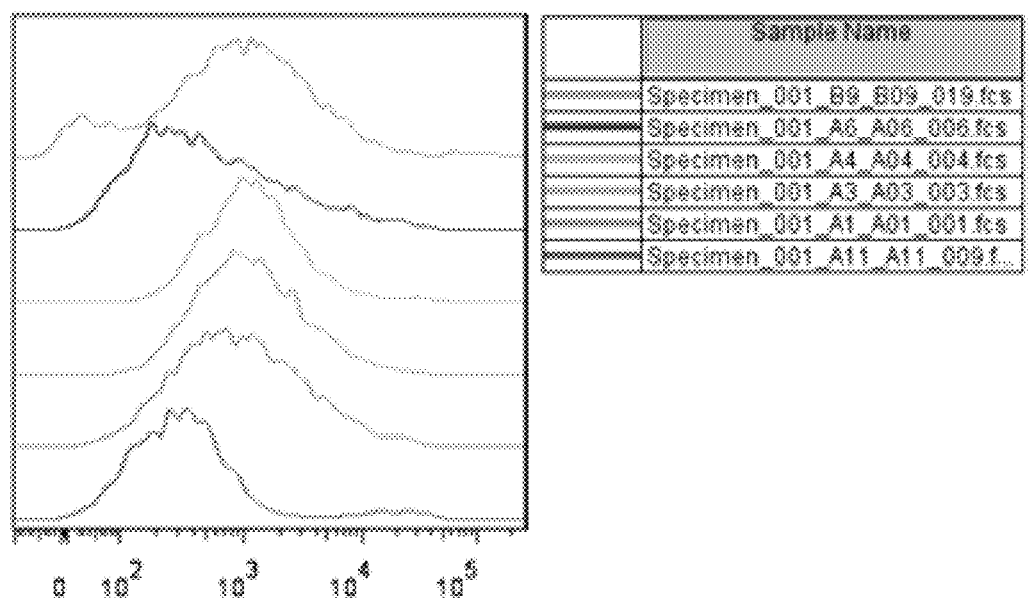
Figure 32C:
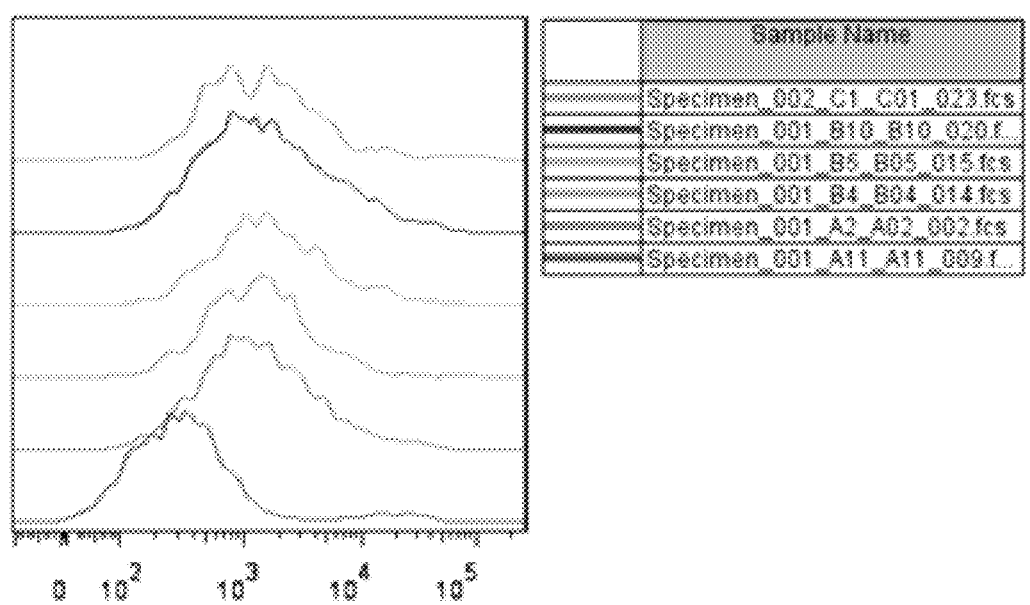
Figure 32D:
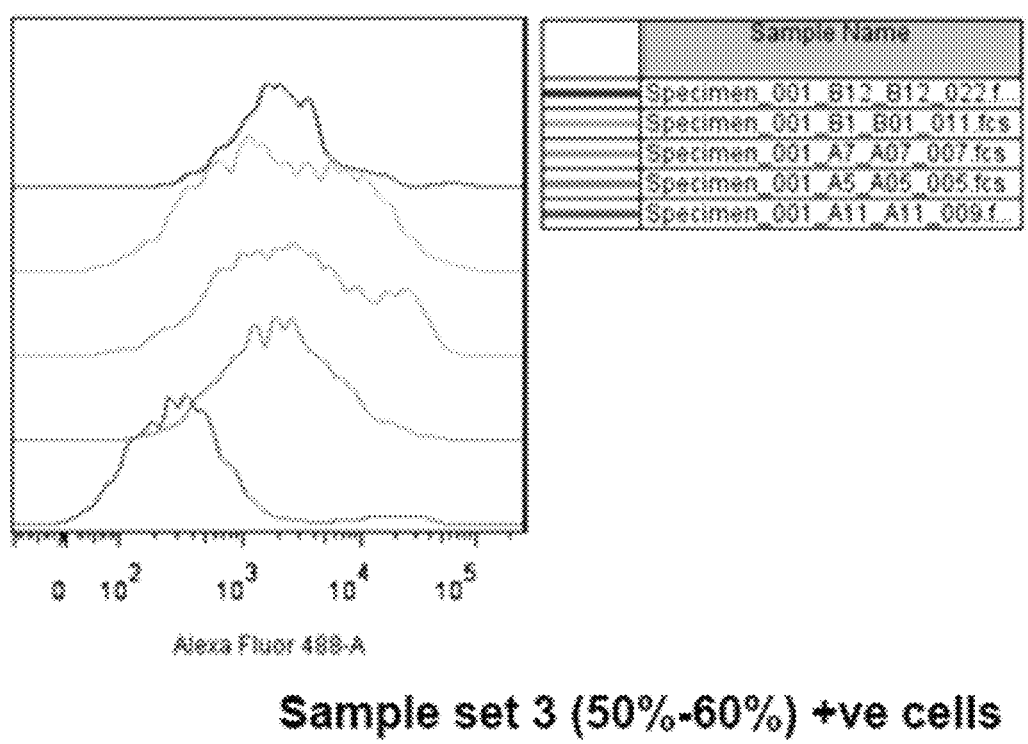
Figure 32E:
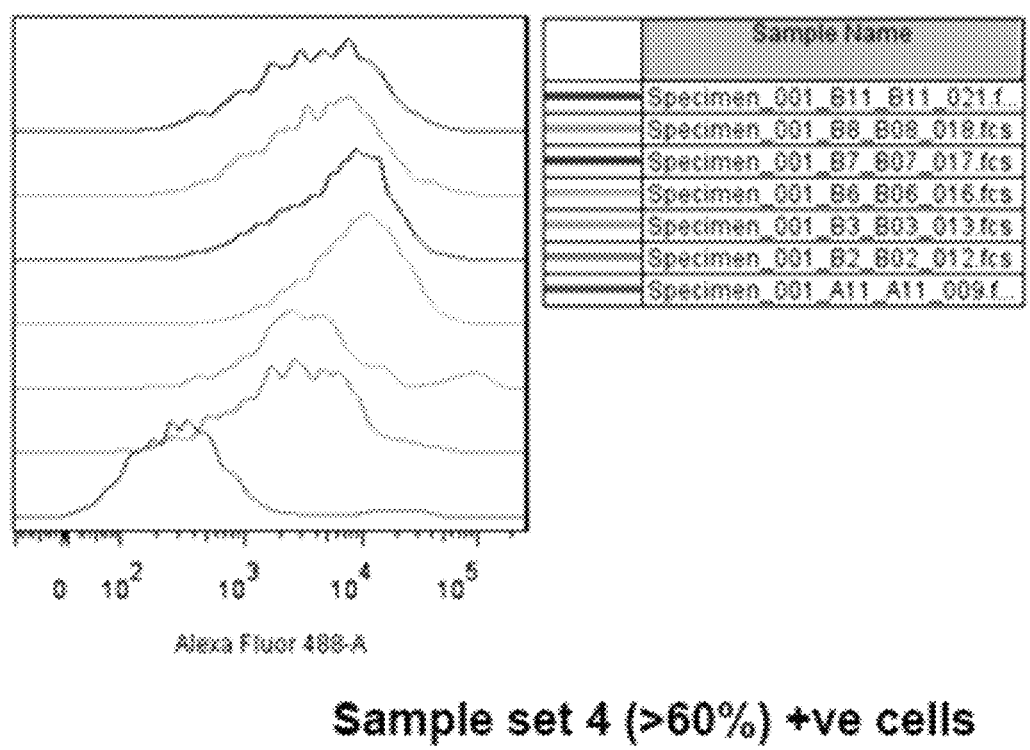

FIGS. 32A-32E shows validation of human PD-L2 over-expression in MC38 cells. FIG. 32A demonstrates a Table showing percentage and mean fluorescent intensity of MC38 cells expressing 21 human PD-L2 individual clones. FIG. 32B demonstrates MC38-hPDL2 cells showing less than 30% of hPD-L2 positive population. FIG. 32C demonstrates MC38-hPD-L2 cells showing less 30%-50% of hPD-L2 positive population. FIG. 32D demonstrates MC38-hPD-L2 cells showing 50%-60% hPD-L2 positive population. FIG. 32E demonstrates MC38-hPD-L2 cells showing more than 60% hPD-L2 positive population.

Figure 33B:
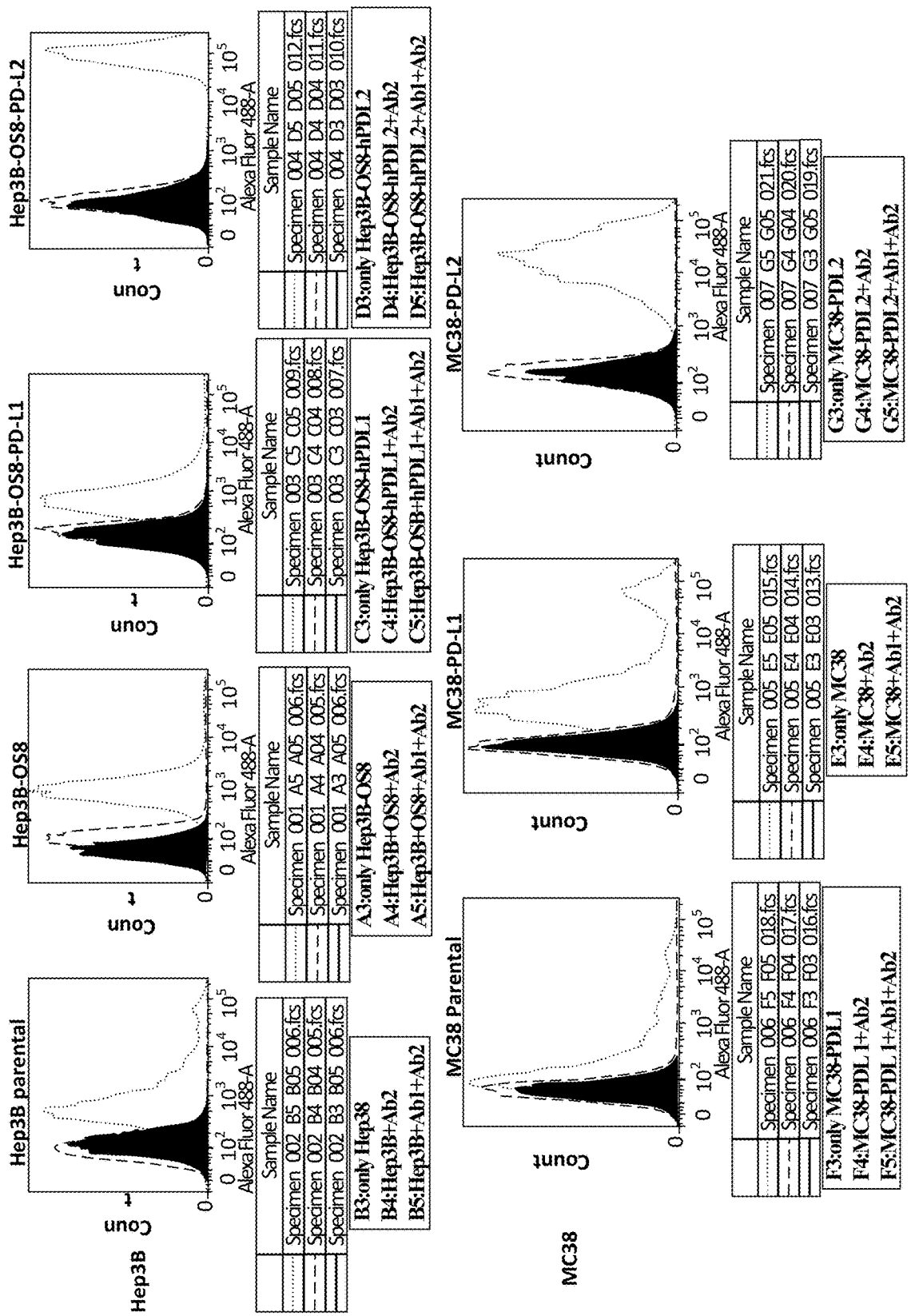

FIGS. 33A and 33B shows validation of human PD-L2 expression in Hep3B-OS8 cells and MC38 cells. FIG. 33A demonstrates a table showing mean fluorescent intensity and percent of Hep3B-OS8 cells transfected with 16 cDNA clones positive for human PD-L2 over-expression. Positive clones were sorted from the lowest efficiency to highest efficiency on the right. Ab1 is anti-human PD-L2 antibody and Ab2 is control IgG. FIG. 33B shows PD-L2 expression on Hep3B parental, Hep3B-OS8 vector only, Hep3B-OS8-hPD-L1 and Hep3B-OS8-hPD-L2 cells (upper panel); and PD-L2 expression on MC38 parental, MC38-hPD-L and MC38-hPD-L2 cells (lower panel). Orange histogram shows positive PD-L2 expression.

Figure 34:
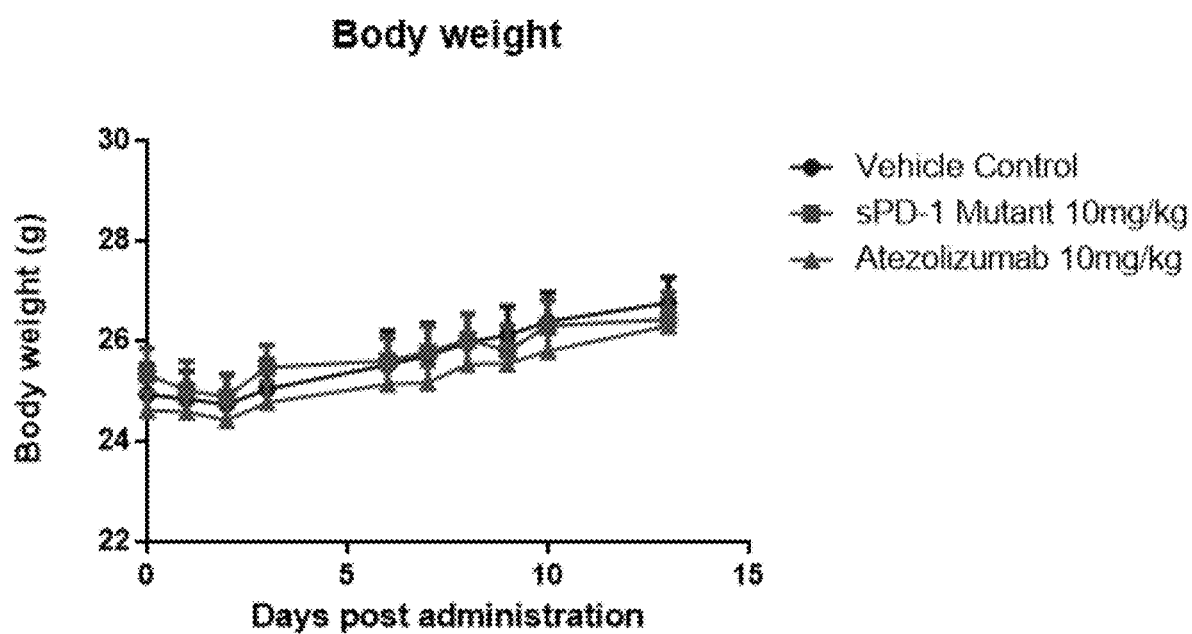

FIG. 34 shows total body weight of mice with MC38-hPD-L1 tumors treated with vehicle control, sPD-1 mutant and Atezolizumab over the course of the experiment. N=10 for each treatment group. Error bar represents mean and standard deviation.

Figure 35A:
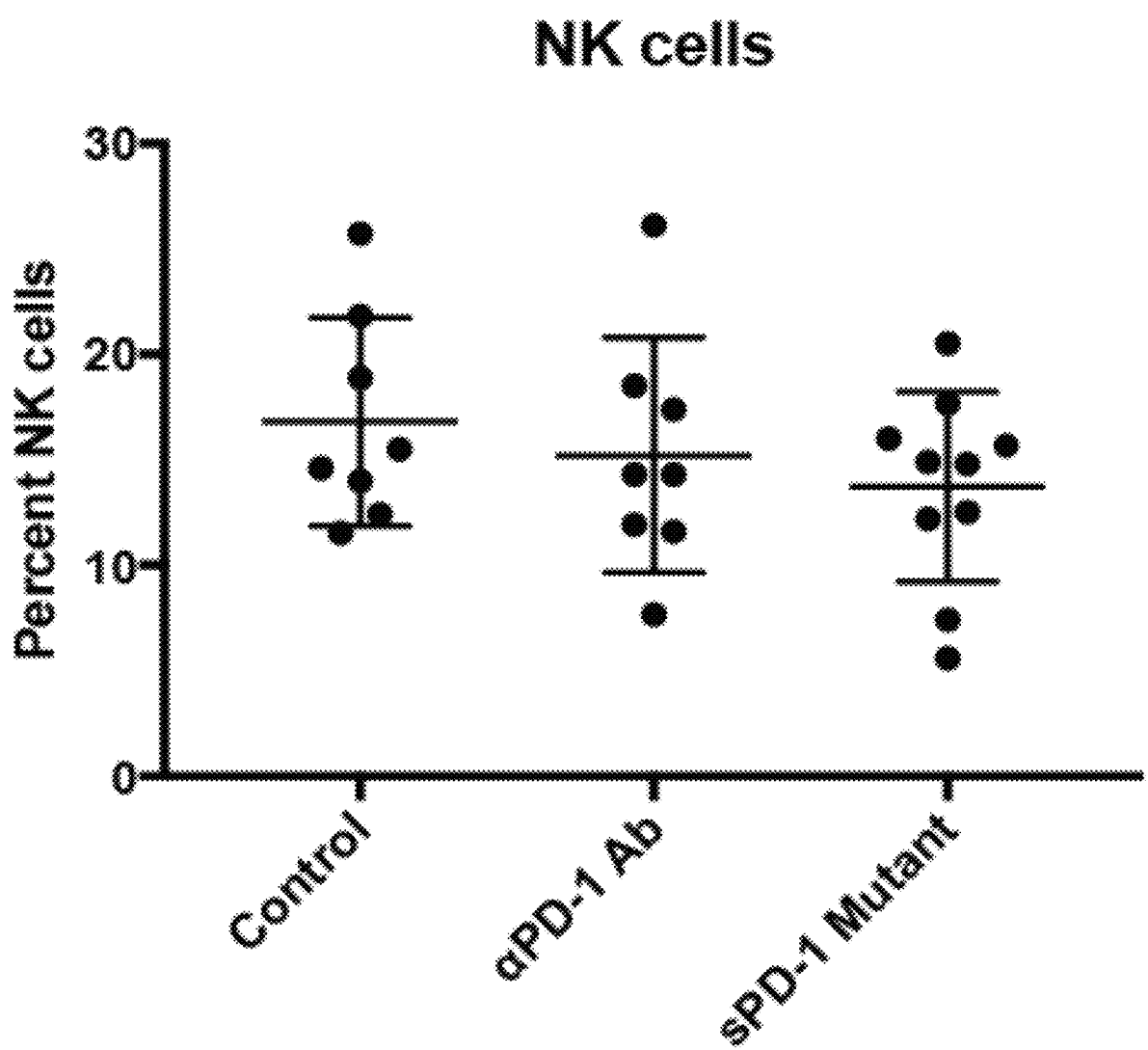
Figure 35B:
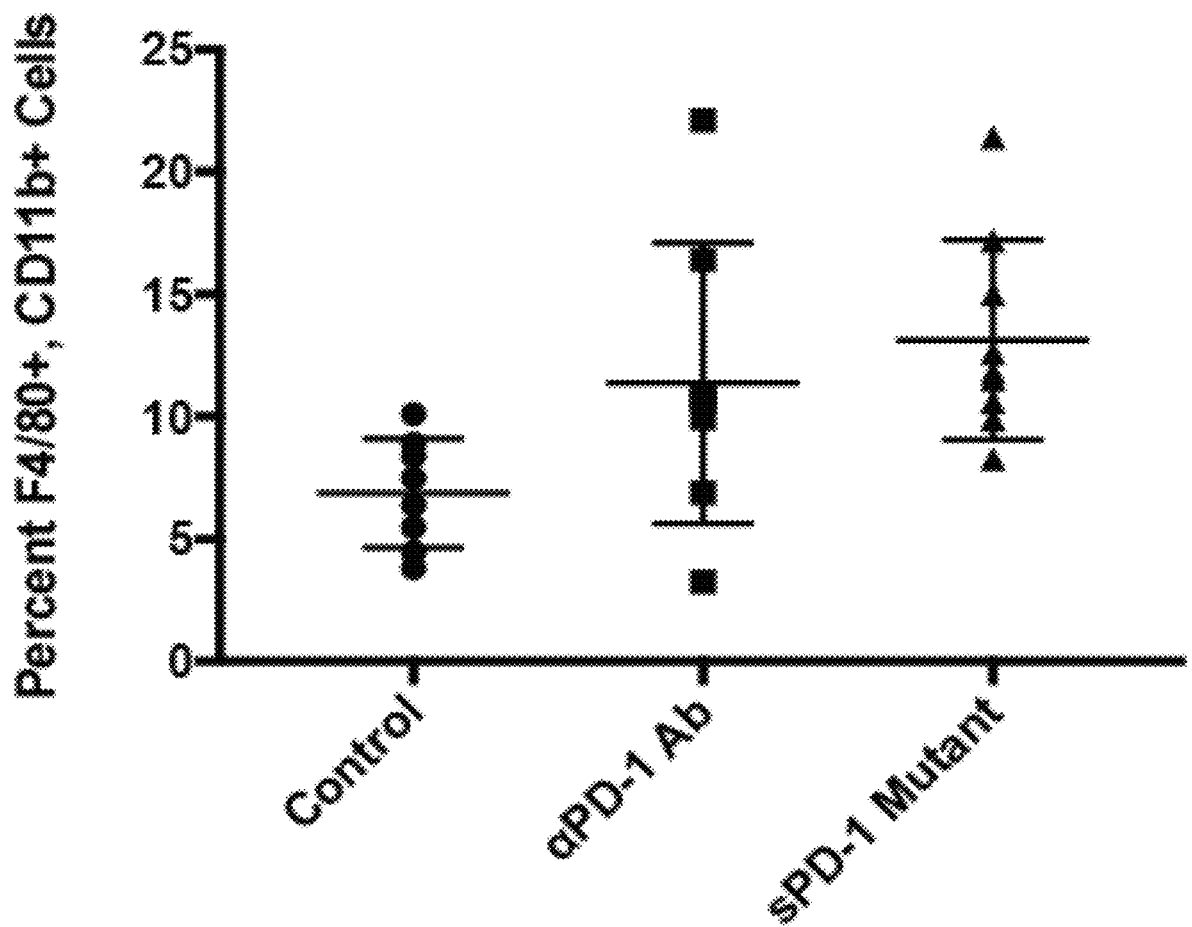

FIGS. 35A-35B shows immune profile of tumor associated NK cells and Macrophages in MC38 parental tumor models treated with anti-mouse PD-1 antibody and sPD-1 mutant. FIG. 35A shows percent positive NK cells in the tumors of each animal treated with vehicle control (N=8), anti-mouse αPD-1 antibody (N=8) and sPD-1 mutant antibody (N=10). Individual data point, mean and standard deviation shown. FIG. 35B shows percent positive macrophages in the tumors of each animal treated with vehicle control (N=8), anti-mouse αPD-1 antibody (N=8) and sPD-1 mutant antibody (N=10). Individual data point, mean and standard deviation shown.

Figure 36A:
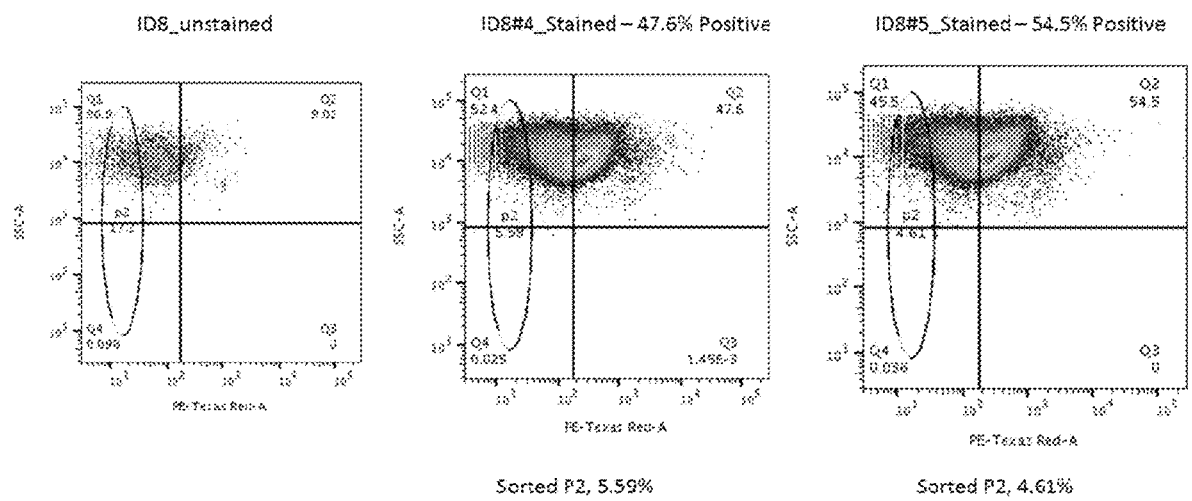
Figure 36B:
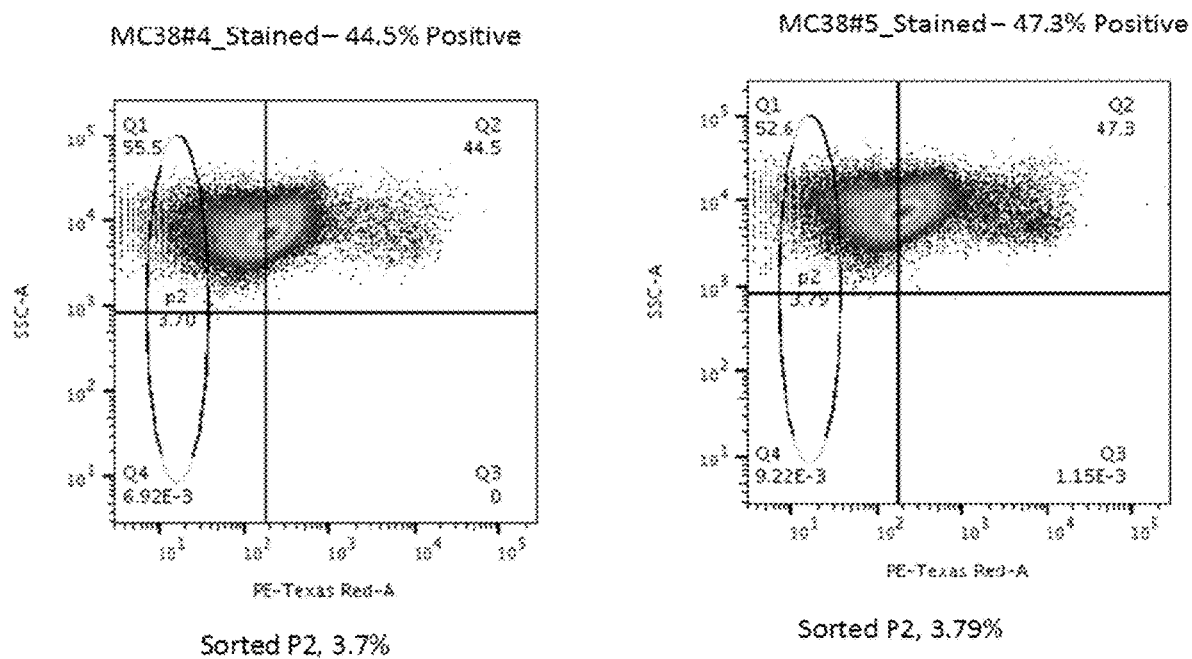

FIGS. 36A and 36B shows isolation of PD-L1 negative cells post PD-L1 CRISPR transfection. FIG. 36A shows PD-L1 negative ID8 cells sorted and collected post PD-L1 CRISPR clone 4 (left) and clone 5 (right) transfection. FIG. 36B shows PD-L1 negative MC38 PD-L2 over-expressing cells sorted and collected post PD-L1 CRISPR clone 4 (left) and clone 5 (right) transfection.

Figure 37:
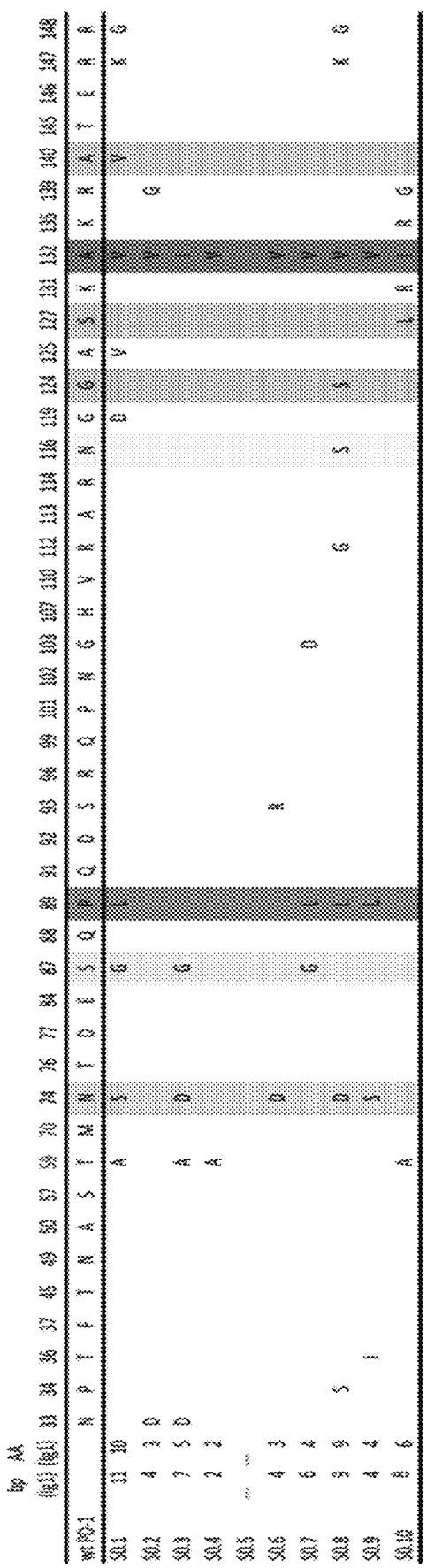
Figure 37:
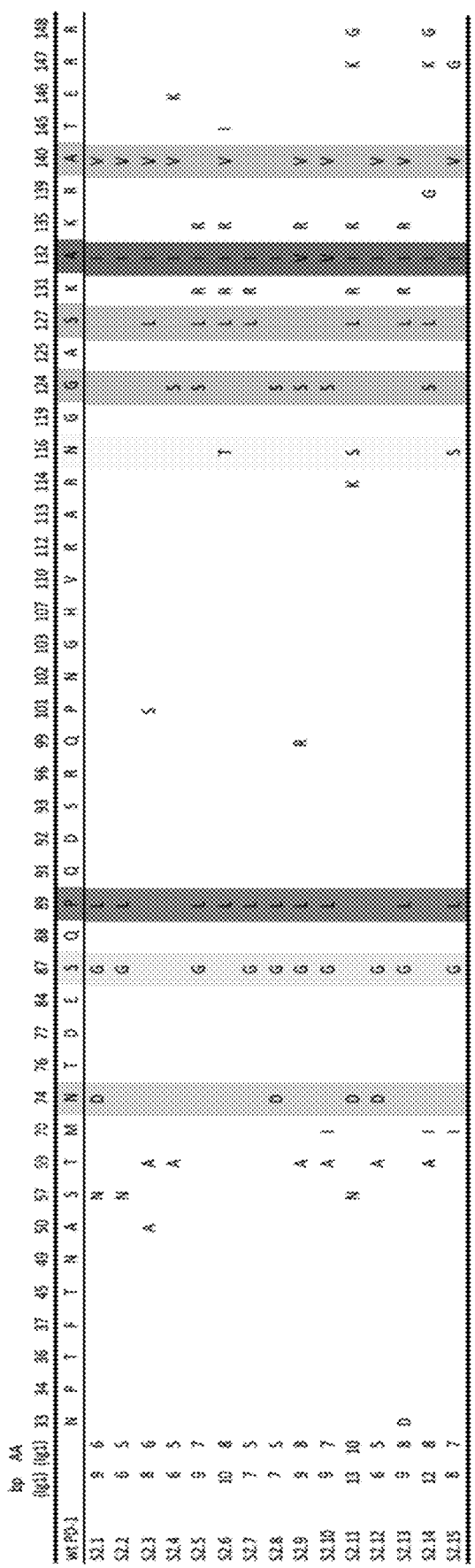

FIG. 37 shows Sequencing of enriched sPD-1 library pool from each consecutive sort round. The residue number is listed at the top and the corresponding wild type amino acid is given.

Figure 38A:
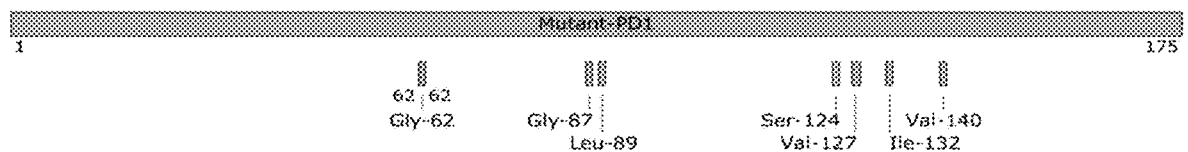

FIG. 38A shows an illustrated map of amino acid mutations present in the initial Mutant PD-1 clone. All mutations were used for generating a library of 128 sPD-1 mutant clones that includes all possible permutations of the 7 mutations. FIG. 38B shows a list of top 5 mutant clones selected from the 128 sPD-1 mutant clone library for further binding analysis.

Figure 39A:
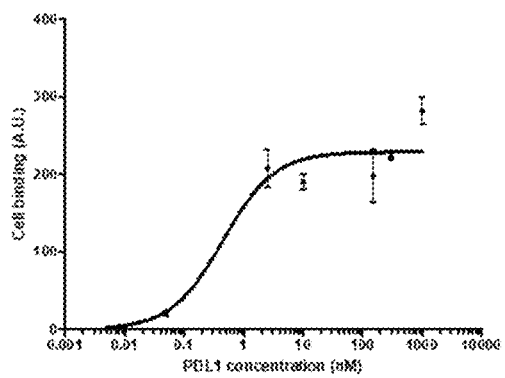
Figure 39B:
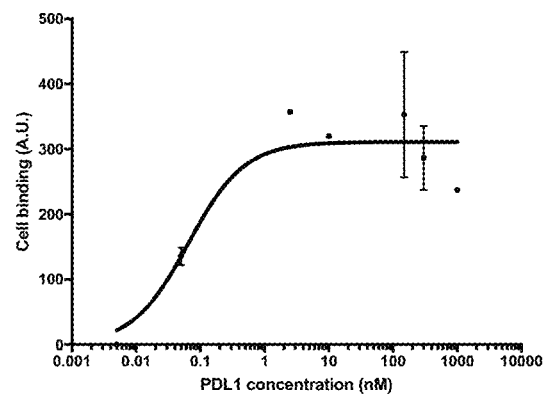
Figure 39C:
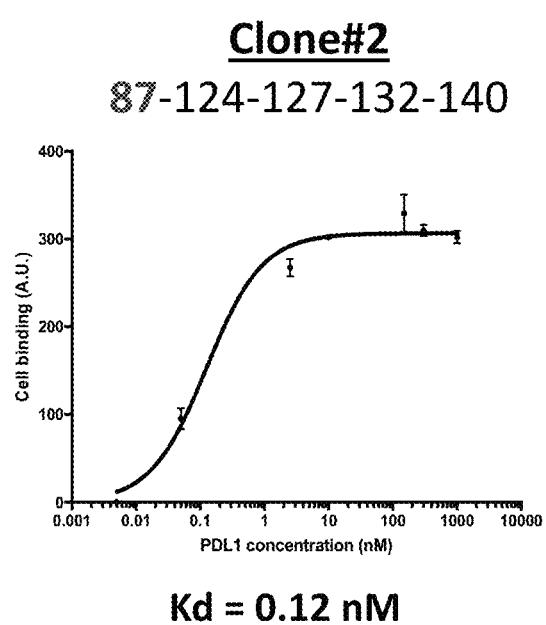
Figure 39D:
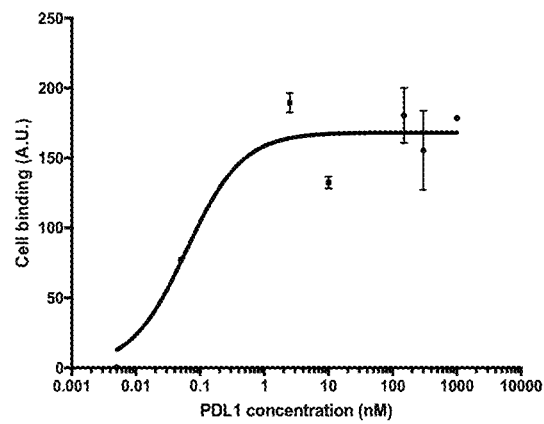
Figure 39E:
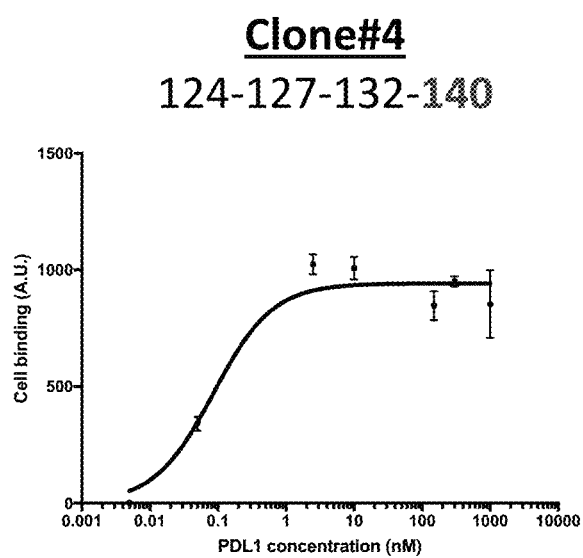
Figure 39F:
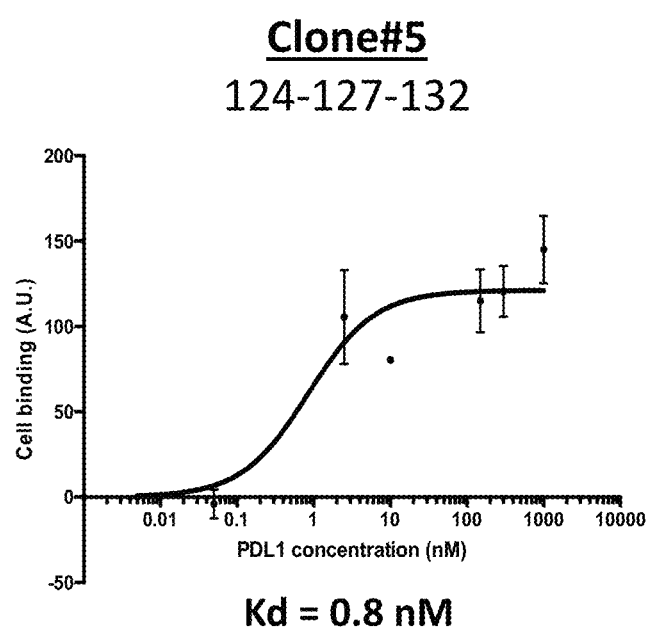

FIG. 39A shows a dose-dependent binding curve and Kd of the original mutant sPD-1 to PD-L1. FIG. 39B shows a dose-dependent binding curve and Kd of Clone #1 to PD-L1. FIG. 39C shows a dose-dependent binding curve and Kd of Clone #2 to PD-L1. FIG. 39D shows a dose-dependent binding curve and Kd of Clone #3 to PD-L1. FIG. 39E shows a dose-dependent binding curve and Kd of Clone #4. FIG. 39F shows a dose-dependent binding curve and Kd of Clone #5 to PD-L1.

Figure 40A:
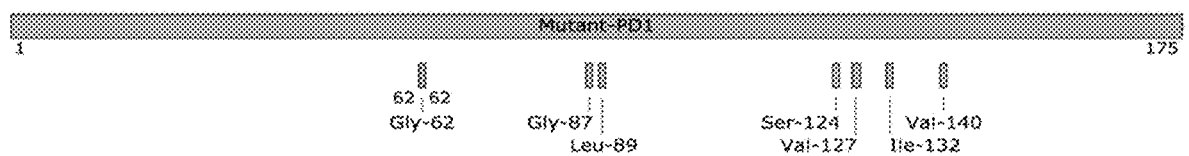

FIG. 40A shows an illustrated map of amino acid mutations present in the initial Mutant PD-1 clone. All mutations were used for generating a library of 128 sPD-1 mutant clones that includes all possible permutations of the 7 mutations. FIG. 40B shows a list of top 5 mutant clones selected from the 128 sPD-1 mutant clone with Kd against human PD-L1 listed.

Figure 41A:
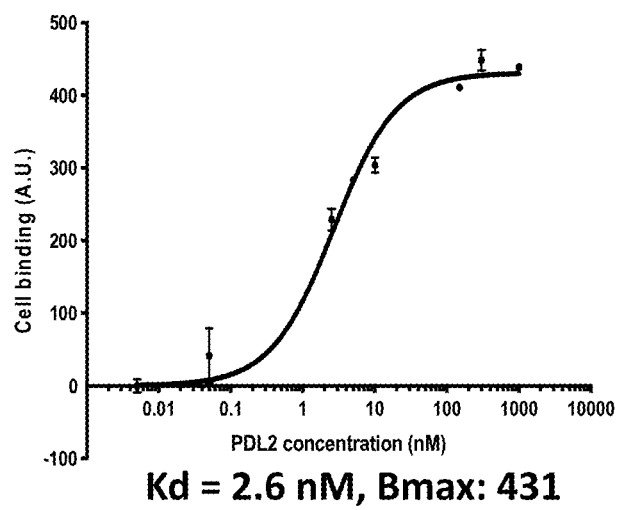
Figure 41B:
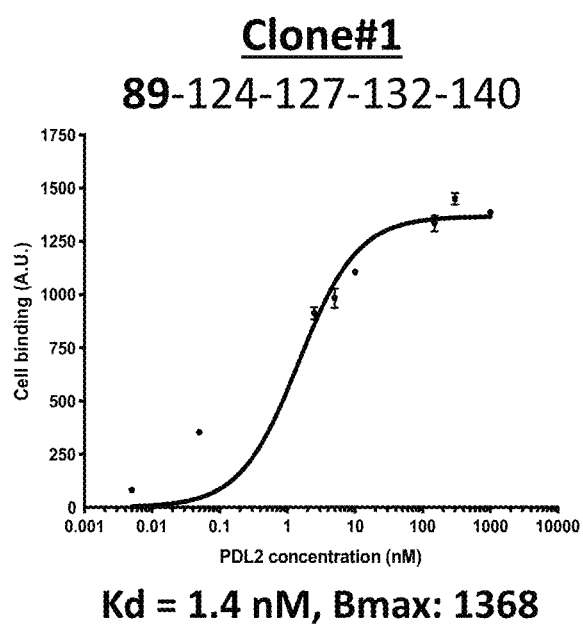
Figure 41C:
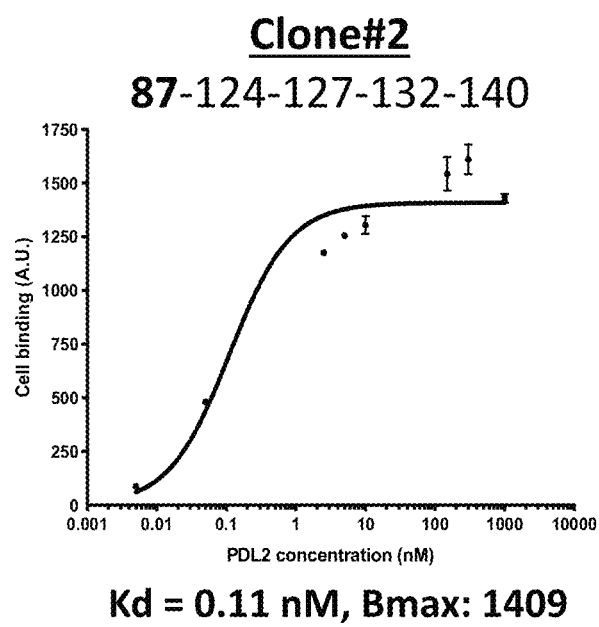
Figure 41D:
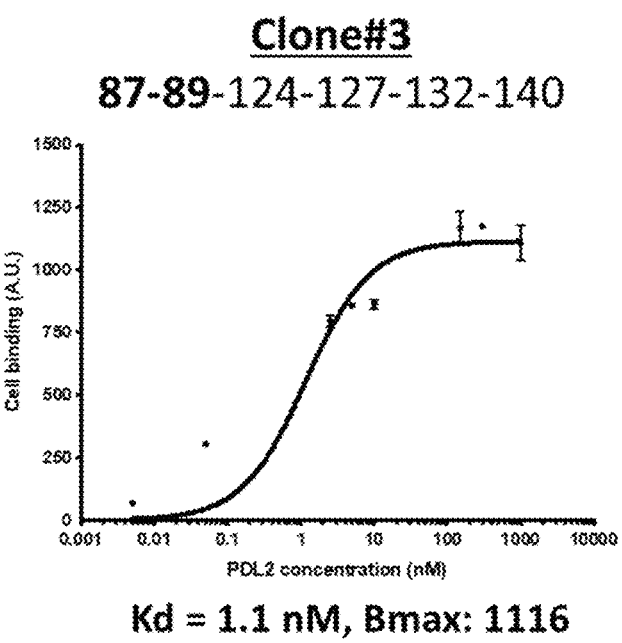
Figure 41E:
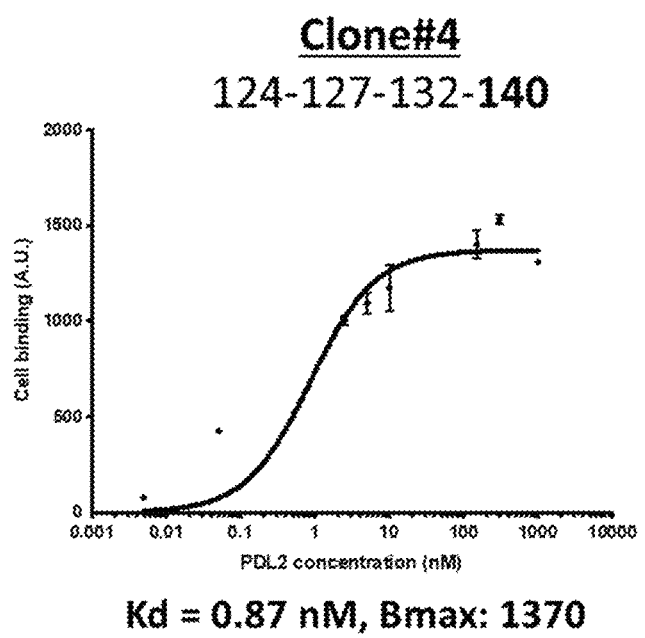
Figure 41F:
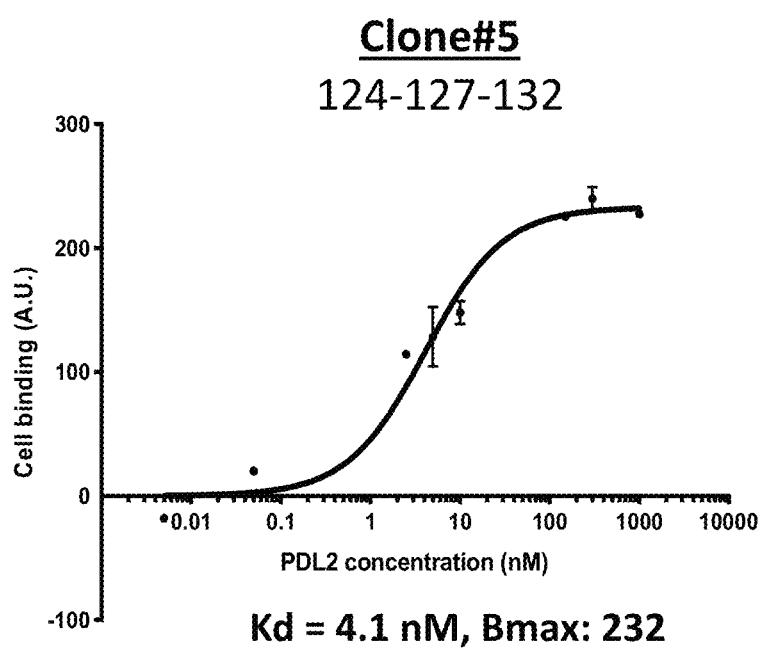

FIG. 41A shows a dose-dependent binding curve, Kd and Bmax of the original mutant sPD-1 to PD-L2. FIG. 41B shows a dose-dependent binding curve, Kd and Bmax of Clone #1 to PD-L2. FIG. 41C shows a dose-dependent binding curve, Kd and Bmax of Clone #2 to PD-L2. FIG. 41D shows a dose-dependent binding curve, Kd and Bmax of Clone #3 to PD-L2. FIG. 41E shows a dose-dependent binding curve, Kd and Bmax of Clone #4 to PD-L2. FIG. 41F shows a dose-dependent binding curve, Kd and Bmax of Clone #5 to PD-L2.

Figure 42A:
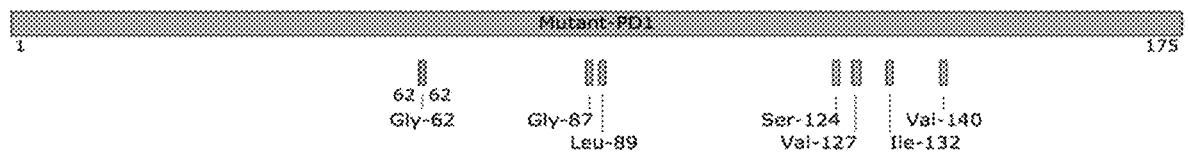

FIG. 42A shows an illustrated map of amino acid mutations present in the initial Mutant PD-1 clone. All mutations were used for generating a library of 128 sPD-1 mutant clones that includes all possible permutations of the 7 mutations. FIG. 42B shows a list of top 5 mutant clones selected from the 128 sPD-1 mutant clone with Kd against human PD-L2 listed.

VI. DETAILED DESCRIPTION OF THE INVENTION

A. Introduction

PD-1 is an inhibitory cell surface receptor involved in controlling T-cell function during immunity and tolerance. Upon binding to its ligand, e.g., PD-L1 or PD-L2, PD-1 inhibits T-cell effector functions. The structure of PD-1 is of a single-pass type 1 membrane protein. PD-1 is encoded by the programmed cell death 1 receptor gene (Entrez Gene ID: 5133). The human PD-1 mRNA (coding) sequence is set forth in, e.g., Genbank Accession No. NM 005018. The human PD-1 polypeptide sequence is set forth in, e.g., Genbank Accession No. NP_005009 or UniProt No. Q15116. PD-1 is also known as programmed cell death 1, PDCD1, PD1, CD279, SLEB2, hPD-1, and hSLE-1. The wild-type human PD-1 polypeptide is 288 amino acids. The signal peptide sequence is from residues 1 to 20 (FIG. 1), the ECD is from residues 21 to 170 (FIG. 1), the transmembrane domain is from residues 171 to 191, and the intracellular domain is from residues 192 to 288 (this is using numbering that starts with the signal peptide region; as will be understood by those in the art, numbering can also be based using the first amino acid of the mature sequence as the first amino acid position as seen in SEQ ID NO:1 to SEQ ID NO:6 of Table 1; that is, the ECD domain can also be from 1 to 150, etc.).

As is known in the art, there are a number of therapeutic antibodies that bind to PD-1 to block the binding of PD-1 to either the PD-L1 or PD-L2 receptor to result in the reduction of immune suppression to effect immune activation. These antibodies include KEYTRUDA® and OPDIVO®, as well as a number of others being tested in the clinic. Similarly, there are anti-PD-L1 antibodies that are approved to result in a similar mechanism and therapeutic effect, such as TECENTRIQ®.

The present invention is directed to a novel mechanism of using the ECD of human PD-1, including variants, to effect similar biological function and therapeutic effect. Thus, the present invention provides fusion proteins. The fusion proteins described herein comprise two general functional components. The first component comprises variants of the soluble, ECD of human PD-1 ("sPD-1 variant" hereinafter). The sPD-1 variants serve to increase the binding affinity for PD-L1 and/or PD-L2 and/or the protein stability. The second component is the Fc domain of a human IgG protein, e.g. human IgG4, to confer a significant increase in half-life of the sPD-1 variant as a fusion protein. These two components, or domains, are generally linked using a domain linker, such as a glycine-serine linker as outlined herein, to form the sPD-1 variant—Fc fusion protein of the invention.

The sPD-1 variant domain herein binds to and block/antagonize PD-1 ligands, i.e., PD-L1 and/or PD-L2, and is linked to the Fc domain (optionally including the hinge domain and optional other linkers) of a human IgG protein. The sPD-1 variants can act as a competitive antagonist of PD-L1 and/or PD-L2, block the immune checkpoint PD-1 pathway, and prevent signal transduction via the PD-1 receptor. Thus, the compositions and methods provided herein block T cell inhibitory signals, and lead to immune mediated antitumor activity. Also, the compositions and methods can activate, enhance or increase an immune response in a subject suffering from an infection, e.g., a chronic infection. The present invention provides compositions and methods for stimulating a T cell response, such as stimulating T cell proliferation, increasing T cell activation, and/or reducing T cell inhibitory signals in patients with cancer or an infection.

B. Definitions

As used herein, the following terms have the meanings ascribed to them unless specified otherwise.

The terms "a", "an", or "the" as used herein not only include aspects with one member, but also include aspects with more than one member. For instance, the singular forms "a", "an", and "the" include plural referents unless the context clearly dictates otherwise. Thus, for example, reference to "a cell" includes a plurality of such cells and reference to "the agent" includes reference to one or more agents known to those skilled in the art, and so forth.

As used herein, "protein" herein is meant at least two covalently attached amino acids, which includes proteins, polypeptides, oligopeptides and peptides.

The term "isolated" refers to a molecule that is substantially free of its natural environment. For instance, an isolated protein is substantially free of cellular material or other proteins from the cell or tissue source from which it is derived. The term "isolated" also refers to preparations where the isolated protein is sufficiently pure to be administered as a pharmaceutical composition, or at least about 70-80%, 80-90%, or 90-95% (w/w) pure, or at least about 95%, 96%, 97%, 98%, 99%, or 100% (w/w) pure.

The term "ligand" refers to a biomolecule that is able to bind to and form a complex with a second biomolecule such as a receptor present on the surface of target cells to serve a biological purpose. A ligand is generally an effector molecule that binds to a site on a target protein, e.g., by intermolecular forces such as ionic bonds, hydrogen bonds, hydrophobic interactions, dipole-dipole bonds, or Van der Waals forces. The sPD-1 variant of the invention can bind to and form a complex with a PD-1 ligand such as PD-L1 and/or PD-L2.

The term "receptor" refers to a biomolecule present on the surface of a target cell that is able to bind to and form a complex with a second biomolecule such as a ligand. A receptor generally activates a specific signal transduction pathway. PD-L1 and PD-L2 are examples of cell surface receptors.

By "position" as used herein is meant a location in the sequence of a protein. Positions may be numbered sequentially, or according to an established format, for example the EU index. In some embodiments of the present invention, positions are numbered sequentially starting with the first amino acid of the mature protein.

By "amino acid modification" herein is meant an amino acid substitution, insertion, and/or deletion in a polypeptide sequence.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution S228P refers to a variant polypeptide, in this case an Fc variant of human IgG4, in which the serine at position 228 is replaced with proline. For clarity, a protein which has been engineered to change the nucleic acid coding sequence but not change the starting amino acid (for example, exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, –233E or 233E designates an insertion of glutamic acid after position 233 and before position 234. Additionally, –233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, E233- or E233 #, E233( ) or E233del designates a deletion of glutamic acid at position 233. Additionally, EDA233- or EDA233 # designates a deletion of the sequence GluAspAla that begins at position 233.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent immunoglobulin" as used herein is meant an unmodified immunoglobulin polypeptide that is modified to generate a variant. In this context, a "parent Fc domain" will be relative to the recited variant; thus, a "variant human IgG Fc domain" is compared to the parent Fc domain of human IgG, for example, a "variant human IgG4 Fc domain" is compared to the parent Fc domain of human IgG4, etc.

By "wild type or WT" herein is meant an amino acid sequence or a nucleotide sequence that is found in nature, including allelic variations. A WT protein has an amino acid sequence or a nucleotide sequence that has not been intentionally modified.

By "variant protein" or "protein variant", or "variant" as used herein is meant a protein that differs from that of a parent protein by virtue of at least one amino acid modification. In some embodiments, the parent proteins are human wild type sequences. In some embodiments, the parent proteins are human sequences with variants. Protein variant may refer to the protein itself, a composition comprising the protein, or the amino sequence that encodes it. Preferably, the protein variant has at least one amino acid modification compared to the parent protein, e.g. from about one to about twenty amino acid modifications, and preferably from about one to about eight amino acid modifications compared to the parent. The protein variant sequence herein will preferably possess at least about 80%, 85%, 90%, 91%, 92%, 93%, 94%, 95%, 96%, 97%, 98% or 99% identity with a parent protein sequence, and most preferably at least about 90% identity, more preferably at least about 95%/97%/98%/99% identity. Sequence identity between two similar sequences (e.g., sPD-1 variable domains) can be measured by algorithms such as that of Smith, T. F. & Waterman, M. S. (1981) "Comparison Of Biosequences," Adv. Appl. Math. 2:482 [local homology algorithm]; Needleman, S. B. & Wunsch, C D. (1970) "A General Method Applicable To The Search For Similarities In The Amino Acid Sequence Of Two Proteins," J. Mol. Biol. 48:443 [homology alignment algorithm], Pearson, W. R. & Lipman, D. J. (1988) "Improved Tools For Biological Sequence Comparison," Proc. Natl. Acad. Sci. (U.S.A.) 85:2444 [search for similarity method]; or Altschul, S. F. et al, (1990) "Basic Local Alignment Search Tool," J. Mol. Biol. 215:403-10, the "BLAST" algorithm, see https:// blast.ncbi.nlm.nih.gov/Blast.cgi. When using any of the aforementioned algorithms, the default parameters (for Window length, gap penalty, etc) are used. In one embodiment, sequence identity is done using the BLAST algorithm, using default parameters.

"IgG variant" or "variant IgG" as used herein is meant an antibody that differs from a parent IgG (again, in many cases, from a human IgG sequence) by virtue of at least one amino acid modification.

"Fc variant" or "variant Fc" as used herein is meant a protein comprising at least one amino acid modification as compared to a parental Fc domain. In some embodiments, the parent Fc domain, is a human wild type Fc sequence, such as the Fc region from IgG1, IgG2, IgG3 or IgG4. Thus, a "variant human IgG4 Fc domain" is one that contains amino acid modifications (generally amino acid substitutions) as compared to the human IgG4 Fc domain. for example, S241P or S228P is a hinge variant with the substitution proline at position 228 relative to the parent IgG4 hinge polypeptide, wherein the numbering S228P is according to the EU index and the S241P is the Kabat numbering. The EU index or EU index as in Kabat or EU numbering scheme refers to the EU numbering (see SEQUENCES OF IMMUNOLOGICAL INTEREST, 5th edition, NIH publication, No. 91-3242, E. A. Kabat et al., hereby entirely incorporated by reference; and see also Edelman et al., 1969, Proc Natl Acad Sci USA 63:78-85, hereby entirely incorporated by reference). In some embodiments, the parent Fc domains are human Fc sequences with variants. For all positions discussed in the present invention that relate to the Fc domain of a human IgG, unless otherwise noted, amino acid position numbering is according to the EU index. The modification can be an addition, deletion, substitution or any combination thereof as outlined herein. Alternatively, the variant Fc domains can have from 1, 2, 3, 4, 5, 6, 7, 8, 9, 10, 11, 12, 13, 14, 15, 16, 11, 12, 13, 14, 15, 16, 17, 18, 19 or 20 amino acid modifications as compared to the parental Fc domain. Additionally, as discussed herein, the variant Fc domains herein still retain the ability to form a dimer with another Fc domain as well as bind to the FcRn receptor as measured using known techniques as described herein, such as non-denaturing gel electrophoresis.

The term "soluble PD-1" or "sPD-1" herein is meant a soluble portion of the programmed cell death 1 (PD-1) polypeptide containing the extracellular domain (ECD) or a fragment or truncated version thereof, but not the transmembrane domain or the cytoplasmic (intracellular) domain of PD-1. The ECD of human wild type PD-1 is shown from residues 21 to 170 in FIG. 1 and also shown as SEQ ID NO:1 in Table 1. In some embodiments, the parent wild type sPD-1 domain can have N-terminal and/or C terminal truncations as long as the truncated wild type sPD-1 retains biological activity, e.g. binding to PD-L1 and/or PD-L2.

The term "sPD-1 variant" refers to a variant of a wild type sPD-1. The sPD-1 variant retains specific binding to a PD-1 ligand, such as PD-L1 and/or PD-L2, but has amino acid substitutions, and can have N- or C-terminal truncations as compared to wild type sPD-1. Specific binding in this case is as determined by a standard binding assay, such as an ELISA, Biacore, Sapidyne KinExA, or Flow Cytometry binding analysis, which assays can also be used to determine binding affinity. As discussed herein, sPD-1 variants may have, in some instances, increased binding affinity as compared to wild type sPD-1.

The term "binding affinity" refers to the ability of a ligand or variant thereof to form coordinated bonds with a protein, e.g., a receptor or a variant thereof. The binding affinity between a ligand and protein can be represented by an equilibrium dissociation constant (KD), a ratio of koff/kon between the ligand and the protein (e.g., receptor or a variant thereof). KD and binding affinity are inversely related. For instance, the KD value relates the concentration of the sPD-1 variant needed to bind to a PD-1 ligand, and a lower KD value (lower PD-1 variant concentration) corresponds to a higher binding affinity for the PD-1 ligand. A high binding affinity corresponds to a greater intermolecular force between the ligand and the protein. A low binding affinity corresponds to a lower intermolecular force between the ligand and the protein. In some cases, an increase in ligand binding affinity can be represented as a decrease of the off-rate by, for example, at least 10-fold, at least 20-fold, at least 50-fold, at least 100-fold, at leak 200-fold, at least 500-fold, or more.

The ability of a sPD-1 variant to bind to PD-L1 and/or PD-L2 can be determined, for example, by the ability of the putative ligand to bind to PD-L1 and/or PD-L2 coated on an assay plate. In one embodiment, the binding activity of sPD-1 variants to PD-L1 and/or PD-L2 can be assayed by either immobilizing the ligand, e.g., PD-L1 and/or PD-L2 or the sPD-1 variant. For example, the assay can include immobilizing PD-L1 and/or PD-L2 fused to a His-tag onto Ni-activated NTA resin beads. Agents can be added in an appropriate buffer and the beads incubated for a period of time at a given temperature. After washes to remove unbound material, the bound protein can be released with, for example, SDS, buffers with a high pH, and the like and analyzed.

Alternatively, binding affinity of a sPD-1 variant for PD-L1 and/or PD-L2 can be determined by displaying the sPD-1 variant on a microbial cell surface, e.g., a yeast cell surface and detecting the bound complex by, for example, flow cytometry. The binding affinity of sPD-1 for PD-1 ligands can be measured using any known method recognized in the art including, but not limited to, the method described in Examples, radioactive ligand binding assays, non-radioactive (fluorescent) ligand binding assays, surface plasmon resonance (SPR), such as Biacore™, Octet™, plasmon-waveguide resonance (PWR), thermodynamic binding assays, whole cell ligand-binding assays, and structure-based ligand binding assays.

"Specific binding" or "specifically binds to" or is "specific for" a particular ligand or variant thereof means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target. In some embodiments, the binding affinity is measured using assays in the art as discussed above, such as a standard Biacore assay.

Specific binding for a particular ligand or variant thereof can be exhibited, for example, by a protein having a KD for another ligand protein of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where KD refers to a dissociation rate of a particular protein-ligand interaction. Typically, a protein that specifically binds a ligand will have a KD that is 20-, 50-, 100-, 200-, 500-, 1000-, 5,000-, 10,000- or more times greater for a control molecule relative to the protein.

By "residue" as used herein is meant a position in a protein and its associated amino acid identity. For example, Asparagine 297 (also referred to as Asn297 or N297) is a residue at position 297 in the human antibody IgG1.

By "hinge" or "hinge region" or "antibody hinge region" or "hinge domain" herein is meant the flexible polypeptide comprising the amino acids between the first and second constant domains of an antibody. Structurally, the IgG CH1 domain ends at EU position 215, and the IgG CH2 domain begins at residue EU position 231. Thus for IgG, the antibody hinge is herein defined to include positions 216 (E216 in IgG1) to 230 (p230 in IgG1), wherein the numbering is according to the EU index as in Kabat. In some cases, a "hinge fragment" is used, which contains fewer amino acids at either or both of the N- and C-termini of the hinge domain. As outlined herein, in some cases, Fc domains inclusive of the hinge are used, with the hinge generally being used as a flexible linker. (Additionally, as further described herein, additional flexible linker components can be used either with or without the hinge).

By "Fc" or "Fc region" or "Fc domain" as used herein is meant the polypeptide comprising the CH2-CH3 domains of an IgG molecule, and in some cases, inclusive of the hinge. In EU numbering for human IgG1, the CH2-CH3 domain comprises amino acids 231 to 447, and the hinge is 216 to 230. Thus the definition of "Fc domain" includes both amino acids 231-447 (CH2-CH3) or 216-447 (hinge-CH2-CH3), or fragments thereof. Thus Fc refers to the last two constant region immunoglobulin domains of IgA, IgD, and IgG, the last three constant region immunoglobulin domains of IgE and IgM, and in some cases, includes the flexible hinge N-terminal to these domains. For IgA and IgM, Fc may include the J chain. For IgG, the Fc domain comprises immunoglobulin domains Cγ2 and Cγ3 and in some cases, includes the lower hinge region between Cγ1 and Cγ2. An "Fc fragment" in this context may contain fewer amino acids from either or both of the N- and C-termini but still retains the ability to form a dimer with another Fc domain or Fc fragment as can be detected using standard methods, generally based on size (e.g. non-denaturing chromatography, size exclusion chromatography, etc.) Human IgG Fc domains are of particular use in the present invention, and can be the Fc domain from human IgG1, IgG2, IgG3 or IgG4. In general, IgG1, IgG2 and IgG4 are used more frequently than IgG3. In some embodiments, amino acid modifications are made to the Fc region, for example to alter binding to one or more FcγR receptors or to the FcRn receptor, and/or to increase the half-life in vivo.

By "IgG subclass modification" or "isotype modification" as used herein is meant an amino acid modification that converts one amino acid of one IgG isotype to the corresponding amino acid in a different, aligned IgG isotype. For example, because IgG1 comprises a tyrosine and IgG2 a phenylalanine at EU position 296, a F296Y substitution in IgG2 is considered an IgG subclass modification. Similarly, because IgG1 has a proline at position 241 and IgG4 has a serine there, an IgG4 molecule with a S241P is considered an IgG subclass modification. Note that subclass modifications are considered amino acid substitutions herein.

By "non-naturally occurring modification" as used herein is meant an amino acid modification that is not isotypic. For example, because none of the IgGs comprise an asparagine at position 297, the substitution N297A in IgG1, IgG2, IgG3, or IgG4 (or hybrids thereof) is considered a non-naturally occurring modification.

By "amino acid" and "amino acid identity" as used herein is meant one of the 20 naturally occurring amino acids that are coded for by DNA and RNA.

By "effector function" as used herein is meant a biochemical event that results from the interaction of an antibody Fc region with an Fc receptor or ligand. Effector functions include but are not limited to ADCC, ADCP, and CDC. In many cases, it is desirable to ablate most or all effector functions using either different IgG isotypes (e.g. IgG4) or amino acid substitutions in the Fc domain; however, preserving binding to the FcRn receptor is desirable, as this contributes to the half-life of the fusion protein in human serum.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65, hereby entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "FcRn" or "neonatal Fc Receptor" as used herein is meant a protein that binds the IgG antibody Fc region and is encoded at least in part by an FcRn gene.

By "linker" or "linker peptide" as used herein have a length that is adequate to link two molecules in such a way that they assume the correct conformation relative to one another so that they retain the desired activity. The linker or linker peptide may predominantly include the following amino acid residues: Gly, Ser, Ala, or Thr. In one embodiment, the linker is from about 1 to 50 amino acids in length, preferably about 1 to 30 amino acids in length. In one embodiment, linkers of 1 to 20 amino acids in length may be used, with from about 4 to about 10 amino acids finding use in some embodiments. Useful linkers include glycine-serine polymers, including for example (GS)n, (GSGGS)n, (GGGGS)n, and (GGGS)n, where n is an integer of at least one (and generally from 3 to 4), glycine-alanine polymers, alanine-serine polymers, and other flexible linkers. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers.

In some embodiments, the linker is a "domain linker", used to link any two domains as outlined herein together, such as to link the sPD-1 variant domain with (variant) Fc domain. While any suitable linker can be used, many embodiments utilize a glycine-serine polymer, including for example (GS)n, (GSGGS)n, (GGGGS)n, and (GGGS)n, where n is an integer of at least one (and generally from 3 to 4 to 5) as well as any peptide sequence that allows for recombinant attachment of the two domains with sufficient length and flexibility to allow each domain to retain its biological function. As discussed herein, a particularly useful domain linker is a GGGGS linker joined to the hinge domain of IgG4.

By "target cell" as used herein is meant a cell that expresses a target polypeptide or protein.

By "host cell" in the context of producing the sPD-1 variant—Fc fusion proteins according to the invention herein is meant a cell that contains the exogenous nucleic acids encoding the components of the sPD-1 variant—Fc fusion protein and is capable of expressing such Fc fusion protein under suitable conditions. Suitable host cells are described below.

Figure 8:
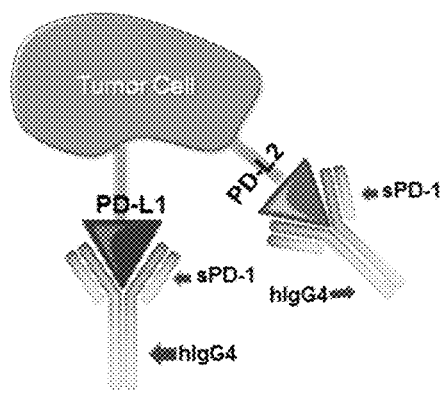

By "improved activity" or "improved function" herein meant a desirable change of at least one biochemical property. An improved function in this context can be measured as a percentage increase or decrease of a particular activity, or as a "fold" change, with increases of desirable properties (e.g. increased binding affinity and/or specificity for PD-L1 and/or PD-L2, increased stability of the fusion protein, increased half-life in vivo, etc.). In general, percentage changes are used to describe changes in biochemical activity of less than 100%, and fold-changes are used to describe changes in biochemical activity of greater than 100% (as compared to the parent protein). In the present invention, percentage changes (usually increases) of biochemical activity of at least about 10%, 20%, 30%, 40%, 50%, 60%, 70%, 80%, 90%, 95%, 98% and 99% can be accomplished. In the present invention, a "fold increase" (or decrease) is measured as compared to the parent protein. In many embodiments, the improvement is at least one and a tenth fold (1.1), one and a half fold (1.5 fold), 2 fold, 3 fold, 4 fold, 5 fold, 6 fold, 7 fold, 8 fold, 9 fold, 10 fold, 50 fold, 100 fold, 200 fold or higher. For example, as shown in FIG. 8, sPD-1 variant—Fc fusion protein demonstrated about 10,000-fold improvement in PD-L1 binding compared with a parent WT PD-1—Fc fusion protein ("parent Fc fusion protein"), and about 200-fold improvement in PD-L2 binding compared with the parent Fc fusion protein.

C. Soluble PD-1 Variant—Fc Fusion Proteins

As described herein, the soluble PD-1 variant—Fc fusion proteins ("sPD-1 variant—Fc fusion protein") of the invention comprise an sPD-1 variant domain, a Fc domain, and optionally a linker linking the sPD-1 variant domain with the Fc domain.

As described herein, the format of the fusion protein can take on several configurations, with the component domains switching order in the protein (from N- to C-terminal). In one embodiment, the fusion protein comprises, from N- to C-terminus, an sPD-1 variant domain-domain linker-Fc domain. In some embodiments, the fusion protein comprises, from N- to C-terminus, Fc domain-domain linker-sPD-1 variant domain. In some embodiments, a linker is not used, in which case the fusion protein comprises from N- to C-terminus, either sPD-1 variant domain-Fc domain or Fc domain-sPD-1 variant domain. Note that in some cases, the same fusion protein can be labeled somewhat differently. For example, in the case where the Fc domain includes a hinge domain, a fusion protein comprising sPD-1 variant domain-Fc domain still includes a linker in the form of the hinge domain. Alternatively, this same protein may not have the hinge domain included in the Fc domain, in which case the fusion protein comprises sPD-1 variant domain-CH2-CH3.

Thus, in some embodiments, the present invention provides an sPD-1 variant—Fc fusion proteins as described herein, where the Fc domain comprises a hinge domain and the sPD-1 variant domain is linked with the Fc domain by the hinge domain: sPD-1 variant domain-hinge domain-CH2-CH3.

In some embodiments, the present invention provides an sPD-1 variant—Fc fusion proteins as described above, where the Fc domain comprises a hinge domain and the sPD-1 variant domain is linked with the Fc domain by an additional linker as described herein. That is, the fusion protein can be, from N- to C-terminal sPD-1 variant domain-domain linker-hinge domain-CH2-CH3; sPD-1 variant domain-domain linker-CH2-CH3; hinge domain-CH2-CH3-domain linker-sPD-1 variant domain or CH2-CH3-domain linker-sPD-1 variant.

In some embodiments, the present invention provides an sPD-1 variant—Fc fusion proteins as described above, where the Fc domain does not comprise a hinge domain and the sPD-1 variant domain is linked with the Fc domain by a domain linker (e.g. non-hinge) as described herein.

1. sPD-1 Variant Domains

The sPD-1 variant domains of the invention comprise the soluble ECD of human PD-1 with variants. The sPD-1 variants serve to increase the binding affinity and/or specificity for PD-L1 and/or PD-L2 compared to the wild-type PD-1 as determined by the binding affinity assays in the art, such as a Biacore assay.

In some embodiments, the sPD-1 variants of the invention are antagonists that bind to and block a PD-1 ligand (e.g., PD-L1 and/or PD-L2) and thereby interfere with or inhibit the binding of the ligand to its receptor PD-1. The antagonists can enhance an immune response by inhibiting the signal transduction pathway mediated by PD-1 via reducing the amount of ligand available to bind the PD-1 receptor. As such, a more robust immune response can be produced by the subject.

In some cases, a useful sPD-1 variant domain specifically binds to PD-L1 and/or PD-L2 on a target cell, e.g., on a cancer cell and thereby reduces (e.g., blocks, prevents, etc.) the interaction between the PD-L1/PD-L2 and PD-1 (e.g., wild-type PD-1 on an immune cell, e.g., on a T cell). Thus, a sPD-1 variant provided herein can act as an engineered decoy receptor for PD-L1 and/or PD-L2. By reducing the interaction between PD-L1 and/or PD-L2 and wild-type PD-1, the sPD-1 variant domain can decrease the immune inhibitory signals produced by the PD-L/PD-1 interaction, and therefore can increase the immune response (e.g., by increasing T cell activation). A suitable sPD-1 variant domain can comprise the portion of PD-1 that is sufficient to bind PD-1 ligand at a recognizable affinity, e.g., high affinity, which normally lies between the signal sequence and the transmembrane domain, or a fragment thereof that retains the binding activity.

The names of the designated proteins/protein domains and corresponding amino acid sequences of SEQ ID NO:1 to SEQ ID NO:10 are listed in Table 1, respectively.

TABLE 1

| SEQ ID numbers, descriptions and corresponding amino acid sequences. | |
|---|---|
| SEQ ID NO (Description) | Amino Acid Sequence |
| SEQ ID NO: 1 (sPD-1 WT ECD) | PGWFLDSPDRPWNPPTFSPALLVVTEGDNATFTCSFSNTSESFV LNWYRMSPSNQTDKLAAFPEDRSQPGQDCRFRVTQLPNGRDF HMSVVRARRNDSGTYLCGAISLAPKAQIKESLRAELRVTERRA EVPTAHPSPSPRPAGQFQTLV |
| SEQ ID NO: 2 (sPD-1 variant version 1 ECD) | PGWFLDSPDRPWNPPTFSPALLVVTEGDNATFTCSFSNTSEGFV LNWYRMSPSNQTDKLAAFPEDRGQLGQDCRFRVTQLPNGRDF HMSVVRARRSDSGTYLCSAIVLAPKIQIKESLRVELRVTERRAE VPTAHPSPSPRPAGQFQTLV |
| SEQ ID NO: 3 (sPD-1 variant version 2 ECD) | PGWFLDSPDRPWNPPTFSPALLVVTEGDNATFTCSFSNTSEGFV LNWYRMSPSNQTDKLAAFPEDRGQLGQDCRFRVTQLPNGRDF HMSVVRARRNDSGTYLCSAIVLAPKIQIKESLRVELRVTERRAE VPTAHPSPSPRPAGQFQTLV |
| SEQ ID NO: 4 (PD-1 WT ECD + domain linker + Fc Fusion Protein) | PGWFLDSPDRPWNPPTFSPALLVVTEGDNATFTCSFSNTSESFV LNWYRMSPSNQTDKLAAFPEDRSQPGQDCRFRVTQLPNGRDF HMSVVRARRNDSGTYLCGAISLAPKAQIKESLRAELRVTERRA EVPTAHPSPSPRPAGQFQTLVGGGGSESKYGPPCPPCPAPEFLG GPSVFLFPPKPKDTLMISRTPEVTCVVVDVSQEDPEVQFNWYV DGVEVHNAKTKPREEQFNSTYRVVSVLTVLHQDWLNGKEYKC KVSNKGLPSSIEKTISKAKGQPREPQVYTLPPSQEEMTKNQVSL TCLVKGFYPSDIAVEWESNGQPENNYKTTPPVLDSDGSFFLYSR LTVDKSRWQEGNVFSCSVMHEALHNHYTQKSLSLSLGK |
| SEQ ID NO: 5 (sPD-1 variant version 1ECD + domain linker + Fc Fusion Protein) | PGWFLDSPDRPWNPPTFSPALLVVTEGDNATFTCSFSNTSEGFV LNWYRMSPSNQTDKLAAFPEDRGQLGQDCRFRVTQLPNGRDF HMSVVRARRSDSGTYLCSAIVLAPKIQIKESLRVELRVTERRAE VPTAHPSPSPRPAGQFQTLVGGGGSESKYGPPCPPCPAPEFLGGP SVFLFPPKPKDTLMISRTPEVTCVVVDVSQEDPEVQFNWYVDG VEVHNAKTKPREEQFNSTYRVVSVLTVLHQDWLNGKEYKCKV SNKGLPSSIEKTISKAKGQPREPQVYTLPPSQEEMTKNQVSLTCL VKGFYPSDIAVEWESNGQPENNYKTTPPVLDSDGSFFLYSRLTV DKSRWQEGNVFSCSVMHEALHNHYTQKSLSLSLGK |
| SEQ ID NO: 6 (sPD-1 variant version 2 ECD + domain linker + Fc Fusion Protein) | PGWFLDSPDRPWNPPTFSPALLVVTEGDNATFTCSFSNTSEGFV LNWYRMSPSNQTDKLAAFPEDRGQLGQDCRFRVTQLPNGRDF HMSVVRARRNDSGTYLCSAIVLAPKIQIKESLRVELRVTERRAE VPTAHPSPSPRPAGQFQTLVGGGGSESKYGPPCPPCPAPEFLGGP SVFLFPPKPKDTLMISRTPEVTCVVVDVSQEDPEVQFNWYVDG VEVHNAKTKPREEQFNSTYRVVSVLTVLHQDWLNGKEYKCKV SNKGLPSSIEKTISKAKGQPREPQVYTLPPSQEEMTKNQVSLTCL VKGFYPSDIAVEWESNGQPENNYKTTPPVLDSDGSFFLYSRLTV DKSRWQEGNVFSCSVMHEALHNHYTQKSLSLSLGK |
| SEQ ID NO: 7 (signal region of PD-1 WT) | MQIPQAPWPVVWAVLQLGWR |
| SEQ ID NO: 8 (signal region of PD-1 WT + PD-1 WT ECD + domain linker + Fc Fusion Protein) | MQIPQAPWPVVWAVLQLGWRPGWFLDSPDRPWNPPTFSPALL VVTEGDNATFTCSFSNTSESFVLNWYRMSPSNQTDKLAAFPED RSQPGQDCRFRVTQLPNGRDFHMSVVRARRNDSGTYLCGAISL APKAQIKESLRAELRVTERRAEVPTAHPSPSPRPAGQFQTLVGG GGSESKYGPPCPPCPAPEFLGGPSVFLFPPKPKDTLMISRTPEVT CVVVDVSQEDPEVQFNWYVDGVEVHNAKTKPREEQFNSTYRV VSVLTVLHQDWLNGKEYKCKVSNKGLPSSIEKTISKAKGQPRE |

TABLE 1-continued

SEQ ID numbers, descriptions and corresponding amino acid sequences.

| SEQ ID NO (Description) | Amino Acid Sequence |
|---|---|
| | PQVYTLPPSQEEMTKNQVSLTCLVKGFYPSDIAVEWESNGQPE NNYKTTPPVLDSDGSFFLYSRLTVDKSRWQEGNVFSCSVMHEA LHNHYTQKSLSLSLGK |
| SEQ ID NO: 9 (signal region of PD-1 WT + sPD-1 variant version 1 ECD + domain linker + Fc Fusion Protein) | MQIPQAPWPVVWAVLQLGWRPGWFLDSPDRPWNPPTFSPALL VVTEGDNATFTCSFSNTSEGFVLNWYRMSPSNQTDKLAAFPED RGQLGQDCRFRVTQLPNGRDFHMSVVRARRSDSGTYLCSAIVL APKIQIKESLRVELRVTERRAEVPTAHPSPSPRPAGQFQTLVGGG GSESKYGPPCPPCPAPEFLGGPSVFLFPPKPKDTLMISRTPEVTC VVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQEEMTKNQVSLTCLVKGFYPSDIAVEWESNGQPEN NYKTTPPVLDSDGSFFLYSRLTVDKSRWQEGNVFSCSVMHEAL HNHYTQKSLSLSLGK |
| SEQ ID NO: 10 (signal region of PD-1 WT + sPD-1 variant version 2 ECD + domain linker + Fc Fusion Protein) | MQIPQAPWPVVWAVLQLGWRPGWFLDSPDRPWNPPTFSPALL VVTEGDNATFTCSFSNTSEGFVLNWYRMSPSNQTDKLAAFPED RGQLGQDCRFRVTQLPNGRDFHMSVVRARRNDSGTYLCSAIVL APKIQIKESLRVELRVTERRAEVPTAHPSPSPRPAGQFQTLVGGG GSESKYGPPCPPCPAPEFLGGPSVFLFPPKPKDTLMISRTPEVTC VVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQEEMTKNQVSLTCLVKGFYPSDIAVEWESNGQPEN NYKTTPPVLDSDGSFFLYSRLTVDKSRWQEGNVFSCSVMHEAL HNHYTQKSLSLSLGK |

In some embodiments, the sPD-1 variants include amino acid substitutions, deletions or insertions or any combination thereof to the WT PD-1 domain as set forth in SEQ ID NO:1 that increases or enhances its binding activity to either PD-L1, PD-L2 or both as compared to wild-type PD-1.

The present invention provides sPD-1 variant domains comprising at least one amino acid substitution at one or more (e.g., several) positions corresponding to positions 120, 112, 107, 104, 67, 69, 96 and 42 as compared to the human wild-type parent PD-1 domain of SEQ ID NO:1, using the numbering starting from the mature region. In some embodiments, the sPD-1 variant has at least 80%, at least 85%, at least 90%, at least 95%, at least 96%, at least 97%, at least 98%, or at least 99%, but less than 100% sequence identity to the parent PD-1 domain. In some embodiments, the parent PD-1 domain is SEQ ID NO:1. In a preferred embodiment, the sPD-1 variant domain has at least 95%, at least 96%, at least 97%, at least 98%, or at least 99%, but less than 100% sequence identity to SEQ ID NO:1. In some embodiments, as noted herein, the variant sPD-1 domain can have N-terminal and/or C terminal truncations compared to wild type sPD-1 as long as the truncated variant sPD-1 retains biological activity (e.g. binding to PD-L1 and/or PD-L2). To be clear, the sPD-1 variants of the invention have at least one amino acid substitution and thus do not have SEQ ID NO:

The present invention provides sPD-1 variant domains comprising at least one amino acid substitution at one or more (e.g., several) positions corresponding to positions 42, 67, 69, 96, 104, 107, 112 and 120 as compared to the human wild type parent PD-1 ECD domain of SEQ ID NO:1.

In some embodiments, the sPD-1 variant domain has amino acid substitution(s) at one of said positions, two of said positions, three of said positions, four of said positions, five of said positions, six of said positions, seven of said positions or eight of said positions as shown in Table 10.

In some embodiments, the present invention provides sPD-1 variant domains comprising one or more of amino acid substitution(s) selected from the group consisting of: A120V, A112I, S107V, G104S, S67G, P69L, N96S and S42G as compared to SEQ ID NO:1.

In some embodiments, the present invention provides sPD-1 variant domains comprising a set of amino acid substitutions selected from the group consisting of S42G/S67G/P69L/G104S/S107V/A112I/A120V, S42G/S67G/P69L/N96S/G104S/S107V/A112I/A120V, S42G/S67G, S42G/P69L, S42G/G104S, S42G/S107V, S42G/A112I, S42G/A120V, S67G/P69L, S67G/G104S, S67G/S107V, S67G/A112I, S67G/A120V, P69L/G104S, P69L/S107V, P69L/A112I, P69L/A120V, G104S/S107V, G104S/A112I, G104S/A120V, S107V/A112I, S107V/A120V, A112I/A120V, S42G/S67G/P69L, S42G/S67G/G104S, S42G/S67G/S107V, S42G/S67G/A112I, S42G/S67G/A120V, S42G/P69L/G104S, S42G/P69L/S107V, S42G/P69L/A112I, S42G/P69L/A120V, S42G/G104S/S107V, S42G/G104S/A112I, S42G/G104S/A120V, S42G/S107V/A112I, S42G/S107V/A120V, S42G/A112I/A120V, S67G/P69L/G104S, S67G/P69L/S107V, S67G/P69L/A112I, S67G/P69L/A120V, S67G/G104S/S107V, S67G/G104S/A112I, S67G/G104S/A120V, S67G/S107V/A112I, S67G/S107V/A120V, S67G/A112I/A120V, P69L/G104S/S107V, P69L/G104S/A112I, P69L/G104S/120V, P69L/S107V/A112I, P69L/S107V/120V, P69L/A112I/A120V, G104S/S107V/A112I, G104S/S107V/A120V, G104S/A112I/A120V, S107V/A112I/A120V, S42G/S67G/P69L/G104S, S42G/S67G/P69L/S107V, S42G/S67G/P69L/A112I, S42G/S67G/P69L/A120V, S42G/S67G/G104S/S107V, S42G/S67G/G104S/A112I, S42G/S67G/G104S/A120V, S42G/S67G/S107V/A112I, S42G/S67G/S107V/A120V, S42G/S67G/A112I/A120V, S42G/P69L/G104S/S107V, S42G/P69L/G104S/A112I, S42G/P69L/G104S/A120V, S42G/P69L/S107V/A112I, S42G/P69L/S107V/A120V, S42G/P69L/A112I/A120V, S42G/G104S/S107V/A112I, S42G/G104S/S107V/A120V, S42G/G104S/A112I/A120V, S42G/S107V/A112I/A120V, S67G/P69L/G104S/S107V, S67G/P69L/G104S/A112I, S67G/P69L/G104S/A120V, S67G/P69L/

S107V/A112I, S67G/P69L/S107V/A120V, S67G/P69L/ A112I/A120V, S67G/G104S/S107V/A112I, S67G/G104S/ S107V/A120V, S67G/G104S/A112I/A120V, S67G/S107V/ A112I/120V, P69L/G104S/S107V/A112I, P69L/G104S/ S107V/A120V, P69L/G104S/A112I/A120V, P69L/S107V/ A112I/A120V, G104S/S107V/A112I/A120V, S42G/S67G/ P69L/G104S/S107V, S42G/S67G/P69L/G104S/A112I, S42G/S67G/P69L/G104S/A120V, S42G/S67G/P69L/ S107V/A112I, S42G/S67G/P69L/S107V/A120V, S42G/ S67G/P69L/A112I/A120V, S42G/S67G/G104S/S107V/ A112I, S42G/S67G/G104S/S107V/A120V, S42G/S67G/ G104S/A112I/A120V, S42G/S67G/S107V/A112I/A120V, S42G/P69L/G104S/S107V/A112I, S42G/P69L/G104S/ S107V/A120V, S42G/P69L/G104S/A112I/A120V, S42G/ P69L/S107V/A112I/A120V, S42G/G104S/S107V/A112I/ A120V, S67G/P69L/G104S/S107V/A112I, S67G/P69L/ G104S/S107V/A120V, S67G/P69L/G104S/A112I /A120V, S67G/P69L/S107V/A112I/A120V, S67G/G104S/S107V/ A112I/A120V, P69L/G104S/S107V/A112I/A120V, S42G/ S67G/P69L/G104S/S107V/A112I, S42G/S67G/P69L/ G104S/S107V/A120V, S42G/S67G/P69L/G104S/A112I/ A120V, S42G/S67G/P69L/S107V/A112I/A120V, S42G/ S67G/G104S/S107V/A112I/A120V, S42G/P69L/G104S/ S107V/A112I/A120V, and S67G/P69L/G104S/S107V/ A112I/A120V as compared to SEQ ID NO:1. In some embodiments, the present invention provides sPD-1 variant-Fc fusion protein(s) comprising the sPD-1 variant domain(s) as disclosed herein, an optional linker, and an Fc domain.

In some embodiments, the present invention provides sPD-1 variant domains comprising a set of amino acid substitutions selected from the group consisting of S42G/ S67G/P69L/G104S/S107V/A112I/A120V, S42G/S67G/ P69L/N96S/G104S/S107V/A112I/A120V, P69L/G104S/ S107V/A112I/A120V, S67G/G104S/S107V/A112I/A120V, S67G/P69L/G104S/S107V/A112I/A120V, G104S/S107V/ A112I/A120V, and G104S/S107V/A112I as compared to SEQ ID NO:1. In some embodiments, the present invention provides sPD-1 variant-Fc fusion proteins comprising the sPD-1 variant domain as disclosed herein, an optional linker, and an Fc domain.

In some embodiments, the present invention provides sPD-1 variant domains comprising amino acid substitutions of S42G/S67G/P69L/G104S/S107V/A112I/A120V as compared to SEQ ID NO:1; and sPD-1 variant-Fc fusion proteins comprising the sPD-1 variant domain as disclosed herein, an optional linker, and an Fc domain.

In some embodiments, the present invention provides sPD-1 variant domains comprising amino acid substitutions of S42G/S67G/P69L/N96S/G104S/S107V/A112I/A120V as compared to SEQ ID NO:1; and sPD-1 variant-Fc fusion proteins comprising the sPD-1 variant domain as disclosed herein, an optional linker, and an Fc domain.

In some embodiments, the present invention provides sPD-1 variant domains comprising amino acid substitutions of P69L/G104S/S107V/A112I/A120V as compared to SEQ ID NO:1; and sPD-1 variant-Fc fusion proteins comprising the sPD-1 variant domain as disclosed herein, an optional linker, and an Fc domain.

In some embodiments, the present invention provides sPD-1 variant domains comprising amino acid substitutions of S67G/G104S/S107V/A112I/A120V as compared to SEQ ID NO:1; and sPD-1 variant-Fc fusion proteins comprising the sPD-1 variant domain as disclosed herein, an optional linker, and an Fc domain.

In some embodiments, the present invention provides sPD-1 variant domains comprising amino acid substitutions of S67G/P69L/G104S/S107V/A112I/A120V as compared to SEQ ID NO:1; and sPD-1 variant-Fc fusion proteins comprising the sPD-1 variant domain as disclosed herein, an optional linker, and an Fc domain.

In some embodiments, the present invention provides sPD-1 variant domains comprising amino acid substitutions of G104S/S107V/A112I/A120V as compared to SEQ ID NO:1; and sPD-1 variant-Fc fusion proteins comprising the sPD-1 variant domain as disclosed herein, an optional linker, and an Fc domain.

In some embodiments, the present invention provides sPD-1 variant domains comprising amino acid substitutions of G104S/S107V/A112I as compared to SEQ ID NO:1; and sPD-1 variant-Fc fusion proteins comprising the sPD-1 variant domain as disclosed herein, an optional linker, and an Fc domain.

In some embodiments, the present invention provides an sPD-1 variant domain having SEQ ID NO:2, and sPD-1 variant-Fc fusion proteins comprising SEQ ID NO:2, an optional linker, and an Fc domain.

In some embodiments, the present invention provides an sPD-1 variant domain having SEQ ID NO:3, and sPD-1 variant-Fc fusion proteins comprising SEQ ID NO:3, an optional linker, and an Fc domain.

In some embodiments, the present invention provides an sPD-1 variant-Fc fusion proteins having SEQ ID NO:5.

In some embodiments, the present invention provides an sPD-1 variant-Fc fusion proteins having SEQ ID NO:6.

In some embodiments, the sPD-1 variant domain comprises an amino acid substitution of the serine at position 42 with the position numbering starting from the mature region. In some embodiments, the substitution is with any other of the 19 naturally occurring amino acids, threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is S42G. In some embodiments, the present invention provides sPD-1 variant-Fc fusion proteins comprising the sPD-1 variant domain as described herein, an optional linker, and an Fc domain.

In some embodiments, the sPD-1 variant domain comprises an amino acid substitution of the serine at position 67 with the position numbering starting from the mature region. In some embodiments, the substitution is with any other of the 19 naturally occurring amino acids, threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is S67G. In some embodiments, the present invention provides sPD-1 variant-Fc fusion proteins comprising the sPD-1 variant domain as described herein, an optional linker, and an Fc domain.

In some embodiments, the sPD-1 variant domain comprises an amino acid substitution of the proline at position 69 with the position numbering starting from the mature region. In some embodiments, the substitution is with any other of the 19 naturally occurring amino acids, serine, threonine, asparagine, glutamic acid, glutamine, aspartic acid, lysine, arginine, histidine, cysteine, glycine, alanine, isoleucine, leucine, methionine, phenylalanine, tryptophan, valine and tyrosine, with some embodiments not utilizing cysteine (due to possible disulfide formation). In some embodiments, the amino acid substitution is P69L. In some embodiments, the present invention provides sPD-1 variant-Fc fusion proteins comprising the sPD-1 variant domain as described herein, an optional linker, and an Fc domain.

In some embodiments, the sPD-1 variant domain comprises an amino acid substitution of the asparagine at position 96 with the position numbering starting from the mature region. In some embodiments, the substitution is with any other of the 19 naturally occurring amino acids, serine, threonine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is N96S. In some embodiments, the present invention provides sPD-1 variant-Fc fusion proteins comprising the sPD-1 variant domain as described herein, an optional linker, and an Fc domain.

In some embodiments, the sPD-1 variant domain comprises an amino acid substitution of the glycine at position 104 with the position numbering starting from the mature region. In some embodiments, the substitution is with any other of the 19 naturally occurring amino acids, serine, threonine, asparagine, glutamic acid, glutamine, aspartic acid, lysine, arginine, histidine, cysteine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is G104S. In some embodiments, the present invention provides sPD-1 variant-Fc fusion proteins comprising the sPD-1 variant domain as described herein, an optional linker, and an Fc domain.

In some embodiments, the sPD-1 variant domain comprises an amino acid substitution of the serine at position 107 with the position numbering starting from the mature region. In some embodiments, the substitution is with any other of the 19 naturally occurring amino acids, threonine, asparagine, glutamic acid, glutamine, aspartic acid, lysine, arginine, histidine, cysteine, glycine, alanine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is S107V. In some embodiments, the present invention provides sPD-1 variant-Fc fusion proteins comprising the sPD-1 variant domain as described herein, an optional linker, and an Fc domain.

In some embodiments, the sPD-1 variant domain comprises an amino acid substitution of the alanine at position 112 with the position numbering starting from the mature region. In some embodiments, the substitution is with any other of the 19 naturally occurring amino acids, serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is A112I. In some embodiments, the present invention provides sPD-1 variant-Fc fusion proteins comprising the sPD-1 variant domain as described herein, an optional linker, and an Fc domain.

In some embodiments, the sPD-1 variant domain comprises an amino acid substitution of the alanine at position 120 with the position numbering starting from the mature region. In some embodiments, the substitution is with any other of the 19 naturally occurring amino acids, serine, threonine, asparagine, glutamic acid, glutamine, aspartic acid, lysine, arginine, histidine, cysteine, glycine, isoleucine, leucine, methionine, proline, phenylalanine, tryptophan, valine and tyrosine, with some embodiments not utilizing cysteine (due to possible disulfide formation) or proline (due to steric effects). In some embodiments, the amino acid substitution is A120V. In some embodiments, the present invention provides sPD-1 variant-Fc fusion proteins comprising the sPD-1 variant domain as described herein, an optional linker, and an Fc domain.

In some embodiments, the sPD-1 variant protein is shorter than the full length ECD. In some embodiments, the sPD-1 variants may comprise a truncated version of the ECD, as long as the truncated form retains the ability to bind human PD-L1 and/or PD-L2 as measured by one of the binding assays outlined herein. As is known in the art, both N- and C-terminal truncations are possible, e.g. from about residue 1, 5, 10, 15, 20, 25, 30, 33, 35, 40, 45, or 50 to about residue 130, 135, 140, 145, 149 or 150 of SEQ ID NO: 1, e.g., residues 33-150. In some cases, only a few amino acids (e.g. 1, 2, 3, 4, 5 or 6) are removed from either or both of the N and C-terminus, as long as activity is retained.

In some embodiments, the sPD-1 variant described herein has a binding affinity for a PD-1 ligand (i.e., PD-L1 and/or PD-L2) that is better than the wild-type PD-1 polypeptide/domain. In some embodiments, the sPD-1 variants have a binding affinity for PD-L1 and/or PD-L2 that is at least 1-fold, 2-fold, 3-fold, 4-fold, 5-fold, 10-fold, 50-fold, 100-fold, 200-fold or greater than that of the wild-type PD-1. In some embodiments, the sPD-1 variants can have a binding affinity for PD-L1 that is at least 1-fold, 2-fold, 3-fold, 4-fold, 5-fold, 10-fold, 50-fold, 100-fold, 200-fold or greater than that of the wild-type PD-1. In some embodiments, the sPD-1 variants can have a binding affinity for PD-L2 that is at least 1-fold, 2-fold, 3-fold, 4-fold, 5-fold, 10-fold, 50-fold, 100-fold, 200-fold or greater than that of the wild-type PD-1.

In certain embodiments, the binding affinity of the sPD-1 variant for PD-L1, PD-L2 or both is increased by at least about 0.5%, 1%, 2%, 3%, 4%, 5%, 6%, 7%, 8%, 9%, 10%, 15%, 20%, 25%, 30%, 35%, 40%, 45%, 50% or higher as compared to that of the wild-type PD-1. In other embodiments, the sPD-1 variants of the present invention have a binding affinity of less than about $1 \times 10^{-8}$ M, $1 \times 10^{-9}$M, $1 \times 10^{-10}$ M or $1 \times 10^{-12}$M for PD-L1 and/or PD-L2. The sPD-1 variants of the present invention can have a binding affinity of less than about $1 \times 10^{-8}$ M, $1 \times 10^{-9}$ M, $1 \times 10^{-10}$M or $1 \times 10^{-12}$M for PD-L1. The sPD-1 variants of the present invention can have a binding affinity of less than about $1 \times 10^{-8}$ M, $1 \times 10^{-9}$M, $1 \times 10^{-10}$ M or $1 \times 10^{-12}$M for PD-L2. In yet other embodiments, the sPD-1 variants inhibit or compete with wild-type PD-1 binding to PD-L1 and/or PD-L2 either in vivo, in vitro or both.

In some embodiments, the sPD-1 variant has a dissociation half-life for PD-L1 and/or PD-L2 that is 2-fold or more (e.g., 5-fold or more, 10-fold or more, 100-fold or more, 500-fold or more, 1000-fold or more, 5000-fold or more, 10000-fold or more etc.) greater than the dissociation half-life for PD-L1 of a wild type PD-1.

2. Fc Domains

As discussed herein, in addition to the sPD-1 variant domains described above, the fusion proteins of the invention also include Fc domains of antibodies that generally are based on the IgG class, which has several subclasses, including, but not limited to IgG1, IgG2, IgG3, and IgG4. As described herein, the Fc domain optionally includes the hinge domain of an IgG antibody.

Human IgG Fc domains are of particular use in the present invention, and can be the Fc domain from human IgG1, IgG2, IgG3 or IgG4. In general, IgG1, IgG2 and IgG4 are used more frequently than IgG3.

The Fc domain of a human IgG protein included in the fusion protein of the present invention confers a significant increase in half-life of the fusion protein, and provides additional binding or interaction with the Ig molecules. In some embodiments, the sPD-1 variant—Fc fusion protein can facilitate purification, multimerization, binding and neutralizing other molecules as compared to a monomeric sPD-variant polypeptide.

The Fc domains that find use in the invention can also contain Fc variants to alter function as needed. However, any Fc variants generally need to retain both the ability to form dimers as well as the ability to bind FcRn. Thus, while many of the embodiments herein rely on the use of a human IgG4 domain so as to avoid effector function, Fc variants can be made that augment or abrogate function in other IgG domains. Thus, for example, ablation variants that reduce or eliminate effector function in IgG1 or IgG2 can be used, and/or Fc variants that confer tighter binding to the FcRn can be used, as will be appreciated by those in the art.

a. IgG4 Fc Domains

The IgG4 subclass is distinguished from the other IgG subclasses, as it exhibits negligible binding to the C1q protein complex and is unable to activate the classical complement pathway (A. Nirula et al., 2011, Current Opinion in Rheumatology 23:119-124, hereby entirely incorporated by reference). As a result, IgG4 finds use in the present invention as it has no significant effector function, and is thus used to block the receptor-ligand binding without cell depletion.

In another embodiment, the Fc domains of the present invention are human IgG4 Fc domains.

In some embodiments, the Fc domain of the present invention comprises the hinge-CH2-CH3 of human IgG4.

In some embodiments, the Fc domain of the present invention comprises the CH2—CH3 of human IgG4.

In another embodiment, the Fc domains of the present invention are variant human IgG4 Fc domains. However, the variant Fc domains herein still retain the ability to form a dimer with another Fc domain as measured using known, as well as the ability to bind to FcRn, as this contributes significantly to the increase in serum half life of the fusion proteins herein.

The variant IgG4 Fc domain can include an addition, deletion, substitution or any combination thereof compared with the parent human IgG4 Fc domain.

In some embodiment, the variant human IgG4 Fc domains of the present invention can have at least about 80%, 85%, 90%, 95%, 95%, 97%, 98% or 99% identity to the corresponding parental human IgG4 Fc domain (using the identity algorithms discussed above, with one embodiment utilizing the BLAST algorithm as is known in the art, using default parameters).

In some embodiment, the variant human IgG4 Fc domains of the present invention can have from 1, 2, 3, 4, 5, 6, 7, 8, 9, 10, 11, 12, 13, 14, 15, 16, 11, 12, 13, 14, 15, 16, 17, 18, 19 or 20 amino acid modifications as compared to the parental human IgG4 Fc domains.

In some embodiments, the variant human IgG4 Fc domain comprises an amino acid substitution of the serine at position 228 to proline according to the EU numbering index.

b. Other IgG Fc Domains

In some embodiments, the Fc domains of the present invention can be the Fc domains from other IgGs than IgG4, such as human IgG1, IgG2 or IgG3. In general, IgG1 and IgG2 are used more frequently than IgG3.

In some embodiments, the Fc domain of the present invention is the Fc domain of human IgG1.

In some embodiments, the Fc domain of the present invention is the Fc domain of human IgG2.

In some embodiments, the Fc domain of the present invention is a variant human IgG1 Fc domain.

In some embodiments, the Fc domain of the present invention is a variant human IgG2 Fc domain.

In some embodiment, the variant human IgG1 Fc domains of the invention can have at least about 80%, 85%, 90%, 95%, 95%, 97%, 98% or 99% identity to the corresponding parental human IgG1 Fc domain (using the identity algorithms discussed above, with one embodiment utilizing the BLAST algorithm as is known in the art, using default parameters).

In some embodiment, the variant human IgG2 Fc domains of the invention can have at least about 80%, 85%, 90%, 95%, 95%, 97%, 98% or 99% identity to the corresponding parental human IgG2 Fc domain (using the identity algorithms discussed above, with one embodiment utilizing the BLAST algorithm as is known in the art, using default parameters).

In some embodiment, the variant human IgG3 Fc domains of the invention can have at least about 80%, 85%, 90%, 95%, 95%, 97%, 98% or 99% identity to the corresponding parental human IgG3 Fc domain (using the identity algorithms discussed above, with one embodiment utilizing the BLAST algorithm as is known in the art, using default parameters).

In some embodiment, the variant human IgG1 Fc domains of the invention can have from 1, 2, 3, 4, 5, 6, 7, 8, 9, 10, 11, 12, 13, 14, 15, 16, 11, 12, 13, 14, 15, 16, 17, 18, 19 or 20 amino acid modifications as compared to the parental human IgG1 Fc domains.

In some embodiment, the variant human IgG2 Fc domains of the invention can have from 1, 2, 3, 4, 5, 6, 7, 8, 9, 10, 11, 12, 13, 14, 15, 16, 11, 12, 13, 14, 15, 16, 17, 18, 19 or 20 amino acid modifications as compared to the parental human IgG2 Fc domains.

In some embodiment, the variant human IgG3 Fc domains of the invention can have from 1, 2, 3, 4, 5, 6, 7, 8, 9, 10, 11, 12, 13, 14, 15, 16, 11, 12, 13, 14, 15, 16, 17, 18, 19 or 20 amino acid modifications as compared to the parental human IgG3 Fc domains.

3. Linkers

The two domains described above (i.e. the sPD-1 variant domain and the Fc domain) are generally linked using a domain linker as described herein. In the context of the invention, what is important is that the two domains are attached using a flexible linker in such a way that the two domains can act independently. This can be accomplished in a variety of ways, using traditional linkers and/or the hinge linker.

While any suitable linker can be used, many embodiments utilize a glycine-serine polymer, including for example (GS)n, (GSGGS)n, (GGGGS)n, and (GGGS)n, where n is an integer of at least one (and generally from 3 to 4 to 5) as well as any peptide sequence that allows for recombinant attachment of the two domains with sufficient length and flexibility to allow each domain to retain its biological function.

In some embodiments, the hinge domain of a human IgG antibody is used. The hinge domains of human IgG1, IgG2, IgG3 and IgG4 are shown in FIG. 12. In some cases, the hinge domain can contain amino acid substitutions as well. For example, as shown in FIG. 1 and Table 1, a hinge domain from IgG4 comprising a S228P variant is used.

In some embodiments, the domain linker is a combination of a hinge domain and a flexible linker, such as an IgG4 hinge with a S228P with a GGGGS linker as well.

In one embodiment, the linker is from about 1 to 50 amino acids in length, preferably about 1 to 30 amino acids in length.

In another embodiment, the linker is from 1 to 20 amino acids in length, preferably from about 5 to about 10 amino acids.

4. Particular Embodiments of the Invention

In some embodiments, the sPD-1 variant—Fc fusion protein of the present invention comprises an sPD-1 variant domain exhibiting at least 80%, 85%, 90%, 95%, 96%, 97%, 98% or 99% identity to SEQ ID NO:1.

In some embodiments, the sPD-1 variant—Fc fusion proteins of the present invention comprise: a) a soluble PD-1 (sPD-1) variant domain comprising an amino acid substitution as compared to SEQ ID NO:1, wherein said amino acid substitution is at a position number selected from the group consisting of 42, 67, 69, 96, 104, 107, 112 and 120, b) a linker, and c) an Fc domain. In some embodiments, the sPD-1 variant—Fc fusion protein comprises from N- to C-terminal: a) said sPD-1 variant domain; b) said linker; and c) said Fc domain. In some embodiments, the sPD-1 variant—Fc fusion protein comprises from N- to C-terminal: a) said Fc domain; b) said linker; and c) said sPD-1 variant domain. In some embodiments, the Fc domain is the Fc domain of a human IgG selected from the group consisting of IgG1, IgG2, IgG3 and IgG4. In some embodiments, the Fc domain is a variant human IgG Fc domain, wherein the human IgG is selected from the group consisting of IgG1, IgG2, IgG3 and IgG4. In some embodiments, the variant human IgG Fc domain as disclosed herein comprises the hinge-CH2-CH3 of human IgG4 with a S228P amino acid substitution. In some embodiments, the linker is a domain linker selected from the group consisting of (GS)n, (GSGGS)n, (GGGGS)n, and (GGGS)n, where n is selected from the group consisting of 1, 2, 3, 4, and 5. In some embodiments, the linker is GGGGS. In some embodiments, the domain linker is a combination of a hinge domain and a flexible linker, such as an IgG4 hinge with a S228P with a GGGGS linker as well.

In some embodiments, the sPD-1 variant—Fc fusion proteins of the present invention comprise a soluble PD-1 (sPD-1) variant domain comprising an amino acid substitution as compared to SEQ ID NO:1, wherein said amino acid substitution is at a position number selected from the group consisting of 42, 67, 69, 96, 104, 107, 112 and 120, and an Fc domain. In some embodiments, the sPD-1 variant—Fc fusion protein comprises from N- to C-terminal: a) said sPD-1 variant domain; and b) said Fc domain. In some embodiments, the sPD-1 variant—Fc fusion protein comprises from N- to C-terminal: a) said Fc domain; and b) said sPD-1 variant domain. In some embodiments, the Fc domain is the Fc domain of a human IgG selected from the group consisting of IgG1, IgG2, IgG3 and IgG4. In some embodiments, the Fc domain is a variant human IgG Fc domain, wherein the human IgG is selected from the group consisting of IgG1, IgG2, IgG3 and IgG4. In some embodiments, the variant human IgG Fc domain as disclosed herein comprises the hinge-CH2-CH3 of human IgG4 with a S228P amino acid substitution.

In some embodiments, the sPD-1 variant—Fc fusion protein of the present invention comprises: a) an sPD-1 variant domain comprising the amino acid substitution selected from the group consisting of S42G, 567G, P69L, N96S, G104S, S107V, A112I, and A120V as compared to SEQ ID NO:1; b) a linker; and c) an Fc domain. In some embodiments, the Fc domain is the Fc domain of a human IgG selected from the group consisting of IgG1, IgG2, IgG3 and IgG4. In some embodiments, the Fc domain is a variant human IgG Fc domain, wherein the human IgG is selected from the group consisting of IgG1, IgG2, IgG3 and IgG4. In some embodiments, the variant human IgG Fc domain as disclosed herein comprises the hinge-CH2-CH3 of human IgG4 with a S228P amino acid substitution. In some embodiments, the linker is a domain linker selected from the group consisting of (GS)n, (GSGGS)n, (GGGGS)n, and (GGGS)n, where n is selected from the group consisting of 1, 2, 3, 4, and 5. In some embodiments, the linker is GGGGS. In some embodiments, the domain linker is a combination of a hinge domain and a flexible linker, such as an IgG4 hinge with a S228P with a GGGGS linker as well.

In some embodiments, the sPD-1 variant—Fc fusion protein of the present invention comprises: an sPD-1 variant domain comprising the amino acid substitution selected from the group consisting of S42G, S67G, P69L, N96S, G104S, S107V, A112I, and A120V as compared to SEQ ID NO:1; and an Fc domain. In some embodiments, the Fc domain is the Fc domain of a human IgG selected from the group consisting of IgG1, IgG2, IgG3 and IgG4. In some embodiments, the Fc domain is a variant human IgG Fc domain, wherein the human IgG is selected from the group consisting of IgG1, IgG2, IgG3 and IgG4. In some embodiments, the variant human IgG Fc domain as disclosed herein comprises the hinge-CH2-CH3 of human IgG4 with a S228P amino acid substitution.

In some embodiments, the sPD-1 variant—Fc fusion protein of the present invention comprises: a) an sPD-1 variant domain comprising a set of amino acid substitutions of S42G/S67G/P69L/G104S/S107V/A112I/A120V, S42G/S67G/P69L/N96S/G104S/S107V/A112I/A120V, S42G/S67G, S42G/P69L, S42G/G104S, S42G/S107V, S42G/A112I, S42G/A120V, S67G/P69L, S67G/G104S, S67G/S107V, S67G/A112I, S67G/A120V, P69L/G104S, P69L/S107V, P69L/A112I, P69L/A120V, G104S/S107V, G104S/A112I, G104S/A120V, S107V/A112I, S107V/A120V, A112I/A120V, S42G/S67G/P69L, S42G/S67G/G104S, S42G/S67G/S107V, S42G/S67G/A112I, S42G/S67G/A120V, S42G/P69L/G104S, S42G/P69L/S107V, S42G/P69L/A112I, S42G/P69L/A120V, S42G/G104S/S107V, S42G/G104S/A112I, S42G/G104S/A120V, S42G/S107V/A112I, S42G/S107V/A120V, S42G/A112I/A120V, S67G/P69L/G104S, S67G/P69L/S107V, S67G/P69L/A112I, S67G/P69L/A120V, S67G/G104S/S107V, S67G/G104S/A112I, S67G/G104S/A120V, S67G/S107V/A112I, S67G/S107V/A120V, S67G/A112I/A120V, P69L/G104S/S107V, P69L/G104S/A112I, P69L/G104S/120V, P69L/S107V/A112I, P69L/S107V/120V, P69L/A112I/A120V, G104S/S107V/A112I, G104S/S107V/A120V, G104S/A112I/A120V, S107V/A112I/A120V, S42G/S67G/P69L/G104S, S42G/S67G/P69L/S107V, S42G/S67G/P69L/A112I, S42G/S67G/P69L/A120V, S42G/S67G/G104S/S107V, S42G/S67G/G104S/A112I, S42G/S67G/G104S/A120V, S42G/S67G/S107V/A112I, S42G/S67G/S107V/A120V, S42G/S67G/A112I/A120V, S42G/P69L/G104S/S107V, S42G/P69L/G104S/A112I, S42G/P69L/G104S/A120V, S42G/P69L/S107V/A112I, S42G/P69L/S107V/A120V, S42G/P69L/A112I/A120V, S42G/G104S/S107V/A112I, S42G/

G104S/S107V/A120V, S42G/G104S/A112I/A120V, S42G/ S107V/A112I/A120V, S67G/P69L/G104S/S107V, S67G/ P69L/G104S/A112I, S67G/P69L/G104S/A120V, S67G/ P69L/S107V/A112I, S67G/P69L/S107V/A120V, S67G/ P69L/A112I/A120V, S67G/G104S/S107V/A112I, S67G/ G104S/S107V/A120V, S67G/G104S/A112I/A120V, S67G/ S107V/A112I/A120V, P69L/G104S/S107V/A112I, P69L/ G104S/S107V/A120V, P69L/G104S/A112I/A120V, P69L/ S107V/A112I/A120V, G104S/S107V/A112I/A120V, S42G/ S67G/P69L/G104S/S107V, S42G/S67G/P69L/G104S/ A112I, S42G/S67G/P69L/G104S/A120V, S42G/S67G/ P69L/S107V/A112I, S42G/S67G/P69L/S107V/A120V, S42G/S67G/P69L/A112I/A120V, S42G/S67G/G104S/ S107V/A112I, S42G/S67G/G104S/S107V/A120V, S42G/ S67G/G104S/A112I/A120V, S42G/S67G/S107V/A112I/ A120V, S42G/P69L/G104S/S107V/A112I, S42G/P69L/ G104S/S107V/A120V, S42G/P69L/G104S/A112I/A120V, S42G/P69L/S107V/A112I/A120V, S42G/G104S/S107V/ A112I/A120V, S67G/P69L/G104S/S107V/A112I, S67G/ P69L/G104S/S107V/A120V, S67G/P69L/G104S/A112I/ A120V, S67G/P69L/S107V/A112I/A120V, S67G/G104S/ S107V/A112I/A120V, P69L/G104S/S107V/A112I/A120V, S42G/S67G/P69L/G104S/S107V/A112I, S42G/S67G/ P69L/G104S/S107V/A120V, S42G/S67G/P69L/G104S/ A112I/A120V, S42G/S67G/P69L/S107V/A112I/A120V, S42G/S67G/G104S/S107V/A112I/A120V, S42G/P69L/ G104S/S107V/A112I/A120V, and S67G/P69L/G104S/ S107V/A112I/A120V as compared to SEQ ID NO:1; b) an optional linker, and c) an Fc domain. In some embodiments, the Fc domain is the Fc domain of a human IgG selected from the group consisting of IgG1, IgG2, IgG3 and IgG4. In some embodiments, the Fc domain is a variant human IgG Fc domain, wherein the human IgG is selected from the group consisting of IgG1, IgG2, IgG3 and IgG4. In some embodiments, the variant human IgG Fc domain as disclosed herein comprises the hinge-CH2-CH3 of human IgG4 with a S228P amino acid substitution. In some embodiments, the linker is a domain linker selected from the group consisting of (GS)n, (GSGGS)n, (GGGGS)n, and (GGGS)n, where n is selected from the group consisting of 1, 2, 3, 4, and 5. In some embodiments, the linker is GGGGS. In some embodiments, the domain linker is a combination of a hinge domain and a flexible linker, such as an IgG4 hinge with a S228P with a GGGGS linker as well.

In some embodiments, the sPD-1 variant—Fc fusion protein of the present invention comprises an sPD-1 variant domain comprising a set of amino acid substitutions of S42G/S67G/P69L/G104S/S107V/A112I/A120V as compared to SEQ ID NO:1, an optional linker, and an Fc domain. In some embodiments, the Fc domain is the Fc domain of a human IgG selected from the group consisting of IgG1, IgG2, IgG3 and IgG4. In some embodiments, the Fc domain is a variant human IgG Fc domain, wherein the human IgG is selected from the group consisting of IgG1, IgG2, IgG3 and IgG4. In some embodiments, the variant human IgG Fc domain as disclosed herein comprises the hinge-CH2-CH3 of human IgG4 with a S228P amino acid substitution. In some embodiments, the linker is a domain linker selected from the group consisting of (GS)n, (GSGGS)n, (GGGGS)n, and (GGGS)n, where n is selected from the group consisting of 1, 2, 3, 4, and 5. In some embodiments, the linker is GGGGS. In some embodiments, the domain linker is a combination of a hinge domain and a flexible linker, such as an IgG4 hinge with a S228P with a GGGGS linker as well.

In some embodiments, the sPD-1 variant—Fc fusion protein of the present invention comprises an sPD-1 variant domain comprising a set of amino acid substitutions of S42G/S67G/P69L/N96G/G104S/S107V/A112I/A120V as compared to SEQ ID NO:1, an optional linker, and an Fc domain. In some embodiments, the Fc domain is the Fc domain of a human IgG selected from the group consisting of IgG1, IgG2, IgG3 and IgG4. In some embodiments, the Fc domain is a variant human IgG Fc domain, wherein the human IgG is selected from the group consisting of IgG1, IgG2, IgG3 and IgG4. In some embodiments, the variant human IgG Fc domain as disclosed herein comprises the hinge-CH2-CH3 of human IgG4 with a S228P amino acid substitution. In some embodiments, the linker is a domain linker selected from the group consisting of (GS)n, (GSGGS)n, (GGGGS)n, and (GGGS)n, where n is selected from the group consisting of 1, 2, 3, 4, and 5. In some embodiments, the linker is GGGGS. In some embodiments, the domain linker is a combination of a hinge domain and a flexible linker, such as an IgG4 hinge with a S228P with a GGGGS linker as well.

In some embodiments, the sPD-1 variant—Fc fusion protein of the present invention comprises an sPD-1 variant domain comprising a set of amino acid substitutions of P69L/G104S/S107V/A112I/A120V as compared to SEQ ID NO:1, an optional linker, and an Fc domain. In some embodiments, the Fc domain is the Fc domain of a human IgG selected from the group consisting of IgG1, IgG2, IgG3 and IgG4. In some embodiments, the Fc domain is a variant human IgG Fc domain, wherein the human IgG is selected from the group consisting of IgG1, IgG2, IgG3 and IgG4. In some embodiments, the variant human IgG Fc domain as disclosed herein comprises the hinge-CH2-CH3 of human IgG4 with a S228P amino acid substitution. In some embodiments, the linker is a domain linker selected from the group consisting of (GS)n, (GSGGS)n, (GGGGS)n, and (GGGS)n, where n is selected from the group consisting of 1, 2, 3, 4, and 5. In some embodiments, the linker is GGGGS. In some embodiments, the domain linker is a combination of a hinge domain and a flexible linker, such as an IgG4 hinge with a S228P with a GGGGS linker as well.

In some embodiments, the sPD-1 variant—Fc fusion protein of the present invention comprises an sPD-1 variant domain comprising a set of amino acid substitutions of S67G/G104S/S107V/A112I/A120V as compared to SEQ ID NO:1, an optional linker, and an Fc domain. In some embodiments, the Fc domain is the Fc domain of a human IgG selected from the group consisting of IgG1, IgG2, IgG3 and IgG4. In some embodiments, the Fc domain is a variant human IgG Fc domain, wherein the human IgG is selected from the group consisting of IgG1, IgG2, IgG3 and IgG4. In some embodiments, the variant human IgG Fc domain as disclosed herein comprises the hinge-CH2-CH3 of human IgG4 with a S228P amino acid substitution. In some embodiments, the linker is a domain linker selected from the group consisting of (GS)n, (GSGGS)n, (GGGGS)n, and (GGGS)n, where n is selected from the group consisting of 1, 2, 3, 4, and 5. In some embodiments, the linker is GGGGS. In some embodiments, the domain linker is a combination of a hinge domain and a flexible linker, such as an IgG4 hinge with a S228P with a GGGGS linker as well.

In some embodiments, the sPD-1 variant—Fc fusion protein of the present invention comprises an sPD-1 variant domain comprising a set of amino acid substitutions of S67G/P69L/G104S/S107V/A112I/A120V as compared to SEQ ID NO:1, an optional linker, and an Fc domain. In some embodiments, the Fc domain is the Fc domain of a human IgG selected from the group consisting of IgG1, IgG2, IgG3 and IgG4. In some embodiments, the Fc domain is a variant human IgG Fc domain, wherein the human IgG is selected from the group consisting of IgG1, IgG2, IgG3 and IgG4. In some embodiments, the variant human IgG Fc domain as disclosed herein comprises the hinge-CH2-CH3 of human IgG4 with a S228P amino acid substitution. In some embodiments, the linker is a domain linker selected from the group consisting of (GS)n, (GSGGS)n, (GGGGS)n, and (GGGS)n, where n is selected from the group consisting of 1, 2, 3, 4, and 5. In some embodiments, the linker is GGGGS. In some embodiments, the domain linker is a combination of a hinge domain and a flexible linker, such as an IgG4 hinge with a S228P with a GGGGS linker as well.

In some embodiments, the sPD-1 variant—Fc fusion protein of the present invention comprises an sPD-1 variant domain comprising a set of amino acid substitutions of G104S/S107V/A112I/A120V as compared to SEQ ID NO:1, an optional linker, and an Fc domain. In some embodiments, the Fc domain is the Fc domain of a human IgG selected from the group consisting of IgG1, IgG2, IgG3 and IgG4. In some embodiments, the Fc domain is a variant human IgG Fc domain, wherein the human IgG is selected from the group consisting of IgG1, IgG2, IgG3 and IgG4. In some embodiments, the variant human IgG Fc domain as disclosed herein comprises the hinge-CH2-CH3 of human IgG4 with a S228P amino acid substitution. In some embodiments, the linker is a domain linker selected from the group consisting of (GS)n, (GSGGS)n, (GGGGS)n, and (GGGS)n, where n is selected from the group consisting of 1, 2, 3, 4, and 5. In some embodiments, the linker is GGGGS. In some embodiments, the domain linker is a combination of a hinge domain and a flexible linker, such as an IgG4 hinge with a S228P with a GGGGS linker as well.

In some embodiments, the sPD-1 variant—Fc fusion protein of the present invention comprises an sPD-1 variant domain comprising a set of amino acid substitutions of G104S/S107V/A112I as compared to SEQ ID NO:1, an optional linker, and an Fc domain. In some embodiments, the Fc domain is the Fc domain of a human IgG selected from the group consisting of IgG1, IgG2, IgG3 and IgG4. In some embodiments, the Fc domain is a variant human IgG Fc domain, wherein the human IgG is selected from the group consisting of IgG1, IgG2, IgG3 and IgG4. In some embodiments, the variant human IgG Fc domain as disclosed herein comprises the hinge-CH2-CH3 of human IgG4 with a S228P amino acid substitution. In some embodiments, the linker is a domain linker selected from the group consisting of (GS)n, (GSGGS)n, (GGGGS)n, and (GGGS)n, where n is selected from the group consisting of 1, 2, 3, 4, and 5. In some embodiments, the linker is GGGGS. In some embodiments, the domain linker is a combination of a hinge domain and a flexible linker, such as an IgG4 hinge with a S228P with a GGGGS linker as well.

In some embodiments, the sPD-1 variant—Fc fusion protein of the present invention comprises an sPD-1 variant domain, an optional linker and an Fc domain, wherein the sPD-1 variant domain comprises an amino acid sequence selected from the group consisting of SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, and SEQ ID NO:139.

In some embodiments, the sPD-1 variant—Fc fusion protein of the present invention comprises an sPD-1 variant domain as set forth in SEQ ID NO:2, an optional linker and an Fc domain.

In some embodiments, the sPD-1 variant—Fc fusion protein of the present invention comprises an sPD-1 variant domain as set forth in SEQ ID NO:3, an optional linker and an Fc domain.

In some embodiments, the sPD-1 variant—Fc fusion protein of the present invention comprises an sPD-1 variant domain as set forth in SEQ ID NO:72, an optional linker and an Fc domain.

In some embodiments, the sPD-1 variant—Fc fusion protein of the present invention comprises an sPD-1 variant domain as set forth in SEQ ID NO:110, an optional linker and an Fc domain.

In some embodiments, the sPD-1 variant—Fc fusion protein of the present invention comprises an sPD-1 variant domain as set forth in SEQ ID NO:130, an optional linker and an Fc domain.

In some embodiments, the sPD-1 variant—Fc fusion protein of the present invention comprises an sPD-1 variant domain as set forth in SEQ ID NO:131, an optional linker and an Fc domain.

In some embodiments, the sPD-1 variant—Fc fusion protein of the present invention comprises an sPD-1 variant domain as set forth in SEQ ID NO:138, an optional linker and an Fc domain.

In some embodiments, the sPD-1 variant—Fc fusion protein of the present invention comprises an sPD-1 variant domain as set forth in SEQ ID NO:12, an optional linker and an Fc domain.

In some embodiments, the sPD-1 variant—Fc fusion protein of the present invention comprises an sPD-1 variant domain as set forth in SEQ ID NO:13, an optional linker and an Fc domain.

In some embodiments, the sPD-1 variant—Fc fusion protein of the present invention comprises an sPD-1 variant domain as set forth in SEQ ID NO:14, an optional linker and an Fc domain.

In some embodiments, the sPD-1 variant—Fc fusion protein of the present invention comprises an sPD-1 variant domain as set forth in SEQ ID NO:15, an optional linker and an Fc domain.

In some embodiments, the sPD-1 variant—Fc fusion protein of the present invention comprises an sPD-1 variant domain as set forth in SEQ ID NO:16, an optional linker and an Fc domain.

In some embodiments, the sPD-1 variant—Fc fusion protein of the present invention comprises an sPD-1 variant domain as set forth in SEQ ID NO:17, an optional linker and an Fc domain.

In some embodiments, the sPD-1 variant—Fc fusion protein of the present invention comprises an sPD-1 variant domain as set forth in SEQ ID NO:18, an optional linker and an Fc domain.

In some embodiments, the sPD-1 variant—Fc fusion protein of the present invention comprises an sPD-1 variant domain as set forth in SEQ ID NO:19, an optional linker and an Fc domain.

In some embodiments, the sPD-1 variant—Fc fusion protein of the present invention comprises an sPD-1 variant domain as set forth in SEQ ID NO:20, an optional linker and an Fc domain.

In some embodiments, the sPD-1 variant—Fc fusion protein of the present invention comprises an sPD-1 variant domain as set forth in SEQ ID NO:21, an optional linker and an Fc domain.

In some embodiments, the sPD-1 variant—Fc fusion protein of the present invention comprises an sPD-1 variant domain as set forth in SEQ ID NO:22, an optional linker and an Fc domain.

In some embodiments, the sPD-1 variant—Fc fusion protein of the present invention comprises an sPD-1 variant domain as set forth in SEQ ID NO:23, an optional linker and an Fc domain.

In some embodiments, the sPD-1 variant—Fc fusion protein of the present invention comprises an sPD-1 variant domain as set forth in SEQ ID NO:24, an optional linker and an Fc domain.

In some embodiments, the sPD-1 variant—Fc fusion protein of the present invention comprises an sPD-1 variant domain as set forth in SEQ ID NO:25, an optional linker and an Fc domain.

In some embodiments, the sPD-1 variant—Fc fusion protein of the present invention comprises an sPD-1 variant domain as set forth in SEQ ID NO:26, an optional linker and an Fc domain.

In some embodiments, the sPD-1 variant—Fc fusion protein of the present invention comprises an sPD-1 variant domain as set forth in SEQ ID NO:27, an optional linker and an Fc domain.

In some embodiments, the sPD-1 variant—Fc fusion protein of the present invention comprises an sPD-1 variant domain as set forth in SEQ ID NO:28, an optional linker and an Fc domain.

In some embodiments, the sPD-1 variant—Fc fusion protein of the present invention comprises an sPD-1 variant domain as set forth in SEQ ID NO:29, an optional linker and an Fc domain.

In some embodiments, the sPD-1 variant—Fc fusion protein of the present invention comprises an sPD-1 variant domain as set forth in SEQ ID NO:30, an optional linker and an Fc domain.

In some embodiments, the sPD-1 variant—Fc fusion protein of the present invention comprises an sPD-1 variant domain as set forth in SEQ ID NO:31, an optional linker and an Fc domain.

In some embodiments, the sPD-1 variant—Fc fusion protein of the present invention comprises an sPD-1 variant domain as set forth in SEQ ID NO:32, an optional linker and an Fc domain.

In some embodiments, the sPD-1 variant—Fc fusion protein of the present invention comprises an sPD-1 variant domain as set forth in SEQ ID NO:33, an optional linker and an Fc domain.

In some embodiments, the sPD-1 variant—Fc fusion protein of the present invention comprises an sPD-1 variant domain as set forth in SEQ ID NO:34, an optional linker and an Fc domain.

In some embodiments, the sPD-1 variant—Fc fusion protein of the present invention comprises an sPD-1 variant domain as set forth in SEQ ID NO:35, an optional linker and an Fc domain.

In some embodiments, the sPD-1 variant—Fc fusion protein of the present invention comprises an sPD-1 variant domain as set forth in SEQ ID NO:36, an optional linker and an Fc domain.

In some embodiments, the sPD-1 variant—Fc fusion protein of the present invention comprises an sPD-1 variant domain as set forth in SEQ ID NO:37, an optional linker and an Fc domain.

In some embodiments, the sPD-1 variant—Fc fusion protein of the present invention comprises an sPD-1 variant domain as set forth in SEQ ID NO:38, an optional linker and an Fc domain.

In some embodiments, the sPD-1 variant—Fc fusion protein of the present invention comprises an sPD-1 variant domain as set forth in SEQ ID NO:39, an optional linker and an Fc domain.

In some embodiments, the sPD-1 variant—Fc fusion protein of the present invention comprises an sPD-1 variant domain as set forth in SEQ ID NO:40, an optional linker and an Fc domain.

In some embodiments, the sPD-1 variant—Fc fusion protein of the present invention comprises an sPD-1 variant domain as set forth in SEQ ID NO:41, an optional linker and an Fc domain.

In some embodiments, the sPD-1 variant—Fc fusion protein of the present invention comprises an sPD-1 variant domain as set forth in SEQ ID NO:42, an optional linker and an Fc domain.

In some embodiments, the sPD-1 variant—Fc fusion protein of the present invention comprises an sPD-1 variant domain as set forth in SEQ ID NO:43, an optional linker and an Fc domain.

In some embodiments, the sPD-1 variant—Fc fusion protein of the present invention comprises an sPD-1 variant domain as set forth in SEQ ID NO:44, an optional linker and an Fc domain.

In some embodiments, the sPD-1 variant—Fc fusion protein of the present invention comprises an sPD-1 variant domain as set forth in SEQ ID NO:45, an optional linker and an Fc domain.

In some embodiments, the sPD-1 variant—Fc fusion protein of the present invention comprises an sPD-1 variant domain as set forth in SEQ ID NO:46, an optional linker and an Fc domain.

In some embodiments, the sPD-1 variant—Fc fusion protein of the present invention comprises an sPD-1 variant domain as set forth in SEQ ID NO:47, an optional linker and an Fc domain.

In some embodiments, the sPD-1 variant—Fc fusion protein of the present invention comprises an sPD-1 variant domain as set forth in SEQ ID NO:48, an optional linker and an Fc domain.

In some embodiments, the sPD-1 variant—Fc fusion protein of the present invention comprises an sPD-1 variant domain as set forth in SEQ ID NO:49, an optional linker and an Fc domain.

In some embodiments, the sPD-1 variant—Fc fusion protein of the present invention comprises an sPD-1 variant domain as set forth in SEQ ID NO:50, an optional linker and an Fc domain.

In some embodiments, the sPD-1 variant—Fc fusion protein of the present invention comprises an sPD-1 variant domain as set forth in SEQ ID NO:51, an optional linker and an Fc domain.

In some embodiments, the sPD-1 variant—Fc fusion protein of the present invention comprises an sPD-1 variant domain as set forth in SEQ ID NO:52, an optional linker and an Fc domain.

In some embodiments, the sPD-1 variant—Fc fusion protein of the present invention comprises an sPD-1 variant domain as set forth in SEQ ID NO:53, an optional linker and an Fc domain.

In some embodiments, the sPD-1 variant—Fc fusion protein of the present invention comprises an sPD-1 variant domain as set forth in SEQ ID NO:54, an optional linker and an Fc domain.

In some embodiments, the sPD-1 variant—Fc fusion protein of the present invention comprises an sPD-1 variant domain as set forth in SEQ ID NO:55, an optional linker and an Fc domain.

In some embodiments, the sPD-1 variant—Fc fusion protein of the present invention comprises an sPD-1 variant domain as set forth in SEQ ID NO:56, an optional linker and an Fc domain.

In some embodiments, the sPD-1 variant—Fc fusion protein of the present invention comprises an sPD-1 variant domain as set forth in SEQ ID NO:57, an optional linker and an Fc domain.

In some embodiments, the sPD-1 variant—Fc fusion protein of the present invention comprises an sPD-1 variant domain as set forth in SEQ ID NO:58, an optional linker and an Fc domain.

In some embodiments, the sPD-1 variant—Fc fusion protein of the present invention comprises an sPD-1 variant domain as set forth in SEQ ID NO:59, an optional linker and an Fc domain.

In some embodiments, the sPD-1 variant—Fc fusion protein of the present invention comprises an sPD-1 variant domain as set forth in SEQ ID NO:60, an optional linker and an Fc domain.

In some embodiments, the sPD-1 variant—Fc fusion protein of the present invention comprises an sPD-1 variant domain as set forth in SEQ ID NO:61, an optional linker and an Fc domain.

In some embodiments, the sPD-1 variant—Fc fusion protein of the present invention comprises an sPD-1 variant domain as set forth in SEQ ID NO:62, an optional linker and an Fc domain.

In some embodiments, the sPD-1 variant—Fc fusion protein of the present invention comprises an sPD-1 variant domain as set forth in SEQ ID NO:63, an optional linker and an Fc domain.

In some embodiments, the sPD-1 variant—Fc fusion protein of the present invention comprises an sPD-1 variant domain as set forth in SEQ ID NO:64, an optional linker and an Fc domain.

In some embodiments, the sPD-1 variant—Fc fusion protein of the present invention comprises an sPD-1 variant domain as set forth in SEQ ID NO:65, an optional linker and an Fc domain.

In some embodiments, the sPD-1 variant—Fc fusion protein of the present invention comprises an sPD-1 variant domain as set forth in SEQ ID NO:66, an optional linker and an Fc domain.

In some embodiments, the sPD-1 variant—Fc fusion protein of the present invention comprises an sPD-1 variant domain as set forth in SEQ ID NO:67, an optional linker and an Fc domain.

In some embodiments, the sPD-1 variant—Fc fusion protein of the present invention comprises an sPD-1 variant domain as set forth in SEQ ID NO:68, an optional linker and an Fc domain.

In some embodiments, the sPD-1 variant—Fc fusion protein of the present invention comprises an sPD-1 variant domain as set forth in SEQ ID NO:69, an optional linker and an Fc domain.

In some embodiments, the sPD-1 variant—Fc fusion protein of the present invention comprises an sPD-1 variant domain as set forth in SEQ ID NO:70, an optional linker and an Fc domain.

In some embodiments, the sPD-1 variant—Fc fusion protein of the present invention comprises an sPD-1 variant domain as set forth in SEQ ID NO:71, an optional linker and an Fc domain.

In some embodiments, the sPD-1 variant—Fc fusion protein of the present invention comprises an sPD-1 variant domain as set forth in SEQ ID NO:73, an optional linker and an Fc domain.

In some embodiments, the sPD-1 variant—Fc fusion protein of the present invention comprises an sPD-1 variant domain as set forth in SEQ ID NO:74, an optional linker and an Fc domain.

In some embodiments, the sPD-1 variant—Fc fusion protein of the present invention comprises an sPD-1 variant domain as set forth in SEQ ID NO:75, an optional linker and an Fc domain.

In some embodiments, the sPD-1 variant—Fc fusion protein of the present invention comprises an sPD-1 variant domain as set forth in SEQ ID NO:76, an optional linker and an Fc domain.

In some embodiments, the sPD-1 variant—Fc fusion protein of the present invention comprises an sPD-1 variant domain as set forth in SEQ ID NO:77, an optional linker and an Fc domain.

In some embodiments, the sPD-1 variant—Fc fusion protein of the present invention comprises an sPD-1 variant domain as set forth in SEQ ID NO:78, an optional linker and an Fc domain.

In some embodiments, the sPD-1 variant—Fc fusion protein of the present invention comprises an sPD-1 variant domain as set forth in SEQ ID NO:79, an optional linker and an Fc domain.

In some embodiments, the sPD-1 variant—Fc fusion protein of the present invention comprises an sPD-1 variant domain as set forth in SEQ ID NO:80, an optional linker and an Fc domain.

In some embodiments, the sPD-1 variant—Fc fusion protein of the present invention comprises an sPD-1 variant domain as set forth in SEQ ID NO:81, an optional linker and an Fc domain.

In some embodiments, the sPD-1 variant—Fc fusion protein of the present invention comprises an sPD-1 variant domain as set forth in SEQ ID NO:82, an optional linker and an Fc domain.

In some embodiments, the sPD-1 variant—Fc fusion protein of the present invention comprises an sPD-1 variant domain as set forth in SEQ ID NO:83, an optional linker and an Fc domain.

In some embodiments, the sPD-1 variant—Fc fusion protein of the present invention comprises an sPD-1 variant domain as set forth in SEQ ID NO:84, an optional linker and an Fc domain.

In some embodiments, the sPD-1 variant—Fc fusion protein of the present invention comprises an sPD-1 variant domain as set forth in SEQ ID NO:85, an optional linker and an Fc domain.

In some embodiments, the sPD-1 variant—Fc fusion protein of the present invention comprises an sPD-1 variant domain as set forth in SEQ ID NO:86, an optional linker and an Fc domain.

In some embodiments, the sPD-1 variant—Fc fusion protein of the present invention comprises an sPD-1 variant domain as set forth in SEQ ID NO:87, an optional linker and an Fc domain.

In some embodiments, the sPD-1 variant—Fc fusion protein of the present invention comprises an sPD-1 variant domain as set forth in SEQ ID NO:88, an optional linker and an Fc domain.

In some embodiments, the sPD-1 variant—Fc fusion protein of the present invention comprises an sPD-1 variant domain as set forth in SEQ ID NO:89, an optional linker and an Fc domain.

In some embodiments, the sPD-1 variant—Fc fusion protein of the present invention comprises an sPD-1 variant domain as set forth in SEQ ID NO:90, an optional linker and an Fc domain.

In some embodiments, the sPD-1 variant—Fc fusion protein of the present invention comprises an sPD-1 variant domain as set forth in SEQ ID NO:91, an optional linker and an Fc domain.

In some embodiments, the sPD-1 variant—Fc fusion protein of the present invention comprises an sPD-1 variant domain as set forth in SEQ ID NO:92, an optional linker and an Fc domain.

In some embodiments, the sPD-1 variant—Fc fusion protein of the present invention comprises an sPD-1 variant domain as set forth in SEQ ID NO:93, an optional linker and an Fc domain.

In some embodiments, the sPD-1 variant—Fc fusion protein of the present invention comprises an sPD-1 variant domain as set forth in SEQ ID NO:94, an optional linker and an Fc domain.

In some embodiments, the sPD-1 variant—Fc fusion protein of the present invention comprises an sPD-1 variant domain as set forth in SEQ ID NO:95, an optional linker and an Fc domain.

In some embodiments, the sPD-1 variant—Fc fusion protein of the present invention comprises an sPD-1 variant domain as set forth in SEQ ID NO:96, an optional linker and an Fc domain.

In some embodiments, the sPD-1 variant—Fc fusion protein of the present invention comprises an sPD-1 variant domain as set forth in SEQ ID NO:97, an optional linker and an Fc domain.

In some embodiments, the sPD-1 variant—Fc fusion protein of the present invention comprises an sPD-1 variant domain as set forth in SEQ ID NO:98, an optional linker and an Fc domain.

In some embodiments, the sPD-1 variant—Fc fusion protein of the present invention comprises an sPD-1 variant domain as set forth in SEQ ID NO:99, an optional linker and an Fc domain.

In some embodiments, the sPD-1 variant—Fc fusion protein of the present invention comprises an sPD-1 variant domain as set forth in SEQ ID NO:100, an optional linker and an Fc domain.

In some embodiments, the sPD-1 variant—Fc fusion protein of the present invention comprises an sPD-1 variant domain as set forth in SEQ ID NO:101, an optional linker and an Fc domain.

In some embodiments, the sPD-1 variant—Fc fusion protein of the present invention comprises an sPD-1 variant domain as set forth in SEQ ID NO:102, an optional linker and an Fc domain.

In some embodiments, the sPD-1 variant—Fc fusion protein of the present invention comprises an sPD-1 variant domain as set forth in SEQ ID NO:103, an optional linker and an Fc domain.

In some embodiments, the sPD-1 variant—Fc fusion protein of the present invention comprises an sPD-1 variant domain as set forth in SEQ ID NO:104, an optional linker and an Fc domain.

In some embodiments, the sPD-1 variant—Fc fusion protein of the present invention comprises an sPD-1 variant domain as set forth in SEQ ID NO:105, an optional linker and an Fc domain.

In some embodiments, the sPD-1 variant—Fc fusion protein of the present invention comprises an sPD-1 variant domain as set forth in SEQ ID NO:106, an optional linker and an Fc domain.

In some embodiments, the sPD-1 variant—Fc fusion protein of the present invention comprises an sPD-1 variant domain as set forth in SEQ ID NO:107, an optional linker and an Fc domain.

In some embodiments, the sPD-1 variant—Fc fusion protein of the present invention comprises an sPD-1 variant domain as set forth in SEQ ID NO:108, an optional linker and an Fc domain.

In some embodiments, the sPD-1 variant—Fc fusion protein of the present invention comprises an sPD-1 variant domain as set forth in SEQ ID NO:109, an optional linker and an Fc domain.

In some embodiments, the sPD-1 variant—Fc fusion protein of the present invention comprises an sPD-1 variant domain as set forth in SEQ ID NO:111, an optional linker and an Fc domain.

In some embodiments, the sPD-1 variant—Fc fusion protein of the present invention comprises an sPD-1 variant domain as set forth in SEQ ID NO:112, an optional linker and an Fc domain.

In some embodiments, the sPD-1 variant—Fc fusion protein of the present invention comprises an sPD-1 variant domain as set forth in SEQ ID NO:113, an optional linker and an Fc domain.

In some embodiments, the sPD-1 variant—Fc fusion protein of the present invention comprises an sPD-1 variant domain as set forth in SEQ ID NO:114, an optional linker and an Fc domain.

In some embodiments, the sPD-1 variant—Fc fusion protein of the present invention comprises an sPD-1 variant domain as set forth in SEQ ID NO:115, an optional linker and an Fc domain.

In some embodiments, the sPD-1 variant—Fc fusion protein of the present invention comprises an sPD-1 variant domain as set forth in SEQ ID NO:116, an optional linker and an Fc domain.

In some embodiments, the sPD-1 variant—Fc fusion protein of the present invention comprises an sPD-1 variant domain as set forth in SEQ ID NO:117, an optional linker and an Fc domain.

In some embodiments, the sPD-1 variant—Fc fusion protein of the present invention comprises an sPD-1 variant domain as set forth in SEQ ID NO:118, an optional linker and an Fc domain.

In some embodiments, the sPD-1 variant—Fc fusion protein of the present invention comprises an sPD-1 variant domain as set forth in SEQ ID NO:119, an optional linker and an Fc domain.

In some embodiments, the sPD-1 variant—Fc fusion protein of the present invention comprises an sPD-1 variant domain as set forth in SEQ ID NO:120, an optional linker and an Fc domain.

In some embodiments, the sPD-1 variant—Fc fusion protein of the present invention comprises an sPD-1 variant domain as set forth in SEQ ID NO:121, an optional linker and an Fc domain.

In some embodiments, the sPD-1 variant—Fc fusion protein of the present invention comprises an sPD-1 variant domain as set forth in SEQ ID NO:122, an optional linker and an Fc domain.

In some embodiments, the sPD-1 variant—Fc fusion protein of the present invention comprises an sPD-1 variant domain as set forth in SEQ ID NO:123, an optional linker and an Fc domain.

In some embodiments, the sPD-1 variant—Fc fusion protein of the present invention comprises an sPD-1 variant domain as set forth in SEQ ID NO:124, an optional linker and an Fc domain.

In some embodiments, the sPD-1 variant—Fc fusion protein of the present invention comprises an sPD-1 variant domain as set forth in SEQ ID NO:125, an optional linker and an Fc domain.

In some embodiments, the sPD-1 variant—Fc fusion protein of the present invention comprises an sPD-1 variant domain as set forth in SEQ ID NO:126, an optional linker and an Fc domain.

In some embodiments, the sPD-1 variant—Fc fusion protein of the present invention comprises an sPD-1 variant domain as set forth in SEQ ID NO:127, an optional linker and an Fc domain.

In some embodiments, the sPD-1 variant—Fc fusion protein of the present invention comprises an sPD-1 variant domain as set forth in SEQ ID NO:128, an optional linker and an Fc domain.

In some embodiments, the sPD-1 variant—Fc fusion protein of the present invention comprises an sPD-1 variant domain as set forth in SEQ ID NO:129, an optional linker and an Fc domain.

In some embodiments, the sPD-1 variant—Fc fusion protein of the present invention comprises an sPD-1 variant domain as set forth in SEQ ID NO:132, an optional linker and an Fc domain.

In some embodiments, the sPD-1 variant—Fc fusion protein of the present invention comprises an sPD-1 variant domain as set forth in SEQ ID NO:133, an optional linker and an Fc domain.

In some embodiments, the sPD-1 variant—Fc fusion protein of the present invention comprises an sPD-1 variant domain as set forth in SEQ ID NO:134, an optional linker and an Fc domain.

In some embodiments, the sPD-1 variant—Fc fusion protein of the present invention comprises an sPD-1 variant domain as set forth in SEQ ID NO:135, an optional linker and an Fc domain.

In some embodiments, the sPD-1 variant—Fc fusion protein of the present invention comprises an sPD-1 variant domain as set forth in SEQ ID NO:136, an optional linker and an Fc domain.

In some embodiments, the sPD-1 variant—Fc fusion protein of the present invention comprises an sPD-1 variant domain as set forth in SEQ ID NO:137, an optional linker and an Fc domain.

In some embodiments, the sPD-1 variant—Fc fusion protein of the present invention comprises an sPD-1 variant domain as set forth in SEQ ID NO:139, an optional linker and an Fc domain.

In some embodiments, the sPD-1 variant—Fc fusion protein of the present invention comprises a human IgG Fc domain or a variant human IgG Fc domain.

In a preferred embodiment, the sPD-1 variant—Fc fusion protein of the present invention comprises a variant human IgG Fc domain.

In some embodiments, the sPD-1 variant—Fc fusion protein of the present invention comprises a human IgG Fc domain comprising the hinge-CH2-CH3 of human IgG4.

In some embodiments, the sPD-1 variant—Fc fusion protein of the present invention comprises a human IgG Fc domain comprising the CH2-CH3 of human IgG4.

In a preferred embodiment, the sPD-1 variant—Fc fusion protein of the present invention comprises a variant human IgG Fc domain comprising the hinge-CH2-CH3 of human IgG4 with a S228P amino acid substitution according to the EU numbering index.

In some embodiments, the sPD-1 variant—Fc fusion protein of the present invention comprises a linker which is selected from the group consisting of (GS)n, (GSGGS)n, (GGGGS)n, and (GGGS)n, where n is selected from the group consisting of 1, 2, 3, 4 and 5.

In a preferred embodiment, the sPD-1 variant—Fc fusion protein of the present invention comprises a linker of GGGGS.

In some embodiments, the sPD-1 variant—Fc fusion protein of the present invention has amino acid sequence as set forth in SEQ ID NO:5.

In some embodiments, the sPD-1 variant—Fc fusion protein of the present invention has amino acid sequence as set forth in SEQ ID NO:6.

In some embodiments, the sPD-1 variant—Fc fusion protein of the present invention has a binding affinity for a PD-1 ligand that is at least about 1.1-fold or more (e.g., 5-fold or more, 10-fold or more, 100-fold or more, 500-fold or more, 1000-fold or more, 5000-fold or more, 10000-fold or more etc.) than that of a parent Fc fusion protein (e.g. the WT PD-1—Fc fusion protein as set forth in SEQ ID NO:4).

In some embodiments, the sPD-1 variant—Fc fusion protein of the present invention has a binding affinity for a PD-1 ligand that is at least about 100-fold stronger than that of a parent fusion protein.

In some embodiments, the sPD-1 variant—Fc fusion protein of the present invention has a binding affinity for a PD-1 ligand that is at least about 200-fold stronger than that of a parent fusion protein.

In some embodiments, the sPD-1 variant—Fc fusion protein of the present invention has a binding affinity for a PD-1 ligand that is at least about 10,000-fold stronger than that of a parent fusion protein.

In some embodiments, the sPD-1 variant—Fc fusion protein of the present invention has a binding affinity for a PD-1 ligand with a KD of $10^{-8}$M or a greater affinity, where the affinity is measured by a standard Biacore assay.

In some embodiments, the sPD-1 variant—Fc fusion protein of the present invention inhibits or prevents binding between a wild-type PD-1 polypeptide and a PD-1 ligand in vitro or in vivo.

The sPD-1 variant domain of the sPD-1 variant—Fc fusion protein serves to increase the binding affinity for PD-L1 and/or PD-L2. The (variant) Fc domain of a human IgG protein significantly increases the half-life of the fusion protein. The fusion proteins of the invention are particular useful for treating a disease or disorder in which the adaptive immune system is suppressed or an increase in the magnitude of level of immune response is needed. In some embodiments, the sPD-1 variant—Fc fusion proteins of the invention can be used to treat cancer or infections.

D. Nucleic Acids

The present invention also provides compositions comprising an sPD-1 variant—Fc fusion protein encoding nucleic acid of the present invention. Such nucleic acids can encode any of the sPD-1 variant—Fc fusion proteins recited in the present application.

The nucleic acids of the present invention may be isolated and obtained in substantial purity. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome.

In some embodiments, the composition comprises a nucleic acid encoding the sPD-1 variant—Fc fusion protein of SEQ ID NO:5. In some embodiments, the composition comprises a nucleic acid encoding the sPD-1 variant—Fc fusion protein of SEQ ID NO:6.

In some embodiments, the nucleic acid encodes the sPD-1 variant-Fc fusion protein including a signal sequence. As is known in the art, signal sequences are used to direct the expression product to the exterior of the cell. In this case, suitable signal sequences for the expression of the fusion proteins of the invention are the signal sequences of wild-type PD-1 as shown in FIG. 1 in italics and in SEQ ID NO:7 of Table 1. As will be appreciated by those in the art, suitable signal sequences for expression of the fusion proteins of the invention can be "matched" to the host cell used for expression. That is, when the fusion proteins of the invention are to be expressed in mammalian host cells such as CHO cells, for example, signal sequences from CHO cells can be used.

In some embodiments, the composition comprises a nucleic acid encoding the sPD-1 variant—Fc fusion protein of SEQ ID NO:9. In some embodiments, the composition comprises a nucleic acid encoding the sPD-1 variant—Fc fusion protein of SEQ ID NO:10.

In some embodiments, the composition comprises a nucleic acid encoding the sPD-1 variant—Fc fusion protein comprising an amino acid sequence selected from the group consisting of SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, and SEQ ID NO:139.

In some embodiments, the sPD-1 variant—Fc fusion protein encoding nucleic acid comprises a codon optimized version or variant.

"Codon optimized" in this context is done in relation to a particular host organism and its generally preferred amino acid codons; that is, the host production organism, e.g. an *Aspergillus* species, may yield higher translation and/or secretion using *Aspergillus* preferred codons as compared to a yeast production organism.

Codon optimization can be employed with any of the sPD-1 variant—Fc fusion protein of the present invention, in order to optimize expression in the host cell employed.

The sPD-1 variant—Fc fusion protein can be prepared generally by construction genes encoding the fusion protein sequence using well known techniques, including site-directed mutagenesis of a parental gene and synthetic gene construction.

Expression of the nucleic acids of the present invention can be regulated by their own or by other regulatory sequences known in the art.

1. Regulatory Sequences

The present invention also relates to nucleic acid constructs comprising a polynucleotide encoding the sPD-1 variant—Fc fusion protein of the present invention operably linked to one or more control sequences that direct the expression of the coding sequence in a suitable host cell under conditions compatible with the control sequences. The control sequence may include a promoter, a polynucleotide which is recognized by a host cell for expression of the polynucleotide. The promoter contains transcriptional control sequences that mediate the expression of the Fc fusion protein. The promoter may be any polynucleotide that shows transcriptional activity in the host cell including mutant, truncated, and hybrid promoters, and may be obtained from genes encoding extracellular or intracellular polypeptides either homologous or heterologous to the host cell.

In some embodiments, the control sequence may also be a signal peptide coding region that encodes a signal peptide linked to the N-terminus of a variant and directs the variant phytase being expressed into the cell's secretory pathway. The 5'-end of the coding sequence of the polynucleotide may inherently contain a signal peptide coding sequence naturally linked in translation reading frame with the segment of the coding sequence that encodes the variant phytase. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant phytase. However, any signal peptide coding sequence that directs the expressed variant into the secretory pathway of a host cell may be used.

E. Expression Vectors

Also provided herein are expression vectors for in vitro or in vivo expression of one or more sPD-1 variant—Fc fusion proteins of the present invention, either constitutively or under one or more regulatory elements. In some embodiments, the present invention relates to expression vectors comprising a polynucleotide encoding the sPD-1 variant—Fc fusion protein, a promoter, and transcriptional and translational stop signals. The various nucleotide and control sequences may be joined together to produce a recombinant expression vector that may include one or more convenient restriction sites to allow for insertion or substitution of the polynucleotide encoding the Fc fusion protein at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector can be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used. Vectors contemplated for use with the methods of the invention include both integrating and non-integrating vectors.

F. Host Cells and Production Strains

As will be appreciated by those in the art, there are a wide variety of production host organisms for the recombinant production of the variant sPD-1 variant—Fc fusion proteins of the invention, including, but not limited to bacterial cells, mammalian cells and fungal cells including yeast.

The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

G. Methods of Making the Fusion Proteins

The present invention also relates to methods of making a sPD-1 variant—Fc fusion protein, comprising: (a) cultivating a host cell of the present invention under conditions suitable for expression of the sPD-1 variant—Fc fusion protein; and (b) optionally recovering the sPD-1 variant—Fc fusion protein.

H. Methods of Treatment

1. Subjects Amenable to Treatment

The increased T cell response achieved as a result of the use of the sPD-1 variant—Fc fusion protein of the invention is sufficient to treat a disease or disorder, including but not limited to cancer, viral infection, bacterial infection, fungal infection and parasitic infection.

The methods of the present invention include administering to a subject in need of treatment a therapeutically effective amount of one or more sPD-1 variant—Fc fusion proteins described herein. In some embodiments, the subject has cancer and administration of a therapeutically effective amount of one or more sPD-1 variant—Fc fusion proteins can treat, reduce or prevent metastasis or invasion of a tumor in the subject. In other embodiments, the sPD-1 variant—Fc fusion protein(s) of the present invention can reduce or inhibit the growth of a solid tumor in a subject with cancer.

In some embodiments, a subject having an infection, e.g., a local or systemic infection, is administered of a therapeutically effective amount of one or more sPD-1 variant—Fc fusion proteins described herein to treat the infection. In other embodiments, the subject has chronic infectious disease caused by a bacterium, virus, protozoan, parasite, or other microbial pathogen.

2. Therapeutic Administration

In certain embodiments, a therapeutically effective composition or formulation comprising one or more sPD-1 variant—Fc fusion proteins of the invention may be administered systemically to the individual in need thereof or via any other route of administration known in the art.

3. Dosing

In some embodiments, an effective dose of the therapeutic entity of the present invention, e.g. for the treatment of metastatic cancer or infection, varies depending upon many different factors, including means of administration, target site, physiological state of the patient, whether the patient is human or an animal, other medications administered, and whether treatment is prophylactic or therapeutic. Treatment dosages can be titrated to optimize safety and efficacy.

VII. EXAMPLES

A. EXAMPLE 1: Modeling of sPD1 Variant with Human PDL1 and PDL2 Complexes

1. Methods

Human PD-1/PD-L1 complex structure is available in Protein Data Bank, the PDBID is 4ZQK and 5IUS. However, in both of the PDB structures, some residues of PD-1 are missing in a loop area, and some of the residues were mutated comparing with wild type PD-1. To better investigate the influence of mutations on binding affinity and protein stability, the missing loop was first fixed and the residue was mutated back to the wild type PD-1 based on crystal structure 4ZQK. The mutated PD-1 structure was modeled using Residue Scanning module in Schrodinger Suite. The residues within 5.0 Å of the mutated residue were refined with side-chain prediction and backbone sampling. The protein interaction analysis was performed for both WT PD-1/PD-L1 complex structure and sPD-1 variant/PD-L1 complex structure. Three PD-1/PD-L1 complex models, WT model, model with 3 interface mutations, model with all 8 mutations, were submitted to 10 ns Molecular Dynamics (MD) simulation using OPLS3 force-field for further refinement and optimization. Each complex was solvated in a periodic, orthorhombic box with SPC water as the solvent. The minimum distance from any complex atom to the box wall was set to 10 Å. Three MD simulations were all carried out at a constant temperature of 300 K and a constant pressure of 1 atm. Trajectory coordinates stored at 1 ps intervals were used for analysis.

Since human PD-L2 structure is not available in Protein Data Bank, the homology model of PD-L2 was built to investigate the interaction between human PD-1 and PD-L2. After homology search in PDB non-redundant data set, three PDB structures of mouse PD-L2 were chosen to be templates. As described previously, the protein interaction analysis was also performed for WT and sPD-1 variant/PD-L2 model.

2. Modeling of Human PD-1/PD-L1 Complex

Figure 2:
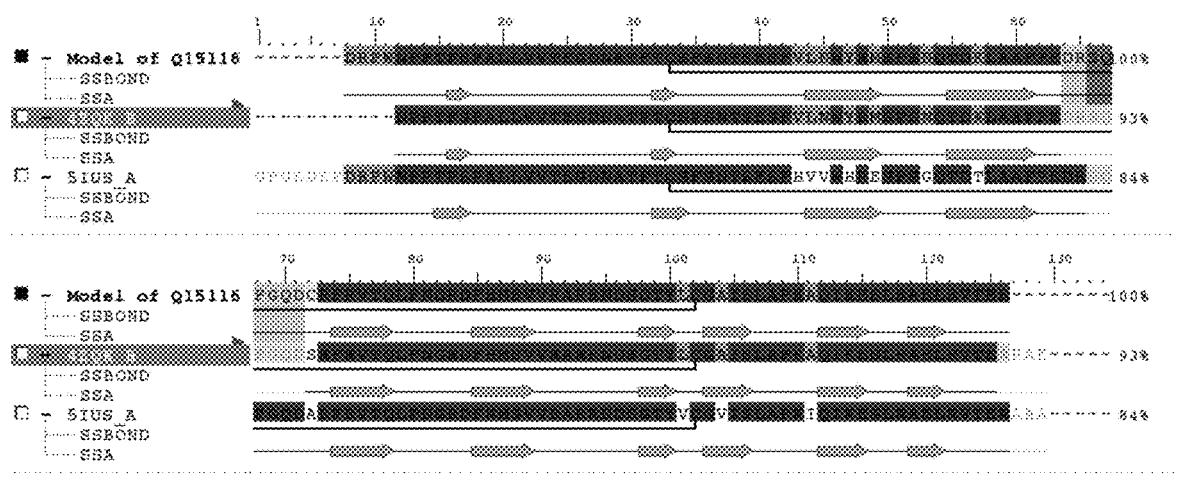

Sequence alignment result of WT PD-1, 4ZQK and 5IUS is show in FIG. 2. The identical residues are marked in blue, the residues missing in both crystal structures are marked in red, residues missing only in 4ZQK are marked in cyan.

Figure 3:
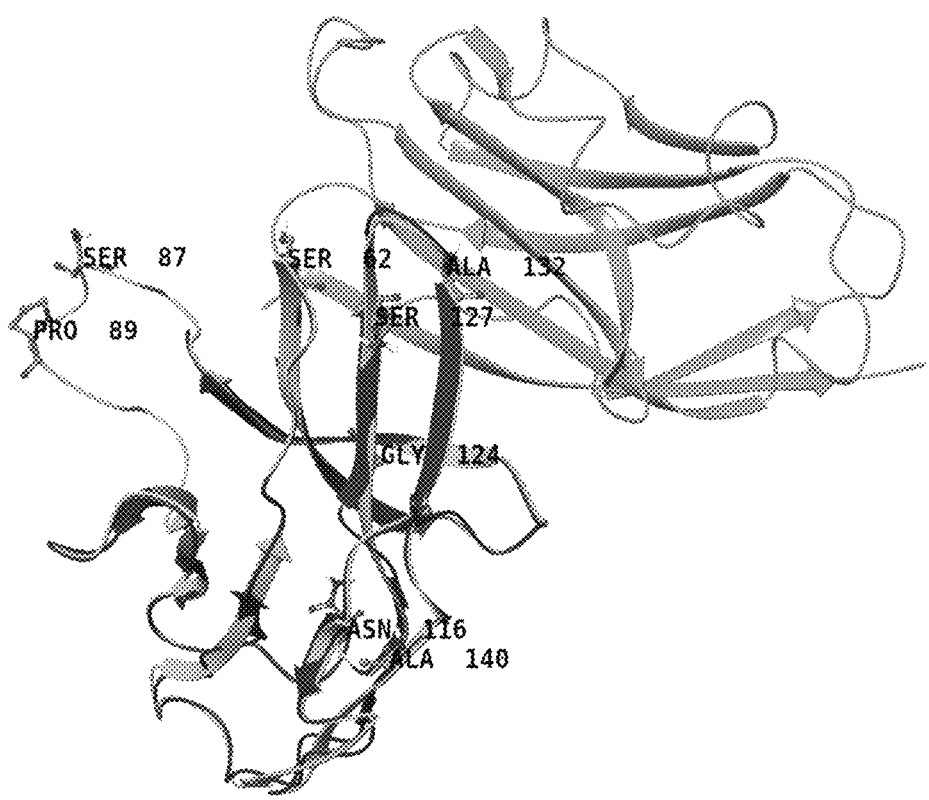
Figure 4:
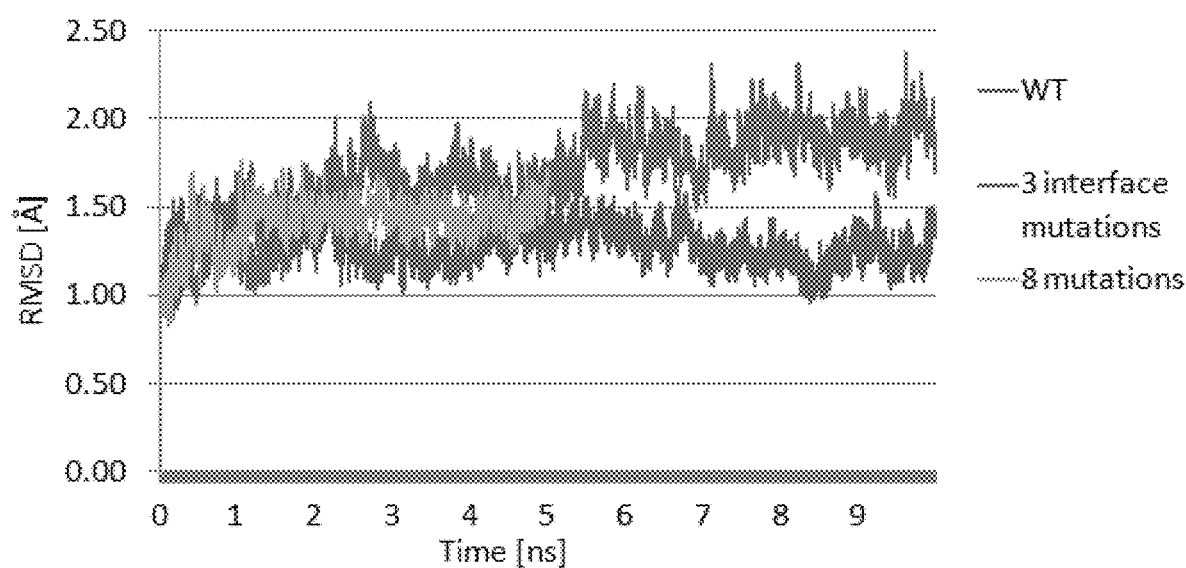

The model of PD-1 with missing loop fixed and residue 93 mutated back to Cys is shown in cyan in FIG. 3. The crystal structures of PD-1 and PD-L1 in 4ZQK are shown in blue and green respectively. The 7 residues (Ser62, Ser87, Pro89, Gly124, Ser127, Ala132 and Ala140 with numbering staring from the signal region; which are equivalent to Ser42, Ser67, Pro69, Gly104, Ser107, Ala112 and Ala120, respectively, with numbering starting from the mature region) on PD-1 for mutation are shown in orange sticks, the N-glycosylation site (Asn116) is shown in magenta sticks.

The mutated PD-1 structure was modeled using Residue Scanning module in Schrodinger Suite. The residues within 5.0 Å of the mutated residue were refined with side-chain prediction and backbone sampling. The protein interaction analysis was performed for both WT PD-1/PD-L1 complex structure and mutated PD-1/PD-L1 complex structure with all 8 residues mutated. The analysis result is listed in Tables 2 and 3 respectively. Mutations G124S, S127V and A132I are considered as interface mutations with the position numbering starting from the signal region. And mutation S62G, S86G, P89L and A140V are considered as outside mutations with the position numbering starting from the signal region. Mutation G124S makes one more hydrogen bond with PD-L1, mutation A132I keeps the hydrogen bond with PD-L1 and increase the surface complementarity.

To further investigate how the mutations influence the PD-1/PD-L1 binding, the variation of binding affinity and protein stability before and after each mutation were calculated. The result is listed in Table 4. The calculation of variation of binding affinity and protein stability were also performed for multiple mutations. The result is listed in Table 5. The more negative value of binding affinity or stability indicates more increase of them. In general, the interface mutations increase both binding affinity and protein stability, and the outside mutations contribute basically only on stability. With all 8 mutations, the binding affinity increases by 19.03 kcal/mol and the protein stability increases by 69.92 kcal/mol.

Three PD-1/PD-L1 complex models, WT model, model with 3 interface mutations, model with all 8 mutations, were submitted to 10 ns Molecular Dynamics (MD) simulation using OPLS3 force-field for further refinement and optimization. Each complex was solvated in a periodic, orthorhombic box with SPC water as the solvent. The minimum distance from any complex atom to the box wall was set to 10 Å. Three MD simulations were all carried out at a constant temperature of 300 K and a constant pressure of 1 atm. Trajectory coordinates stored at 1 ps intervals were used for analysis. The time-evolution of backbone atom-positional RMSD is shown in FIG. 4. MD result also shows that the mutations increase the model stability.

TABLE 2

Protein interaction analysis of WT human PD-1/PD-L1 model.

| Residue | Closest | Distance | Specific Interactions | # HB | # Salt | # Pi | # | # vdW | Surface | Buried |
|---|---|---|---|---|---|---|---|---|---|---|
| B:64:Val | A:121:Ala | 4.0 A | | 0 | 0 | 0 | 0 | 0 | 0.87 | 59.50% |
| B:66:Asn | A:121:Ala | 2.9 A | 1x hb to A:121:Ala | 1 | 0 | 0 | 0 | 0 | 0.76 | 98.20% |
| B:68:Tyr | A:122:Asp | 2.8 A | 1x hb to A:122:Asp | 1 | 0 | 0 | 0 | 0 | 0.82 | 100.00% |
| B:70:Met | A:125:Arg | 3.5 A | | 0 | 0 | 0 | 0 | 0 | 0.84 | 33.00% |
| B:73:Ser | A:26:Asp | 3.0 A | 1x hb to A:26:Asp | 1 | 0 | 0 | 0 | 0 | 0.69 | 32.90% |

TABLE 2-continued

Protein interaction analysis of WT human PD-1/PD-L1 model.

| Residue | Closest | Distance | Specific Interactions | # HB | # Salt | # Pi | # | # vdW | Surface | Buried |
|---|---|---|---|---|---|---|---|---|---|---|
| B:74:Asn | A:125:Arg | 3.7 A | | 0 | 0 | 0 | 0 | 0 | 0.86 | 18.10% |
| B:75:Gln | A:125:Arg | 3.0 A | 1x hb to A:26:Asp | 3 | 0 | 0 | 0 | 0 | 0.8 | 89.60% |
| | A:26:Asp | 3.0 A | 2x hb to A:125:Arg | | | | | | | |
| | A:123:Tyr | 3.2 A | 1x hb to A:123:Tyr | | | | | | | |
| B:76:Thr | A:125:Arg | 3.3 A | 2x hb to A:124:Lys | 2 | 0 | 0 | 0 | 0 | 0.82 | 100.00% |
| B:77:Asp | A:124:Lys | 3.0 A | 1x hb to A:124:Lys | 1 | 0 | 0 | 0 | 0 | 0.69 | 24.40% |
| | A:19:Phe | 2.9 A | 1x hb to A:19:Phe | | | | | | | |
| B:78:Lys | A:121:Ala | 2.9 A | 1x hb to A:121:Ala | 2 | 0 | 0 | 0 | 0 | 0.67 | 78.30% |
| | A:120:Gly | 3.5 A | 1x hb to A:19:Phe | | | | | | | |
| B:84:Glu | A:18:Ala | 3.6 A | 1x hb to A:120:Gly | 2 | 0 | 0 | 0 | 0 | 0.68 | 68.70% |
| B:122:Leu | A:123:Tyr | 3.8 A | | 0 | 0 | 0 | 0 | 0 | 0.87 | 80.20% |
| B:124:Gly | A:123:Tyr | 3.7 A | | 0 | 0 | 0 | 0 | 0 | 0.93 | 100.00% |
| B:126:Ile | A:123:Tyr | 3.6 A | | 0 | 0 | 0 | 0 | 0 | 0.92 | 99.90% |
| B:127:Ser | A:115:Met | 3.7 A | | 0 | 0 | 0 | 0 | 0 | 0.89 | 4.60% |
| B:128:Leu | A:117:Ser | 3.5 A | | 0 | 0 | 0 | 0 | 0 | 0.85 | 83.00% |
| B:130:Pro | A:66:Gln | 4.0 A | | 0 | 0 | 0 | 0 | 0 | 0.06 | 19.40% |
| B:131:Lys | A:66:Gln | 3.4 A | | 0 | 0 | 0 | 0 | 0 | 0.87 | 43.10% |
| B:132:Ala | A:56:Tyr | 3.4 A | 1x hb to A:66:Gln | 1 | 0 | 0 | 0 | 0 | 0.72 | 99.80% |
| B:133:Gln | A:56:Tyr | 4.3 A | | 0 | 0 | 0 | 0 | 0 | 0.37 | 16.10% |
| B:134:Ile | A:113:Arg | 3.6 A | | 0 | 0 | 0 | 0 | 0 | 0.85 | 90.90% |
| | A:123:Tyr | 2.9 A | 1x hb, 1x salt bridge to A:113:Arg | | | | | | | |
| | A:125:Arg | 2.9 A | 1x hg to A:123:Tyr | | | | | | | |
| B:136:Glu | A:113:Arg | 3.1 A | 1x hb, 1x salt bridge to A:125:Arg | 3 | 2 | 0 | 0 | 0 | 0.75 | 56.80% |
| B:139:Arg | A:125:Arg | 3.3 A | | 0 | 0 | 0 | 0 | 0 | 0.72 | 11.40% |

TABLE 3

Protein interaction analysis of mutated (S62G, S87G, P89L, G124S, S127V, A1321, A140V and N116S with the position numbering starting from the signal region) human PD-1/PD-L1 model.

| Residue | Closes | Distance | Specific Interactions | # HB | # Salt | # Pi | # | # vdW | Surface | Buried |
|---|---|---|---|---|---|---|---|---|---|---|
| B:64:Val | A:121:Ala | 3.7 A | | 0 | 0 | 0 | 0 | 0 | 0.85 | 94.10% |
| B:66:Asn | A:121:Ala | 2.9 A | 1x hb to A:121:Ala | 1 | 0 | 0 | 0 | 0 | 0.74 | 100.00% |
| B:68:Tyr | A:122:Asp | 2.7 A | 1x hb to A:121:Asp | 1 | 0 | 0 | 0 | 0 | 0.75 | 100.00% |
| B:70:Met | A:125:Arg | 3.5 A | | 0 | 0 | 0 | 0 | 0 | 0.82 | 18.10% |
| B:73:Ser | A:26:Asp | 3.0 A | 1x hb to A:26:Asp | 1 | 0 | 0 | 0 | 0 | 0.28 | 32.90% |
| B:74:Asn | A:125:Arg | 3.7 A | | 0 | 0 | 0 | 0 | 0 | 0.85 | 18.10% |
| B:75:Gln | A:125:Arg | 3.0 A | 1x hb to A:26 :Asp | 3 | 0 | 0 | 0 | 0 | 0.8 | 89.60% |
| B:76:Thr | A:124:Lys | 2.9 A | 1x hb to A:124:Lys | 1 | 0 | 0 | 0 | 0 | 0.78 | 100.00% |
| B:77:Asp | A:124:Lys | 3.5 A | | 0 | 0 | 0 | 0 | 0 | 0.89 | 18.30% |
| B:78:Lys | A:19:Phe | 2.9 A | 1x hb to A:19:Phe | 2 | 0 | 0 | 0 | 0 | 0.69 | 76.10% |
| B:80:Ala | | | | 0 | 0 | 0 | 0 | 0 | 0 | 10.20% |
| B:84:Glu | A:19:Phe | 3.1 A | 1x hb to A:19:Phe | 2 | 0 | 0 | 0 | 0 | 0.81 | 80.90% |
| B:85:Asp | | | | 0 | 0 | 0 | 0 | 0 | 0 | 8.10% |
| B:86:Arg | A:120:Gly | 3.7 A | | 0 | 0 | 0 | 0 | 0 | 0.55 | 16.30% |
| B:92:Asp | | | | 0 | 0 | 0 | 0 | 0 | 0 | 0.90% |
| B:122:Leu | A:123:Tyr | 3.5 A | | 0 | 0 | 0 | 0 | 0 | 0.8 | 78.80% |
| B:124:Ser | A:123:Tyr | 2.9 A | 1x hb to A:123:Tyr | 1 | 0 | 0 | 0 | 0 | 0.71 | 100.00% |
| B:126:Ile | A:115:Me | 3.5 A | | 0 | 0 | 0 | 0 | 0 | 0.93 | 100.00% |
| B:127:Val | A:115:Met | 4.4 A | | 0 | 0 | 0 | 0 | 0 | 0.33 | 0.00% |
| B:128:Leu | A:115:Me | 3.5 A | | 0 | 0 | 0 | 0 | 0 | 0.93 | 75.00% |
| B:129.Ala | | | | 0 | 0 | 0 | 0 | 0 | 0 | 1.50% |
| B:130:Pro | A:66:Gln | 4.9 A | | 0 | 0 | 0 | 0 | 0 | 0 | 0.00% |
| B:131:Lys | A:63:Asn | 3.5 A | | 0 | 0 | 0 | 0 | 0 | 0.75 | 36.00% |
| B:132:Ile | A:66:Gln | 2.8 A | 1x hb to A:66:Gln | 1 | 0 | 0 | 0 | 0 | 0.86 | 98.60% |
| B:133:Gln | A:56:Tyr | 3.0 A | | 0 | 0 | 0 | 0 | 0 | 0.74 | 50.00% |
| B:134:Ile | A:123:Tyr | 3.5 A | | 0 | 0 | 0 | 0 | 0 | 0.86 | 91.90% |
| B:136:Glu | A:123:Tyr | 2.8 A | 1x hb, 1x salt bridge to A:113:Arg | 3 | 2 | 0 | 0 | 0 | 0.68 | 62.10% |
| B:139:Arg | A:125:Arg | 3.1 A | | 0 | 0 | 0 | 0 | 0 | 0.79 | 10.70% |

TABLE 4

Variation of binding affinity and protein stability (in kcal/mol) of human PD-1/PD-L1 for each single mutation.

| Residue | Original | Mutated | d Affinity | d Stability (solvated) |
|---|---|---|---|---|
| 62 | SER | GLY | −1.37 | 0.5 |
| 87 | SER | GLY | 0.94 | 5.56 |
| 89 | PRO | LEU | 0 | −7.06 |
| 116 | ASN | SER | −0.02 | 0.82 |
| 124 | GLY | SER | −4.27 | −10.24 |
| 127 | SER | VAL | −0.12 | −1.82 |
| 132 | ALA | ILE | −10.94 | −11.9 |
| 140 | ALA | VAL | −0.77 | −25.89 |

TABLE 5

Variation of binding affinity and protein stability (in kcal/mol) of human PD-1/PD-L1 for multiple mutations.. The more negative value of binding affinity or stability indicates more increase of them.

| Mutations | d Affinity | d Stability (solvated) |
|---|---|---|
| 8 mutations | −19.03 | −69.92 |
| 7 mutations (N116S excluded) | −20.08 | −66.99 |
| 4 outsied mutations | −1.61 | −30.66 |
| 4 interface mutations | −24.78 | −30.58 |
| 2 mutations on missing loop | 1.31 | −12.08 |

3. Modeling of Human PD-1/PD-L2 Complex

Figure 5A:
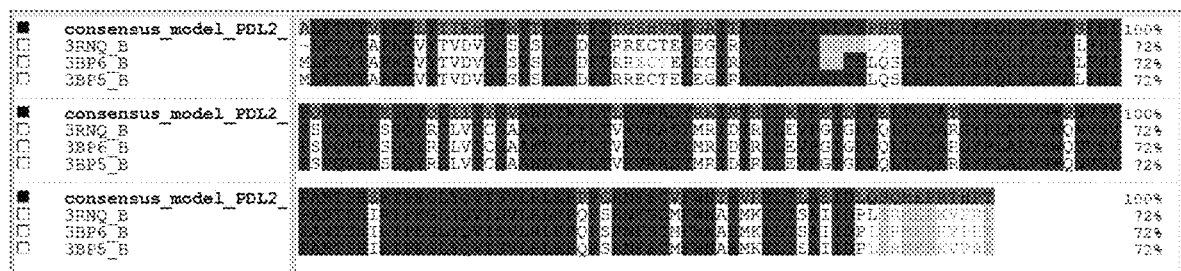
Figure 5B:

The sequence alignment results are shown in FIG. 5A. The sequence identity between human PD-L2 and mouse PD-L2 is about 72%. The consensus model of human PD-L2 is shown in FIG. 5B. The identical residues are marked in blue. The residues in missing loop are marked in red.

Figure 6:
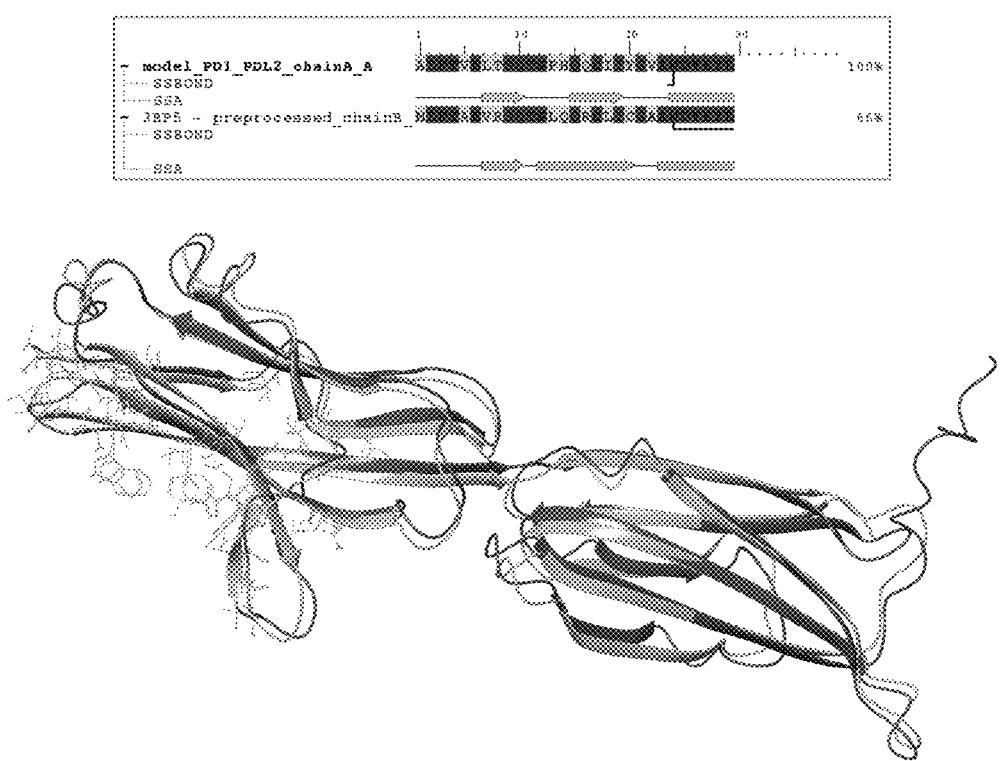
Figure 7:
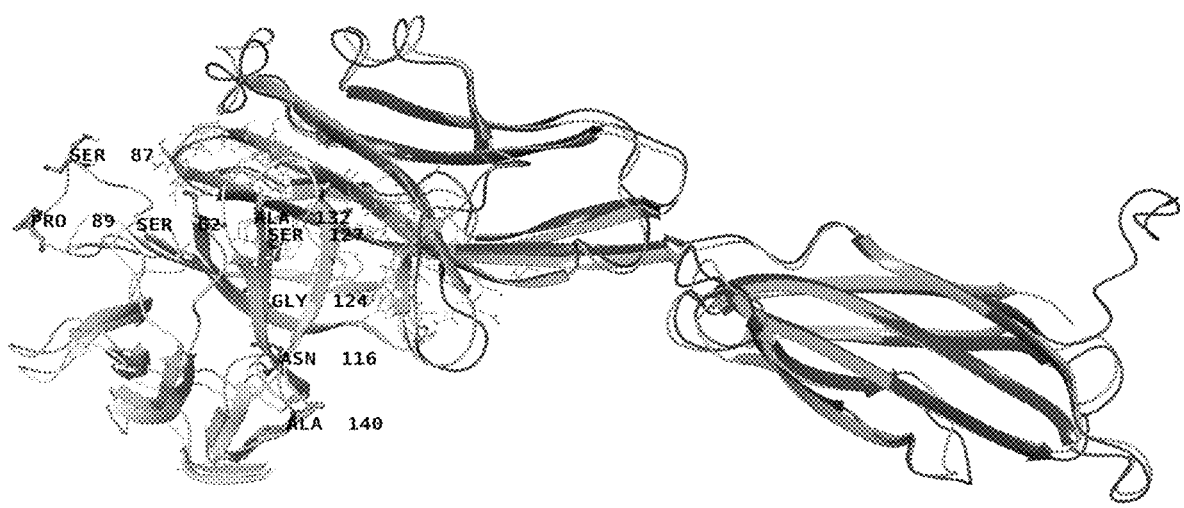

PD-1 binding interface comparison between human PD-L2 model and mouse PD-L2 crystal structure (PDBID: 3BP5) is shown in FIG. 6. The interface residues are shown in lines. The interface residues are marked in green in the human PD-L2 model (shown in dark blue). The crystal structure of mouse PD-L2 is shown in pink. The sequence identity on interface is 66%. The human PD-1/PD-L2 complex model was built based on human PD-1 model (described in Part I) and the consensus human PD-L2 model by superposing to mouse PD-1/PD-L2 crystal structure (PDBID: 3BP5). The Overlay of human PD-1/PD-L2 model and mouse PD-1/PD-L2 crystal structure (PDBID: 3BP5) is shown in FIG. 7. Human PD-1 and PD-L2 models are shown in cyan and dark blue, mouse PD-1 and PD-L2 structures are shown in yellow and pink, respectively.

As described in the method section, the protein interaction analysis was also performed for WT and mutated human PD-1/PD-L2 model. The results are listed in Tables 6 and 7. Mutation G124S and A132I slightly increase the surface complementarity. The calculation of variation of binding affinity and protein stability were also performed for each single mutation and multiple mutations. The results are listed in Tables 8 and 9. In general, the interface mutations increase binding affinity, and the outside mutations increase stability. With all 8 mutations, the binding affinity increases by 10.62 kcal/mol and the protein stability increases by 10.7 kcal/mol. The variation of binding affinity and stability of PD-1/PD-L2 is not as significant as those of PD-1/PD-L1. It may due to the structural precision difference between homology model and crystal structure.

TABLE 6

Protein interaction analysis of WT human PD-1/PD-L2 model.

| Residue | Closes | Distance | Specific Interactions | # HB | # Salt | # Pi | # | # vdW | Surface | Buried |
|---|---|---|---|---|---|---|---|---|---|---|
| B:64:Val | A:110:Trp | 3.5 A |  | 0 | 0 | 0 | 0 | 0 | 0.77 | 71.80% |
| B:65:Leu | A:110:Trp | 3.9 A |  | 0 | 0 | 0 | 0 | 0 | 0.79 | 23.00% |
| B:66:Asn | A:110:Trp | 2.8 A | 1x hb to A:110:Trp | 1 | 0 | 0 | 0 | 0 | 0.84 | 100.00% |
| B:68:Tyr | A:111:Asp | 2.8 A | 1x hb to A:111:Asp | 1 | 0 | 1 | 0 | 0 | 0.84 | 100.00% |
| B:70:Met | A:114:Tyr | 4.2 A |  | 0 | 0 | 0 | 0 | 0 | 0.9 | 14.10% |
| B:73:Ser | A:28:Glu | 3.0 A | 1x hb to A:28:Glu | 1 | 0 | 0 | 0 | 0 | 0.82 | 30.50% |
| B:74:Asn | A:99:Gln | 2.8 A | 1x hb to A:99:Gln | 1 | 0 | 0 | 0 | 0 | 0.88 | 49.60% |
| B:75:Gln | A:114:Tyr | 2.8 A | 1x hb to A:28:Glu | 3 | 0 | 0 | 0 | 0 | 0.76 | 87.60% |
| B:76:Thr | A:113:Lys | 3.0 A | 1x hb to A:112:Tyr | 2 | 0 | 0 | 0 | 0 | 0.87 | 100.00% |
| B:77:Asp | A:113:Lys | 4.6 A |  | 0 | 0 | 0 | 0 | 0 | 0 | 13.00% |
| B:78:Lys | A:110:Trp | 2.9 A | 1x hb to A:21:Phe | 2 | 0 | 0 | 0 | 0 | 0.7 | 68.10% |
| B:83:Pro | A:108:Val | 3.5 A |  | 0 | 0 | 0 | 0 | 0 | 0.73 | 34.50% |
| B:84:Glu | A:21:Phe | 2.8 A | 1x hb to A:21:Phe | 1 | 0 | 0 | 0 | 0 | 0.72 | 99.90% |
| B:85:Asp | A:19:Ala | 3.3 A |  | 0 | 0 | 0 | 0 | 0 | 0.86 | 65.20% |
| B:86:Arg | A:108:Val | 3.6 A |  | 0 | 0 | 0 | 0 | 0 | 0.97 | 12.70% |
| B:92:Asp | A:20:Leu | 3.3A |  | 0 | 0 | 0 | 0 | 0 | 0.89 | 38.70% |
| B93:Cys | A:20:Leu | 4.3 A |  | 0 | 0 | 0 | 0 | 0 | 0.91 | 22.90% |
| B:122:Leu |  |  |  | 0 | 0 | 0 | 0 | 0 | 0.49 | 100.00% |
| B:124:Gly | A:110:Trp | 3.6 A |  | 0 | 0 | 0 | 0 | 0 | 0.8 | 100.00% |
| B:125:Ala | A:110:Trp | 3.6 A |  | 0 | 0 | 0 | 0 | 0 | 0.86 | 100.00% |
| B:126:Ile | A:110:Trp | 3.4 A |  | 0 | 0 | 0 | 0 | 0 | 0.91 | 100.00% |
| B:127:Ser | A:105:Ile | 4.6 A |  | 0 | 0 | 0 | 0 | 0 | 0.93 | 0.00% |
| B:128:Leu | A:105:Ile | 3.6 A |  | 0 | 0 | 0 | 0 | 0 | 0.88 | 55.70% |
| B:131:Lys | A:68:Pro | 3.9 A |  | 0 | 0 | 0 | 0 | 0 | 0.87 | 29.70% |
| B:132:Ala | A:60:Gln | 2.7 A | 1x hb to A:60:Gln | 1 | 0 | 0 | 0 | 0 | 0.83 | 83.70% |
| B:133:Gln | A:67:Ser | 2.8 A | 1x hb to A:67:Ser | 1 | 0 | 0 | 0 | 0 | 0.87 | 53.60% |
| B:134:Ile | A:103:Ile | 3.4A |  | 0 | 0 | 0 | 0 | 0 | 0.88 | 92.90% |
| B:136:Glu | A:112:Tyr | 2.8 A | 1x hb to A:112:Tyr | 2 | 0 | 0 | 0 | 0 | 0.76 | 41.20% |
| B:139:Arg | A:114:Tyr | 3.5 A |  | 0 | 0 | 0 | 0 | 0 | 0.89 | 10.20% |

TABLE 7

Protein interaction analysis of mutated (S62G, S87G, P89L, G124S, S127V, A132I, A140V and N116S with position numbering starting from the signal region, which are equivalent to S42G, S67G, P69L, G104S, S107V, A112I, A120V and N96S, respectively, with position numbering starting from the mature region) human PD-1/PD-L2 model.

| Residue | Closes | Distance | Specific Interactions | # HB | # Salt | # Pi | # | # vdW | Surface | Buried |
|---|---|---|---|---|---|---|---|---|---|---|
| B:64:Val | A:110:Trp | 3.3 A | 1x hb to A:110:Trp | 1 | 0 | 0 | 0 | 0 | 0.76 | 71.20% |
| B:65:Leu | A:110:Trp | 4.0 A | | 0 | 0 | 0 | 0 | 0 | 0.29 | 13.20% |
| B:66:Asn | A:110:Trp | 2.9 A | 1x hb to A:110:Trp | 1 | 0 | 0 | 0 | 0 | 0.83 | 100.00% |
| B:68:Tyr | A:111:Asp | 2.9 A | 1x hb to A:111:Asp | 1 | 0 | 1 | 0 | 0 | 0.86 | 100.00% |
| B:70:Met | A:114:Tyr | 4.2 A | | 0 | 0 | 0 | 0 | 0 | 0.89 | 10.90% |
| B:73:Ser | A:28:Glu | 3.0 A | 1x hb to A:28:Glu | 1 | 0 | 0 | 0 | 0 | 0.87 | 30.50% |
| B:74:Asn | A:99:Gln | 2.8 A | 1x hb to A:99:Gln | 1 | 0 | 0 | 0 | 0 | 0.88 | 49.60% |
| B:75:Gln | A:114:Tyr | 2.8 A | 1x hb to A:28:Glu | 3 | 0 | 0 | 0 | 0 | 0.77 | 87.70% |
| B:76:Thr | A:113:Lys | 3.0 A | 1x hb to A:112:Tyr | 2 | 0 | 0 | 0 | 0 | 0.85 | 100.00% |
| B:77:Asp | A:113:Lys | 4.6 A | | 0 | 0 | 0 | 0 | 0 | 0 | 13.20% |
| B:78:Lys | A:110:Trp | 2.9 A | 1x hb to A:21:Phe | 2 | 0 | 0 | 0 | 0 | 0.68 | 68.10% |
| B:81:Ala | A:109:Ala | 4.9 A | | 0 | 0 | 0 | 0 | 0 | 0.08 | 97.90% |
| B:82:Phe | A:109:Ala | 4.8 A | | 0 | 0 | 0 | 0 | 0 | 0.29 | 3.00% |
| B:83:Pro | A:108:Val | 3.5 A | | 0 | 0 | 0 | 0 | 0 | 0.77 | 37.80% |
| B:84:Glu | A:21:Phe | 2.8 A | 1x hb to A:21:Phe | 1 | 0 | 0 | 0 | 0 | 0.74 | 99.90% |
| B:85:Asp | A:19:Ala | 3.3 A | | 0 | 0 | 0 | 0 | 0 | 0.8 | 54.80% |
| B:86:Arg | A:108:Val | 3.5 A | | 0 | 0 | 0 | 0 | 0 | 0.92 | 15.80% |
| B:92:Asp | A:20:Leu | 3.4 A | | 0 | 0 | 0 | 0 | 0 | 0.89 | 39.50% |
| B:93:Cys | A:20:Leu | 4.3 A | | 0 | 0 | 0 | 0 | 0 | 0 | 22.20% |
| B:124:Ser | A:110:Trp | 3.5 A | | 0 | 0 | 0 | 0 | 0 | 0.85 | 100.00% |
| B:125:Ala | A:110:Trp | 3.7 A | | 0 | 0 | 0 | 0 | 0 | 0.89 | 100.00% |
| B:126:Ile | A:110:Trp | 3.4 A | | 0 | 0 | 0 | 0 | 0 | 0.92 | 100.00% |
| B:128:Leu | A:105:Ile | 3.6 A | | 0 | 0 | 0 | 0 | 0 | 0.8 | 48.80% |
| B:131:Lys | A:69:Hie | 3.6 A | | 0 | 0 | 0 | 0 | 0 | 0.83 | 36.70% |
| B:132:Ile | A:60:Gln | 2.8 A | 1x hb to A:60:Gln | 1 | 0 | 0 | 0 | 0 | 0.85 | 75.50% |
| B:133:Gln | A:67:Ser | 3.0 A | 1x hb to A:67:Ser | 1 | 0 | 0 | 0 | 0 | 0.76 | 61.30% |
| B134:Ile | A:103:Ile | 3.4 A | | 0 | 0 | 0 | 0 | 0 | 0.9 | 96.00% |
| B:135:Lys | | | | 0 | 0 | 0 | 0 | 0 | 0 | 16.30% |
| B:136:Glu | A:112:Tyr | 2.8 A | 1x hb to A:112:Tyr | 2 | 0 | 0 | 0 | 0 | 0.79 | 38.50% |
| B:139:Arg | A:114:Tyr | 3.4 A | | 0 | 0 | 0 | 0 | 0 | 0.89 | 12.10% |

TABLE 8

Variation of binding affinity and protein stability (in kcal/mol) of human PD-1/PD-L2 for each single mutation.

| Residue | Original | Mutated | d Affinity | d Stability (solvated) |
|---|---|---|---|---|
| 62 | SER | GLY | 0.3 | 4.21 |
| 87 | SER | GLY | 0 | −0.68 |
| 89 | PRO | LEU | 0.28 | −4.71 |
| 116 | ASN | SER | 0 | 0.85 |
| 124 | GLY | SER | −3.06 | 6.47 |
| 127 | SER | VAL | 1.65 | −4.42 |
| 132 | ALA | ILE | −9.47 | −0.55 |
| 140 | ALA | VAL | 0.25 | −11.76 |

TABLE 9

Variation of binding affinity and protein stability (in kcal/mol) of human PD-1/PD-L2 for multiple mutations.

| Mutations | d Affinity | d Stability (solvated) |
|---|---|---|
| 8 mutations | −10.62 | −10.7 |
| 7 mutations (N116S excluded) | −10.21 | −12.19 |
| 4 outsied mutations | 0.59 | −10

TABLE 10-continued

Colony tracking numbers, SEQ ID numbers and amino acid mutations in different colonies with respect to wild type (SEQ ID NO: 11). The signal peptide region is from residues 1 to 20, and the mature extracellular domain (ECD) starts from residues 21 to 170. The linker domain starts from residues 171 to 175. The sequence numbering for amino acid mutation(s) in each sequence starts from its mature region.

| Colony Tracking No. | SEQ ID No. | AA mutations with respect to 1-WT (SEQ ID NO: 11) |
|---|---|---|
| 27-2 mutations | SEQ ID NO: 37 | G104S/A120V |
| 28-2 mutations | SEQ ID NO: 38 | S107V/A112I |
| 29-2 mutations | SEQ ID NO: 39 | S107V/A120V |
| 30-2 mutations | SEQ ID NO: 40 | A112I/A120V |
| 31-3 mutations | SEQ ID NO: 41 | S42G/S67G/P69L |
| 32-3 mutations | SEQ ID NO: 42 | S42G/S67G/G104S |
| 33-3 mutations | SEQ ID NO: 43 | S42G/S67G/S107V |
| 34-3 mutations | SEQ ID NO: 44 | S42G/S67G/A112I |
| 35-3 mutations | SEQ ID NO: 45 | S42G/S67G/A120V |
| 36-3 mutations | SEQ ID NO: 46 | S42G/P69L/G104S |
| 37-3 mutations | SEQ ID NO: 47 | S42G/P69L/S107V |
| 38-3 mutations | SEQ ID NO: 48 | S42G/P69L/A112I |
| 39-3 mutations | SEQ ID NO: 49 | S42G/P69L/A120V |
| 40-3 mutations | SEQ ID NO: 50 | S42G/G104S/S107V |
| 41-3 mutations | SEQ ID NO: 51 | S42G/G104S/A112I |
| 42-3 mutations | SEQ ID NO: 52 | S42G/G104S/A120V |
| 43-3 mutations | SEQ ID NO: 53 | S42G/S107V/A112I |
| 44-3 mutations | SEQ ID NO: 54 | S42G/S107V/A120V |
| 45-3 mutations | SEQ ID NO: 55 | S42G/A112I/A120V |
| 46-3 mutations | SEQ ID NO: 56 | S67G/P69L/G104S |
| 47-3 mutations | SEQ ID NO: 57 | S67G/P69L/S107V |
| 48-3 mutations | SEQ ID NO: 58 | S67G/P69L/A112I |
| 49-3 mutations | SEQ ID NO: 59 | S67G/P69L/A120V |
| 50-3 mutations | SEQ ID NO: 60 | S67G/G104S/S107V |
| 51-3 mutations | SEQ ID NO: 61 | S67G/G104S/A112I |
| 52-3 mutations | SEQ ID NO: 62 | S67G/G104S/A120V |
| 53-3 mutations | SEQ ID NO: 63 | S67G/S107V/A112I |
| 54-3 mutations | SEQ ID NO: 64 | S67G/S107V/A120V |
| 55-3 mutations | SEQ ID NO: 65 | S67G/A112I/A120V |
| 56-3 mutations | SEQ ID NO: 66 | P69L/G104S/S107V |
| 57-3 mutations | SEQ ID NO: 67 | P69L/G104S/A112I |
| 58-3 mutations | SEQ ID NO: 68 | P69L/G104S/120V |
| 59-3 mutations | SEQ ID NO: 69 | P69L/S107V/A112I |
| 60-3 mutations | SEQ ID NO: 70 | P69L/S107V/120V |
| 61-3 mutations | SEQ ID NO: 71 | P69L/A112I/A120V |
| 62-3 mutations (clone #5) | SEQ ID NO: 72 | G104S/S107V/A112I |
| 63-3 mutations | SEQ ID NO: 73 | G104S/S107V/A120V |
| 64-3 mutations | SEQ ID NO: 74 | G104S/A112I/A120V |
| 65-3 mutations | SEQ ID NO: 75 | S107V/A112I/A120V |
| 66-4 mutations | SEQ ID NO: 76 | S42G/S67G/P69L/G104S |
| 67-4 mutations | SEQ ID NO: 77 | S42G/S67G/P69L/S107V |
| 68-4 mutations | SEQ ID NO: 78 | S42G/S67G/P69L/A112I |
| 69-4 mutations | SEQ ID NO: 79 | S42G/S67G/P69L/A120V |
| 70-4 mutations | SEQ ID NO: 80 | S42G/S67G/G104S/S107V |
| 71-4 mutations | SEQ ID NO: 81 | S42G/S67G/G104S/A112I |
| 72-4 mutations | SEQ ID NO: 82 | S42G/S67G/G104S/A120V |
| 73-4 mutations | SEQ ID NO: 83 | S42G/S67G/S107V/A112I |
| 74-4 mutations | SEQ ID NO: 84 | S42G/S67G/S107V/A120V |
| 75-4 mutations | SEQ ID NO: 85 | S42G/S67G/A112I/A120V |
| 76-4 mutations | SEQ ID NO: 86 | S42G/P69L/G104S/S107V |
| 77-4 mutations | SEQ ID NO: 87 | S42G/P69L/G104S/A112I |
| 78-4 mutations | SEQ ID NO: 88 | S42G/P69L/G104S/A120V |
| 79-4 mutations | SEQ ID NO: 89 | S42G/P69L/S107V/A112I |
| 80-4 mutations | SEQ ID NO: 90 | S42G/P69L/S107V/A120V |
| 81-4 mutations | SEQ ID NO: 91 | S42G/P69L/A112I/A120V |
| 82-4 mutations | SEQ ID NO: 92 | S42G/G104S/S107V/A112I |
| 83-4 mutations | SEQ ID NO: 93 | S42G/G104S/S107V/A120V |
| 84-4 mutations | SEQ ID NO: 94 | S42G/G104S/A112I/A120V |
| 85-4 mutations | SEQ ID NO: 95 | S42G/S107V/A112I/A120V |
| 86-4 mutations | SEQ ID NO: 96 | S67G/P69L/G104S/S107V |
| 87-4 mutations | SEQ ID NO: 97 | S67G/P69L/G104S/A112I |
| 88-4 mutations | SEQ ID NO: 98 | S67G/P69L/G104S/A120V |
| 89-4 mutations | SEQ ID NO: 99 | S67G/P69L/S107V/A112I |
| 90-4 mutations | SEQ ID NO: 100 | S67G/P69L/S107V/A120V |
| 91-4 mutations | SEQ ID NO: 101 | S67G/P69L/A112I/A120V |
| 92-4 mutations | SEQ ID NO: 102 | S67G/G104S/S107V/A112I |
| 93-4 mutations | SEQ ID NO: 103 | S67G/G104S/S107V/A120V |
| 94-4 mutations | SEQ ID NO: 104 | S67G/G104S/A112I/A120V |
| 95-4 mutations | SEQ ID NO: 105 | S67G/S107V/A112I/A120V |
| 96-4 mutations | SEQ ID NO: 106 | P69L/G104S/S107V/A112I |
| 97-4 mutations | SEQ ID NO: 107 | P69L/G104S/S107V/A120V |
| 98-4 mutations | SEQ ID NO: 108 | P69L/G104S/A112I/A120V |
| 99-4 mutations | SEQ ID NO: 109 | P69L/S107V/A112I/A120V |
| 100-4 mutations (clone #4) | SEQ ID NO: 110 | G104S/S107V/A112I/A120V |
| 101-5 mutations | SEQ ID NO: 111 | S42G/S67G/P69L/G104S/S107V |
| 102-5 mutations | SEQ ID NO: 112 | S42G/S67G/P69L/G104S/A112I |
| 103-5 mutations | SEQ ID NO: 113 | S42G/S67G/P69L/G104S/A120V |
| 104-5 mutations | SEQ ID NO: 114 | S42G/S67G/P69L/S107V/A112I |
| 105-5 mutations | SEQ ID NO: 115 | S42G/S67G/P69L/S107V/A120V |
| 106-5 mutations | SEQ ID NO: 116 | S42G/S67G/P69L/A112I/A120V |
| 107-5 mutations | SEQ ID NO: 117 | S42G/S67G/G104S/S107V/A112I |
| 108-5 mutations | SEQ ID NO: 118 | S42G/S67G/G104S/S107V/A120V |
| 109-5 mutations | SEQ ID NO: 119 | S42G/S67G/G104S/A112I/A120V |
| 110-5 mutations | SEQ ID NO: 120 | S42G/S67G/S107V/A112I/A120V |
| 111-5 mutations | SEQ ID NO: 121 | S42G/P69L/G104S/S107V/A112I |
| 112-5 mutations | SEQ ID NO: 122 | S42G/P69L/G104S/S107V/A120V |
| 113-5 mutations | SEQ ID NO: 123 | S42G/P69L/G104S/A112I/A120V |
| 114-5 mutations | SEQ ID NO: 124 | S42G/P69L/S107V/A112I/A120V |
| 115-5 mutations | SEQ ID NO: 125 | S42G/G104S/S107V/A112I/A120V |
| 116-5 mutations | SEQ ID NO: 126 | S67G/P69L/G104S/S107V/A112I |
| 117-5 mutations | SEQ ID NO: 127 | S67G/P69L/G104S/S107V/A120V |
| 118-5 mutations | SEQ ID NO: 128 | S67G/P69L/G104S/A112I/A120V |
| 119-5 mutations | SEQ ID NO: 129 | S67G/P69L/S107V/A112I/A120V |
| 120-5 mutations (clone #2) | SEQ ID NO: 130 | S67G/G104S/S107V/A112I/A120V |
| 121-5 mutations (clone #1) | SEQ ID NO: 131 | P69L/G104S/S107V/A112I/A120V |
| 122-6 mutations | SEQ ID NO: 132 | S42G/S67G/P69L/G104S/S107V/A112I |
| 123-6 mutations | SEQ ID NO: 133 | S42G/S67G/P69L/G104S/S107V/A120V |
| 124-6 mutations | SEQ ID NO: 134 | S42G/S67G/P69L/G104S/A112I/A120V |
| 125-6 mutations | SEQ ID NO: 135 | S42G/S67G/P69L/S107V/A112I/A120V |
| 126-6 mutations | SEQ ID NO: 136 | S42G/S67G/G104S/S107V/A112I/A120V |
| 127-6 mutations | SEQ ID NO: 137 | S42G/P69L/G104S/S107V/A112I/A120V |
| 128-6 mutations (clone #3) | SEQ ID NO: 138 | S67G/P69L/G104S/S107V/A112I/A120V |
| 129-8 mutations | SEQ ID NO: 139 | S42G/S67G/P69L/N96S/G104S/S107V/A112I/A120V |

B. EXAMPLE 2: Binding Affinity of sPD-1 Variant to PD-L1 and PD-L2

Binding affinity assay was performed according to the Manufacture's assay protocol. Machine model is Biacore T200, GE Healthcare Life sciences. Experiments were performed at 25° C. Analytes were human PD-L1 and human PD-L2. Running buffer was HBS-EP+. Briefly, Anti-human Fc IgG was immobilized on CM5 sensor chip. sPD-1 variants were captured to the immobilized sensor chip. Multiple cycle kinetics were performed with injection of serial diluted analyte.

sPD-1 variant—Fc fusion protein demonstrated about 10,000-fold improvement in PD-L1 binding compared with a WT PD-1—Fc fusion protein ("parent Fc fusion protein"), and about 200-fold improvement in PD-L2 binding compared with the parent Fc fusion protein (FIG. 8).

C. EXAMPLE 3: Binding Activity of sPD-1 Variant—Fc Fusion Protein on MC38 Cells FACS binding analysis was performed to assess the binding activity of sPD-1 variant—Fc fusion protein with MC38 mouse colorectal cancer cell line and MC38 cells with human PD-L1 knock-in.

Figure 9A:
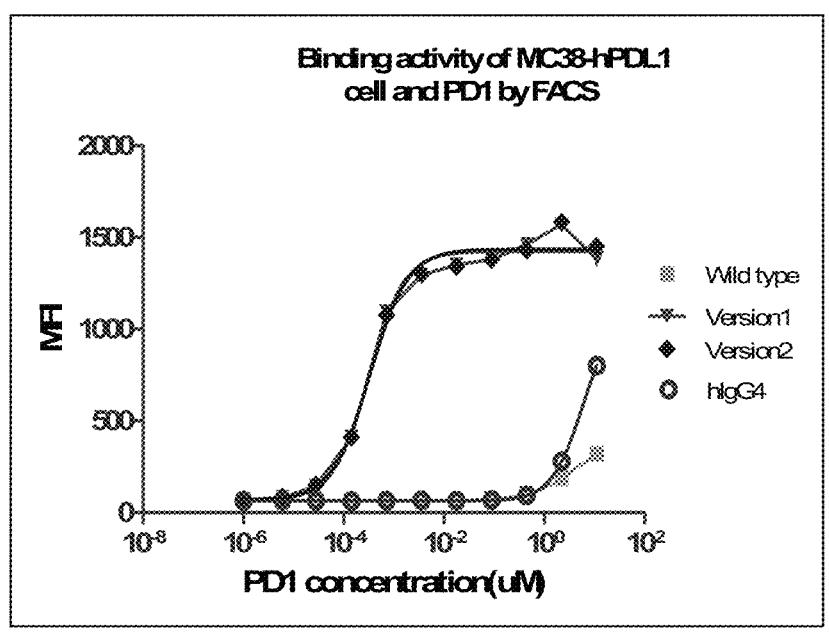
Figure 9B:
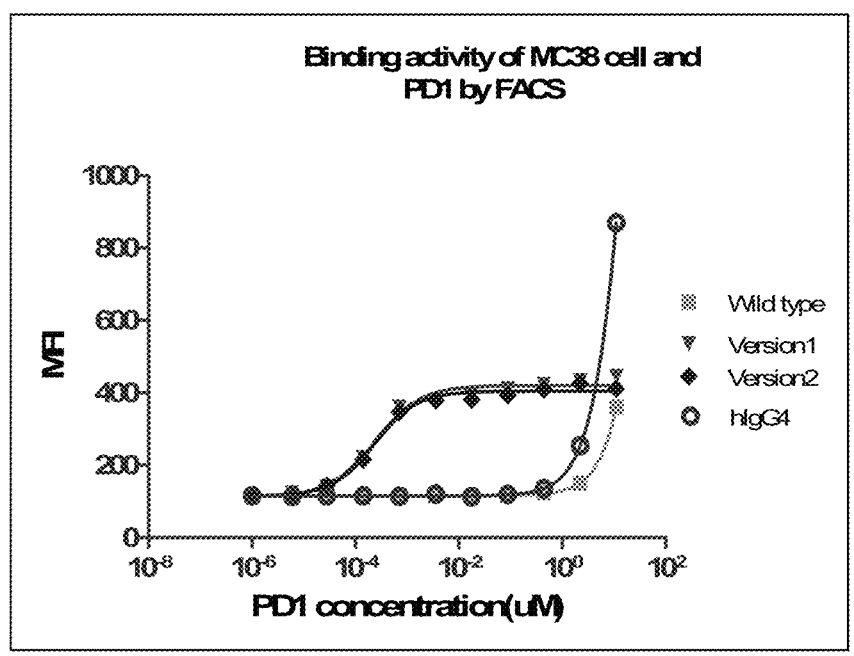

Briefly, the cells were cultured at 37° C. with 5% $CO_2$. Cells were harvested according to standard procedures, and the supernatant was discarded. Cells were dispensed into staining plates at 0.3 million cells per well. The plates were centrifuged at 300 g at 4° C. for 5 minutes. A series concentration of sPD-1 variant—Fc fusion protein and a negative control in FACS buffer containing 2% FBS were titrated 1:5 from 500 ug/ml. 100 ul were added to each well and cells were incubated for 1 hour at 4° C. The cells were washed twice with 200 ul FACS buffer, centrifuged at 300 g for 5 minutes and the supernatant was discarded before and after each wash. Cells were then re-suspended with anti-human IgG-Alexa 488. Plates were incubated for 1 hour at 4° C. Cells were then washed twice for FACS analysis. FACS analyses were performed with FACS Canto II, BD Biosciences per manufactures instruction.

sPD-1 variant—Fc fusion proteins (e.g. sPD-1 variant version 1—Fc fusion protein, and sPD-1 variant version 2—Fc fusion protein) demonstrated higher binding affinity for MC38-PD-L1 Knock-In cells than the wild type PD-1 group (i.e. wild type PD-1—Fc fusion protein as set forth in SEQ ID NO:4) (FIG. 9A), though sPD-1 variant—Fc fusion proteins also bind to parental MC38 but at a lower extent (FIG. 9B).

D. EXAMPLE 4: T Cell Activation Assay

PBMC isolation: The blood sample from an individual donor was diluted by the same volume of sterile PBS, for instance, 25 ml sterile PBS was added into 25 ml fresh whole blood and mixed sufficiently by gentle shake. 15 ml Ficoll-Pague medium was transferred into a new 50 ml centrifuge tube to make sure the Ficoll and blood volume ratio is 3:4, then the diluted blood sample was carefully added onto the surface of the Ficoll medium, avoiding mixing by being added as soft as possible so that the layer of two liquid could be seen clearly. The tube was gently moved to centrifuge, at 400×g, 30 min, 20° C., with the Max acceleration and Min deceleration settings during the centrifugation. The layer of mononuclear cells was carefully absorbed and transferred into another new sterile centrifuge tube. The sterile PBS buffer was added into the collected PBMCs for washing at a volume ratio of 3:1 and centrifuged at 300×g, 10 min, 20° C. The cells were then resuspended with 10% FBS+RPMI 1640 for assay.

Preparation of Hep3B human PD-L1 knock-in cells: mycoplasma-free Hep3b-hPDL1-OS8 cells were prepared in a 15 cm dish, and the confluency was kept at 60~80% before use. The cells were trypsinized with TrypLE™ Express Enzyme, the trypsin was then neutralized and the cells were collected to a 50 ml centrifuge tube by centrifuging at 1000 rpm for 5 min. The supernatant was discarded, and the cells were resuspended with mitomycin, 10 ug/ml (in 5-10 ml 10% FBS+RPMI1640 medium). The cells were incubated at 37° C. for 1 hr. The cells were washed with 15-20 ml PBS 4 times before cell counting with cytometer, and then centrifuged at 1000 rpm, 5 min, at 20° C. The cells were resuspended with 10% FBS+RPMI 1640 for assay.

PBMC stimulation: PBMC were added at 50,000 cell/well, 100 ul/well and then series of 5× sPD-1 variant version 2 (PD1 V2), 5× PD1 WT or hIgG4 protein solution 50 ul/well were added followed by Hep3b-hPDL1 cells at 5000 cell/well for 50 ul/well. The mixed solution was incubated at a 37° C. incubator for 72 hrs. The supernatant was harvested and freezed below −20° C. before ELISA test. The IFN-gamma concentration was tested by ELISA kit. Quantification of IFN-γ were determined by Quantifkine ELISA kits purchased from R&D. Procedures were performed according to the assay procedure of Human IFN-γ ELISA kit, R&D, Cat #DY285.

Figure 10:
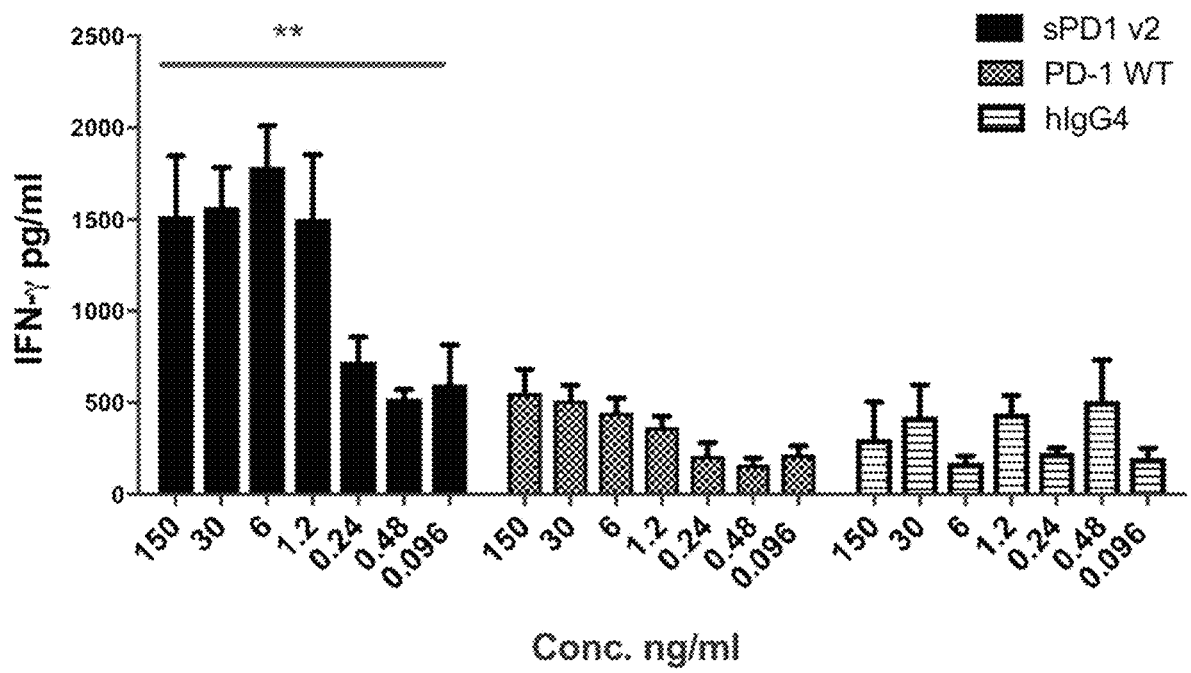

FIG. 10 shows that sPD-1 variant version 2—Fc fusion proteins is capable of activating T cells isolated from Human PBMC.

E. EXAMPLE 5: In Vivo Tumor Study Using MC38-hPD-L1 Colorectal Tumor Cell Line All animals were purchased and housed in AAALC accredited, temperature controlled and pathogen free environment. Animals were removed from the study once the tumor size reaches ethical limit. C57/B6 mice were inoculated with MC38-hPD-L1 tumor cells and observed for 5 days to confirm tumor growth, and then assigned to each of the three treatment groups with 10 animals in each group: vehicle control, anti-PD-L1 antibody 10 mg/kg (group of positive control), and sPD-1 Variant 2—Fc fusion protein 10 mg/kg (group of PD1-ECD-Fc 10 mg/kg). Treatment started day 6 post tumor inoculation and animals were removed from the study once the tumor size exceeds 2000 $mm^3$. Tumor growth overtime and survival were recorded as experimental endpoint.

sPD-1 Variant 2—Fc fusion protein demonstrated superior anti-tumor activity compared to the positive control group (i.e. anti-PD-L1 antibody), as evidenced by reduced tumor volume, increased tumor growth inhibition, increased survival rate and reduced body weight in the group of sPD-1 Variant 2—Fc fusion protein (i.e. PD-1-ECD-Fc group) compared to that in the group of anti-PD-L1 antibody.

F. EXAMPLE 6: Expression of PD-L2 in Lentiviral Transduced Hep3B-OS8 Cells and MC38 Cells Hep3B-OS8 cells and MC38 cells were transduced with lentiviral plasmid with human PD-L2 expression.

The expression of PDL2 in single clones of Hep3B-OS8 cells and MC38 cells were analyzed using FACS. Briefly, cells were harvested according to standard procedures, and the supernatant was discarded. The cells were dispensed into staining plate at 0.3 million cells per well, and the plate was centrifuged at 300 g at 4° C. for 5 min. 100 ul/well rabbit anti-hPD-L2 (1 ug/test) antibody was added in FACS buffer titrated, and incubated for 1 hour at 4° C. The cells were washed twice with 200 μl FACS buffer, centrifuged at 300 g for 5 min and the supernatant was discarded before and after each wash. The cells were resuspended at 100 μl/well with 1:1000 dilution of secondary antibody. The plates were incubated for 30 min at 4° C. The cells were washed 2 times with 200 μl FACS buffer, centrifuged at 300 g for 5 min, and the supernatant was discarded before and after each wash. The cells were resuspended in 100 μl PBS. The cells were kept in dark and submitted for FACS analysis. FACS analyses were performed with FACS Canto II, BD Biosciences per manufactures instruction.

Figure 13:
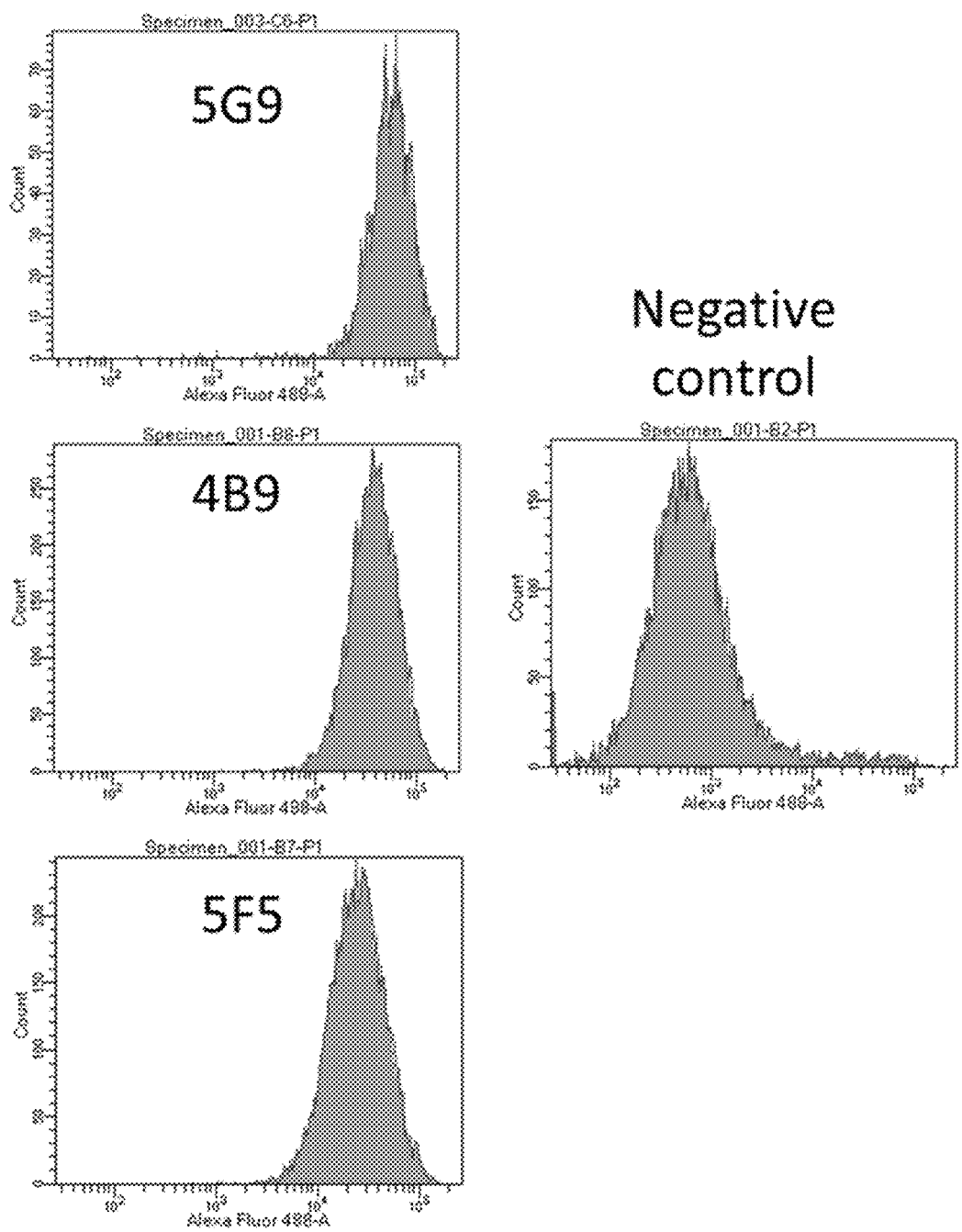
FIG. 13 shows that human PD-L2 were overexpressed in Hep3B and MC38 cell lines. Positive clones were selected by Fluorescence-activated cell sorting (FACS).

FIG. 13 shows that human PD-L2 were overexpressed in Hep3B and MC38 cell lines.

G. EXAMPLE 7: Binding Activity of sPD-1 Variant—Fc Fusion Protein on Hep3b Cells Over-Expressing Human PD-L2 (Hep3B-hPDL2)

FACS binding analysis was performed to assess the binding activity of sPD-1 variant—Fc fusion protein with human hepatocellular cancer cell line Hep3b cells overexpressing human PD-L2 (Hep3B-hPDL2).

Briefly, the cells were cultured at 37° C. with 5% $CO_2$. Cells were harvested according to standard procedures, and the supernatant was discarded. Cells were dispensed into staining plates at 0.3 million cells per well. The plates were centrifuged at 300 g at 4° C. for 5 minutes. A series concentration of sPD-1 variant—Fc fusion protein, wild type PD-1, PDL2 tab1 and a negative control human IgG4 in FACS buffer containing 2% FBS were titrated 1:5 from 500 µg/ml. 100 µl were added to each well and cells were incubated for 1 hour at 4° C. The cells were washed twice with 200 µl FACS buffer, centrifuged at 300 g for 5 minutes and the supernatant was discarded before and after each wash. Cells were then re-suspended with anti-human IgG-Alexa 488. Plates were incubated for 1 hour at 4° C. Cells were then washed twice for FACS analysis. FACS analyses were performed with FACS Canto II, BD Biosciences per manufactures instruction.

Figure 14:
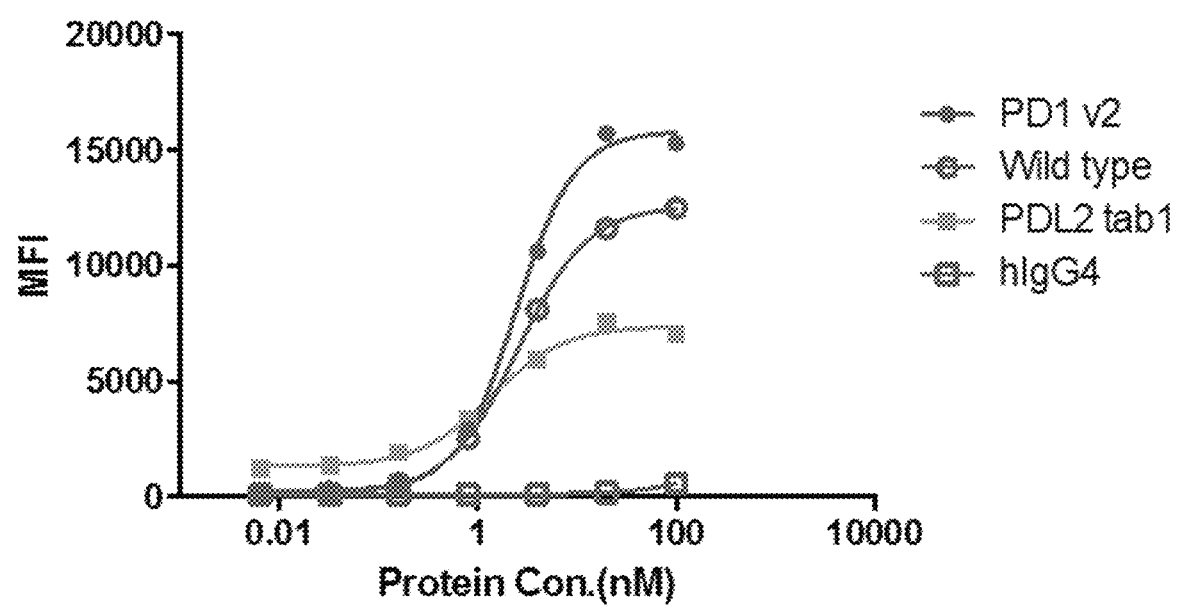
FIG. 14 shows that sPD-1 variant 2—Fc fusion protein binds strongly to Hep3b-hPDL2 cells in PD1 protein and PDL2 tab1 binding test on Hep3b-hPDL2 cell.

FIG. 14 shows that sPD-1 variant—Fc fusion protein (e.g. sPD-1 variant version 2—Fc fusion protein) demonstrated higher binding affinity for Hep3B-hPDL2 cells than the wild type PD-1 group.

H. EXAMPLE 8: T Cell Activation Assay in Cocultured of PBMC and Hep3B-OS8-PDL2 4B9

PBMC isolation: The blood sample from an individual donor was diluted by the same volume of sterile PBS, for instance, 25 ml sterile PBS was added into 25 ml fresh whole blood and mixed sufficiently by gentle shake. 15 ml Ficoll-Pague medium was transferred into a new 50 ml centrifuge tube to make sure the Ficoll and blood volume ratio is 3:4, then the diluted blood sample was carefully added onto the surface of the Ficoll medium, avoiding mixing by being added as soft as possible so that the layers of two liquids could be seen clearly. The tube was gently moved to centrifuge, at 400×g, 30 min, 20° C., with the Max acceleration and Min deceleration settings during the centrifugation. The layer of mononuclear cells was carefully absorbed and transferred into another new sterile centrifuge tube. The sterile PBS buffer was added into the collected PBMCs for washing at a volume ratio of 3:1 and centrifuged at 300×g, 10 min, 20° C. The cells were then resuspended with 10% FBS+RPMI 1640 for assay.

Preparation of Hep3B hPD-L2 cells: mycoplasma-free Hep3b-hPDL2-OS8 cells were prepared in a 15 cm dish, and the confluency was kept at 60~80% before use. The cells were trypsinized with TrypLE™ Express Enzyme, the trypsin was then neutralized and the cells were collected to a 50 ml centrifuge tube by centrifuging at 1000 rpm for 5 min. The supernatant was discarded, and the cells were resuspended with mitomycin, 10 µg/ml (in 5-10 ml 10% FBS+RPMI1640 medium). The cells were incubated at 37° C. for 1 hr. The cells were washed with 15-20 ml PBS 4 times before cell counting with cytometer, and then centrifuged at 1000 rpm, 5 min, at 20° C. The cells were resuspended with 10% FBS+RPMI 1640 for assay.

PBMC stimulation: PBMC were added at 50,000 cell/well, 100 µl/well and then series of 5× sPD-1 variant version 2 (PD1 V2), 5× PD1 WT or hIgG4 protein solution 50 µl/well were added followed by Hep3b-hPDL2 cells at 5000 cell/well for 50 µl/well. The mixed solution was incubated at a 37° C. incubator for 72 hrs. The supernatant was harvested and freezed below −20° C. before ELISA test. The IFN-gamma concentration was tested by ELISA kit. Quantification of IFN-γ were determined by Quantifkine ELISA kits purchased from R&D. Procedures were performed according to the assay procedure of Human IFN-γ ELISA kit, R&D, Cat #DY285.

Figure 15:
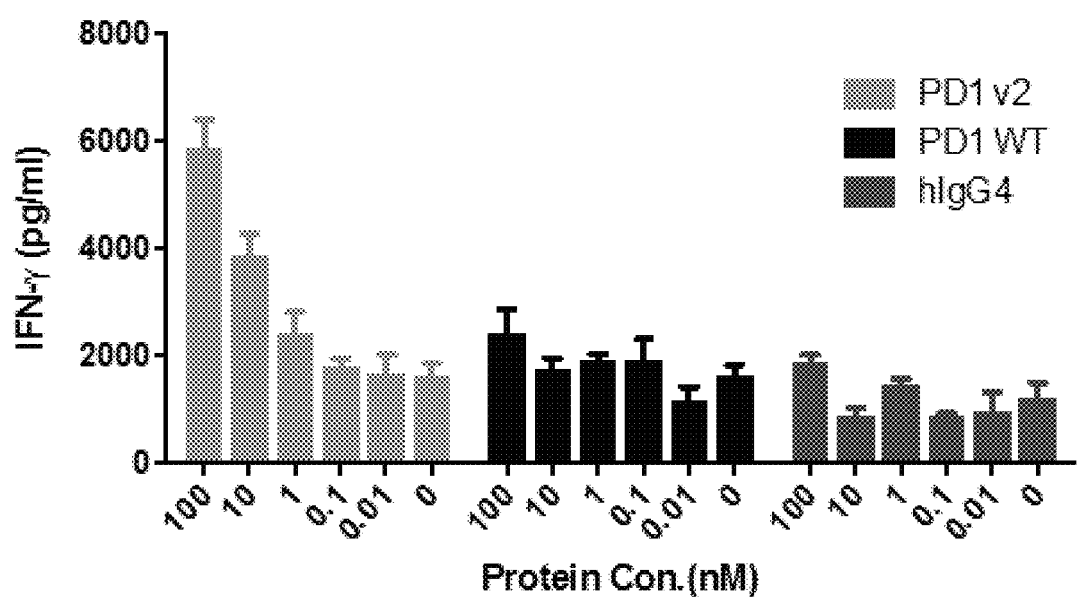
FIG. 15 shows T cell activation test in coculture of PBMC and Hep3B-OS8-PDL2 4B9.

FIG. 15 shows that sPD-1 variant version 2—Fc fusion proteins is capable of activating T cells in a T cell activation test with coculture of PBMC and Hep3B-OS8-PDL2 4B9.

I. EXAMPLE 9: In Vivo Tumor Study Using MC38-hPDL2 Colorectal Tumor Cell Line All animals were purchased and housed in AAALC accredited, temperature controlled and pathogen free environment. Animals were removed from the study once the tumor size reaches ethical limit. C57/B6 mice were inoculated with MC38-hPD-L2 tumor cells and observed for 5 days to confirm tumor growth, and then assigned to each of the three treatment groups with 10 animals in each group: vehicle control, anti-PD-1 antibody 10 mg/kg (group of positive control), and sPD-1 Variant 2—Fc fusion protein 10 mg/kg (group of PD1-ECD-Fc 10 mg/kg). Treatment started day 6 post tumor inoculation and animals were removed from the study once the tumor size exceeds 2000 $mm^3$. Tumor growth overtime and survival were recorded as experimental endpoint.

Figure 16:
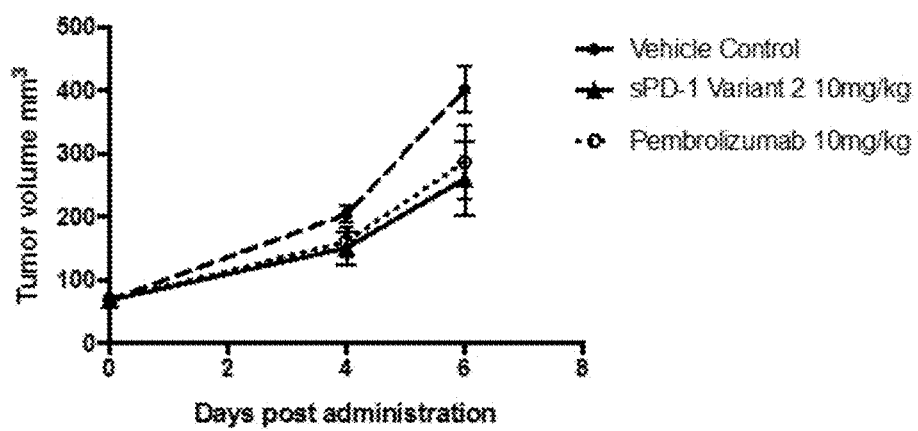
FIG. 16 shows tumor volumes on different days post-administration of a vehicle control, an sPD-1 variant 2-Fc fusion protein or Pembrolizumab in an in vivo tumor model using MC38-hPDL2 colorectal tumor cell line.

FIG. 16 shows that sPD-1 Variant 2—Fc fusion protein demonstrated equivalent anti-tumor activity compared to the positive control group (i.e. anti-PD-1 antibody, pembrolizumab), as evidenced by reduced tumor volume.

J. EXAMPLE 10: Neutralizing PD-L1 and PD-L2 for Enhancing the Efficacy of Immune Checkpoint Inhibitors 1. Abstract Immune checkpoint inhibitors that target PD-1 and PD-L1 have contributed significantly to the treatment of cancer, becoming one of the most widely used immunotherapy. Unfortunately, low patient response rate has presented itself as a major clinical challenge and to address such shortcoming, much of research efforts have been focused on improving the efficacy and response rate for patients receiving immune checkpoint therapies. In this study, we presented both clinical and biological evidences that PD-L2 is highly expressed in cancer types such as ovarian, gastric and esophageal cancer, all of which are poor responders to both PD-1 and PD-L1 inhibitors. We are hypothesizing that such lack of efficacy is partly due to the overwhelming levels of PD-L2 present in the tumors. Consistent with the previous finding that PD-L2 has 10 fold higher native binding affinity to PD-1 compared with PD-L1, high levels of PD-L2 leads to insufficient blockade of the PD-1 signaling pathway. To overcome this clinical shortcoming, we engineered a mutant soluble PD-1 decoy molecule that binds and neutralizes both PD-L1 and PD-L2 with an improved binding affinity of 10000 and 200 folds respectively when compared to their wildtype interaction. Such enhancement in binding affinity is contributed in part by conserved amino acid mutations both within and outside of the binding interface. Furthermore, we demonstrated that the sPD-1 mutant molecules are capable of stimulating T-cell mediated killing without affecting T-cell viability, subsequently resulted in superior in vivo efficacies in multiple syngenic cancer models driven by both PD-L2 and PD-L1.

2. Introduction

Therapeutic inhibition of PD-1 signaling pathway has proven to be a successful strategy in treating malignant diseases (Berger and Pu 2018, Gene 638: 20-25, hereby entirely incorporated by reference) showing unprecedented durable response in the clinic (Abdel-Rahman 2016, Immunotherapy 8(12): 1383-1391, hereby entirely incorporated by reference). Therapeutic antibodies against PD-1 and PD-L1 are approved for the treatment of various cancer types as a monotherapy or in combination with current standard-of-care (Abdel-Rahman 2016, Immunotherapy 8(12): 1383-1391, hereby entirely incorporated by reference). Unfortunately, clinical response to PD-1/PD-L1 inhibitors can be as diverse as the heterogeneous nature of the malignant diseases itself, further revealing the complexity of immune regulation and dysregulation associated with cancer progression (Ruiz de Galarreta, Bresnahan et al. 2019, Cancer Discov 9(8): 1124-1141, hereby entirely incorporated by reference). It has being clearly demonstrated that the activation of PD-1 signaling pathway requires the binding and the activation of PD-L1 and PD-L2 (Latchman, Wood et al. 2001, Nat Immunol 2(3): 261-268; Ishida, Iwai et al. 2002, Immunol Lett 84(1): 57-62, hereby entirely incorporated by reference). PD-L1 is the predominant ligand for PD-1 and is well studied and recognized as a biomarker for therapeutic response to PD-1 (Freeman, Long et al. 2000, J Exp Med 192(7): 1027-1034, hereby entirely incorporated by reference). However, the role of PD-L2 in tumor immune biology remains unclear (Bardhan, Anagnostou et al. 2016, Front Immunol 7: 550, hereby entirely incorporated by reference).

A continuous effort trying to boost the response rate of PD-1/PD-L1 inhibitors was made in the clinic through testing these inhibitors in combinations with a cocktail of cytotoxic drugs, targeted therapies and radiation treatment, aiming to improve the therapeutic efficacy while preserving a manageable toxicity profile (Sullivan, Hamid et al. 2019, Nat Med 25(6): 929-935, hereby entirely incorporated by reference). Yet despite all efforts, it is still puzzling that certain cancer types such as ovarian cancer, esophageal cancer and gastric cancer still experiencing sub-optimal clinical response, showing minimal infiltration of CD8+ cytotoxic T cells and limited T-cell activity (Meza-Perez and Randall 2017, Trends Immunol 38(7): 526-536; Sato, Olson et al. 2005, Proc Natl Acad Sci USA 102(51): 18538-18543, hereby entirely incorporated by reference). Interestingly, immunohistochemistry analysis of patient tumors revealed additional information regarding both the PD-L1 and PD-L2 expression in tumors. While the expression of PD-L1 remains high in many malignancy. PD-L2, a largely understudied second ligand of PD-1 also reported to be highly expressed in these cancers that are known to be poor responders to PD-1/PD-L1 inhibitors (Mak, Tong et al. 2016, Clin Cancer Res 22(3): 609-620, hereby entirely incorporated by reference) Although the common perception is that the treatment of αPD-1 antibodies is sufficient to block both PD-L1 and PD-L2 mediated activation of PD-1 (Garon, Rizvi et al. 2015, N Engl J Med 372(21): 2018-2028, hereby entirely incorporated by reference). However, binding studies done by us and others showed significant higher in binding affinities between PD-1 and PD-L2 compared to PD-1 and PD-L1 (Lazar-Molnar, Yan et al. 2008, Proc Natl Acad Sci USA 105(30): 10483-10488, hereby entirely incorporated by reference), giving PD-L2 an significant advantage when competing with PD-1 antibodies for receptor binding.

In this study, we demonstrate that the overexpression of PD-L2 is a clinically relevant observation in ovarian, esophageal and gastric cancer and is correlated with high PD-L1 expression as well as the exclusion of CD8+ cytotoxic T-cells. This observation prompted us to develop a soluble PD-1 ligand trap with enhanced binding affinity to PD-L1 and PD-L2. the soluble PD-1 Mutant showed ×10,000 and ×200 fold improvement in binding affinity to PD-1 receptor when compared to the wildtype binding between PD-L1 and PD-L2 respective. Structural modeling of the receptor-ligand complex revealed unique mutations in both binding interface and non-binding sites contributing to such affinity enhancement. This enhancement in binding affinity translated into improved inhibition of PD-1 receptor activity both in vitro and in vivo, outperforming antibodies targeting PD-L1 and PD-1 in multiple cancer types. More importantly, through both genetic and pharmacological approaches, we solidified the biological requirement of PD-L2 as an independent contributor to PD-1 signaling and demonstrated that the use of high affinity soluble PD-1 mutant is a clinically viable strategy for targeting cancers expressing both PD-L1 and PD-L2.

3. Results

PD-L2 is Abundantly Expressed in Human Ovarian, Esophageal, Gastric and Brain Tumors.

Although PD-L1 mediated PD-1 signaling has been the subject of extensive study in the field of immune-oncology, less is known about the status of PD-L2, especially in cancers that are poor responders to anti-PD-1/PD-L1 therapies (Derks, Nason et al. 2015, Cancer Immunol Res 3(10): 1123-1129; Lingohr, Dohmen et al. 2019, Epigenomics 11(6): 639-653; hereby entirely incorporated by reference). In the current study, we wanted to examine the clinical relevance of PD-L2 during tumor progression, and in particular cancer types that showed sub-optimal anti-tumor effect in response to check point inhibitors. We have chosen human cancer TMAs from ovarian cancer (n=156), esophageal cancer (n=72), gastric cancer (n=76) and glioblastomas (n=152). Each specimen was co-stained with PD-L1 (Latchman, Wood et al.), PD-L2 (Grey) and pan-cytokeratin (Red) as a marker of epithelial cells. The specificity of anti-PD-L1 and anti-PD-L2 antibodies were validated in human tonsil tissue to avoid possible cross-reactivity between the two antibodies (FIG. 24E). The expression level of PD-L1 and PD-L2 were scored according to the staining intensity and further stratified according to tumor grade. In ovarian, esophageal and gastric cancer, the expression of PD-L1 is elevated in the cancerous tissue but significantly lower in the non-malignant specimens (FIGS. 18A-18C). Interestingly, PD-L2 expression levels was also significantly increased in cancer, and its expression pattern tracts with PD-L1 for ovarian, gastric and esophageal cancer (FIGS. 18A-18C) with the exception of glioblastoma (FIG. 18D). In glioblastoma, only PD-L2 expression was significantly elevated in tumors regardless of its grade. No change was detected in PD-L1 expression between normal versus different grades of glioblastoma specimens (FIG. 18D with quantification shown on the right side). Although the non-malignant brain tissue had very few cells in the specimen, however those cells had intense signal for PD-L1 hence the high score of PD-L1 in normal tissue. The Pearson correlations between PD-L1 and PD-L2 were also calculated and plotted for each of the cancer type (FIGS. 24A-24D). Consistent with the Immunostaining findings, we found positive correlation between the PD-L1 and PD-L2 across all four cancer types, confirm our hypothesis that PD-L2 is present in abundance in tumors respond poorly to immune check point therapies (FIGS. 24A-24D). Functionally, we examined whether the presence of PD-L1 and PD-L2 expression resulted in changes in the infiltrating CD8$^+$ T cells. We stained ovarian (FIG. 18E) and esophageal cancer (FIG. 18F) specimens from the same TMAs and again quantified CD8$^+$ cells stratified according to tumor grades. In ovarian cancer, non-malignant ovary tissue with blood vessels were included as positive control showing the majority of CD8$^+$ T cells confined to the blood stream (FIG. 18E top panel). Representative pictures of ovarian cancers positive and negative for infiltration CD8+ T cells are shown in FIG. 18E and was again quantified according to tumor grade (FIG. 25A). In esophageal cancer TMA, most esophageal cancer samples had low CD8+ T cell staining with the exception of few showing higher CD8 cells (FIG. 18F and FIG. 25B). Inflammatory esophagitis tissues were included in the TMA as positive control. Lack of CD8$^+$ T cells in tumor suggests that the presence of both PD-L1 and PD-L2 can be contributing factors towards T-cell exclusion. In summary, our results demonstrated the high expression of both PD-L1 and PD-L2 in multiple cancer types with known sub-optimal clinical response to PD-1/PD-L1 therapies, and this may also play a role in the immune exclusion of CD8$^+$ cytotoxic T cells in cancer tissues.

Engineering sPD-1 Mutants with Superior Binding Affinity to PD-L1 and PD-L2

A sophisticated way of antagonizing both PD-L1 and PD-L2 in a biological system is to utilize the soluble component of the PD-1 receptor (FIG. 19A). Unfortunately, the native affinity of wild type soluble PD-1 and both of its ligands are low in the micromolar range, making wild type sPD-1 an ineffective antagonist for blocking PD-1/PD-L1/PD-L2 signaling axis (Lazar-Molnar, Yan et al. 2008, Proc Natl Acad Sci USA 105(30): 10483-10488, hereby entirely incorporated by reference). In an attempt to develop antagonists with high binding affinity towards neutralizing both PD-L1 and PD-L2, we generated a library of mutants by introducing random mutations throughout the extracellular component of the PD-1 molecule (soluble PD-1). Adopting a similar strategy we have previously published (Kariolis, et al. 2014, Nat Chem Biol 10(11): 977-983, hereby entirely incorporated by reference) mutant library was displayed as fusion proteins on yeast cell surface and further enriched for clones with enhanced binding to PD-L1 (FIG. 19B and FIG. 26). After six rounds of sorting, clones with superior binding affinity were sequenced for further characterization and analysis (FIG. 37). Eight residues were mutated on the sPD-1 domain corresponding to Ser62, Ser87, Pro89, Asn116, Gly124, Ser127, Ala132 and Ala140 with the position numbering starting from the signal region (Table 4). An updated version of the sPD-1 mutant (version 2) was generated by removing the mutation on Asn116 to avoid mutating a N-glycosylation site. Both mutant versions were fused onto the Fc domain of human IgG4 for improved stability and apparent affinities. The apparent affinities of both mutant V1 and V2 IgG4 towards human PD-L1 and PD-L2 were quantitatively measured using the BIAcore® surface plasmon resonance technology and compared to wild type sPD-1 IgG4. A significant improvement in binding affinities to human PD-L1 and PD-L2 was detected in both mutant V1 and V2 when compared to wild type sPD-1, exhibiting approximately 10,000 fold and 200 fold improvement in binding affinity towards PD-L1 and PD-L2 respectively (FIG. 8). In both instances this improvement in affinities were primarily driven by a slower dissociation rate (FIGS. 19C and 19D). Since we saw no significant differences in the KDs between the sPD-1 mutant V1 and sPD-1 mutant V2. All cell based and in vivo studies were carried-out using sPD-1 mutant V2. Collectively, using yeast-surface display based technology, we identified sPD-1 mutant clones exhibiting high binding affinity towards PD-L1 and PD-L2. These clones sill be characterized further to evaluate both structural and biological enhancement as a result of site-specific mutations.

Computational Based Modeling to Identify Structural Basis for High Affinity Binding To determine the changes in structural confirmation that result in such affinity increase between PD-1/PD-L1 and PD-L2, we performed computational modeling comparing human PD-L1 and PD-L2 in co-complex with the sPD-1 mutant. Wild type human PD-1/PD-L1 complex structure is available in PDB (4ZQK and 5IUS). However, since there are missing and mutated residues in the loop area of PD-1, we first fixed the missing loop and mutated the residue back to the wild type PD-1 based on 4ZQK. Sequence alignment of 4ZQK and 5IUS is shown in FIG. 2. The sPD-1 mutant structure was modeled using the Residue Scanning module in Schrodinger Suite. The crystal structure of PD-1 and PD-L1 are shown in blue and green respectively with the 8 mutations (Ser62, Ser87, Pro89, Asn116, Gly124, Ser127, Ala132 and Ala140 with the position numbering starting from the signal region) are shown in orange sticks (FIG. 3). Combining the knowledge from previous published literature and our structural modeling data, we identified residue G124S, S127V and A132I as mutations within the binding interface, S62G, S87G, P89L and A140V lies outside of the binding interface. G124S and A132I each make one additional hydrogen bond with Tyr 123 and Gln 66 of PD-L1 respectively (FIG. 20A left and right panel). Mutation A132I also resulted in an increase in surface complementary with PD-L1 from 0.72 to 0.85 (FIG. 20B, FIG. 29). To further investigate how these mutations influence the overall binding between PD-1 and PD-L1, the variation of the binding affinity and complex stability before and after individual mutation were calculated with results listed in Table 4. The calculation of variation of binding affinity and complex stability were also performed for grouped mutations within and outside of the binding interface (Table 5). A higher negative value is indicative of increased binding affinity and stability. Overall, the interface mutations contributed to both binding affinity and protein stability as expected, and the mutations outside of the binding interface lead to increased stability. Interestingly, the mutation A140V outside of the binding interface significantly improves the stability of the complex by 25.89 kcal/mol. This observation further reinforced the importance of a non-biased screening approach for identifying mutations outside of binding interface for improving overall stability of the co-complex.

Since human PD-L2 protein structure is not available in PDB, a model of human PD-L2 was built using available mouse PD-L2 structures as templates (FIG. 5A). The sequence identity between human PD-L2 and mouse PD-L2 is about 72% (FIG. 6, FIG. 5A). The overlay of proposed human PD-1/PD-L2 model and mouse PD-1/PD-L2 crystal structure (PDBID:3BP5) is shown in FIG. 6 and FIG. 5B. The mutant sPD-1 with proposed human PD-L2 co-complex crystal structure is shown in FIG. 7. When compared with proposed wild type human PD-1/PD-L2, similar to PD-1/PD-L1 binding, mutation A132I again retained the same additional hydrogen bond with PD-L2, resulted in an increased of surface complementarity (FIG. 20C and FIG.

Figure 11A:
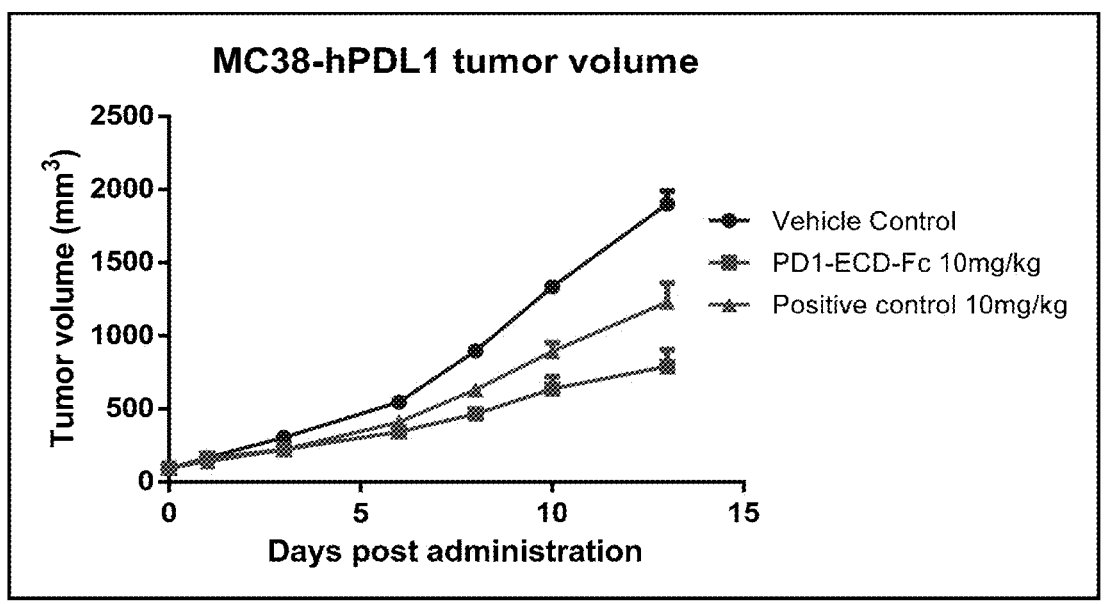
Figure 11B:
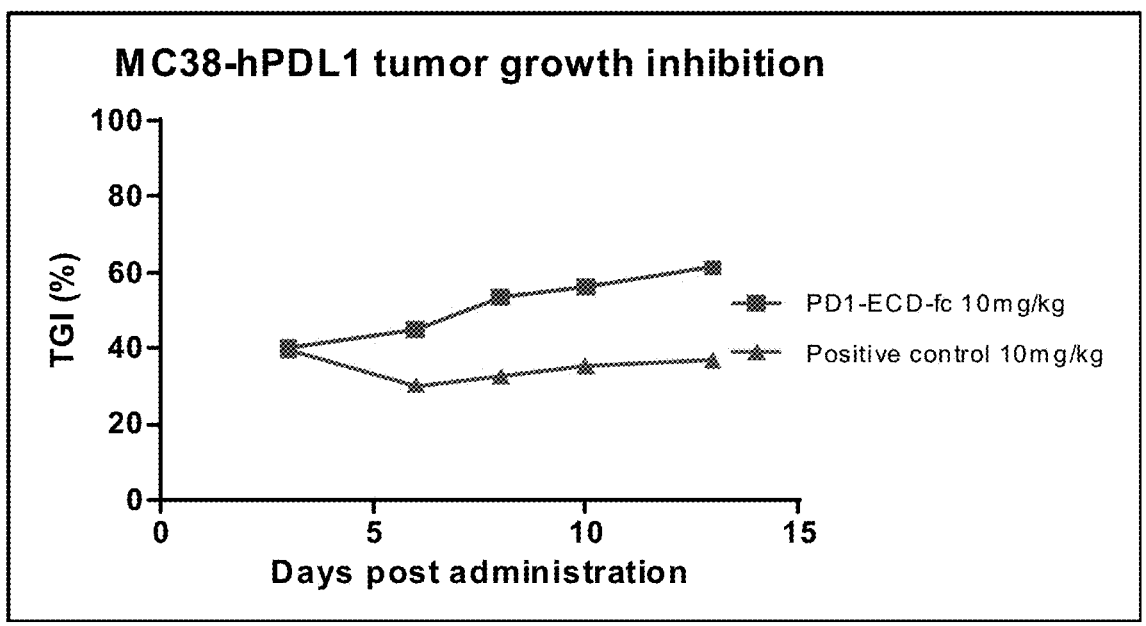
Figure 11C:
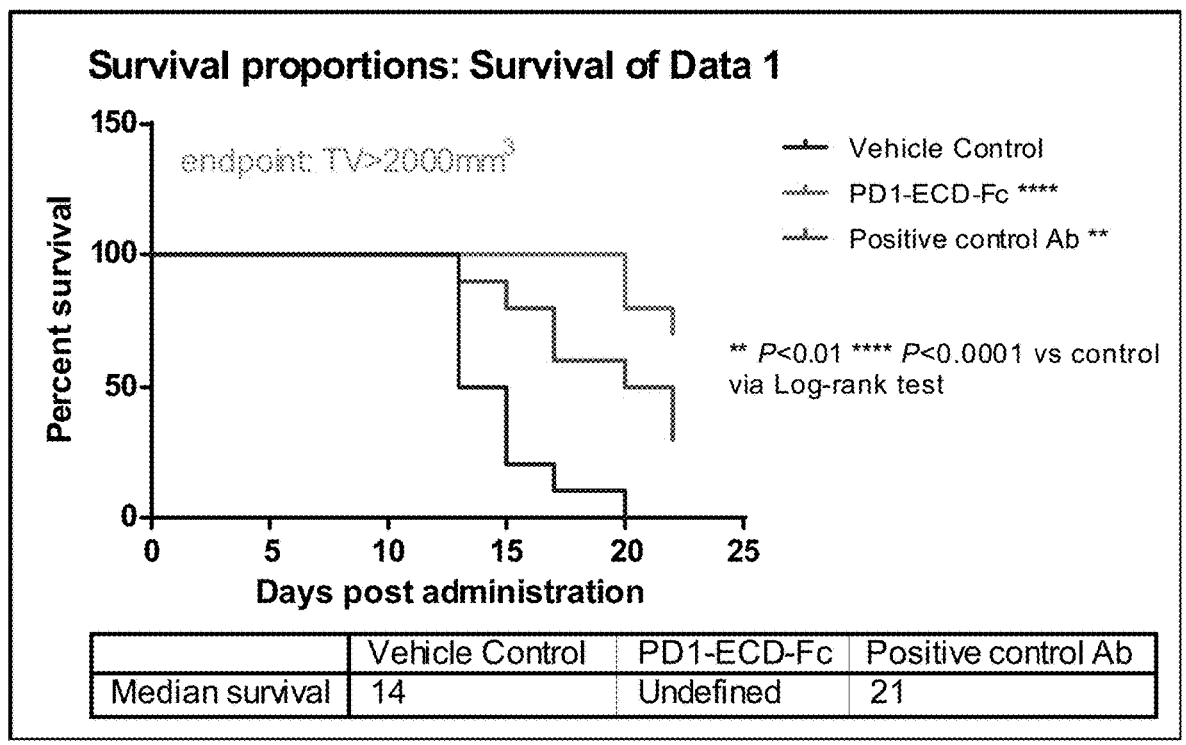
Figure 11D:
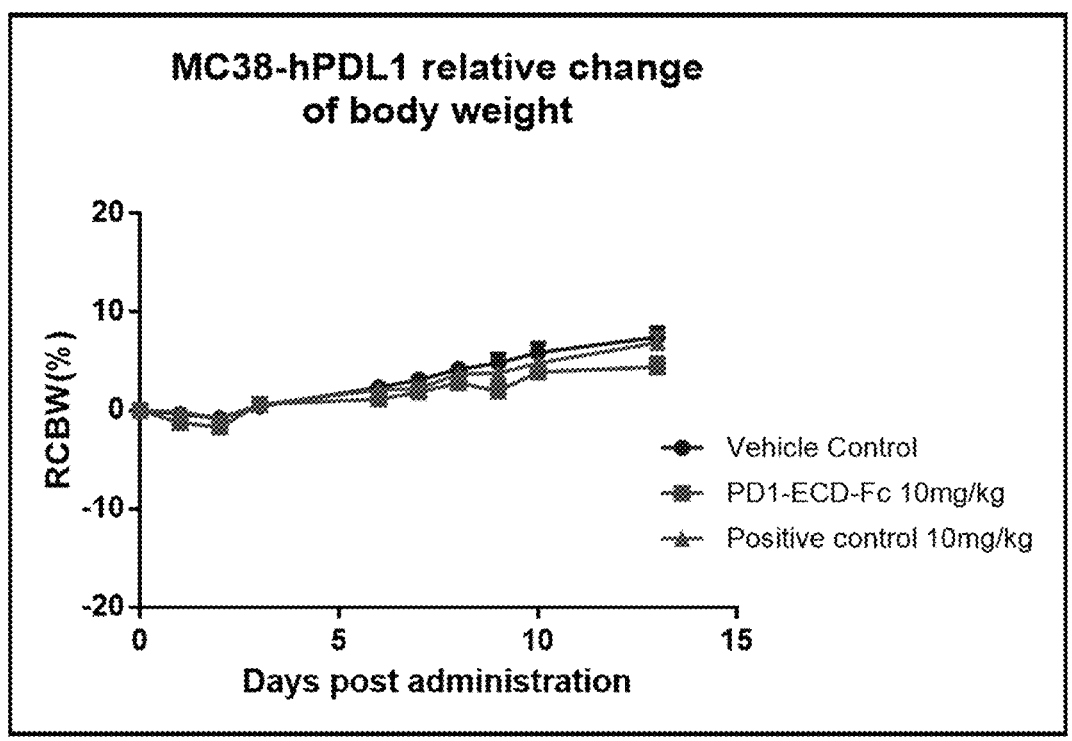

30). The calculation of the binding affinity variation and protein stability were also performed for single mutation and grouped mutations within and outside of the binding interface (Table 8 and Table 9). Based on structural simulation analysis, we have shown that the mutations both within and outside of the binding interface contribute to the improvement of overall binding affinity and stability.

sPD-1 Mutants Block PD-L1 and PD-L2 Mediated PD-1 Activation and Induce T-Cell Activation In order to demonstrate that the sPD-1 mutants can effectively disrupt the interactions between PD-L1/PD-L2 and PD-1, we first assessed the binding activity of sPD-1 mutants to PD-L1 using MC38 cells with knock-in human PD-L1 (provided by ChemPartner, Shanghai). Both versions of the sPD-1 mutants, the wildtype sPD-1 and the hIgG4 controls were tested using FACS based binding analysis. A significant improvement in binding signal was observed with both versions of the sPD-1 mutants compared with the wild type sPD-1 and the hIgG4 control, where no fluorescent signal can be detected up to µM range for the wild type sPD-1 (FIG. 9A). In order to validate the binding of sPD-1 to mouse PD-L1 for conducting in vivo testing downstream, we also analyzed sPD-1 mutant binding against wild type parental MC38 expressing mouse PD-L1 and PD-L2. Increase in binding signal was also detected with both version 1 and 2 compared to wild type sPD-1 with overall lower intensity (FIG. 9B). Binding analysis was also repeated in hepatocellular carcinoma cell line Hep3B-OS8-hPD-L1 (ChemPartner, Shanghai) with similar outcomes (FIG. 31). To test whether the sPD-1 mutants are capable of blocking receptor mediated interaction between PD-L1 and PD-1. We conducted Receptor Binding Assay (RBA) using sPD-1 mutants, wildtype sPD-1 and hIgG4 control. Both sPD-1 mutants showed superior inhibition of PD-L1 mediated receptor binding towards PD-1 when compared to wildtype sPD-1 and hIgG4 (FIG. 21A). To demonstrate that the sPD-1 mutant is capable of binding to PD-L2 and blocking PD-L2 mediated PD-1 activation, we overexpressed human PD-L2 in both MC38 and Hep3B cells (FIGS. 32 and 33). For binding analysis, we tested sPD-1 mutant V2 along with wild type sPD-1, αPD-L2 antibody as positive control and hIgG4 as negative control. sPD-1 mutant showed better binding to MC38-PD-L2, wild type sPD-1 and the αPD-L2 antibody binds to MC38-PD-L2 with less potency (FIG. 14). Similarly, sPD-1 mutant also exhibited enhanced ability to block PD-L2 mediated activation of PD-1 in receptor binding assay (FIG. 21B). To test whether the sPD-1 mutant is capable of activating human cytotoxic T-cells through blocking PD-L1 or PD-L2 mediated signaling, human PBMCs were collected from healthy donors and incubated with Hep3B-OS8-hPDL1 and Hep3B-OS8-hPDL2 cells. sPD-1 mutant, wildtype PD-1 and IgG4 were added and cytotoxic T cell activity measured by Interfereon-γ level. sPD-1 mutant is highly capable of activating T-cell in the presence of PD-L1 and PD-L2 respectively when compared to both wildtype sPD-1 and IgG4 in a dose dependent manner (FIGS. 10 and 15), supporting the argument that the sPD-1 mutant can functionally stimulate T-cell activity through blocking the interaction between PD-L1/PD-L2 and PD-1. Since prolonged stimulation of T-cell activity through direct binding using αPD-1 antibodies and PD-1 receptors on T-cells can potentially affect T-cell functionality and viability over time, our sPD-1 mutant was designed only to target cancer cells expressing PD-L1 and PD-L2, aiming to preserve T-cell longevity and functionality. To test this hypothesis, we first manufactured both sPD-1 mutants (V1 and V2) and wild type sPD-1 all fused to human IgG4 Fc with high purity and low endotoxin (FIG. 28). Then treated activated human T-cells (through stimulation with CD3/CD28 cocktail) with either αPD-1 antibody or sPD-1 mutant in the presence or absence of PD-L1 over a period of 12 days. Continuous treatment with αPD-1 slowed T-cell proliferation over-time while sPD-1 mutant treatment did not affect T-cell growth, showing similar growth rate as the CD3/CD28 stimulated T-cells. As expected, native T cells did not proliferate in the absence of CD3/CD28 stimulation (FIG. 21C). These observations reinforced the concept that the sPD-1 mutant is capable of binding and blocking PD-1/PD-L1 and PD-L2 signaling cascade and stimulate T-cell activity, while preserving T-cell viability and functionality.

sPD-1 Mutant Demonstrates Superior Anti-Tumor Efficacy in Syngenic Mouse Cancer Models The therapeutic potency of the sPD-1 mutant was evaluated in several syngenic mouse tumor models. sPD-1 mutant without mutation at the N-glycosylation site (Asn116) was used for all in vivo studies. In order to determine the dosing schedule and the pharmacokinetics of the sPD-1 mutant in vivo. The molecule was labelled with fluorescent dye and a single dose of 10 mg/kg was injected into mice and imaged at 30 minutes, 8 hours, 24 hours and 72 hours post treatment (FIG. 22A). Additionally, ELISA detecting human IgG4 portion of the sPD-1 mutant molecule was also performed on serum taken over time from animal treated with the same dosing (FIG. 22B). Both fluorescent imagine and ELISA analysis reached similar conclusion that the half-life of the sPD-1 mutant molecule is approximately 24 hours post dosing, provided the rationale for in vivo dosing at 10 mg/kg every 48 hours. Mice inoculated subcutaneously with MC38-hPDL1 colorectal cancers were treated with vehicle control, sPD-1 mutant or Atezolizumab. Significant reduction in tumor growth was observed in both sPD-1 mutant and Atezolizumab treated tumors (FIG. 11A). Compared to Atezolizumab treatment, tumors treated with sPD-1 mutant showed superior efficacy in suppressing tumor growth and prolonged survival with no severe toxicity defined by change in body weight (FIGS. 11C, 35, 11B), further providing rationale for targeting both PD-L1 and PD-L2 for optimal antitumor activities (FIG. 11B). The ability for sPD-1 mutant to antagonize PD-L2 mediated tumor growth was demonstrated in in vivo models inoculated with MC38 tumors overexpressing human PD-L2 (FIG. 22C). Significant delays in tumor growth were observed in tumor bearing mice treated with sPD-1 mutant or αPD-1 antibody Pembrolizumab. Although statistically not significant, there was trend towards better suppression of tumor growth in sPD-1 mutant treated group compared to the Pembrolizumab treated group that may warrant further investigation (FIG. 22C). The antitumor efficacy of sPD-1 mutant was also tested in mouse B16/OVA melanoma model and ID8 ovarian cancer model. Melanoma tumors treated with sPD-1 mutant fail to sustain tumor growth when compared to vehicle treated groups (FIG. 22D). Clinically, ovarian cancer patients are known to respond poorly to PD-1 inhibition. In this study we wanted to test the efficacy of sPD-1 mutant in a syngenic ovarian cancer model. Animals with orthotopically inoculated ID8 ovarian tumor cells were treated with vehicle control; sPD-1 mutant or mouse αPD-1 antibody and animals were terminated upon the development of ascites. Kaplan meier survival analysis showed improvement in overall survival for both mouse αPD-1 antibody treated and sPD-1 mutant treated groups. However most significant survival advantages were seen in animals treated with sPD-1 mutant group, suggesting that sPD-1 mutant is more efficacious that targeting ovarian cancer then blocking PD-1 receptor (FIG. 22E). Tumor infiltrating T cells (TILs) were analyzed in mice bearing B16/OVA (FIG. 22F) and MC38 (FIGS. 22G and 22H) tumors treated with αPD-1 antibody or sPD-1 mutant. Treatment from both inhibitors resulted in increased infiltration of $CD4^+$, $CD8^+$ cytotoxic T-cells again with most significant changes observed in the sPD-1 mutant treatment groups. Other tumor-associated immune cells were also profiled but no significant differences were detected between treatment groups (FIG. 36). Collectively we demonstrated superior antitumor efficacy of sPD-1 mutant tested in multiple syngenic mouse tumor models, partly contributed by better infiltration of TILs and has the potential to replace both αPD-L1 and αPD-1 antibodies as a new form of checkpoint inhibitor.

sPD-1 Mutant is Efficacious in PD-L2 Driven Animal Models of Human Cancer (FIG. 23)

To demonstrate that PD-L2 is a functionally important ligand of PD-1 and PD-L2 along is capable of facilitating PD-1 mediated tumor growth, especially in cancers types that are poor responder to PD-L1 inhibition. We genetically ablated PD-L1 in ID8 ovarian tumor cells using CRISPR-CAS9 technology and inoculated tumor cells into PD-L1 knockout mice, eliminating PD-L1 expression in both the tumor and the host (FIGS. 23A and 37A). Interestingly, complete loss of PD-L1 did result in slower tumor growth rate and smaller tumors formed compared to wildtype ID8 tumor grown in normal C57/B6 mice. Nonetheless satisfactory tumor growth did occur when mice inoculated with higher number of ID8 cells possible due to elevated PD-L2 expression (FIG. 2). Tumors treated with sPD-1 mutant fail to grow and showed significant tumor regression in some treated animals, as expected tumors treated with αPD-L1 antibody remains largely unresponsive (FIGS. 23B and 23C). In a separate study where ID8 PD-L1 CRISPR cells were orthotopically inoculated i.p., only three out of eight mice in the sPD-1 mutant treated group developed ascites, compared to seven out of eight mice in the αPD-L1 treated group. Significantly boosting the survival outcome of mice bearing ovarian cancer that was solely driving by PD-L2 (FIG. 23D). Finally, when ID8 tumors were stained for both PD-L2 and CD8 expression. As expected, all tumors regardless of treatment groups showed positive PD-L2 expression, however, only tumors treated with sPD-1 mutant saw infiltration of CD8+ T cells into the tumor due to the loss of both PD-L1 and PD-L2 (FIG. 23E).

In this study, we demonstrated the clinical relevance of PD-L2 in cancers that are considered poor responders to immune checkpoint inhibitor, and presented a therapeutic strategy that preferentially targets both PD-L1 and PD-L2 at ultra-high affinity. Structural and biological analysis of the sPD-1 mutant strongly supported our hypothesis that the improvement in the binding affinity leads to superior inhibition of the PD-1 pathway through blocking both of its ligands. Together with in vivo data demonstrating enhanced anti-tumor effects, sPD-1 mutant present itself as a viable clinical approach for targeting cancer types that lacks satisfactory response to PD-1/PD-L1 inhibitors as result of high PD-L2 expression.

4. Discussion

Immunotherapies such as the inhibitors of the PD-1 signaling pathway has revolutionized the cancer treatment landscape and dramatically improved the survival outcome for cancer patients who enjoyed durable response to the treatment (Topalian, Hodi et al. 2012, N Engl J Med 366(26): 2443-2454, hereby entirely incorporated by reference). However, while immunotherapy truly deserves to be named as "a breakthrough" in the battle against cancer, there is certainly no "one-size-fits-all" approach that promotes adequate immune response in all patients who receive the treatment. Response to PD-1/PD-L1 inhibitors varys between cancer types as well as individual patient within the same treatment cohort depending on the immunogenic nature of the malignant diseases (Pitt, Vetizou et al. 2016, Immunity 44(6): 1255-1269, hereby entirely incorporated by reference). Heterogeneity observed with checkpoint inhibitors maybe attributed to several factors including 1), genetic mutations within certain cancer cells causing microinstability (MSI-H) are more immunogenic and therefore showing better response to PD-1 inhibitors (Diaz and Le 2015, N Engl J Med 373(20): 1979, hereby entirely incorporated by reference). 2), Factors secreted by both cancer and cancer-associated stromal cells within the tumor microenvironment such as PD-L1 and PD-L2 protects cancer cells from immune surveillance, preventing cytotoxic T-cells recruitment and activation (Tumeh, Harview et al. 2014, Nature 515(7528): 568-571, hereby entirely incorporated by reference). Collectively, strategies that can promote host immune response to target cancer cells is vital to the success of immune checkpoint therapy.

In this study we are focusing on understanding both the expression level and the correlation of PD-L1 and PD-L2 in cancer types that are clinically poor responders to the PD-1 checkpoint therapies (Imai, Hasegawa et al. 2018, Oncol Lett 15(5): 6457-6468, hereby entirely incorporated by reference). In contrast to PD-L1, which is the better known ligand of PD-1, the role of PD-L2 in cancer remains elusive (Yearley, Gibson et al. 2017, Clin Cancer Res 23(12): 3158-3167, hereby entirely incorporated by reference). Interestingly, contrast to the common belief that PD-L1 is the predominant PD-1 ligand that is upregulated by cancer cells. We observed significantly elevation of PD-L2 expression in all of the patient samples we examined and its expression level is highly correlative to PD-L1 expression. Interestingly, we also observed PD-L1 expression in both cancer and non-cancerous tissue, whereas elevated PD-L2 expression seems to be restricted to cancer tissues, suggesting that the PD-L2 expression can be induced during malignant diseases. Based on these observations, we believe PD-L2 expression is highly expressed in cancers that respond poorly to PD-1 inhibitors and the adequate inhibition of both PD-L1 and PD-L2 is necessary for optimal antagonizing the PD-1 signaling pathway.

It is possible to achieve optimal suppression of the PD-1 signaling pathway though disrupting the receptor ligand interaction between PD-1 and PD-L1/L2. While blocking PD-1 receptors on T-cells using PD-1 antibodies have resulted in durable clinical response for a subset of patients, our patient data showed high levels of PD-L2 expression in cancers with poor response rate to PD-1/PD-L1 inhibition, suggesting that the presence of PD-L2 can potentially undermine the effort of PD-1 inhibition. Indeed, our data showed 10 folds increase in the native binding affinity between PD-L2 and PD-1 than the binding affinity between PD-L1 and PD-1. Although most αPD-1 antibodies undergoes affinity maturation enhancing their ability to bind PD-1 in the presence of its ligands, high level of PD-L2 expressed by cancer cells can significantly impede the ability of αPD-1 antibodies to compete for PD-1 binding. Instead of blocking PD-1 receptor on T-cells, we generated sPD-1 mutants with significant enhancement in binding affinity to both PD-L1 and PD-L2. Utilizing yeast surface display platform with directed evolution approaches (Kariolis, et al. 2014, Nat Chem Biol 10(11): 977-983, hereby entirely incorporated by reference), mutant clones displaying significant enhancement in binding affinity to both PD-L1 and PD-L2 were selected and the structural basis that confers such high affinity binding were analysed through computational structural modeling. The comparison of protein interaction between wildtype and mutated sPD-1 with PD-L1 revealed that the changes in binding affinity was a result of both gaining an additional hydrogen bond at Ala 132 and the improvement in the stability of co-complex as a result of mutations at Ser127 and Ala140 with the position numbering starting from the signal region. Similar findings were observed when comparing protein interaction between wild-type and mutated PD1/PD-L2 complex, again reinforcing the concept that while mutations occurring at the binding interface can improve the receptor-ligand binding affinity, mutations resides outside of the binding interface can be equally important in promoting stability of the overall structure. Interestingly, there has been reports of two additional studies that has generated high affinity binding sPD-1 clones (Maute, Gordon et al. 2015, Proc Natl Acad Sci USA 112(47): E6506-6514; Li, Liang et al. 2018, Cancer Sci 109(8): 2435-2445, hereby entirely incorporated by reference). Both studies reported unique mutation sites contributing to their enhanced binding affinity that does not overlap with our current study, again supporting a non-biased approach is essential for generating affinity enhanced therapeutics with desired biological properties.

The concept of enhanced affinity translates into superior biological activity is reinforced when in vitro FACS binding analysis and RBA assay clearly demonstrated that the sPD-1 mutants resulted in an enhancement in the binding affinity and their abilities to block interactions between PD-1 and PD-L1/L2. Functionally, sPD-1 mutant also resulted in heightened T-cell activity, a hallmark of immune checkpoint inhibition. In all scenario, it was evident that both PD-L1 or PD-L2 along were sufficient to activate the PD-1 pathway and the addition of the sPD-1 mutant effectively disrupt the signaling mediated by both ligands. In our study, we observed reduced viability of T-cells after continuous treatment with αPD-1 antibodies, whereas T-cells treated with sPD-1 treatment did not affect cell growth. While it is difficult to confirm whether the reduction in T-cell viability post αPD-1 treatment was a result of T cell exhaustion. Given that the αPD-1 antibody are known to directly bind and stimulate T-cells whereas sPD-1 mutant only targets PD-L1/L2 on cancer cells, avoiding direct interact with T-cell maybe at beneficial in preserving T-cell viability and functionality.

Current study evaluated the anti-tumor activity of sPD-1 mutant against both αPD-L1 or αPD-1 antibodies to address two questions. 1) Can sPD-1 mutant outperform both αPD-L1 and αPD-1 antibodies due to its enhanced ability to block PD-L1 and PD-L2? 2) Can sPD-1 mutant affect tumor growth in tumor models solely driven by PD-L2? Indeed, the sPD-1 mutant out performed both αPD-L1 and αPD-1 antibodies in multiple syngenic mouse tumor models, affirming the argument that the enhanced receptor-ligand binding affinity improves therapeutic outcome of PD-1 inhibition. More importantly, since the contribution of PD-L2 in tumor growth remains undefined, we evaluated the functional relevance of PD-L2 using PD-L1 knockout mice inoculated with PD-L1 CRISPR tumors, proving that PD-L2 along is capable of promoting tumor growth in the absence of PD-L1 and can be successfully targeted using sPD-1 mutants but not αPD-L1 antibody. However it is worth noting that both higher tumor cell number and delayed tumor growth was observed in tumor models lacking PD-L1, yet eventually the presence of PD-L2 is capable of maintaining tumor growth that can be effectively targeted using the sPD-1 mutant.

In summary, this study identified PD-L2 as a potential risk factor associated with poor clinical response towards PD-1 inhibitors in multiple cancer types. This observation prompt us to develop sPD-1 mutants with superior binding affinity to both PD-L1 and PD-L2 as a strategy to abolish the interaction between PD-1 and PD-L1/L2. The mutations both within and outside of the binding interface contributed to the enhancement of binding affinity and resulted in superior anti-tumor activities when compared with both αPD-L1 and αPD-1 antibodies. Furthermore, the observation that tumors expressing PD-L2 was able to grow in a PD-L1 independent manner in vivo and its growth inhibited by sPD-1 mutant but not αPD-L1 antibody further solidified the tumor protective role of PD-L2 in cancer. These data collectively provided justification for evaluating sPD-1 mutant as an alternative to PD-1 inhibitors in the treatment of cancer expressing PD-L1 and/or PD-L2.

5. Materials and Methods

Study Design

This study was designed to evaluate the involvement of PD-L2 both in in vivo models and human clinical specimens and to characterize structural, biochemical, functional and therapeutic efficacy of a soluble PD-1 mutants with ultra-high binding affinity to both PD-L1 and PD-L2. All tumor microarray specimens were commercially purchased from US Biomax (Derwood, Md.). A board certified veterinarian pathologist performed the Immunohistochemical scoring of the stained tumor microarray specimens. Mouse in vivo studies were conducted under the approval of AAAPLAC at Stanford University and ChemPartner, Shanghai. Sample size for animal studies was based on previous experience with similar in vivo studies. All animals were randomly assigned to treatment groups. Samples were not excluded from studies except for animals that required early termination due to illness that is unrelated to the study. Endpoints of experiments were defined in advance for each experiments. Tumor growth curves were presented for studies where tumor growth was measurable and Kaplan-Meier curves were used for ID8 orthotropic ovarian cancer model. Appropriate statistical analysis was used for each experimental study.

Cell Lines

MC38, IDB, ID8-PDL1 CRISPR, B16/OVA, MC38-hPD-L1, MC38-hPD-L2, MC38-hPD-L2-PD-L1 CRISPR, Hep3B-OS8-hPD-L1, Hep3B-OS8-hPD-L2 were maintained in Dulbecco's Modified Eagle's Medium (DMEM) supplemented with 10% fetal bovine serum (FBS) and 1% antibiotics in a humidified 37° C., 5% CO2 incubator. Cells were trypsinized and passaged at 80% confluency.

Synthesis of Yeast-Displayed sPD-1 Library

DNA encoding human PD-1 extracellular domain, amino acids Leu25-Val170, was cloned into the pCT yeast display plasmid using NheI and BamHI restriction sites. Sequence numbering was done to match that used in Mihalis S. Kariolis et al. (Kariolis, et al. 2014, Nat Chem Biol 10(11): 977-983, hereby entirely incorporated by reference) to facilitate comparisons to their work with the wild-type proteins. An error-prone library was created using the PD-1 extracellular domain DNA as a template and mutations were introduced by using low-fidelity Taq polymerase (Invitrogen) and the nucleotide analogs 8-oxo-dGTP and dPTP (TriLink Biotech). Six separate PCR reactions were performed in which the concentration of analogs and the number of cycles were varied to obtain a range of mutation frequencies; five cycles (200 µM), ten cycles (2, 20, or 200 µM), and 20 cycles (2 or 20 µM). Products from these reactions were amplified using forward and reverse primers each with 50 bp homology to the pCT plasmid in the absence of nucleotide analogs. Amplified DNA was purified using gel electrophoresis and pCT plasmid was digested with NheI and BamHI. Purified mutant cDNA and linearized plasmid were electroporated in a 5:1 ratio by weight into EBY100 yeast where they were assembled in vivo through homologous recombination (Kariolis, et al. 2014, Nat Chem Biol 10(11): 977-983, hereby entirely incorporated by reference) Library size was estimated to be 7.4×10$^7$ by dilution plating.

Library Screening

Yeast displaying high affinity PD-1 mutants were isolated from the library using fluorescence-activated cell sorting (FACS). For FACS rounds 1-3, equilibrium binding sorts were performed in which yeast were incubated at room temperature in phosphate buffered saline with 1 mg/ml BSA (PBSA) with the following nominal concentrations of Gas6 (R&D Systems): sort 1) 10 nM PD-L1 for 3 h; sort 2) 2 nM PD-L1 for 3 h; sort 3) 0.2 nM PD-L1 for 24 h. After incubation with PD-L1, yeast were pelleted, washed, and resuspended in PBSA with 1:250 of chicken anti-c-Myc (Invitrogen) for 1 h at 4° C. Yeast were then washed, pelleted and secondary labeling was performed for on ice for 30 min using PBSA with a 1:100 dilution of goat anti-chicken Alexa Fluor 555 (Invitrogen) and mouse anti-HIS Hilyte Fluor 488 (Anaspec).

For FACS rounds 4-6, kinetic off-rate sorts were conducted in which yeast were incubated with 2 nM PD-L1 for 3 hours at room temperature, after which cells were washed twice to remove excess unbound Gas6, and resuspended in PBSA containing a ~50 fold molar excess of PD-1 (R&D Systems) to render unbinding events irreversible. The length of the unbinding step was as follows: sort 4) 4 h; sort 5) 4 h; sort 6) 24 h, with all unbinding reactions performed at room temperature. During the last hour of the dissociation reaction, chicken anti-c-Myc was added to a final dilution of 1:250. Yeast were pelleted, washed, and secondary labeling was performed as previously described. Labeled yeast were sorted by FACS using a Vantage SE flow cytometer (Stanford FACS Core Facility) and CellQuest software (Becton Dickinson). Sorts were conducted such that the 1-3% of clones with the highest Gas6 binding/c-Myc expression ratio were selected, enriching the library for clones with the highest binding affinity to Gas6. In sort 1, 108 cells were screened and subsequent rounds analyzed a minimum of ten-fold the number of clones collected in the prior sort round to ensure adequate sampling of the library diversity. Selected clones were propagated and subjected to further rounds of FACS. Following sorts 5 and 6, plasmid DNA was recovered using a Zymoprep kit (Zymo Research Corp.), transformed into XL-1 blue supercompetent cells, and isolated using plasmid miniprep kit (Qiagen). Sequencing was performed by Sequetech Corp.

Analysis of yeast-displayed sort products was performed using the same reagents and protocols and described for the library sorts. Samples were analyzed on a FACSCalibur (BD Biosciences) and data was analyzed using FlowJo software (Treestar Inc.).

Recombinant Protein Production

Soluble PD-1 wild type and mutants linked to hIgG4Fc were cloned into the pCPC plasmid with signaling peptide (ChemPartner, Shanghai) and transiently transfected into HEK293 Human embryonic kidney cells and cultured in 4 L OPM-293 CD03. Products were then purified through protein A resin MabSelect SuRe (GE Healthcare) and further isolated using superdex 200 size exclusion chromatography. Each purification steps were followed by SDS-PAGE confirmation and SEC-HPLC analysis. Final products were endotoxin tested and confirmed at 0.09 EU/mg.

Computational Modeling Analysis

Human PD1/PDL1 complex structure is available in Protein Data Bank, the PDBID is 4ZQK and 5IUS. However, in both of the PDB structures, some residues of PD1 are missing in a loop area, and some of the residues were mutated comparing with wild type PD1. The missing loop and mutated the residue were reconstructed back to the wild type PD1 based on crystal structure 4ZQK. The mutated PD1 structure was modeled using Residue Scanning module in Schrodinger Suite. The residues within 5.0 Å of the mutated residue were refined with side-chain prediction and backbone sampling. The calculation of variation of binding affinity and complex stability were also performed for multiple mutations. The more negative value of binding affinity or stability indicates more increase of them. The homology model of PDL2 was built to investigate the interaction between human PD1 and PDL2. After homology search in PDB non-redundant data set, three PDB structures of mouse PDL2 were chosen to be templates. PD1 binding interface comparison between human PDL2 model and mouse PDL2 crystal structure (PDBID: 3BP5).

Immunoassays

Slides were de-paraffined and antigen retrieval carried out using 10 mM Citric Acid Buffer, 0.05% Tween 20, pH 6 Slides were removed from buffer and cooled at room temperature for 15 minutes. Quenched endogenous peroxidase with 1:10 dilution of 34% hydrogen peroxide and water for 15 minutes. Avidin and Biotin blocker were added for 15 minutes each. Protein block using 2% fetal calf serum was added for 20 minutes. The serum and antibodies were diluted in PBT (1×PBS, 0.1% BSA, 0.2% , 0.01% Tween 20). αHuman PD-L1 1:500 (#AF154, R&D systems, Minneapolis, Minn.), αHuman PD-L2 1:500 (#MABC1120, EMD Millipore, Mass.), αHuman CD8 1:500 (#Ab4005, Abcam, Cambridge, Mass.), αMouse PD-L1 1:750 (#17952-1-AP, Proteintech, Ill.), αMouse PD-L2 1:750 (#Ab21107, Abcam, Cambridge, Mass.) and αMouse CD8 1:500 (#Ab203035, Abcam, Cambridge, Mass.) antibodies incubated overnight at ° C. For immunohistochemistry, anti-rabbit and anti-rat were added on each slide and incubated at 37° C. for 30 minutes then incubated with STREP-HRP for 30 minutes at 37° C. and signals developed using DAB substrate kit (#34002, ThermoFisher Scientific, Waltham, Mass.). For immunofluorescence detection, all staining were carried out in dark, Secondary antibody1:400 diluted in 2% BSA and 0.1% tween 20 in PBS was incubated at room temperature for 1 hour. Sudan Black B 0.2% solution in 70% ethanol through syringe filter, pre-warmed to RT was added to the slides for 10 minutes at room temperature. DAPI (#F6057, Sigma-Aldrich, St. Louis, Mo.) 0.1 µg/mL was used for counterstain and coverslip applied. ELISA quantification of human IgG4 (#BMS2059, ThermoFisher Scientific, Waltham, Mass.) was carried out per manufacturer's instruction.

Surface Plasmon Resonance

Human PD-L1 (#10084-H08H, SinoBiological, Wayne, Pa.) and human PD-L2 (#10292-H08H, SinoBiological, Wayne, Pa.) were used as analyte. Running buffer HBS-EP+ (10 mM HEPES, 150 mM NaCl, 3 mM EDTA and 0.05% P20, pH 7.4) was prepared. Flow rate was performed at 30 µL/min. Immobilization of anti-human Fc IgG on CMS sensorchip. PD1-Fc was captured to the immobilized sensorchip. An injection of serial diluted analyte was used.

Glycine pH 1.5 for 30 s was used as the surface regeneration. Multiple cycle kinetics was carried out on Biacore T200. Kd analysis calculated using the Biacore T200 Evaluation Software (GE Healthcare Life Sciences).

Flow Cytometry Based Binding Analysis

The MC38-hPD-L1, MC38-hPD-L2, Hep3B-OS8-hPD-L1, Hep3B-OS8-hPD-L2 and parental MC38 cells were cultured in standard tissue culture condition. Cells were harvested and the supernatant discarded then dispensed onto a staining plate at 3×105 cells per well. The plate was centrifuged at 300 g at 4° C. for 5 minutes. Various concentrations of sPD-1 mutants and negative control were diluted in FACS buffer containing 2% FBS, 100 µL/well was added. Cells were incubated for 1 hour at 4° C. and washed twice with 200 µL FACS buffer and centrifuged at 300 g for 5 minutes. The supernatant was discarded before and after each wash. Cells were re-suspended at 1004/well with 1:1000 diluent with anti-human IgG-Alexa 488 (#A28175, ThermoFisher, Waltham, Mass.). Plates were incubated for 1 hour at 4° C. Cells were washed twice with FACS buffer and centrifuged at 300 g for 5 minutes. Supernatant was discarded and cells were re-suspended in 100 µL cold PBS. The cells were kept in the dark and FACS analysis carried out on FACS CantoII, (BD Biosciences, San Jose, Calif.).

Receptor Blocking Assay

Hep3B-OS8-hPD-L1, Hep3B-OS8-hPD-L2, MC38-hPD-L1 and MC38-hPD-L2 cells were cultured in PRMI 1640 medium, 10% FBS, G418 and hygro, in T175 flask to a confluency of 60-80%. The cells were harvested and re-suspended into dilution buffer. cells were dispensed into round bottom 96-well plate corning #3799 at the density of $2 \times 10^5$ cells/well. sPD-1 mutant at multiple concentration: 600, 120, 24, 4.8, 0.96, 0.192, 0.00384 nM and 0 nM were re-suspended in dilution Buffer. sPD-1 wild type were also prepared in dilution Buffer. The plate was centrifuged at 500 g for 3 minutes and supernatants discarded. Cells were re-suspended with 50 µL antibody followed by adding 50 µL of ligand. The plates were incubated at 4° C. for 2 hours followed by centrifugation and washed. Streptavidin-Alexa Flour 488 (#S11223, Thermo Fisher, Waltham, Mass.) diluted 1:1000 in dilution Buffer was prepare and incubated with cells at 4° C. for 1 hour. The plate was centrifuged and washed then re-suspended in 200 µL FACS buffer. Cells ran on FACS Canto II (BD Biosciences, San Jose, Calif.). Curves with MFI values were drawn and IC50s and tops were calculated.

T Cell Stimulation and T Proliferation Assay

Blood sample from healthy donors were diluted by equal volume of sterile PBS and mixed by gentle shaking. 15 mL of Ficoll-Paque PLUS (−1440-02, GE Healthcare, Pittsburgh, Pa.) medium was transferred into a fresh 50 mL centrifuge tube with a Ficoll and blood volume ration of 3:4. The diluted blood sample was then carefully layered onto the surface of the Ficoll medium to avoid mixing. The tube was centrifuged at 400 g for 30 minutes at 20° C. with the max acceleration and min deceleration settings during the centrifugation. 4 interfaces was observed after the centrifugation with layers of plasma, mononuclear cells, Ficoll medium, and RBCs seen from top to bottom. Gently removing the layer of mononuclear cells were carefully transferred into a new sterile centrifuge tube. Sterile PBS buffer was added into the collected PBMCs for washing. The tube was centrifuged at 300×g for 10 minutes at 20° C. with the max acceleration and min deceleration settings during the centrifugation. Cells were re-suspended with 10% FBS+RPMI 1640 for assay. Mycoplasma-free Hep3b-hPDL1-OS8 cells were prepared in a 15 cm dish with the confluency kept at 60-80% before use. Cells were trypsinized with TrypLE™ Express, (#12605-036, Thermo Fisher, Waltham, Mass.) were collected to a 50 mL centrifuge tube and centrifuged at 1000 rpm for 5 minutes. The supernatant was discarded and cells were re-suspended with mitomycin (#H33020786, Zhejiang, China) 10 µg/mL in 5-10 mL 10% FBS+RPMI 1640 medium. Cells were incubated at 37° C. for an hour. After incubation, cells were washed in PBS cell counting with cytometer. Cells were centrifuged at 1000 rpm for 5 minutes at 20° C. Cells were then re-suspended with 10% FBS+RPMI 1640 assay. PBMC stimulation was performed by adding PBMC at 5E4 cell/well with 100 µL/well on a 96 well microplate. 50 µL/well of a series of 5× OD1 v2, 5× PD1 WT, or hIgG4 protein solution was added followed by APC Hep3b-hPDL1-OS8 at 5000 cell/well for 50 µL/well. The mixed solution was incubated at 37° C. for 72 hours. The supernatant was harvested and placed in −20° C. before ELISA test. The IFN-γ concentration was tested with the ELISA kit. Quantification of IFN-γ was determined by quantikine ELISA kits purchased from R&D. The assay procedure outlined by the Human IFN-γ ELISA kit, R&D, Cat #DY285 was followed. The plate was read with the ELISA plate reader at 450 nm wavelength.

Expression of PD-L2 in Lentiviral Transduced Hep3B-OS8 Cells and MC38 Cells

Hep3B-OS8(4E8) cell line was transduced with pLVX-IRES-hygro-hPDL2:CP in house, raising in 1640 medium. MC38 cells were transduced with pLVX-IRES-hygro-hPDL2. Cells were harvested according to standard procedures and the supernatant was discarded. Cells were dispensed into a round bottom 96-well staining plate: corning, REF #3799 with 3e5 cells per well. The plate was placed in the centrifuge at 300 g at 4° C. for 5 minutes. 100 µL of rabbit anti-hPD-L2 in titrated 1×PBS+2% FBS FACS buffer was added to each well and incubated for one hour at 4° C. Cells were washed twice with 200 µL FACS buffer and centrifuged at 300 g for 5 minutes. Supernatant was discarded before and after each wash. Cells were re-suspended at 100 µL/well with 1:1000 dilution of secondary donkey-anti-rabbit IgG(H+L) Alexa488 life technology antibody and incubated for 1 hour at 4° C. Cells were again washed twice with 200 µL FACS buffer and centrifuged at 300 g for 5 minutes. Supernatant was discarded before and after each wash. Cells were re-suspended in 100 µL PBS. Cells were kept in the dark and submitted for FACS analysis.

In Vivo Tumor Studies

All animal experiments were reviewed and approved by the Institutional Animal Care and Use Committee (IACUC) at Stanford University and animal ethical committee at ChemPartner, Shanghai. C57B/6 mice with hPD-L1 knock-in were purchased from Biocytogen (Beijing, China) and wild type C57/B6 mice were purchased from Biocytogen (Beijing, China) or The Jackson Laboratory (Bar Harbor, Me.). PD-L1 knockout mice on C57B/6 background were kindly gifted by (Dr. Dean W. Felsher at Stanford University). Female mice age 6-8 weeks were used for ID8 ovarian tumor studies and male mice aged 6-8 weeks were used for MC38 colorectal studies and B16/OVA melanoma studies. Mice were housed in pathogen-free animal facility, kept under constant temperature and humidity and controlled 12 h light-dark cycles. For MC38, MC38-hPD-L1, MC38-hPD-L2 colorectal study, and B16/OVA melanoma study, 1×10^6 cells were injected subcutaneously and randomly assigned to control or appropriate treatment group upon confirmation of tumor growth approximately 7 days post tumor inoculation. Tumor growth was measured throughout the study and body weight recorded. Animals were sacrificed at the same time when majority of tumors reached ethical endpoint. For ID8 ovarian study, 5×10^6 cells were injected intraperitoneal, and each animal terminated upon development of peritoneal ascite for survival analysis. For tumor studies conducted in PD-L1 knockout mice, 10×10^6 ID8 cells were injected subcutaneously or intraperitoneal for two separate studies.

Statistical Analysis

The Pearson correlation was used for all correlation analysis of tumor specimens. IHC H score values were determined by a board certified veterinarian pathologist. All tumor volume, survival, quantification of in vivo immunohistochemistry were conducted using Prism software (GraphPad Software Inc). ANOVA with Tukey-Kramer test was used for comparing multiple treatment groups with each other. P <0.05 was considered significant. Repeated measure ANOVA was used for comparing multiple treatment groups measured over time. Statistical analysis of survival curves was conducted in the ID8 survival study. A log-rank (Mantel-Cox) test was performed to compare mean survival among groups; P <0.05 was considered statistically significant.

K. EXAMPLE 11: Neutralizing PD-L1 and PD-L2 for Enhancing the Efficacy of Immune Checkpoint Inhibitors 1. Mutant Clone Screening Against Human PD-L1 and PD-L2

Yeast displaying libraries of 128 sPD-1 mutants comprised of all possible combinations of the permutations arose from the high affinity binding sPD-1 mutant with the 7 mutation (62-87-89-124-127-132-140 with the position numbering starting from the signal region) were isolated from the library using fluorescence-activated cell sorting (FACS). Equilibrium binding sorts were performed in which yeast were incubated at room temperature in phosphate buffered saline with 1 mg/ml BSA (PBSA) with the following nominal concentrations of PDL1-Fc and PD-L2-Fc. Highest binding clones were collected and sequenced for further analysis.

2. Characterization of Selected Clones

FIG. 38A illustrates the amino acid mutations present in the initial mutant PD-1 clone and all mutations were used for generating a library of 128 sPD-1 mutant clones that includes all possible permutations of the 7 mutations. FIG. 38B shows a list of top 5 mutant clones selected from the 128 sPD-1 mutant clone library for further binding analysis. FIG. 39 shows dose-dependent binding curves of the original mutant sPD-1 and clones #1-5 to PD-L1, and FIG. 40 summarizes the Kd values of the original mutant sPD-1 and clones #1-5 binding to PD-L1. FIG. 41 shows dose-dependent binding curves of the original mutant sPD-1 and clones #1-5 to PD-L2, and FIG. 42 summarizes the Kd values of the original mutant sPD-1 and clones #1-5 binding to PD-L2.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only.

---

What is claimed is:

1. An sPD-1 variant—Fc fusion protein comprising:
   a) a soluble PD-1 (sPD-1) variant domain comprising an amino acid substitution as compared to SEQ ID NO:1, wherein said amino acid substitution is at a position number selected from the group consisting of 120, 112, 107, 104, 67, 69, 96 and 42; and wherein said sPD-1 variant domain comprises a set of amino acid substitutions G104S/S107V/A112I/A120V as compared to SEQ ID NO:1;
   b) an optional linker; and
   c) an Fc domain.

2. The Fc fusion protein according to claim 1, wherein said Fc fusion protein comprises, from N- to C-terminal:
   a) said sPD-1 variant domain;
   b) said optional linker; and
   c) said Fc domain.

3. The Fc fusion protein according to claim 1, wherein said Fc fusion protein comprises, from N- to C-terminal:
   a) said Fc domain;
   b) said optional linker; and
   c) said sPD-1 variant domain.

4. The Fc fusion protein according to claim 1, wherein said sPD-1 variant domain exhibits at least 95% identity to SEQ ID NO:1.

5. The Fc fusion protein according to claim 1, wherein said sPD-1 variant domain has amino acid substitutions at five of said positions, six of said positions, seven of said positions or eight of said positions.

6. The Fc fusion protein according to claim 1, wherein said sPD-1 variant domain further comprises one or more amino acid substitutions selected from the group consisting of: S67G, P69L, N96S and S42G.

7. The Fc fusion protein according to claim 1, wherein said sPD-1 variant domain consists of a set of amino acid substitutions selected from the group consisting of
   S42G/S67G/P69L/G104S/S107V/A112I/A120V,
   S42G/S67G/P69L/N96S/G104S/S107V/A112I/A120V,
   P69L/G104S/S107V/A112I/A120V,
   S67G/G104S/S107V/A112I/A120V,
   S67G/P69L/G104S/S107V/A112I/A120V, and
   G104S/S107V/A112I/A120V.

8. The Fc fusion protein according to claim 1, wherein said sPD-1 variant domain comprises a set of amino acid substitutions of S42G/S67G/P69L/G104S/S107V/A112I/A120V.

9. The Fc fusion protein according to claim 1, wherein said sPD-1 variant domain comprises a set of amino acid substitutions of S42G/S67G/P69L/N96S/G104S/S107V/A112I/A120V.

10. The Fc fusion protein according to claim 1, wherein said sPD-1 variant domain comprises a set of amino acid substitutions of P69L/G104S/S107V/A112I/A120V.

11. The Fc fusion protein according to claim 1, wherein said sPD-1 variant domain comprises a set of amino acid substitutions of S67G/G104S/S107V/A112I/A120V.

12. The Fc fusion protein according to claim 1, wherein said sPD-1 variant domain comprises a set of amino acid substitutions of S67G/P69L/G104S/S107V/A112I/A120V.

13. The Fc fusion protein according to claim 1, wherein said sPD-variant domain consists of a set of amino acid substitutions of G104S/S107V/A112I/A120V.

14. The Fc fusion protein according to claim 1, wherein said sPD-1 variant domain has SEQ ID NO:2.

15. The Fc fusion protein according to claim 1, wherein said sPD-1 variant domain has SEQ ID NO:3.

16. The Fc fusion protein according to claim 1, wherein said sPD-1 variant domain has SEQ ID NO:110.

17. The Fc fusion protein according to claim 1, wherein said sPD-1 variant domain has SEQ ID NO:130.

18. The Fc fusion protein according to claim 1, wherein said sPD-1 variant domain has SEQ ID NO:131.

19. The Fc fusion protein according to claim 1, wherein said sPD-1 variant domain has SEQ ID NO:138.

20. The Fc fusion protein according to claim 1, wherein said Fc domain is a human IgG Fc domain or a variant human IgG Fc domain.

21. The Fc fusion protein according to claim 20, wherein said human IgG Fc domain comprises the hinge-CH2-CH3 of human IgG4.

22. The Fc fusion protein according to claim 20, wherein said Fc domain is a variant human IgG Fc domain.

23. The Fc fusion protein according to claim 22, wherein said variant human IgG Fc domain comprises the hinge-CH2-CH3 of human IgG4 with a S228P amino acid substitution.

24. The Fc fusion protein according to claim 1, wherein said linker comprises a linker selected from the group consisting of (GS)n, SEQ ID NO:146, SEQ ID NO:147, and SEQ ID NO:148, wherein n is selected from the group consisting of 2, 3, 4 and 5.

25. The Fc fusion protein according to claim 24, wherein said linker comprises SEQ ID NO:147.

26. The Fc fusion protein according to claim 1, wherein said Fc fusion protein comprises SEQ ID NO:5.

27. The Fc fusion protein according to claim 1, wherein said Fc fusion protein comprises SEQ ID NO:6.

28. A nucleic acid encoding said Fc fusion protein according to claim 1.

29. An expression vector comprising said nucleic acid of claim 28.

30. A host cell comprising said nucleic acid of claim 28.

31. A method of making an sPD-1 variant—Fc fusion protein comprising: a) culturing said host cell of claim 30 under conditions wherein said Fc fusion protein is expressed; and b) recovering said Fc fusion protein.

32. A method of treating, reducing or preventing metastasis or invasion of a tumor in a subject with cancer, the method comprising administering to the subject a therapeutically effective dose of one or more said Fc fusion proteins of claim 1.

33. The method of claim 32, wherein the cancer is selected from the group consisting of melanoma, glioma, lymphoma, myeloma, head and neck cancer, esophageal cancer, kidney cancer, lung cancer, breast cancer, liver cancer, colorectal cancer, gallbladder cancer, gastric cancer, pancreatic cancer, prostate cancer, cervical cancer, uterine cancer, ovarian cancer, testicular cancer, and any other solid tumor cancer.

34. A method of treating a subject with an infection, the method comprising administering to the subject a therapeutically effective dose of one or more said Fc fusion proteins of claim 1.

35. The method of claim 34, wherein the infection is selected from the group consisting of a fungal infection, bacterial infection and viral infection.

36. The method of claim 35, wherein the viral infection is selected from the group consisting of a hepatitis B virus infection, hepatitis C virus infection, human papilloma virus infection, human immunodeficiency virus (HIV) infection, human T-lymphotrophic virus (HTLV) infection, Epstein-Barr virus infection, herpes virus infection, cytomegalovirus infection, and any other chronic viral infection.

37. The method of claim 32, wherein the effective dose of the one or more Fc fusion proteins inhibits, reduces, or modulates signal transduction mediated by the wild-type PD-1 in the subject.

38. The method of claim 32, wherein the effective dose of the one or more Fc fusion proteins increases a T cell response in the subject.

* * * * *